(12) United States Patent
Blomgren et al.

(10) Patent No.: US 11,578,069 B2
(45) Date of Patent: Feb. 14, 2023

(54) COMPOUNDS FOR INHIBITION OF α4 β7 INTEGRIN

(71) Applicant: Gilead Sciences, Inc., Foster City, CA (US)

(72) Inventors: Peter A. Blomgren, Issaquah, WA (US); Taryn L. Campbell, Seattle, WA (US); Jayaraman Chandrasekhar, Redmond, WA (US); Christopher T. Clark, Seattle, WA (US); Kevin S. Currie, North Bend, WA (US); Jeffrey E. Kropf, Issaquah, WA (US); Yasamin Moazami, Seattle, WA (US); Nicole A. Nava, Seattle, WA (US); Leena Patel, Seattle, WA (US); Jason K. Perry, San Francisco, CA (US); Natalie Seeger, Seattle, WA (US); Kirk L. Stevens, Bothell, WA (US); Zhongdong Zhao, Bellevue, WA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 16/991,708

(22) Filed: Aug. 12, 2020

(65) Prior Publication Data
US 2021/0053967 A1 Feb. 25, 2021

Related U.S. Application Data

(60) Provisional application No. 62/886,798, filed on Aug. 14, 2019.

(51) Int. Cl.
C07D 471/04 (2006.01)
C07C 233/87 (2006.01)
C07D 213/64 (2006.01)
C07D 215/227 (2006.01)
C07D 239/54 (2006.01)
C07D 239/96 (2006.01)
C07D 413/12 (2006.01)
C07D 413/14 (2006.01)
C07D 491/052 (2006.01)

(52) U.S. Cl.
CPC .......... C07D 471/04 (2013.01); C07C 233/87 (2013.01); C07D 213/64 (2013.01); C07D 215/227 (2013.01); C07D 239/54 (2013.01); C07D 239/96 (2013.01); C07D 413/12 (2013.01); C07D 413/14 (2013.01); C07D 491/052 (2013.01)

(58) Field of Classification Search
CPC ................ C07D 471/04; C07D 213/64; C07D 215/227; C07D 239/54; C07D 239/96; C07D 413/12; C07D 413/14; C07D 491/052; C07C 233/87
See application file for complete search history.

(56) References Cited

U.S. PATENT DOCUMENTS

| 6,511,961 | B1 | 1/2003 | Takahashi et al. |
| 6,521,666 | B1 | 2/2003 | Sircar et al. |
| 6,806,312 | B2 | 10/2004 | Sasagawa et al. |
| 7,105,520 | B2 | 9/2006 | Suzuki et al. |
| 7,335,673 | B2 | 2/2008 | Hoshina et al. |
| 7,361,679 | B2 | 4/2008 | Ikegami et al. |
| 7,566,724 | B2 | 7/2009 | Hirano et al. |
| 8,546,610 | B2 | 10/2013 | Kataoka et al. |
| 9,216,174 | B2 | 12/2015 | Shen et al. |
| 9,533,985 | B2 | 1/2017 | Ueno et al. |
| 9,822,110 | B2 | 11/2017 | Ueno et al. |
| 11,116,760 | B2 | 9/2021 | Blomgren et al. |
| 11,174,256 | B2 | 11/2021 | Blomgren et al. |
| 11,179,383 | B2 | 11/2021 | Blomgren et al. |

(Continued)

FOREIGN PATENT DOCUMENTS

| CN | 105483206 A | 4/2016 |
| CN | 106995439 A | 8/2017 |

(Continued)

OTHER PUBLICATIONS

Examination Report dated Aug. 12, 2021 for GCC Appl. No. 2019-38568.

(Continued)

Primary Examiner — Brandon J Fetterolf
Assistant Examiner — Lauren Wells

(57) ABSTRACT

The present disclosure provides a compound of Formula (I):

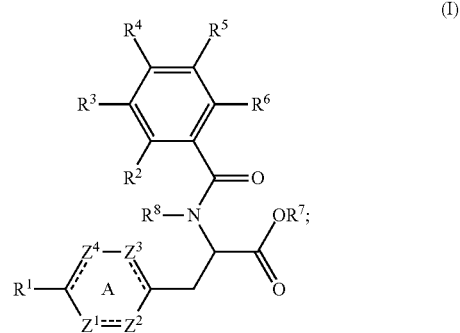

or a pharmaceutically acceptable salt thereof as described herein. The present disclosure also provides pharmaceutical compositions comprising a compound of Formula (I), processes for preparing compounds of Formula (I), therapeutic methods for treating inflammatory disease.

11 Claims, No Drawings

(56) References Cited

U.S. PATENT DOCUMENTS

| | | |
|---|---|---|
| 11,224,600 B2 | 1/2022 | Blomgren et al. |
| 11,370,773 B1 | 6/2022 | Bursavich et al. |
| 2003/0114490 A1 | 6/2003 | Tanaka et al. |
| 2003/0130320 A1 | 7/2003 | Suzuki et al. |
| 2003/0149083 A1 | 8/2003 | Tanaka et al. |
| 2003/0220268 A1 | 11/2003 | Makino et al. |
| 2003/0220318 A1 | 11/2003 | Suzuki et al. |
| 2004/0039040 A1 | 2/2004 | Takahashi et al. |
| 2004/0077693 A1 | 4/2004 | Artis et al. |
| 2004/0087574 A1 | 5/2004 | Takahashi et al. |
| 2004/0110945 A1 | 6/2004 | Nakayama et al. |
| 2004/0132783 A1 | 7/2004 | Ono et al. |
| 2004/0235848 A1 | 11/2004 | Okuzumi et al. |
| 2004/0236147 A1 | 11/2004 | Chiba et al. |
| 2004/0259908 A1 | 12/2004 | Ikegami et al. |
| 2005/0101779 A1 | 5/2005 | Sagi et al. |
| 2005/0187284 A1 | 8/2005 | Artis et al. |
| 2005/0222141 A1 | 10/2005 | Sag et al. |
| 2005/0261291 A1 | 11/2005 | Kawahara et al. |
| 2006/0009476 A1 | 1/2006 | Kataoka et al. |
| 2006/0204572 A1 | 9/2006 | Higuchi et al. |
| 2006/0204574 A1 | 9/2006 | Ogawa et al. |
| 2006/0223836 A1 | 10/2006 | Makino et al. |
| 2006/0241132 A1 | 10/2006 | Ishigaki et al. |
| 2007/0105936 A1 | 5/2007 | Ono et al. |
| 2007/0232601 A1 | 10/2007 | Yoneda et al. |
| 2007/0269835 A1 | 11/2007 | Katayama et al. |
| 2008/0075719 A1 | 3/2008 | Chan et al. |
| 2008/0108634 A1 | 5/2008 | Sagi et al. |
| 2008/0108637 A1 | 5/2008 | Fujita et al. |
| 2008/0161566 A1 | 7/2008 | Kotake et al. |
| 2008/0280909 A1 | 11/2008 | Okuzumi et al. |
| 2009/0048236 A1 | 2/2009 | Suzuki et al. |
| 2009/0163715 A1 | 6/2009 | Nagai et al. |
| 2009/0233901 A1 | 9/2009 | Maohinaga et al. |
| 2009/0318688 A1 | 12/2009 | Kataoka et al. |
| 2009/0325962 A1 | 12/2009 | Jackson et al. |
| 2010/0022783 A1 | 1/2010 | Ono et al. |
| 2010/0137593 A1 | 6/2010 | Takahashi et al. |
| 2010/0204505 A1 | 8/2010 | Kataoka et al. |
| 2010/0267754 A1 | 10/2010 | Wakabayashi et al. |
| 2011/0009434 A1 | 1/2011 | Fujita et al. |
| 2011/0065918 A1 | 3/2011 | Makino et al. |
| 2011/0313154 A1 | 12/2011 | Kataoka et al. |
| 2012/0157437 A1 | 6/2012 | Maohinaga et al. |
| 2012/0253041 A1 | 10/2012 | Makino et al. |
| 2013/0030013 A1 | 1/2013 | Aburatani et al. |
| 2013/0065882 A1 | 3/2013 | Machinaga et al. |
| 2013/0066072 A1 | 3/2013 | Kataoka et al. |
| 2014/0206705 A1 | 7/2014 | Kataoka et al. |
| 2015/0045435 A1 | 2/2015 | Scott et al. |
| 2015/0051395 A1 | 2/2015 | Ueno et al. |
| 2016/0367517 A1 | 12/2016 | Thompson |
| 2017/0196870 A1 | 7/2017 | Kageyama et al. |
| 2018/0244648 A1 | 8/2018 | Harrison et al. |
| 2018/0312498 A1 | 11/2018 | Biediger et al. |
| 2020/0155538 A1 | 5/2020 | Blomgren et al. |
| 2020/0155563 A1 | 5/2020 | Blomgren et al. |
| 2020/0163953 A1 | 5/2020 | Blomgren et al. |
| 2020/0165248 A1 | 5/2020 | Blomgren et al. |
| 2022/0119383 A1 | 4/2022 | Blomgren et al. |
| 2022/0135561 A1 | 5/2022 | Blomgren et al. |
| 2022/0152014 A1 | 5/2022 | Blomgren et al. |
| 2022/0226337 A1 | 7/2022 | Blomgren et al. |

FOREIGN PATENT DOCUMENTS

| | | |
|---|---|---|
| EP | 1209147 A1 | 5/2002 |
| EP | 1323711 A1 | 7/2003 |
| EP | 1889827 B1 | 8/2010 |
| EP | 3064491 A1 | 9/2016 |
| EP | 2842945 B1 | 10/2016 |
| IN | 2966/DEL/2005 | 7/2009 |
| JP | 2001089368 A | 4/2001 |
| JP | 2003048889 A | 2/2003 |
| JP | 2003277340 A | 10/2003 |
| JP | 2003-321358 A | 11/2003 |
| JP | 2004277338 A | 10/2004 |
| JP | 2015083970 A | 4/2015 |
| JP | 201637467 A | 3/2016 |
| JP | 201637468 A | 3/2016 |
| JP | 2019031449 A | 2/2019 |
| WO | WO-94/012181 A1 | 6/1994 |
| WO | WO-96/000581 A1 | 1/1996 |
| WO | WO-97/003094 A1 | 1/1997 |
| WO | WO-97/005865 A1 | 2/1997 |
| WO | WO-98/004247 A1 | 2/1998 |
| WO | WO-98/042656 A1 | 10/1998 |
| WO | WO-98/053814 A1 | 12/1998 |
| WO | WO-98/053817 A1 | 12/1998 |
| WO | WO-98/053818 A1 | 12/1998 |
| WO | WO-98/058902 A1 | 12/1998 |
| WO | WO-99/006431 A1 | 2/1999 |
| WO | WO-99/006434 A1 | 2/1999 |
| WO | WO-99/006436 A1 | 2/1999 |
| WO | WO-99/006437 A1 | 2/1999 |
| WO | WO-99/010312 A1 | 3/1999 |
| WO | WO-99/010313 A1 | 3/1999 |
| WO | WO-99/013898 A1 | 3/1999 |
| WO | WO-99/025731 A1 | 5/1999 |
| WO | WO-99/026615 A1 | 6/1999 |
| WO | WO-99/026921 A1 | 6/1999 |
| WO | WO-99/030713 A1 | 6/1999 |
| WO | WO-99/036393 A1 | 7/1999 |
| WO | WO-99/052898 A1 | 10/1999 |
| WO | WO-99/061421 A1 | 12/1999 |
| WO | WO-99/062901 A1 | 12/1999 |
| WO | WO-99/064395 A1 | 12/1999 |
| WO | WO-99/067230 A1 | 12/1999 |
| WO | WO-2000/002903 A1 | 1/2000 |
| WO | WO-2000/005223 A2 | 2/2000 |
| WO | WO-2000/015612 A1 | 3/2000 |
| WO | WO-2000/035855 A1 | 6/2000 |
| WO | WO-2000/037444 A1 | 6/2000 |
| WO | WO-2000/043354 A2 | 7/2000 |
| WO | WO-2000/043369 A1 | 7/2000 |
| WO | WO-2000/043371 A2 | 7/2000 |
| WO | WO-2000/043372 A1 | 7/2000 |
| WO | WO-2000/043413 A2 | 7/2000 |
| WO | WO-2000/048994 A1 | 8/2000 |
| WO | WO-2000/051974 A1 | 9/2000 |
| WO | WO-2000/063234 A2 | 10/2000 |
| WO | WO-2000/064866 A1 | 11/2000 |
| WO | WO-2000/067746 A1 | 11/2000 |
| WO | WO-2000/071572 A1 | 11/2000 |
| WO | WO-2001/000206 A1 | 1/2001 |
| WO | WO-2001/007400 A1 | 2/2001 |
| WO | WO-2001/012183 A1 | 2/2001 |
| WO | WO-2001/012186 A1 | 2/2001 |
| WO | WO-2001/014328 A2 | 3/2001 |
| WO | WO-2001/021584 A1 | 3/2001 |
| WO | WO-2001/032610 A1 | 5/2001 |
| WO | WO-2001/042215 A1 | 6/2001 |
| WO | WO-2001/042225 A2 | 6/2001 |
| WO | WO-2001/043774 A1 | 6/2001 |
| WO | WO-2001/047868 A1 | 7/2001 |
| WO | WO-2001/047887 A1 | 7/2001 |
| WO | WO-2001/053279 A1 | 7/2001 |
| WO | WO-2001/053295 A1 | 7/2001 |
| WO | WO-2001/055121 A1 | 8/2001 |
| WO | WO-2001/056994 A1 | 8/2001 |
| WO | WO-2001/068586 A2 | 9/2001 |
| WO | WO-2001/070670 A1 | 9/2001 |
| WO | WO-2002/002556 A2 | 1/2002 |
| WO | WO-2002/008201 A2 | 1/2002 |
| WO | WO-2002/008203 A2 | 1/2002 |
| WO | WO-2002/008206 A1 | 1/2002 |
| WO | WO-2002/014262 A1 | 2/2002 |
| WO | WO-2002/016329 A1 | 2/2002 |
| WO | WO-2002/018320 A2 | 3/2002 |
| WO | WO-2002/022563 A1 | 3/2002 |
| WO | WO-2002/024697 A1 | 3/2002 |
| WO | WO-2002/028830 A1 | 4/2002 |
| WO | WO-2002/053534 A1 | 7/2002 |

(56) References Cited

FOREIGN PATENT DOCUMENTS

| | | |
|---|---|---|
| WO | WO-2002/057242 A2 | 7/2002 |
| WO | WO-2002/068393 A1 | 9/2002 |
| WO | WO-2003/008380 A1 | 1/2003 |
| WO | WO-2003/010135 A1 | 2/2003 |
| WO | WO-2003/011815 A1 | 2/2003 |
| WO | WO-2003/024933 A1 | 3/2003 |
| WO | WO-2003/048126 A1 | 6/2003 |
| WO | WO-2003/053926 A1 | 7/2003 |
| WO | WO-2003/070709 A1 | 8/2003 |
| WO | WO-2003/072536 A1 | 9/2003 |
| WO | WO-2003/080611 A1 | 10/2003 |
| WO | WO-2003/089410 A1 | 10/2003 |
| WO | WO-2003/093237 A1 | 11/2003 |
| WO | WO-2003/099231 A2 | 12/2003 |
| WO | WO-2003/099809 A1 | 12/2003 |
| WO | WO-2004/006918 A1 | 1/2004 |
| WO | WO-2004/007428 A1 | 1/2004 |
| WO | WO-2004/007494 A1 | 1/2004 |
| WO | WO-2004/014844 A2 | 2/2004 |
| WO | WO-2004/014859 A2 | 2/2004 |
| WO | WO-2004/062601 A2 | 7/2004 |
| WO | WO-2004/066931 A2 | 8/2004 |
| WO | WO-2004/066932 A2 | 8/2004 |
| WO | WO-2004/074264 A1 | 9/2004 |
| WO | WO-2004/099126 A1 | 11/2004 |
| WO | WO-2004/103967 A2 | 12/2004 |
| WO | WO-2005/000244 A2 | 1/2005 |
| WO | WO-2005/009992 A1 | 2/2005 |
| WO | WO-2005/014532 A1 | 2/2005 |
| WO | WO-2005/040135 A1 | 5/2005 |
| WO | WO-2005/042529 A1 | 5/2005 |
| WO | WO-2005/044817 A1 | 5/2005 |
| WO | WO-2005/061440 A1 | 7/2005 |
| WO | WO-2005/061466 A1 | 7/2005 |
| WO | WO-2005/063705 A1 | 7/2005 |
| WO | WO-2005/070921 A1 | 8/2005 |
| WO | WO-2005/077914 A1 | 8/2005 |
| WO | WO-2005/077915 A1 | 8/2005 |
| WO | WO-2005/087760 A1 | 9/2005 |
| WO | WO-2005/097162 A2 | 10/2005 |
| WO | WO-2005/107762 A2 | 11/2005 |
| WO | WO-2005/121135 A1 | 12/2005 |
| WO | WO-2006/010054 A2 | 1/2006 |
| WO | WO-2006/019632 A2 | 2/2006 |
| WO | WO-2006/023396 A2 | 3/2006 |
| WO | WO-2006/028393 A1 | 3/2006 |
| WO | WO-2006/052962 A2 | 5/2006 |
| WO | WO-2006/066780 A1 | 6/2006 |
| WO | WO-2006/068058 A1 | 6/2006 |
| WO | WO-2006/068213 A1 | 6/2006 |
| WO | WO-2006/081986 A1 | 8/2006 |
| WO | WO-2006/090234 A1 | 8/2006 |
| WO | WO-2006/096807 A1 | 9/2006 |
| WO | WO-2006/112738 A1 | 10/2006 |
| WO | WO-2006/113199 A1 | 10/2006 |
| WO | WO-2006/115918 A2 | 11/2006 |
| WO | WO-2006/126635 A1 | 11/2006 |
| WO | WO-2006/127584 A1 | 11/2006 |
| WO | WO-2006/131200 A1 | 12/2006 |
| WO | WO-2007/004958 A1 | 1/2007 |
| WO | WO-2007/069635 A1 | 6/2007 |
| WO | WO-2007/082809 A1 | 7/2007 |
| WO | WO-2007/100763 A2 | 9/2007 |
| WO | WO-2007/101165 A1 | 9/2007 |
| WO | WO-2008/062859 A1 | 5/2008 |
| WO | WO-2008/064830 A1 | 6/2008 |
| WO | WO-2008/125210 A1 | 10/2008 |
| WO | WO-2008138591 A2 * 11/2008 ........... C07D 263/56 |
| WO | WO-2008/154642 A1 | 12/2008 |
| WO | WO-2009/075806 A1 | 6/2009 |
| WO | WO-2009/124755 A1 | 10/2009 |
| WO | WO-2009/140621 A2 | 11/2009 |
| WO | WO-2010/104306 A2 | 9/2010 |
| WO | WO-2010/105363 A1 | 9/2010 |
| WO | WO-2010/112865 A1 | 10/2010 |
| WO | WO-2010/126914 A1 | 11/2010 |
| WO | WO-2011/048091 A1 | 4/2011 |
| WO | WO-2011/094890 A1 | 8/2011 |
| WO | WO-2011/122619 A1 | 10/2011 |
| WO | WO-2011/143274 A1 | 11/2011 |
| WO | WO-2011/150499 A1 | 12/2011 |
| WO | WO-2011/159781 A2 | 12/2011 |
| WO | WO-2012/011123 A1 | 1/2012 |
| WO | WO-2012/068251 A2 | 5/2012 |
| WO | WO-2012/106343 A2 | 8/2012 |
| WO | WO-2013/070842 A1 | 5/2013 |
| WO | WO-2013/110680 A1 | 8/2013 |
| WO | WO-2013/110681 A1 | 8/2013 |
| WO | WO-2013/148978 A1 | 10/2013 |
| WO | WO-2013/161904 A1 | 10/2013 |
| WO | WO-2013/178816 A1 | 12/2013 |
| WO | WO-2014/051056 A1 | 4/2014 |
| WO | WO-2014/052605 A1 | 4/2014 |
| WO | WO-2015/064580 A1 | 5/2015 |
| WO | WO-2015/138882 A1 | 9/2015 |
| WO | WO-2015/172196 A1 | 11/2015 |
| WO | WO-2016/040505 A1 | 3/2016 |
| WO | WO-2016/051828 A1 | 4/2016 |
| WO | WO-2016/145258 A1 | 9/2016 |
| WO | WO-2017/006272 A1 | 1/2017 |
| WO | WO-2017/070518 A1 | 4/2017 |
| WO | WO-2017/126637 A1 | 7/2017 |
| WO | WO-2017/132620 A1 | 8/2017 |
| WO | WO-2017/135471 A1 | 8/2017 |
| WO | WO-2017/135472 A1 | 8/2017 |
| WO | WO-2018/049068 A1 | 3/2018 |
| WO | WO-2018/064119 A1 | 4/2018 |
| WO | WO-2018/085552 A1 | 5/2018 |
| WO | WO-2018/085574 A2 | 5/2018 |
| WO | WO-2018/089353 A1 | 5/2018 |
| WO | WO-2018/089355 A1 | 5/2018 |
| WO | WO-2018/089357 A1 | 5/2018 |
| WO | WO-2018/089358 A1 | 5/2018 |
| WO | WO-2018/089360 A1 | 5/2018 |
| WO | WO-2018/160522 A1 | 9/2018 |
| WO | WO-2018/200625 A1 | 11/2018 |
| WO | WO-2018/201167 A2 | 11/2018 |
| WO | WO-2019/085441 A1 | 5/2019 |
| WO | WO-2019/094319 A1 | 5/2019 |
| WO | WO-2019/173653 A1 | 9/2019 |
| WO | WO-2019/178248 A1 | 9/2019 |
| WO | WO-2019/200202 A1 | 10/2019 |
| WO | WO-2019246455 A1 * 12/2019 ............. A61K 47/02 |
| WO | WO-2020/033724 A1 | 2/2020 |
| WO | WO-2020/043533 A1 | 3/2020 |
| WO | WO-2020/047207 A1 | 3/2020 |
| WO | WO-2020/047208 A1 | 3/2020 |
| WO | WO-2020/047239 A1 | 3/2020 |
| WO | WO-2020/092375 A1 | 5/2020 |
| WO | WO-2020/092383 A1 | 5/2020 |
| WO | WO-2020/092394 A1 | 5/2020 |
| WO | WO-2020/092401 A1 | 5/2020 |
| WO | WO-2021/030438 A1 | 2/2021 |

OTHER PUBLICATIONS

Intl. Preliminary Report on Patentability dated May 14, 2021 for Intl. Appl. No. PCT/US2019/058573.
Intl. Preliminary Report on Patentability dated May 14, 2021 for Intl. Appl. No. PCT/US2019/058583.
Intl. Preliminary Report on Patentability dated May 14, 2021 for Intl. Appl. No. PCT/US2019/058599.
Intl. Preliminary Report on Patentability dated May 14, 2021 for Intl. Appl. No. PCT/US2019/058610.
Intl. Search Re port-Written Opinion dated Jan. 21, 2021 for Intl. Appl. No. PCT/US2020/045938.
Non-Final Office Action dated Mar. 19, 2021 for U.S. Appl. No. 16/667,532.
Notice of Allowance and Fees Due dated Feb. 24, 2021 for U.S. Appl. No. 16/667,306.
Notice of Allowance and Fees Due dated Mar. 12, 2021 for U.S. Appl. No. 16/667,373.

(56) References Cited

OTHER PUBLICATIONS

Notice of Allowance and Fees Due dated Mar. 19, 2021 for U.S. Appl. No. 16/667,572.
Notice of Allowance and Fees Due dated Jun. 14, 2021 for U.S. Appl. No. 16/667,306.
Notice of Allowance dated Mar. 26, 2021 for Taiwanese Appl. No. 108139358.
Notice of Allowance and Fees Due dated Jul. 15, 2021 for U.S. Appl. No. 16/667,532.
Examination Report dated Aug. 27, 2021 for Australian Appl. No. 2019373244.
Examination Report dated Nov. 11, 2021 for Indian Appl. No. 202117022534.
Examination Report dated Aug. 23, 2021 for Australian Appl. No. 2019373245.
Examination Report dated Nov. 16, 2021 for Indian Appl. No. 202117023382.
Non-Final Office Action dated Jul. 9, 2021 for U.S. Appl. No. 16/667,373.
Final Office Action dated Aug. 12, 2021 for U.S. Appl. No. 16/667,373.
Notice of Allowance and Fees Due dated Sep. 15, 2021 for U.S. Appl. No. 16/667,373.
Examination Report dated Nov. 15, 2021 for Indian Appl. No. 202117023381.
Office Action dated Jul. 14, 2021 for Taiwanese Appl. No. 109127810.
Ravi C. et al. (2017), "Synthesis of Imidazo[1,2-a]pyridines: C—H Functionalization in the Direction of C—S Bond Formation", The Chemical Record, 17(10), 1019-1038.
Hatley R J D et al. (2019), "The Design of Potent, Selective and Drug-Like RGD αvβ1 Small-Molecule Inhibitors Derived from non-RGD α4β1 Antagonists", Chem MedChem, 14, 1-7.
Intl. Search Re port-Written Opinion dated Jan. 14, 2020 for Intl. Appl. No. PCT/US2019/058610.
Intl. Search Re port-Written Opinion dated Jan. 21, 2020 for Intl. Appl. No. PCT/US2019/058573.
Intl. Search Re port-Written Opinion dated Jan. 23, 2020 for Intl. Appl. No. PCT/US2019/058583.
Intl. Search Re port-Written Opinion dated Jan. 28, 2020 for Intl. Appl. No. PCT/US2019/058599.
Li H et al. (2018), "$\alpha_{4\beta7}$ integrin inhibitors: a patent review", Expert Opinion on Therapeutic Patents, 28:12, 903-917.
Notice of Allowance and Search Report dated Nov. 4, 2020 for Taiwanese Appl. No. 108139338.
Office Action dated Aug. 4, 2020 for Taiwanese Appl. No. 108139359.
Office Action dated Sep. 11, 2020 for Taiwanese Appl. No. 108139358.
Office Action dated Sep. 18, 2020 for Taiwanese Appl. No. 108139336.
Sircar Ila et al. (2002), "Synthesis and SAR of N-Benzoyl-L-Biphenylalanine Derivatives: Discovery of TR-14035, A Dual α4β7/α4β1 Integrin Antagonist", Bioorganic & Medicinal Chemistry, vol. 10, No. 6, pp. 2051-2066.
Xu Y-Z et al. (2013), "Orally available and efficacious α4β1/α4β7 integrin inhibitors", Bioorganic & Medicinal Chemistry Letters 23:4370-4373.
Examination Report dated Jan. 28, 2022 for Indian Appl. No. 202117019649.
Intl. Preliminary Report on Patentability dated Feb. 24, 2022 for Intl. Appl. No. PCT/US2020/045938.
Office Action dated Mar. 17, 2022 for Taiwanese Appl. No. 109127810.
Examination Report dated Apr. 22, 2022 for Australian Appl. No. 2019373240.
Office Action dated May 6, 2022 for Japanese Appl. No. 2021-548535.
Office Action dated May 6, 2022 for Japanese Appl. No. 2021-548531.
Examination Report dated Apr. 27, 2022 for Indian Appl. No. 202217010515.

* cited by examiner

COMPOUNDS FOR INHIBITION OF α4 β7 INTEGRIN

CROSS REFERENCE TO RELATED APPLICATIONS

This application claims the benefit of U.S. Provisional Application No. 62/886,798, filed on Aug. 14, 2019, the entire content of which is hereby incorporated by reference in its entirety.

FIELD

The present disclosure relates generally to novel compounds that have α4β7 integrin inhibitory action, prodrugs of compounds having α4β7 integrin inhibitory action, and methods of use and manufacture thereof.

BACKGROUND

Integrins are heterodimeric cell surface proteins involved in numerous cellular processes including cell-cell and cell-extracellular matrix interactions. Upon binding of an extracellular ligand, integrins mediate signal transduction to the cell interior resulting in lymphocyte cell capture, adhesion, and infiltration into the tissue.

Integrins are heterodimeric proteins consisting of an alpha and a beta subunit. There are 18 known alpha subunits and 8 known beta subunits. The α4β7 integrin is expressed on the surface of lymphocytes and recognizes the extracellular ligand mucosal addressing cell adhesion molecule-1 (MAdCAM-1). α4β7 integrin governs lymphocyte trafficking to and retention in gut tissues through its interaction with MAdCAM-1, which is expressed on venules in the intestinal mucosa and high endothelial venules (HEV) in the gut-associated lymphoid tissues (GALT). Inhibiting the interactions of integrins with their respective ligands has been proposed as an effective method of treating a variety of autoimmune and inflammatory diseases, and blocking the α4β7-MAdCAM-1 interaction has shown therapeutic benefit in inflammatory bowel disease (Crohn's disease and ulcerative colitis).

There is a need to for improved α4β7 integrin antagonist molecules for the treatment of autoimmune and inflammatory diseases, including inflammatory bowel disease.

SUMMARY

The present disclosure provides compounds that are inhibitors for α4β7 integrin. The disclosure also provides compositions, including pharmaceutical compositions, kits that include the compounds, and methods of using (or administering) and making the compounds. The compounds provided herein are useful in treating diseases, disorders, or conditions that are mediated by α4β7 integrin. The disclosure also provides compounds for use in therapy. The disclosure further provides compounds for use in a method of treating a disease, disorder, or condition that is mediated by α4β7 integrin. Moreover, the disclosure provides uses of the compounds in the manufacture of a medicament for the treatment of a disease, disorder or condition that is mediated by α4β7 integrin.

In one aspect, provided is a compound having the structure of Formula (I), or a pharmaceutically acceptable salt thereof:

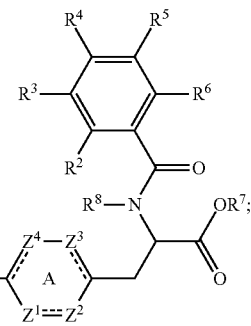

(I)

or a pharmaceutically acceptable salt thereof, wherein:
$\mathrel{\overline{\overline{\phantom{=}}}}$ is a single or double bond; wherein A is an aromatic ring;
each $Z^1$, $Z^2$, $Z^3$, and $Z^4$ is independently selected from N, $N(CR^c)$, $C(O)$, and $CR^c$; wherein each $R^c$ is independently selected from H, halo, cyano, hydroxyl, $-NR^{a1}R^{a2}$, $C_{1-4}$alkyl, $C_{1-4}$alkoxyl, $C_{1-4}$haloalkyl, and $C_{1-4}$haloalkoxyl;
$R^1$ is 5-10 membered heteroaryl or 6-10 membered heterocyclyl;
wherein each 5-10 membered heteroaryl and 6-10 membered heterocyclyl of $R^1$ contains one to four N and optionally one to three C(O) as a ring member(s); and
wherein each 5-10 membered heteroaryl and 6-10 membered heterocyclyl of $R^1$ is optionally substituted with one to four $R^a$; and wherein each $R^a$ is independently selected from halo, cyano, hydroxyl, $-NR^{a1}R^{a2}$, $C_{1-4}$alkyl, $C_{1-4}$alkoxyl, $C_{1-4}$haloalkyl, $C_{1-4}$haloalkoxyl, $-C_{1-4}$alkylene-O-$C_{1-4}$alkyl, and $C_{3-10}$cycloalkyl;
each $R^2$, $R^3$, $R^5$, and $R^6$ is independently selected from H, halo, cyano, hydroxyl, $-NR^{a1}R^{a2}$, $C_{1-4}$alkyl, $C_{1-4}$alkoxyl, $C_{1-4}$haloalkyl, and $C_{1-4}$haloalkoxyl;
$R^4$ is selected from 3-10 membered heterocyclyl, 5-10 membered heteroaryl, and $-NR^{b1}R^{b2}$.
wherein the 3-10 membered heterocyclyl and 5-10 membered heteroaryl of $R^4$ is optionally substituted with one to six $R^b$; and wherein each $R^b$ is independently selected from halo, cyano, hydroxyl, $-NR^{a1}R^{a2}$, $C_{1-6}$alkyl, $C_{1-6}$alkoxyl, $C_{1-8}$haloalkyl, and $C_{1-8}$haloalkoxyl; and
wherein each $R^{b1}$ and $R^{b2}$ is independently selected from H, $C_{1-6}$alkyl, $C_{1-6}$haloalkyl, $C_{3-10}$cycloalkyl, $-C_{1-6}$alkylene-phenyl, and $-C_{1-6}$haloalkylene-phenyl;
$R^7$ is selected from H, $C_{1-10}$alkyl, $C_{1-10}$haloalkyl, $C_{3-10}$cycloalkyl, 3-14 membered heterocyclyl, $C_{6-10}$aryl, 5-10 membered heteroaryl, $-C_{1-4}$alkylene-$NR^{a1}R^{a2}$, $-C_{1-4}$alkylene-$C(O)NR^{a1}R^{a2}$, $-C_{1-4}$alkylene-$C_{3-10}$cycloalkyl, $-C_{1-4}$alkylene-3-14 membered heterocyclyl, $-C_{1-4}$alkylene-$C_{6-10}$aryl, $-C_{1-4}$alkylene-5-10 membered heteroaryl, and $-L^1-R^9$;
wherein $L^1$ is selected from $-C_{1-4}$alkylene-O-, $-C_{1-4}$alkylene-C(O)-, $-C_{1-4}$alkylene-O-C(O)-, $-C_{1-4}$alkylene-O-C(O)-$C_4$alkylene-, $-C_{1-4}$alkylene-C(O)-O-, $-C_{1-4}$alkylene-C(O)-O-$C_{1-4}$alkylene-, $-C_{1-4}$alkylene-O-C(O)-O-, $-C_{1-4}$alkylene-O-C(O)-O-$C_{1-4}$alkylene-, $-C_{1-4}$alkylene-$NR^{a1}C(O)$-O-, and $-C_{1-4}$alkylene-O-C(O)-$NR^{a1}$-;
$R^9$ is selected from $C_{1-6}$alkyl, $C_{1-6}$haloalkyl, $C_{3-10}$cycloalkyl, 3-14 membered heterocyclyl, $C_{6-10}$aryl, and 5-10 membered heteroaryl;
wherein each $C_{3-10}$cycloalkyl, 3-14 membered heterocyclyl, $C_{6-10}$aryl, and 5-10 membered heteroaryl of $R^7$ and $R^9$ is optionally substituted with one to four groups independently selected from halo, hydroxyl, $C_{1-4}$alkyl, $C_{1-4}$alkoxyl, $C_{1-4}$haloalkyl, $C_{1-4}$haloalkoxyl, —$NR^{a1}R^{a2}$, and —$C_{1-4}$alkylene-$NR^{a1}R^{a2}$;

$R^8$ is selected from H, $C_{1-6}$alkyl, and $C_{1-6}$haloalkyl; and each $R^{a1}$ and $R^{a2}$ is independently selected from H, $C_{1-6}$alkyl, $C_{1-6}$haloalkyl, and $C_{3-10}$cycloalkyl.

DETAILED DESCRIPTION

Definitions and General Parameters

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —$CONH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

The prefix "$C_{u-v}$" indicates that the following group has from u to v carbon atoms. For example, "$C_{1-8}$ alkyl" indicates that the alkyl group has from 1 to 8 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Alkylene" (including those which are part of other groups) refers to branched and unbranched divalent "alkyl" groups. As used herein, alkylene has 1 to 20 carbon atoms (i.e., $C_{1-20}$alkylene), 1 to 8 carbon atoms (i.e., $C_{1-8}$ alkylene), 1 to 6 carbon atoms (i.e., $C_{1-6}$ alkylene), or 1 to 4 carbon atoms (i.e., $C_{1-4}$ alkylene). Examples include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propylene also includes 1-methylethylene and butylene includes 1-methylpropylene, 1,1-dimethylethylene, and 1,2-dimethylethylene.

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" and "alkoxyl" are used interchangeably and refer to the group "alkyl-O—". Examples of alkoxyl and alkoxy groups include methoxy, ethoxy, n-propoxy, isopropoxy, n-butoxy, tert-butoxy, sec-butoxy, n-pentoxy, n-hexoxy, and 1,2-dimethylbutoxy. "Haloalkoxyl" refers to an alkoxyl group as defined above, wherein one or more hydrogen atoms are replaced by a halogen.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Azido" refers to the group —$N_3$.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl. Cycloalkyl groups also include partially unsaturated ring systems containing one or more double bonds, including fused ring systems with one aromatic ring and one non-aromatic ring, but not fully aromatic ring systems.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

The term "fused" refers to a ring which is bound to an adjacent ring.

"Halogen" or "halo" includes fluoro, chloro, bromo, and iodo.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—$CHF_2$) and trifluoromethyl (—$CF_3$).

"Haloalkylene" refers to an unbranched or branched alkylene group as defined above, wherein one or more hydrogen atoms are replaced by a halogen.

The term "heterocyclyl" or "heterocycle" as used herein refers to a single saturated or partially unsaturated non-aromatic ring or a non-aromatic multiple ring system that has at least one heteroatom in the ring (i.e., at least one annular heteroatom selected from O, N, S, S(O), S(O)$_2$, and N-oxide groups). Unless otherwise specified, a heterocyclyl group has from 3 to about 20 annular atoms, for example from 3 to 12 annular atoms, for example from 3 to 10 annular atoms, for example from 5 to 10 annular atoms or for example from 5 to 6 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms independently selected from the group consisting of O, N, S, S(O), S(O)$_2$, and N-oxide in the ring. The rings of the multiple condensed ring (e.g. bicyclic heterocyclyl) system can be connected to each other via fused, spiro and bridged bonds when allowed by valency requirements. Heterocycles include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, N-bromopyrrolidine, N-chloropiperidine, and the like. Heterocycles include spirocycles, such as, for example, aza or oxo-spiroheptanes. Heterocyclyl groups also include partially unsaturated ring systems containing one or more double bonds, including fused ring systems with one aromatic ring and one non-aromatic ring, but not fully aromatic ring systems. Examples include dihydroquinolines, e.g. 3,4-dihydroquinoline, dihydroisoquinolines, e.g. 1,2-dihydroisoquinoline, dihydroimidazole, tetrahydroimidazole, etc., indoline, isoindoline, isoindolones (e.g. isoindolin-1-one), isatin, dihydrophthalazine, quinolinone, spiro[cyclopropane-1,1'-isoindolin]-3'-one, and the like. Additional examples of heterocycles include 3,8-diazabicyclo[3.2.1]octanyl, 2,5-diazabicyclo [2.2.1]heptanyl, 3,6-diazabicyclo [3.1.1]heptanyl, 3-oxa-7,9-diazabicyclo[3.3.1]nonanyl, and hexahydropyrazino[2,1-c][1,4]oxazinyl, for example.

"Hydroxyl" and "hydroxy" are used interchangeably and refer to —OH. "Oxo" refers to the group (=O) or (O). Where tautomeric forms of the compound exist, hydroxyl and oxo groups are interchangeable.

"Heteroaryl" refers to an aromatic group, including groups having an aromatic tautomer or resonance structure, having a single ring, multiple rings, or multiple fused rings, with at least one heteroatom in the ring, i.e., one or more ring heteroatoms independently selected from nitrogen, oxygen, and sulfur, wherein the nitrogen or sulfur may be oxidized. Thus, the term includes rings having one or more annular O, N, S, S(O), S(O)$_2$, and N-oxide groups. The term includes rings having one or more annular C(O) groups. As used herein, heteroaryl include 5 to 20 ring atoms (i.e., 5- to 20-membered heteroaryl), 5 to 12 ring atoms (i.e., 5- to 12-membered heteroaryl), or 5 to 10 ring atoms (i.e., 5- to 10-membered heteroaryl), and 1 to 5 heteroatoms independently selected from nitrogen, oxygen, and sulfur, and oxidized forms of the heteroatoms. Examples of heteroaryl groups include pyridin-2(1H)-one, pyridazin-3(2H)-one, pyrimidin-4(3H)-one, quinolin-2(1H)-one, pyrimidinyl, purinyl, pyridyl, pyridazinyl, benzothiazolyl, and pyrazolyl. Heteroaryl does not encompass or overlap with aryl as defined above.

"Sulfonyl" refers to the group —S(O)$_2$R, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, the term "substituted alkyl" refers to an alkyl group having one or more substituents including hydroxyl, halo, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, alkoxy, halo, oxo, and hydroxyl; "substituted heterocyclyl" refers to a heterocyclyl group having one or more substituents including alkyl, haloalkyl, heterocyclyl, cycloalkyl, aryl, heteroaryl, alkoxy, halo, oxo, and hydroxyl; "substituted aryl" refers to an aryl group having one or more substituents including halo, alkyl, haloalkyl, cycloalkyl, heterocyclyl, heteroaryl, alkoxy, and cyano; "substituted heteroaryl" refers to an heteroaryl group having one or more substituents including halo, alkyl, haloalkyl, heterocyclyl, heteroaryl, alkoxy, and cyano and "substituted sulfonyl" refers to a group —$S(O)_2R$, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of the present disclosure, in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of the present disclosure, when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of the present disclosure.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl)

amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of α4β7 integrin activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of α4β7 integrin" or variants thereof refers to a decrease in activity of α4β7 integrin as a direct or indirect response to the presence of a compound of the present application relative to the activity of α4β7 integrin in the absence of the compound of the present application. "Inhibition of α4β7" refers to a decrease in α4β7 integrin activity as a direct or indirect response to the presence of a compound described herein relative to the activity of α4β7 integrin in the absence of the compound described herein. In some embodiments, the inhibition of α4β7 integrin activity may be compared in the same subject prior to treatment, or other subjects not receiving the treatment.

Compounds

Provided herein are compounds that function as inhibitors of α4β7 integrin. In one aspect, provided is a compound having structure of Formula (I), or a pharmaceutically acceptable salt thereof:

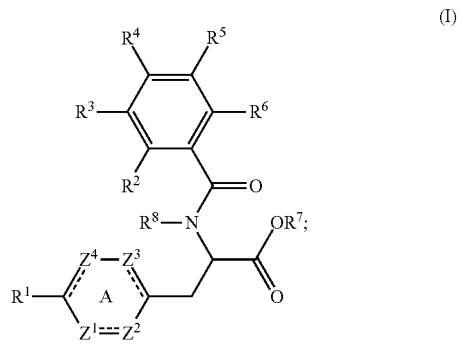

or a pharmaceutically acceptable salt thereof, wherein: $\equiv\equiv\equiv$ is a single or double bond; wherein A is an aromatic ring;

each $Z^1$, $Z^2$, $Z^3$, and $Z^4$ is independently selected from N, N(CR$^c$), C(O), and CR$^c$; wherein each R$^c$ is independently selected from H, halo, cyano, hydroxyl, —NR$^{a1}$R$^{a2}$, $C_{1-4}$alkyl, $C_{1-4}$alkoxyl, $C_{1-4}$haloalkyl, and $C_{1-4}$haloalkoxyl;

R$^1$ is 5-10 membered heteroaryl or 6-10 membered heterocyclyl;

wherein each 5-10 membered heteroaryl and 6-10 membered heterocyclyl of R$^1$ contains one to four N and optionally one to three C(O) as a ring member(s); and wherein each 5-10 membered heteroaryl and 6-10 membered heterocyclyl of R$^1$ is optionally substituted with one to four R$^a$; and wherein each R$^a$ is independently selected from halo, cyano, hydroxyl, —NR$^{a1}$R$^{a2}$, $C_{1-4}$alkyl, $C_{1-4}$alkoxyl, $C_{1-4}$haloalkyl, $C_{1-4}$haloalkoxyl, —$C_{1-4}$alkylene-O—$C_{1-4}$alkyl, and $C_{3-10}$cycloalkyl;

each R$^2$, R$^3$, R$^5$, and R$^6$ is independently selected from H, halo, cyano, hydroxyl, —NR$^{a1}$R$^{a2}$, $C_{1-4}$alkyl, $C_{1-4}$alkoxyl, $C_{1-4}$haloalkyl, and $C_{1-4}$haloalkoxyl;

R$^4$ is selected from 3-10 membered heterocyclyl, 5-10 membered heteroaryl, and —NR$^{b1}$R$^{b2}$;

wherein the 3-10 membered heterocyclyl and 5-10 membered heteroaryl of $R^4$ is optionally substituted with one to six $R^b$; and wherein each $R^b$ is independently selected from halo, cyano, hydroxyl, $-NR^{a1}R^{a2}$, $C_{1-6}$alkyl, $C_{1-6}$alkoxyl, $C_{1-8}$haloalkyl, and $C_{1-8}$haloalkoxyl; and wherein each $R^{b1}$ and $R^{b2}$ is independently selected from H, $C_{1-6}$alkyl, $C_{1-6}$haloalkyl, $C_{3-10}$cycloalkyl, $-C_{1-6}$alkylene-phenyl, and $-C_{1-6}$haloalkylene-phenyl;

$R^7$ is selected from H, $C_{1-10}$alkyl, $C_{1-10}$haloalkyl, $C_{3-10}$cycloalkyl, 3-14 membered heterocyclyl, $C_{6-10}$aryl, 5-10 membered heteroaryl, $-C_{1-4}$alkylene-$NR^{a1}R^{a2}$, $-C_{1-4}$alkylene-$C(O)NR^{a1}R^{a2}$, $-C_{1-4}$alkylene-$C_{3-10}$cycloalkyl, $-C_{1-4}$alkylene-3-14 membered heterocyclyl, $-C_{1-4}$alkylene-$C_{6-10}$aryl, $-C_{1-4}$alkylene-5-10 membered heteroaryl, and $-L^1-R^9$;

wherein $L^1$ is selected from $-C_{1-4}$alkylene-O—, $-C_{1-4}$alkylene-C(O)—, $-C_{1-4}$alkylene-O—C(O)—, $-C_{1-4}$alkylene-O—C(O)—$C_{1-4}$alkylene-, $-C_{1-4}$alkylene-C(O)—O—, $-C_{1-4}$alkylene-C(O)—O—$C_{1-4}$alkylene-, $-C_{1-4}$alkylene-O—C(O)—O—, $-C_{1-4}$alkylene-O—C(O)—O—$C_{1-4}$alkylene-, $-C_{1-4}$alkylene-$NR^{a1}$C(O)—O—, and $-C_{1-4}$alkylene-O—C(O)—$NR^{a1}$—;

$R^9$ is selected from $C_{1-6}$alkyl, $C_{1-6}$haloalkyl, $C_{3-10}$cycloalkyl, 3-14 membered heterocyclyl, $C_{6-10}$aryl, and 5-10 membered heteroaryl;

wherein each $C_{3-10}$cycloalkyl, 3-14 membered heterocyclyl, $C_{6-10}$aryl, and 5-10 membered heteroaryl of $R^7$ and $R^9$ is optionally substituted with one to four groups independently selected from halo, hydroxyl, $C_{1-4}$alkyl, $C_{1-4}$alkoxyl, $C_{1-4}$haloalkyl, $C_{1-4}$haloalkoxyl, $-NR^{a1}R^{a2}$, and $-C_{1-4}$alkylene-$NR^{a1}R^{a2}$;

$R^8$ is selected from H, $C_{1-6}$alkyl, and $C_{1-6}$haloalkyl; and each $R^{a1}$ and $R^{a2}$ is independently selected from H, $C_{1-6}$alkyl, $C_{1-6}$haloalkyl, and $C_{3-10}$cycloalkyl.

In another aspect, provided are compounds of Formula (II), or pharmaceutically acceptable salts thereof:

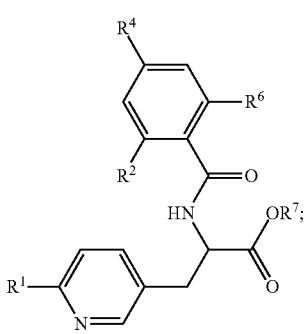

(II)

wherein $R^1$, $R^2$, $R^4$, $R^6$, and $R^7$ are as defined above in formula (I), or elsewhere in this disclosure.

In another aspect, provided are compounds of Formula (IIa), or pharmaceutically acceptable salts thereof:

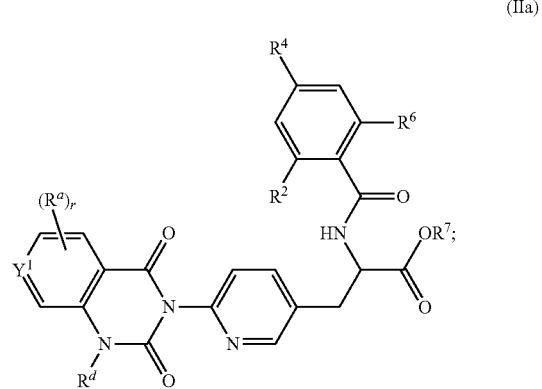

(IIa)

wherein $R^2$, $R^4$, $R^6$, $R^7$, and $R^a$ are as defined above in formula (I), (II), or elsewhere in this disclosure. $Y^1$ is N or CH. $R^d$ is selected from H, $C_{1-4}$alkyl, and $C_{1-4}$haloalkyl; and r is selected from 0, 1, 2, and 3.

In another aspect, provided are compounds of Formula (IIb), or pharmaceutically acceptable salts thereof:

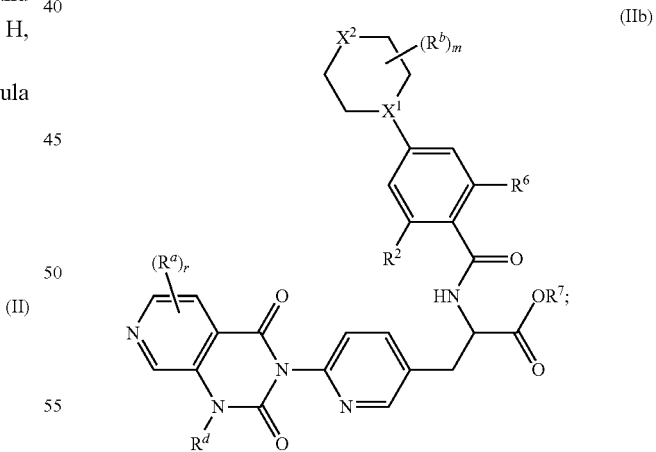

(IIb)

wherein $R^a$, $R^2$, $R^6$, $R^7$, and $R^b$ are as defined above in formula (I), (II), or elsewhere in this disclosure. $X^1$ is selected from $CR^{x1}$, and N. $X^2$ is selected from $CR^{x1}R^{x2}$, $NR^{x2}$, and O. $R^{x1}$ is selected from H, and $R^b$; and $R^{x2}$ is selected from H, $C_{1-4}$alkyl, and $C_{1-4}$haloalkyl. $R^d$ is selected from H, $C_{1-4}$alkyl, and $C_{1-4}$haloalkyl. r is selected from 0, 1, 2, and 3; and m is selected from 0, 1, 2, 3, and 4.

In another aspect, provided are compounds of Formula (IIc), or pharmaceutically acceptable salts thereof:

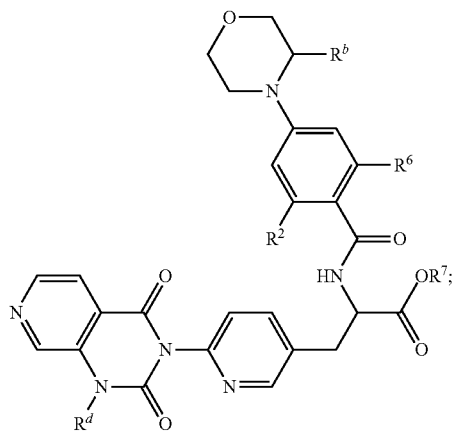

(IIc)

wherein $R^2$, $R^6$, and $R^7$ are as defined above in formula (I), (II), or elsewhere in this disclosure. $R^b$ is $C_{1-4}$alkyl, or $C_{1-6}$haloalkyl. $R^d$ is selected from H, $C_{1-4}$alkyl, and $C_{1-4}$haloalkyl.

In another aspect, provided are compounds of Formula (Id), or pharmaceutically acceptable salts thereof:

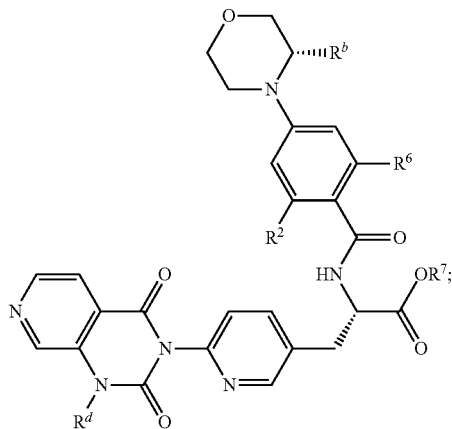

(IId)

wherein $R^7$ is as defined above in formula (I), (II), or elsewhere in this disclosure. Each $R^2$ and $R^6$ is independently selected from halo, $C_{1-4}$alkyl and $C_{1-4}$haloalkyl. $R^b$ is $C_{1-4}$alkyl, or $C_{1-6}$haloalkyl. $R^d$ is H, $C_{1-4}$alkyl, or $C_{1-4}$haloalkyl.

In another aspect, provided are compounds of Formula (III), or pharmaceutically acceptable salts thereof:

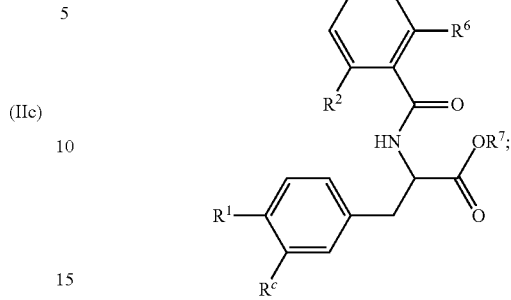

(III)

wherein $R^1$, $R^2$, $R^4$, $R^6$, $R^7$, and $R^c$ are as defined above in formula (I), or elsewhere in this disclosure.

In another aspect, provided are compounds of Formula (IIIa), or pharmaceutically acceptable salts thereof:

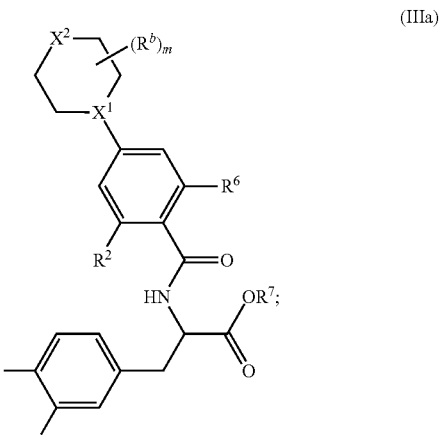

(IIIa)

wherein $R^1$, $R^2$, $R^6$, $R^7$, $R^b$, and $R^c$ are as defined above in formula (I), or elsewhere in this disclosure. $X^1$ is selected from $CR^{x1}$, and N. $X^2$ is selected from $CR^{x1}R^{x2}$, $NR^{x2}$, and O. $R^{x1}$ is selected from H, and $R^b$. $R^{x2}$ is selected from H, $C_{1-4}$alkyl, and $C_{1-4}$haloalkyl. m is selected from 0, 1, and 2.

In another aspect, provided are compounds of Formula (IIIb), or pharmaceutically acceptable salts thereof:

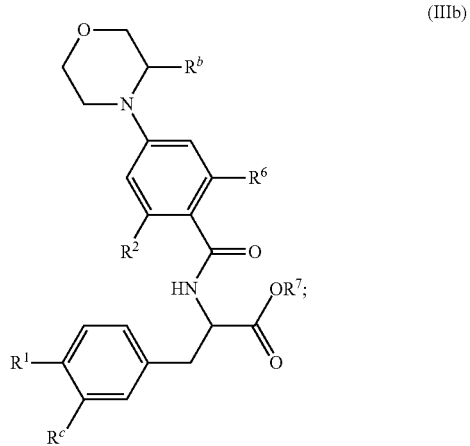

(IIIb)

wherein $R^1$, $R^2$, $R^6$, $R^7$, and $R^c$ are as defined above in formula (I), or elsewhere in this disclosure. $R^7$. $R^b$ is $C_{1-4}$alkyl, or $C_{1-6}$haloalkyl.

In another aspect, provided are compounds of Formula (IV), or pharmaceutically acceptable salts thereof:

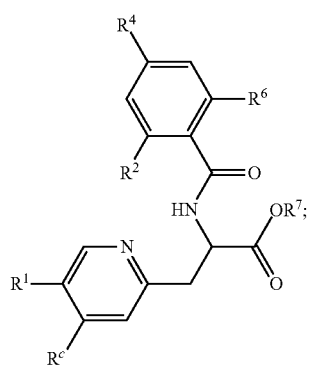
(IV)

wherein $R^1$, $R^2$, $R^4$, $R^6$, $R^7$, and $R^c$ are as defined above in formula (I), or elsewhere in this disclosure.

In some embodiments of formula (I), (II), (III), (IIIa), or (IIIb), $R^1$ is selected from pyridinyl, pyridazinyl, pyrazinyl, pyrimidinyl, quinolinyl, isoquinolinyl, isoxazolyl, triazolyl, pyrazolyl, benzothiazolyl, pyridinonyl, quinolinonyl, isoquinolinonyl, quinazolinedionyl, pyrazinonyl, pyrimidinonyl, pyrimidinedionyl, pyridazinonyl, and quinazolinonyl. Each $R^1$ is independently optionally substituted with one to four $R^a$.

In some embodiments of formula (I), (II), (III), (IIIa), or (IIIb), $R^1$ is selected from:

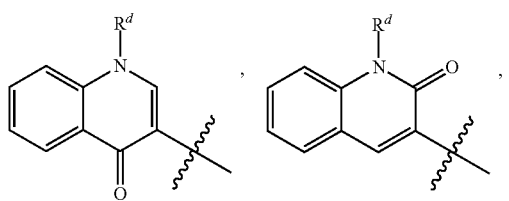

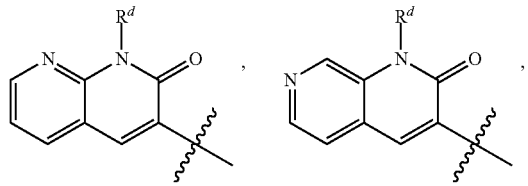

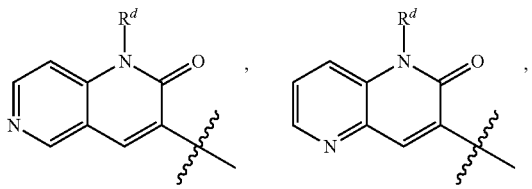

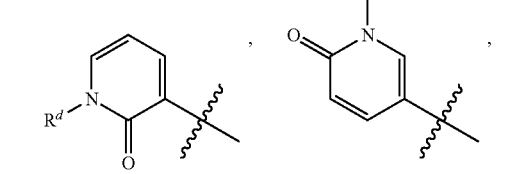

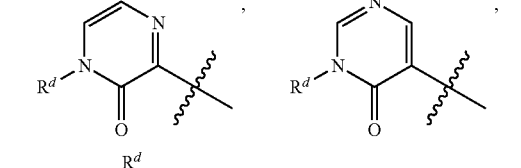

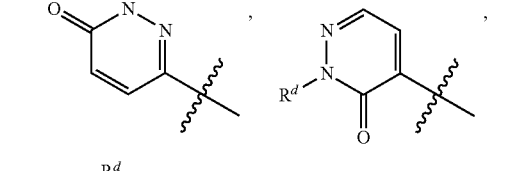

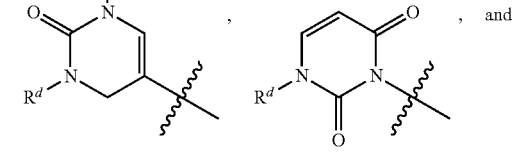

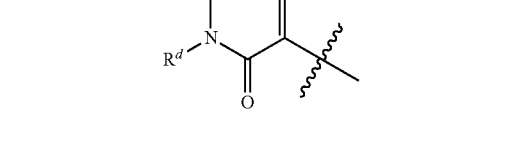

wherein each $R^1$ is independently optionally substituted with one to three $R^a$. In some embodiments, $R^1$ is selected from:

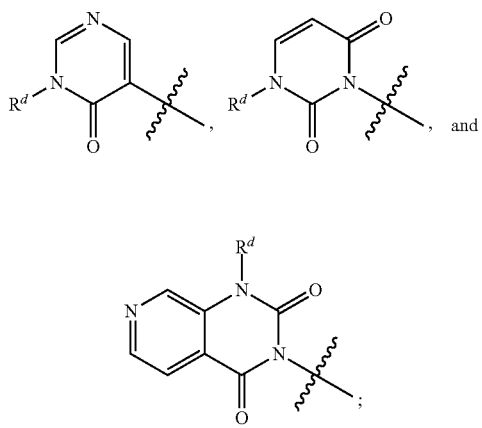

wherein each R¹ is independently optionally substituted with one to three $R^a$. In some embodiments, each $R^a$ is independently selected from halo, CN, —OH, $NR^{a1}R^{a2}$, $C_{1-4}$alkyl, $C_{1-4}$alkoxyl, $C_{1-4}$haloalkyl, and $C_{1-4}$haloalkoxyl. In some embodiments, each $R^a$ is independently selected from F, C, OH, CN, —NH₂, —N(CH₃)₂, —CH₃, —CH₂F, —CHF₂, —CF₃, —OCH₃, and —OCF₃.

In some embodiments of formula (I), (II), (III), (IIIa), or (IIIb), R¹ is

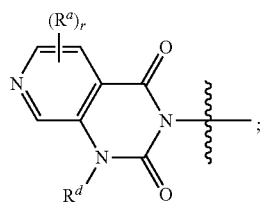

and $R^d$ is $C_{1-4}$alky. In some embodiments, $R^d$ is methyl or ethyl. In some embodiments, $R^d$ is methyl. In some embodiments, R¹ is

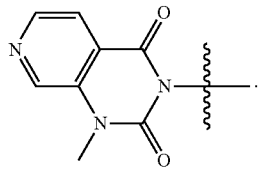 [SMILES: *n1c(=O)c2ccncc2n(C)c1=O]

In some embodiments of formula (I), (II), (III), (IIIa), or (IIIb), R¹ is

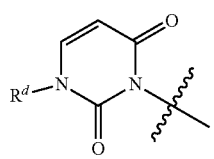

optionally substituted with one to three $R^a$. In some embodiments, R¹ is selected from

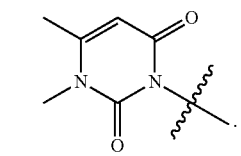 [SMILES: *n1c(=O)cc(C)n(C)c1=O]

In some embodiments, R¹ is

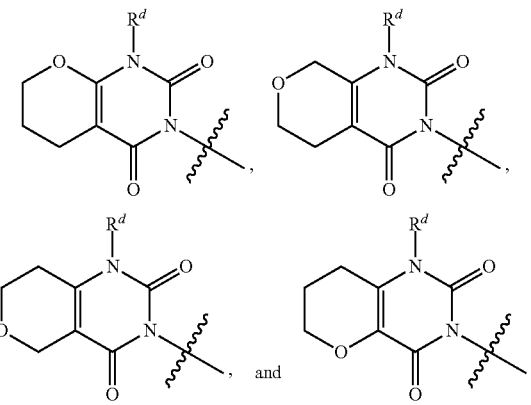

In some embodiments of formula (I), (II), (III), (IIIa), or (IIIb), R¹ is 10 membered heterocyclyl containing two N and two C(O) as ring members, and R¹ is optionally substituted with one to three $R^a$. In some embodiments, each $R^a$ is independently selected from F, Cl, OH, CN, —NH₂, —N(CH₃)₂, —CH₃, —CH₂F, —CHF₂, —CF₃, —OCH₃, and —OCF₃. In some embodiments, R¹ is selected from

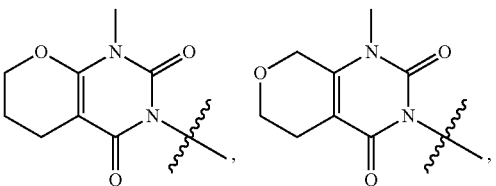

each of which is optionally substituted with one to three $R^a$. In some embodiments, $R^d$ is —CH₃. In some embodiments, R¹ is

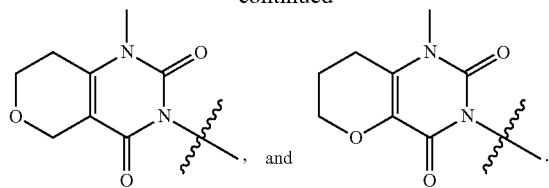, and.

In some embodiments, $R^1$ is

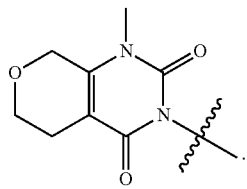 [SMILES: *n1c(=O)c2c(n(C)c1=O)COCC2].

In some embodiments of formula (I), (II), (III), (IIIa), or (IIIb), $R^1$ is

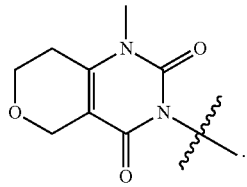 [SMILES: *n1c(=O)c2c(n(C)c1=O)CCOC2].

In some embodiments of formula (I), (II), (III), (IIIa), or (IIIb), $R^1$ is

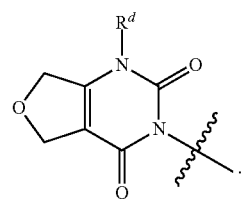.

In some embodiments, $R^d$ is —$CH_3$. In some embodiments, $R^1$ is

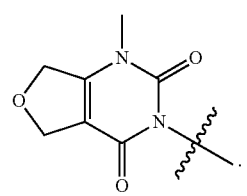 [SMILES: *n1c(=O)c2c(n(C)c1=O)COC2].

In some embodiments of formula (I), $Z^1$ is N. $Z^2$, $Z^3$, and $Z^4$ are $CR^c$. In some embodiments, $Z^1$ is N; and $Z^2$, $Z^3$, and $Z^4$ are CH. In some embodiments, $Z^3$ is N; and $Z^1$, $Z^2$, and $Z^4$ are $CR^c$. In some embodiments, $Z^1$ and $Z^2$ are N. In some embodiments, $Z^1$ and $Z^3$ are N. In some embodiments, $Z^1$ is $CR^c$; and $R^c$ is selected from $C_{1-4}$alkyl, $C_{1-4}$alkoxyl, $C_{1-4}$haloalkyl, and $C_{1-4}$haloalkoxyl. In some embodiments, $Z^1$ is $CR^c$, and $R^c$ is selected from —$CH_3$, —$OCH_3$, and —$CF_3$. In some embodiments, $Z^1$ is C—$OCH_3$.

In some embodiments of formula (I), each $R^3$ and $R^5$ is independently selected from H, and halo. In some embodiments, each $R^3$ and $R^5$ is H.

In some embodiments of formula (I), (II), (IIa), (IIb), (IIc), (IId), (III), (IIIa), or (IIIb), each $R^2$ and $R^6$ is independently selected from H, halo, $C_{1-4}$alkyl, $C_{1-4}$alkoxyl, $C_{1-4}$haloalkyl, and $C_{1-4}$haloalkoxyl. In some embodiments, each $R^2$ and $R^6$ is independently selected from F, and —$CH_3$. In some embodiments, $R^2$ is F, and $R^6$ is —$CH_3$.

In some embodiments of formula (I), (II), (IIa), or (III), $R^4$ is 3-8 membered heterocyclyl optionally substituted with one to three $R^b$. In some embodiments, the 3-8 membered heterocyclyl of $R^4$ contains one to two heteroatoms or groups independently selected from S, N, O, and $S(O)_2$. In some embodiments, each $R^b$ is independently selected from halo, hydroxyl, cyano, —$NR^{a1}R^{a2}$, $C_{1-4}$alkyl, $C_{1-4}$alkoxyl, and $C_{1-4}$haloalkyl. In some embodiments, each $R^b$ is independently selected from F, Cl, CN, —OH, —$CH_3$, —CH$(CH_3)_2$, —$CF_3$, and —$CH_2CF_3$.

In some embodiments of formula (I), (II), (IIa), or (II), $R^4$ is 6-membered heterocyclyl optionally substituted with one to three $R^b$. In some embodiments, $R^4$ is selected from

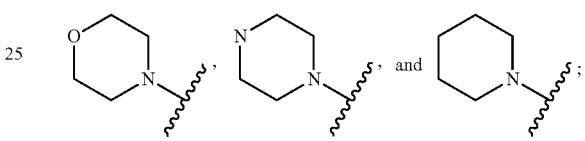

and each of which is optionally substituted with one to three $R^b$. In some embodiments, each $R^b$ is independently selected from halo, $C_{1-4}$alkyl, and $C_{1-4}$haloalkyl. In some embodiments, $R^4$ is

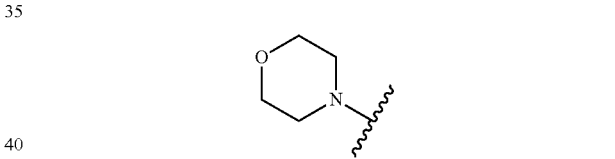

optionally substituted with $R^b$; and $R^b$ is selected from —$CH_3$, —$CHF_2$, —$CF_3$, and —$CH_2CF_3$. In some embodiments, $R^b$ is selected from —$CH_3$, —$CHF_2$, and —$CF_3$. In some embodiments, $R^b$ is selected from —$CH_2CHF_2$, and —$CH_2CF_3$. In some embodiments, $R^4$ is selected from

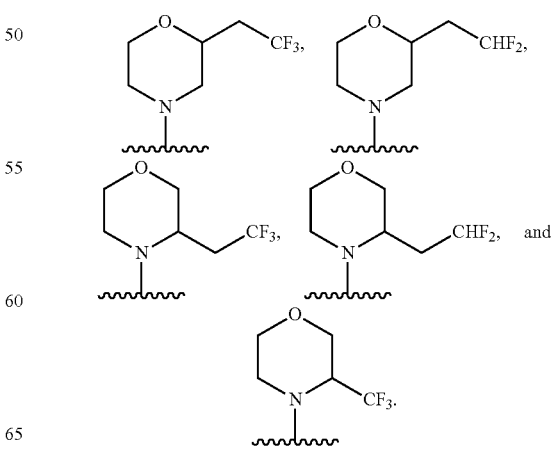

In some embodiments, R⁴ is

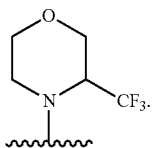 [SMILES: *N1CCOCC1C(F)(F)F]

In some embodiments, R⁴ is

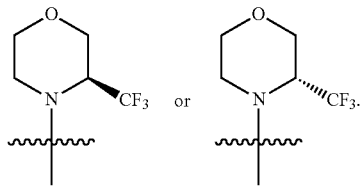 [SMILES: *N1CCOC[C@H]1C(F)(F)F ; *N1CCOC[C@@H]1C(F)(F)F]

In some embodiments, R⁴ is

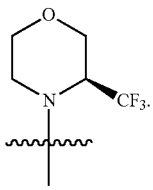 [SMILES: *N1CCOC[C@H]1C(F)(F)F]

In some embodiments, R⁴ is

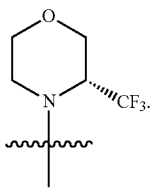

In some embodiments of formula (I), (II), (IIa), or (III), R⁴ is

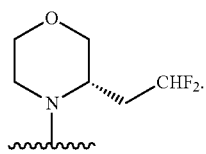 [SMILES: *N1CCOC[C@@H]1CC(F)F]

In some embodiments

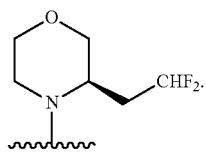 [SMILES: *N1CCOC[C@H]1CC(F)F]

In some embodiments of formula (I), (II), (IIa), or (III), R⁴ is —NR$^{b1}$R$^{b2}$. In some embodiments, each R$^{b1}$ and R$^{b2}$ is independently selected from H, $C_{1-6}$alkyl, $C_{1-6}$haloalkyl, and $C_{3-6}$cycloalkyl. In some embodiments, R$^{b1}$ is H and R$^{b2}$ is $C_{1-6}$haloalkyl. In some embodiments, R⁴ is

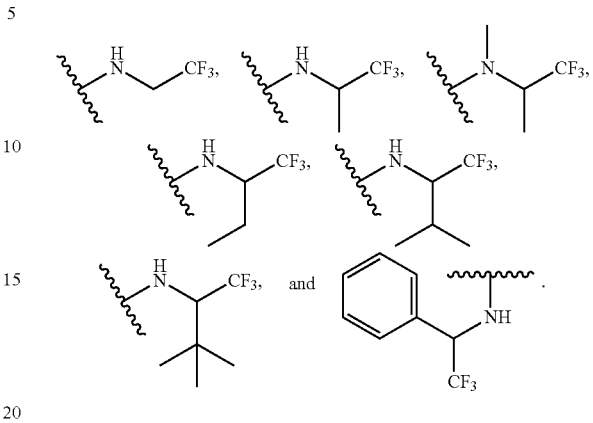

In some embodiments, R⁴ is

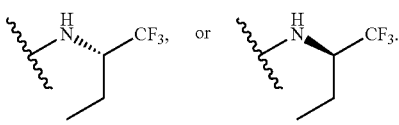

In some embodiments of formula (I), (II), (IIa), or (III), R⁴ is 5-10 membered heteroaryl optionally substituted with one to three R$^b$; and each R$^b$ is independently selected from halo, $C_{1-4}$alkyl, and $C_{1-4}$haloalkyl. In some embodiments, R⁴ is 5 membered heteroaryl optionally substituted with one to three R$^b$. In some embodiments, R⁴ is pyrrolyl optionally substituted with one to three R$^b$. In some embodiments, R⁴ is imidazolyl optionally substituted with one to three R$^b$. In some embodiments, each R$^b$ is independently selected from —CH₃, —CHF₂, —CF₃, and —CH₂CF₃. In some embodiments, R⁴ is

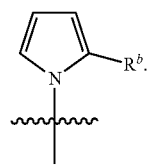

In some embodiments, R⁴ is

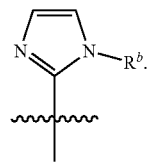

In some embodiments, R$^b$ is selected from —CH₃, —CHF₂, —CF₃, and —CH₂CF₃.

In some embodiments of formula (IIb), or (IIa), X¹ is N, and X² is O. In some embodiments, X¹ is N. In some embodiments, X¹ and X² are N. In some embodiments, X² is O. In some embodiments, X² is CR$^{x1}$R$^{x2}$, R$^{x1}$ is selected from H and $C_{1-4}$alkyl, and R$^{x2}$ is H. In some embodiments, X² is —CH₂—.

In some embodiments of formula (III), (IIIa), or (IIIb), $R^c$ is selected from halo, $C_{1-4}$ alkyl, $C_{1-4}$alkoxyl, $C_{1-4}$haloalkyl, and $C_{1-4}$haloalkoxyl. In some embodiments, $R^c$ is selected from F, Cl, $CH_3$, —$OCH_3$, —$OCF_3$, and —$CF_3$. In some embodiments, $R^c$ is —$OCH_3$.

In some embodiments of formula (I), (II), (IIa), (IIb), (IIc), (Id), (III), (IIIa), or (IIIb), $R^7$ is selected from H, $C_{1-6}$alkyl, and $C_{3-6}$cycloalkyl. In some embodiments, $R^7$ is selected from H, $C_{1-6}$alkyl, and $C_{3-6}$cycloalkyl. $R^7$ is selected from H, methyl, ethyl, propyl, butyl, cyclopropyl, —$CH_2$—O—$C(O)C(CH)_3$, and phenyl. In some embodiments, $R^7$ is selected from H, methyl, ethyl, propyl, and cyclopropyl. In some embodiments, $R^7$ is selected from H, methyl, ethyl, propyl, butyl, —$CH_2C(O)N(CH_3)_2$, —$(CH_2)_2N(CH_2CH_3)_2$, —$CH_2$—O—$C(O)CH_3$, —$(CH_2)_2$—O—$C(O)CH_3$, —$CH_2$—O—$C(O)C(CH_3)_3$, —$(CH_2)_2$—O—$C(O)C(CH_3)_3$, —$CH_2$—O—$C(O)$—O—$CH_3$, —$CH(CH_3)$—O—$C(O)$—O—$CH_3$, —$CH_2$—O—$C(O)$—O—$CH_2CH_3$, —$CH_2$—O—$C(O)$—O—$CH(CH_3)_2$, —$CH_2$—O—$C(O)$—O—$C(CH_3)_3$, and —$(CH_2)_2C(O)CH_3$. In some embodiments, $R^7$ is H. In some embodiments, $R^7$ is methyl. In some embodiments, $R^7$ is ethyl. In some embodiments, $R^7$ is cyclopropyl. In some embodiments, $R^7$ is phenyl.

In some embodiments of formula (I), $R^8$ is H.

In some embodiments, the compound of the present disclosure is selected from examples 1-53.

In some embodiments, the compound of the present disclosure is selected from examples 54-93.

Provided are also compounds described herein or pharmaceutically acceptable salts, isomer, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

In some embodiments, the compound of the present disclosure contains one to six deuterium ($^2$H, or D). In some embodiments, one of $R^2$, $R^3$, $R^4$, $R^5$, and $R^6$ contains one to six D. In some embodiments, $R^6$ contains one to six D. In some embodiments, $R^6$ is $CD_3$.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

A "solvate" is formed by the interaction of a solvent and a compound. Solvates of salts of the compounds described herein are also provided. Hydrates of the compounds described herein are also provided.

A "prodrug" is a biologically inactive derivative of a drug that upon administration to the human body is converted to the biologically active parent drug according to some chemical or enzymatic pathway.

In certain embodiments, provided are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution of the racemate. Resolution of racemates can be accomplished, for example, by conventional methods such as crystallization in the presence of a resolving agent, or chromatography, using, for example a chiral high pressure liquid chromatography (HPLC) column. In addition, provided are also Z- and E-forms (or cis- and trans-forms) of the compounds described herein. Specifically, Z- and E-forms are included even if only one designation is named for both carbon-carbon double bonds.

Where chirality is not specified but is present, it is understood that the embodiment is directed to either the specific diastereomerically or enantiomerically enriched form; or a racemic or scalemic mixture of such compound(s).

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

"Atropisomers" are stereoisomers arising due to hindered rotation about a single bond, where the barrier to rotation about the bond is high enough to allow for isolation of individual stereoisomers. Provided includes atropisomers of the compounds described herein.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

In certain embodiments, provided are also chelates, non-covalent complexes, and mixtures thereof, of the compounds described herein or pharmaceutically acceptable salts, isomer, or a mixture thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

Therapeutic Uses of the Compounds

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo to determine the optimal schedule and/or dosing of administration of an α4β7 integrin inhibitor for a given indication, cell type, individual, and other parameters. Information gleaned from such use may be used for experimental purposes or in the clinic to set protocols for in vivo treatment. Other ex vivo uses for which the invention may be suited are described below or will become apparent to those skilled in the art. The selected compounds may be further characterized to examine the safety or tolerance dosage in human or non-human subjects. Such properties may be examined using commonly known methods to those skilled in the art.

In some embodiments, compounds described herein, or a pharmaceutically acceptable salt, stereoisomer, mixture of stereoisomers, tautomer, or deuterated analog thereof, may be used to treat subjects who have or are suspected of having disease states, disorders, and conditions (also collectively referred to as "indications") responsive or believed to be responsive to the inhibition of α4β7 integrin activity. In some embodiments, the compounds described herein may be used to inhibit the activity of α4β7 integrin. In some embodiments, the compounds described herein may be used to inhibit excessive or destructive immune reactions or growth or a proliferation of a cell, such as a cancer cell, or inhibit immunosuppression.

In some embodiments, compounds described herein, or a pharmaceutically acceptable salt, stereoisomer, mixture of stereoisomers, tautomer, or deuterated analog thereof, may be used to treat subjects who have or are suspected of having disease states, disorders, and conditions (also collectively referred to as "indications") responsive or believed to be responsive to the inhibition of α4β7 integrin activity. In some embodiments, the compounds described herein may be used to inhibit the activity of α4β7 integrin. In some embodiments, the compounds described herein may be used to inhibit excessive or destructive immune reactions or growth or a proliferation of a cell, such as a cancer cell, or inhibit immunosuppression.

Methods

In some embodiments, the present disclosure provides a compound described herein useful as an inhibitor of α4β7 integrin. In some embodiments, the present disclosure provides a method of treating an inflammatory disease or condition comprising administering a compound described herein.

In some embodiments, the present disclosure provides a pharmaceutical composition comprising a compound described herein and a pharmaceutically acceptable carrier.

In some embodiments, the present disclosure provides a pharmaceutical composition comprising a compound described herein and at least one additional therapeutic agent and at least one pharmaceutically acceptable excipient.

The present disclosure provides a compound described herein for use in therapy.

In another embodiment, the present disclosure provides a compound described herein for use in the manufacture of a medicament for treating a disease or condition provided herein.

In some embodiments, provided is a compound described herein useful for the treatment of a disease or condition in a patient that is amenable to treatment by inhibiting α4β7 integrin. Diseases or conditions that may be treated with the compounds described herein include a solid tumor, diabetes, an inflammatory disease, graft versus host disease, primary sclerosing cholangitis, HIV, an autoimmune disease, inflammatory bowel disease (IBD), alcoholic hepatitis, hepatic steatosis, nonalcoholic fatty liver disease (NAFLD), nonalcoholic steatohepatitis (NASH), systemic lupus erythematosus (SLE), and lupus nephritis.

In some embodiments, provided is a compound described herein useful for the treatment of an inflammatory disease or condition in a patient that is mediated, at least in part, by α4β7 integrin.

"Administering" or "administration" refers to the delivery of one or more therapeutic agents to a patient. In some embodiments, the administration is a monotherapy wherein a compound described herein is the only active ingredient administered to the patient in need of therapy. In another embodiment, the administration is co-administration such that two or more therapeutic agents are delivered together during the course of the treatment. In some embodiments, two or more therapeutic agents may be co-formulated into a single dosage form or "combined dosage unit", or formulated separately and subsequently combined into a combined dosage unit, as is typically for intravenous administration or oral administration as a mono or bilayer tablet or capsule.

In some embodiments, the compound described herein is administered to a human patient in need thereof in an effective amount, such as, from about 0.1 mg to about 1000 mg per dose of said compound. In some embodiments, the effective amount is from about 0.1 mg to about 400 mg per dose. In some embodiments, the effective amount is from about 0.1 mg to about 300 mg per dose. In some embodiments, the effective amount is from about 0.1 mg to about 200 mg per dose. In some embodiments, the effective amount is from about 1 mg to about 100 mg per dose. In other embodiments, the effective amount is about 1 mg, about 3 mg, about 5 mg, about 10 mg, about 15 mg, about 18 mg, about 20 mg, about 30 mg, about 40 mg, about 60 mg, about 80 mg, about 100 mg, about 200 mg, or about 300 mg per dose.

In some embodiments, the compound described herein and at least one additional therapeutic agent is administered to a human patient in need thereof in an effective amount of each agent, independently from about 0.1 mg to about 1000 mg per dose of a compound or formulation per dose per compound. In some embodiments, the effective amount of the combination treatment of a compound described herein and an additional compound is independently from about 0.1 mg to about 200 mg per compound per dose. In some embodiments, the effective amount of the combination treatment of a compound described herein and an additional compound is independently from about 1 mg to about 100 mg per compound per dose. In other embodiments, the effective amount of the combination treatment of a compound described herein and an additional compound is for each component, about 1 mg, about 3 mg, about 5 mg, about 10 mg, about 15 mg, about 18 mg, about 20 mg, about 30 mg, about 40 mg, about 60 mg, about 80 mg, about 100 mg, about 200 mg, or about 500 mg each per dose.

In some embodiments, the dose of a compound described herein and/or a combination of the dose of the compound described herein and/or the dose of an additional therapeutic agent is administered once per day, twice per day, or thrice per day. In yet another embodiment, the dose of a compound described herein and/or the dose of an additional therapeutic agent is administered as a loading dose of from about 0.1 mg to about 1000 mg per compound on the first day and each day or on alternate days or weekly for up to a month followed by a regular regimen of a compound described herein and/or one or more additional therapeutic agents or therapies. The maintenance dose may be about 0.1 mg to about 1000 mg once per day, twice per day, thrice per day, or weekly, for each component of a multi component drug regimen. A qualified care giver or treating physician is aware of what dose regimen is best for a particular patient or particular presenting conditions and will make appropriate treating regimen decisions for that patient. Thus, in another embodiment, the qualified caregiver is able to tailor a dose regimen of the compound described herein and/or an additional therapeutic agent(s) as disclosed herein to fit with the particular needs of the patient. Thus, it will be understood that the amount of the dose of a compound described herein and the amount of the dose of an additional therapeutic agent actually administered will usually be determined by a physician, in light of the relevant circumstances, including the condition(s) to be treated, the chosen route of administration, the actual compound (e.g., salt or free base) administered and its relative activity, the age, weight, and response of the individual patient, the severity of the patient's symptoms, and the like.

Co-administration may also include administering component drugs e.g., one on more compounds described herein and one or more additional (e.g., a second, third, fourth or fifth) therapeutic agent(s). Such combination of one on more compounds described herein and one or more additional therapeutic agent(s) may be administered simultaneously or in sequence (one after the other) within a reasonable period of time of each administration (e.g., about 1 minute to 24 hours) depending on the pharmacokinetic and/or pharmacodynamics properties of each agent or the combination. Co-administration may also involve treatment with a fixed combination wherein agents of the treatment regimen are combinable in a fixed dosage or combined dosage medium e.g., solid, liquid or aerosol. In some embodiments, a kit may be used to administer the drug or drug components.

Thus, some embodiments of the present disclosure is a method of treating a disease or condition mediated, at least in part, by α4β7 integrin, comprising administering therapeutically effective amounts of formulations of one on more compounds described herein and one or more additional therapeutic agents, including for example, via a kit to a patient in need thereof. It will be understood that a qualified care giver will administer or direct the administration of a therapeutically effective amount of any of the compound(s) or combinations of compounds of the present disclosure.

"Intravenous administration" is the administration of substances directly into a vein, or "intravenously." Compared with other routes of administration, the intravenous (IV) route is a faster way to deliver fluids and medications throughout the body. An infusion pump can allow precise control over the flow rate and total amount of medication delivered. However, in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, as a "flush", following the injection to push the medicine into the bloodstream more quickly. Thus, in some embodiments, compound(s) or combination of compounds described herein may be administered by IV administration alone or in combination with administration of certain components of the treatment regimen by oral or parenteral routes.

"Oral administration" is a route of administration where a substance is taken through the mouth, and includes buccal, sub labial, and sublingual administration, as well as enteral administration and that through the respiratory tract, unless made through e.g., tubing so the medication is not in direct contact with any of the oral mucosa. Typical form for the oral administration of therapeutic agents includes the use of tablets or capsules. Thus, in some embodiments, compound(s) or combination of compounds described herein may be administered by oral route alone or in combination with administration of certain components of the treatment regimen by IV or parenteral routes.

Pharmaceutical Formulations

The compounds described herein may be administered in a pharmaceutical formulation. Pharmaceutical formulations/compositions contemplated by the present disclosure comprise, in addition to a carrier, the compound described herein or a combination of compounds described herein optionally in combination with an additional therapeutic agent.

Pharmaceutical formulations/compositions contemplated by the present disclosure may also be intended for administration by injection and include aqueous solutions, oil suspensions, emulsions (with sesame oil, corn oil, cottonseed oil, or peanut oil) as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component compound(s) in the required amount in the appropriate solvent with various other ingredients as enumerated above or as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient(s) plus any additional desired ingredient from a previously sterile-filtered solution thereof.

In making pharmaceutical compositions that comprise compound described herein optionally in combination with an additional agent/therapy useful for the purpose or pharmaceutically acceptable salt thereof, the active ingredient is usually diluted by an excipient or carrier and/or enclosed or mixed with such a carrier that may be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 20% by weight of the active compounds, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the disclosure may be formulated so as to provide quick, sustained or delayed release of the active ingredient after administration to the patient by employing procedures known in the art. In some embodiments, sustained release formulations are used. Controlled release drug delivery systems for oral administration include osmotic pump systems and dissolutional systems containing polymer-coated reservoirs or drug-polymer matrix formulations.

Certain compositions are preferably formulated in a unit dosage form. The term "unit dosage forms" or "combined dosage unit" refers to physically discrete units suitable as unitary dosages for human subjects and other mammals, each unit containing a predetermined quantity of one or more of the active materials (e.g., a compound described herein, optionally in combination with an additional therapeutic agent calculated to produce the desired effect, in association with a suitable pharmaceutical excipient in for example, a tablet, capsule, ampoule or vial for injection. It will be understood, however, that the amount of each active agent actually administered will be determined by a physician, in the light of the relevant circumstances, including the condition to be treated, the chosen route of administration, the actual compounds administered and their relative activity, the age, weight, and response of the individual patient, the severity of the patient's symptoms, and the like.

For preparing solid compositions such as tablets, the principal active ingredient(s) is/are mixed with a pharmaceutical excipient to form a solid pre-formulation composition containing a homogeneous mixture of a compound of the present disclosure. When referring to these pre-formulation compositions as homogeneous, it is meant that the active ingredient(s) are dispersed evenly throughout the composition so that the composition may be readily subdivided into equally effective unit dosage forms such as tablets, pills and capsules.

The tablets or pills comprising compound described herein of the present disclosure optionally in combination with the second agent may be coated or otherwise compounded to provide a dosage form affording the advantage of prolonged action, or to protect from the acidic conditions of the stomach. For example, the tablet or pill can comprise an inner dosage and an outer dosage element, the latter being in the form of an envelope over the former. In some embodiments, the inner dosage element may comprise the compound described herein and the outer dosage element may comprise the second or additional therapeutic agent or vice versa. Alternatively, the combined dosage unit may be side by side configuration as in a capsule or tablet where one portion or half of the tablet or capsule is filled with a formulation of the compound described herein while the other portion or half of the table or capsule comprises the additional therapeutic agent.

A variety of materials may be used for such enteric layers or coatings, such materials including a number of polymeric acids and mixtures of polymeric acids with such materials as shellac, cetyl alcohol, and cellulose acetate. One of ordinary skill in the art is aware of techniques and materials used in the manufacture of dosages of formulations disclosed herein.

A "sustained release formulation" or "extended release formulation" is a formulation which is designed to slowly release a therapeutic agent into the body over an extended period of time, whereas an "immediate release formulation" is a formulation which is designed to quickly release a therapeutic agent into the body over a shortened period of time. In some cases, the immediate release formulation may be coated such that the therapeutic agent is only released once it reaches the desired target in the body (e.g., the stomach). One of ordinary skill in the art is able to develop sustained release formulations of the presently disclosed compounds without undue experimentation. Thus in some embodiments, compound(s) or combination of compounds described herein may be delivered via sustained released formulations alone or in combination with administration of certain components of the treatment regimen by oral, IV or parenteral routes.

A lyophilized formulation may also be used to administer a compound described herein singly or in combination with an additional therapeutic agent. One of skill in the art is aware of how to make and use lyophilized formulations of drug substances amenable to lyophilization.

Spray-dried formulation may also be used to administer a compound described herein singly or in combination with an additional therapeutic agent. One of skill in the art is aware of how to make and use spray-dried formulations of drug substances amenable to spray-drying. Other known formulation techniques may also be employed to formulate a compound or combination of compounds disclosed herein.

The compounds disclosed herein are useful for the treatment of diseases or conditions mediated, at least in part, by α4β7 integrin. Non-limiting examples of diseases or conditions mediated, at least in part, by α4β7 integrin include, without limitation, acne, acid-induced lung injury, Addison's disease, adrenal hyperplasia, adrenocortical insufficiency, adult-onset Still's disease, adult respiratory distress syndrome (ARDS), age-related macular degeneration, aging, alcoholic hepatitis, alcoholic liver disease, allergen-induced asthma, allergic bronchopulmonary, allergic conjunctivitis, allergic contact dermatitis, allergies, allergic encephalomyelitis, allergic neuritis, allograft rejection, alopecia, alopecia areata, Alzheimer's disease, amyloidosis, amyotrophic lateral sclerosis, angina pectoris, angioedema, angiofibroma, anhidrotic ectodermal dysplasia-ill, antiglomerular basement membrane disease, antigen-antibody complex mediated diseases, ankylosing spondylitis, antiphospholipid syndrome, aphthous stomatitis, appendicitis, arthritis, ascites, aspergillosis, asthma, atherosclerosis, atherosclerotic plaques, atopic dermatitis, atrophic thyroiditis, autoimmune diseases, autoimmune hemolytic anemia (immune pancytopenia, paroxysmal nocturnal hemoglobinuria), autoimmune polyendocrinopathies, autoimmune thrombocytopenia (idiopathic thrombocytopenic purpura, immune-mediated thrombocytopenia), autoimmune hepatitis, autoimmune thyroid disorders, autoinflammatory diseases, back pain, *Bacillus anthracis* infection, Bechet's disease, bee sting-induced inflammation, Behçet's syndrome, Bell's palsy, berylliosis, Blau syndrome, bone pain, bronchiolitis, bullous pemphigoid (BP) asthma, burns, bursitis, cardiac hypertrophy, carpal tunnel syndrome, Castleman's disease, catabolic disorders, cataracts, Celiac disease, cerebral aneurysm, chemical irritant-induced inflammation, chorioretinitis, chronic atypical neutrophilic dermatosis with lipodystrophy and elevated temperature (CANDLE) syndrome, chronic heart failure, chronic lung disease of prematurity, chronic obstructive pulmonary disease (COPD), chronic pancreatitis, chronic prostatitis, chronic recurrent multifocal osteomyelitis, cicatricial alopecia, colitis, complex regional pain syndrome, complications of organ transplantation, conjunctivitis, connective tissue disease, contact dermatitis, corneal graft neovascularization, corneal ulcer, Crohn's disease, cryopyrin-associated periodic syndromes, cutaneous lupus erythematosus (CLE), cryptococcosis, cystic fibrosis, deficiency of the interleukin-1 receptor antagonist (DIRA), dermatitis, dermatitis endotoxemia, dermatomyositis, diabetic macular edema, diverticulitis, eczema, encephalitis, endometriosis, endotoxemia, eosinophilic pneumonias, epicondylitis, epidermolysis bullosa, erythema multiforme, erythroblastopenia, esophagitis, familial amyloidotic polyneuropathy, familial cold urticarial, familial Mediterranean fever, fetal growth retardation, fibromyalgia, fistulizing Crohn's disease, food allergies, giant cell arteritis, glaucoma, glioblastoma, glomerular disease, glomerular nephritis, glomerulonephritis, gluten-sensitive enteropathy, gout, gouty arthritis, graft-versus-host disease (GVHD), granulomatous hepatitis, Graves' disease, growth plate injuries, Guillain-Barre syndrome. gut diseases, hair loss, Hashimoto's thyroiditis, head injury, headache, hearing loss, heart disease, hemangioma, hemolytic anemia, hemophilic joints, Henoch-Scholein purpura, hepatitis, hepatic steatosis, nonalcoholic fatty liver disease (NAFLD), nonalcoholic steatohepatitis (NASH), hereditary periodic fever syndrome, heritable disorders of connective tissue, herpes zoster and simplex, hidradenitis suppurativa (HS), hip replacement, Hodgkin's disease, Huntington's disease, hyaline membrane disease, hyperactive inflammatory response, hyperammonemia, hypercalcemia, hypercholesterolemia, hypereosinophilic syndrome (HES), hyperimmunoglobulinemia D with recurrent fever (HIDS), hypersensitivity pneumonitis, hypertropic bone formation, hypoplastic and other anemias, hypoplastic anemia, ichthyosis, idiopathic demyelinating polyneuropathy, Idiopathic inflammatory myopathies (dermatomyositis, polymyositis), idiopathic pulmonary fibrosis, idiopathic thrombocytopenic purpura, immunoglobulin nephropathies, immune complex nephritis, immune thrombocytopenic purpura (ITP), incontinentia pigmenti (IP, Bloch-Siemens syndrome), infectious mononucleosis, infectious diseases including viral diseases such as AIDS (HIV infection), hepatitis A, B, C, D, and E, herpes; inflammation, inflammation of the CNS, inflammatory bowel disease (IBD), inflammatory disease of the lower respiratory tract including bronchitis or chronic obstructive pulmonary diseases, inflammatory disease of the upper respiratory tract including the nose and sinuses such as rhinitis or sinusitis, inflammatory diseases of the respiratory tract, inflammatory ischemic event such as stroke or cardiac arrest, inflammatory lung disease, inflammatory myopathy such as myocarditis, inflammatory liver disease, inflammatory neuropathy, inflammatory pain, insect bite-induced inflammation, interstitial cystitis, interstitial lung disease, iritis, irritant-induced inflammation, ischemia/reperfusion, joint replacement, juvenile arthritis, juvenile rheumatoid arthritis, keratitis, kidney injury caused by parasitic infections, kidney transplant rejection, leptospirosis, leukocyte adhesion deficiency, lichen sclerosus (LS), Lambert-Eaton myasthenic syndrome, Loeffler's syndrome, lupus, lupus nephritis, Lyme disease, Marfan syndrome (MFS), mast cell activation syndrome, mastocytosis, meningitis, meningioma, mesothelioma, mixed connective tissue disease, Muckle-Wells syndrome (urticaria deafness amyloidosis), mucositis, multiple organ injury syndrome, multiple sclerosis, muscle wasting, muscular dystrophy, myasthenia gravis (MG), myelodysplastic syndrome, myocarditis, myositis, nasal sinusitis, necrotizing enterocolitis, neonatal onset multisystem inflammatory disease (NOMID), neovascular glaucoma, nephrotic syndrome, neuritis, neuropathological diseases, non-allergen induced asthma, obesity, ocular allergy, optic neuritis, organ transplant rejection, Osier-Weber syndrome, osteoarthritis, osteogenesis imperfecta, osteonecrosis, osteoporosis, osteoarthritis, otitis, pachyonychia congenita, Paget's disease, Paget's disease of bone, pancreatitis, Parkinson's disease, pediatric rheumatology, pelvic inflammatory disease, pemphigus, pemphigus vulgaris (PV), bullous pemphigoid (BP), pericarditis, periodic fever, periodontitis, peritoneal endometriosis, pernicious anemia (Addison's disease), pertussis, PFAPA (periodic fever aphthous pharyngitis and cervical adenopathy), pharyngitis and adenitis (PFAPA syndrome), plant irritant-induced inflammation, pneumocystis infection, pneumonia, pneumonitis, poison ivy/urushiol oil-induced inflammation, polyarthritis nodosa, polychondritis, polycystic kidney disease, polymyalgia rheumatic, giant cell arteritis, polymyositis, pouchitis, reperfusion injury and transplant rejection, primary biliary cirrhosis, primary pulmonary hypertension, primary sclerosing cholangitis (PSC), proctitis, psoriasis, psoriasis vulgaris, psoriatic arthritis, psoriatic epidermis, psychosocial stress diseases, pulmonary disease, pulmonary fibrosis, pulmonary hypertension, pyoderma gangrenosum, pyogenic granuloma retrolental fibroplasias, pyogenic sterile arthritis, Raynaud's syndrome, Reiter's disease, reactive arthritis, renal disease, renal graft rejection, reperfusion injury, respiratory distress syndrome, retinal disease, retrolental fibroplasia, Reynaud's syndrome, rheumatic carditis, rheumatic diseases, rheumatic fever, rheumatoid arthritis, rhinitis, rhinitis psoriasis, rosacea, sarcoidosis, Schnitzler syndrome, scleritis, sclerosis, scleroderma, scoliosis, seborrhea, sepsis, septic shock, severe pain, Sezary syndrome, sickle cell anemia, silica-induced disease (Silicosis), Sjogren's syndrome, skin diseases, skin irritation, skin rash, skin sensitization (contact dermatitis or allergic contact dermatitis), sleep apnea, spinal cord injury, spinal stenosis, spondyloarthropathies, sports injuries, sprains and strains, Stevens-Johnson syndrome (SJS), stroke, subarachnoid hemorrhage, sunburn, synovial inflammation, systemic inflammatory response syndrome (SIRS), systemic lupus erythematosus, systemic mast cell disease (SMCD), systemic vasculitis, systemic-onset juvenile idiopathic arthritis, temporal arteritis, tendinitis, tenosynovitis, thrombocytopenia, thyroditis, thyroiditis, tissue transplant, toxoplasmosis, trachoma, transplantation rejection, traumatic brain injury, tuberculosis, tubulointerstitial nephritis, tumor necrosis factor (TNF) receptor associated periodic syndrome (TRAPS), type 1 diabetes, type 2 diabetes, complications from type 1 or type 2 diabetes, ulcerative colitis, urticaria, uterine fibroids, uveitis, uveoretinitis, vascular restenosis, vasculitis, vasculitis (NHLBI), vitiligo, Wegener's granulomatosis, and Whipple's disease.

In further embodiments, the methods are provided for alleviating a symptom of a disease or disorder mediated, at least in part, by $\alpha 4\beta 7$ integrin. In some embodiments, the methods include identifying a mammal having a symptom of a disease or disorder mediated, at least in part, by $\alpha 4\beta 7$ integrin, and providing to the mammal an amount of a compound as described herein effective to ameliorate (i.e., lessen the severity of) the symptom.

In some embodiments, the disease or condition mediated, at least in part, by $\alpha 4\beta 7$ integrin is an inflammatory disease or LPS induced endotoxin shock. In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), inflammatory bowel disease (IBD), sepsis, psoriasis, Sjoegren's syndrome, autoimmune hemolytic anemia, asthma, or chronic obstructive pulmonary disease (COPD), ankylosing spondylitis, acute gout and ankylosing spondylitis, reactive arthritis, monoarticular arthritis, osteoarthritis, gouty arthritis, juvenile arthritis, juvenile onset rheumatoid arthritis, juvenile rheumatoid arthritis or psoriatic arthritis. In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

In some embodiments, the disease or condition mediated, at least in part, by $\alpha 4\beta 7$ integrin is inflammatory bowel disease (IBD). The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the presently disclosed compounds, compositions and methods include diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

Treating or preventing IBD also includes ameliorating or reducing one or more symptoms of IBD. As used herein, the term "symptoms of IBD" refers to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The term "wherein said symptoms are reduced" refers to a qualitative or quantitative reduction in detectable symptoms, including but not limited to a detectable impact on the rate of recovery from disease (e.g. rate of weight gain). The diagnosis is typically determined by way of an endoscopic observation of the mucosa, and pathologic examination of endoscopic biopsy specimens.

The course of IBD varies, and is often associated with intermittent periods of disease remission and disease exacerbation. Various methods have been described for characterizing disease activity and severity of IBD as well as response to treatment in subjects having IBD. Treatment according to the present methods is generally applicable to a subject having IBD of any level or degree of disease activity.

In some embodiments, the disease or condition treated by the administration of a compound of composition described herein includes acute gout and ankylosing spondylitis, allergic disorders, Alzheimer's disease, Amyotrophic lateral sclerosis (ALS), Amyotrophic lateral sclerosis and multiple sclerosis, atherosclerosis, bacterial infections, bone cancer pain and pain due to endometriosis, BRAF resistant melanoma, brain stem glioma or pituitary adenomas, burns, bursitis, cancer of the anal region, cancer of the endocrine system, cancer of the kidney or ureter (e.g. renal cell carcinoma, and carcinoma of the renal pelvis), cancer of the penis, cancer of the small intestine, cancer of the thyroid, cancer of the urethra, cancers of the blood such as acute myeloid leukemia, cancers of the tongue, carcinoma of the cervix, carcinoma of the endometrium, carcinoma of the fallopian tubes, carcinoma of the renal pelvis, carcinoma of the vagina or carcinoma of the vulva, chronic myeloid leukemia, chronic or acute leukemia, chronic pain, classic Bartter syndrome, common cold conjunctivitis, coronary heart disease, cutaneous or intraocular melanoma, dermatitis, dysmenorrhea, eczema, endometriosis, familial adenomatous polyposis, fibromyalgia, fungal infections, gout, gynecologic tumors, uterine sarcomas, carcinoma of the fallopian tubes, headache, hemophilic arthropathy, Parkinson's disease, AIDS, herpes zoster, Hodgkin's disease, Huntington's, hyperprostaglandin E syndrome, influenza, iritis, juvenile arthritis, juvenile onset rheumatoid arthritis, juvenile rheumatoid arthritis, low back and neck pain, lymphocytic lymphomas, myofascial disorders, myositis, neuralgia, neurodegenerative disorders such as Alzheimer's disease, neuroinflammatory disorders, neuropathic pain, carcinoma of the vulva, Parkinson's disease, pediatric malignancy, pulmonary fibrosis rectal cancer, rhinitis, sarcoidosis, sarcomas of soft tissues, scleritis, skin cancer, solid tumors of childhood, spinal axis tumors, sprains and strains, stomach cancer, stroke, subacute and chronic musculoskeletal pain syndromes such as bursitis, surgical or dental procedures, symptoms associated with influenza or other viral infections, synovitis, toothache, ulcers, uterine cancer, uterine sarcomas, uveitis, vasculitis, viral infections, viral infections {e.g. influenza) and wound healing.

Criteria useful for assessment of disease activity in subjects with ulcerative colitis can be found in, e.g., Truelove et al. (1955) Br Med J 2:1041-1048.) Using these criteria, disease activity can be characterized in a subject having IBD as mild disease activity or severe disease activity. Subjects who do not meet all the criteria for severe disease activity, and who exceed the criteria for mild disease activity are classified as having moderate disease activity.

The presently disclosed treatment methods can also be applied at any point in the course of the disease. In some embodiments, the methods are applied to a subject having IBD during a time period of remission (i.e., inactive disease). In such embodiments, the present methods provide benefit by extending the time period of remission (e.g., extending the period of inactive disease) or by preventing, reducing, or delaying the onset of active disease. In other embodiments, methods may be applied to a subject having IBD during a period of active disease. Such methods provide benefit by reducing the duration of the period of active disease, reducing or ameliorating one or more symptoms of IBD, or treating IBD.

Measures for determining efficacy of treatment of IBD in clinical practice have been described and include, for example, the following: symptom control; fistula closure; extent of corticosteroid therapy required; and, improvement in quality of life. Heath-related quality of life (HRQL) can be assessed using the Inflammatory Bowel Disease Questionnaire (IBDQ), which is extensively used in clinical practice to assess quality of life in a subject with IBD. (See Guyatt et al. (1989) Gastroenterology 96:804-810.) In some embodiments, the disease or condition is immune-mediated liver injury, disease or condition.

In some embodiments, the disease or condition mediated, at least in part, by α4β7 integrin is alcoholic hepatitis. Alcoholic hepatitis is a clinical syndrome characterized by jaundice and liver failure that develops in subjects with chronic and active alcohol abuse. (See Akriviadis E. et. al, Ann Gastroenterol. 2016 April-June; 29(2): 236-237). Alcoholic hepatitis can cause cirrhosis and fibrosis of the liver cells. Glucocorticoids, (e.g. prednisolone) and phosophodiesterase inhibitors (e.g. pentoxifylline) can be used to treat alcoholic hepatitis. The compounds herein can be used as stand-alone treatments or in combination with the current treatments for alcoholic hepatitis.

In some embodiments, the disease or condition mediated, at least in part, by α4β7 integrin is fatty liver disease. In some embodiments, the diseases are hepatic steatosis, non-alcoholc fatty liver disease (NAFLD) and nonalcoholic steatohepatitis (NASH). The compounds herein can be used as stand-alone treatments or in combination with the current treatments for fatty liver diseases.

In one aspect, the present disclosure provides methods of treating or preventing a human immunodeficiency virus (HIV) infection in a subject in need thereof, comprising administering to the subject a therapeutically effective amount of a compound provided herein, or a pharmaceutically acceptable salt thereof, or a pharmaceutical composition provided herein.

In some embodiments, the disease or condition mediated, at least in part, by α4β7 integrin is systemic lupus erythematosus (SLE), lupus nephritis, lupus-related, or other autoimmune disorders or a symptom of SLE. Symptoms of systemic lupus erythematosus include joint pain, joint swelling, arthritis, fatigue, hair loss, mouth sores, swollen lymph nodes, sensitivity to sunlight, skin rash, headaches, numbness, tingling, seizures, vision problems, personality changes, abdominal pain, nausea, vomiting, abnormal heart rhythms, coughing up blood and difficulty breathing, patchy skin color and Raynaud's phenomenon.

Combination Therapy

Also provided are methods of treatment in which a compound described herein is given to a patient in combination with one or more additional active agents or therapy.

Thus in some embodiments, a method of treating diseases or conditions mediated, at least in part, by α4β7 integrin and/or diseases or symptoms that co-present or are exacerbated or triggered by the diseases or conditions mediated, at least in part, by α4β7 integrin, e.g., an allergic disorder and/or an autoimmune and/or inflammatory disease, and/or an acute inflammatory reaction, comprises administering to a patient in need thereof an effective amount of a compound described herein optionally in combination with an additional agent (e.g., a second, third, fourth or fifth active agent) which can be useful for treating diseases or conditions mediated, at least in part, by α4β7, an allergic disorder and/or an autoimmune and/or inflammatory disease, and/or an acute inflammatory reaction incident to or co-presenting with diseases or conditions mediated, at least in part, by α4β7 integrin. Treatment with the second, third, fourth or fifth active agent may be prior to, concomitant with, or following treatment with a compound described herein. In some embodiments, a compound described herein is combined with another active agent in a single dosage form. Suitable therapeutics that may be used in combination with a compound described herein include, but are not limited to, therapeutic agents provided herein, or a combination comprising at least one therapeutic agent provided herein.

Included herein are methods of treatment in which a compound described herein is administered in combination with an agent for treatment of an inflammatory disease or condition. Examples of agents for treatment of an inflammatory disease or condition that can be used in combination with compounds described herein, include alpha-fetoprotein modulators; adenosine A3 receptor antagonist; adrenomedullin ligands; AKT1 gene inhibitors; antibiotics; antifungals; ASK1 inhibitors; ATPase inhibitors; beta adrenoceptor antagonists; BTK inhibitors; calcineurin inhibitors; carbohydrate metabolism modulators; cathepsin S inhibitors; CCR9 chemokine antagonists; CD233 modulators; CD29 modulators; CD3 antagonists; CD40 ligand inhibitors; CD40 ligand receptor antagonists; chemokine CXC ligand inhibitors; CHST15 gene inhibitors; collagen modulators; CSF-1 antagonists; CX3CR1 chemokine modulators; ecobiotics; eotaxin ligand inhibitors; EP4 prostanoid receptor agonists; F1F0 ATP synthase modulators; farnesoid X receptor agonists; fecal microbiota transplantation (FMT); fractalkine ligand inhibitors; free fatty acid receptor 2 antagonists; GATA 3 transcription factor inhibitors; glucagon-like peptide 2 agonists; glucocorticoid agonists; Glucocorticoid receptor modulators; guanylate cyclase receptor agonists; HIF prolyl hydroxylase inhibitors; histone deacetylase inhibitors; HLA class II antigen modulators; hypoxia inducible factor-1 stimulator; ICAM1 gene inhibitors; IL-1 beta ligand modulators; IL-12 antagonists; IL-13 antagonists; IL-18 antagonists; IL-22 agonists; IL-23 antagonists; IL-23A inhibitors; IL-6 antagonists; IL-7 receptor antagonists; IL-8 receptor antagonists; integrin alpha-4/beta-1 antagonists; integrin alpha-4/beta-7 antagonists; integrin antagonists; interleukin ligand inhibitors; interleukin receptor 17A antagonists; interleukin-1 beta ligands; interleukin 1 like receptor 2 inhibitors; IL-6 receptor modulators; JAK tyrosine kinase inhibitors; Jak1 tyrosine kinase inhibitors;

Jak3 tyrosine kinase inhibitors; lactoferrin stimulators; LanC like protein 2 modulators; leukocyte elastate inhibitors; leukocyte proteinase-3 inhibitors; MAdCAM inhibitors; melanin concentrating hormone (MCH-1) antagonist; melanocortin agonists; metalloprotease-9 inhibitors; microbiome-targeting therapeutics; natriuretic peptide receptor C agonists; neuregulin-4 ligands; NLPR3 inhibitors; NKG2 D activating NK receptor antagonists; NR1H4 receptor (FXR) agonists or modulators; nuclear factor kappa B inhibitors; opioid receptor antagonists; OX40 ligand inhibitors; oxidoreductase inhibitors; P2X7 purinoceptor modulators; PDE 4 inhibitors; Pellino homolog 1 inhibitors; PPAR alpha/delta agonists; PPAR gamma agonists; protein fimH inhibitors; P-selectin glycoprotein ligand-1 inhibitors; Ret tyrosine kinase receptor inhibitors; RIP-1 kinase inhibitors; RIP-2 kinase inhibitors; RNA polymerase inhibitors; sphingosine 1 phosphate phosphatase 1 stimulators; sphingosine-1-phosphate receptor-1 agonists; sphingosine-1-phosphate receptor-5 agonists; sphingosine-1-phosphate receptor-1 antagonists; sphingosine-1-phosphate receptor-1 modulators; stem cell antigen-1 inhibitors; superoxide dismutase modulators; SYK inhibitors; TLR-3 antagonists; TLR-4 antagonists; Toll-like receptor 8 (TLR8) inhibitors; TLR-9 agonists; TNF alpha ligand inhibitors; TNF ligand inhibitors; TNF alpha ligand modulators; TNF antagonists; TPL-2 inhibitors; tumor necrosis factor 14 ligand modulators; tumor necrosis factor 15 ligand inhibitors; Tyk2 tyrosine kinase inhibitors; type I IL-1 receptor antagonists; vanilloid VR1 agonists; and zonulin inhibitors, and combinations thereof.

Adenosine A3 receptor antagonists include PBF-677.
Adrenomedullin ligands include adrenomedullin.
Antibiotics include ciprofloxacin, metronidazole, vancomycin, rifaximin.
ASK1 inhibitors include GS-4997.
Alpha-fetoprotein modulators include ACT-101.
Anti-CD28 inhibitors include JNJ-3133
Beta adrenoceptor antagonists include NM-001.
BTK inhibitors include GS-4059.
Calcineurin inhibitors: include tacrolimus, and ciclosporin.
Carbohydrate metabolism modulators include ASD-003.
Cathepsin S inhibitors include VBY-129.
CCR9 chemokine antagonists include CCX-507.
CD233 modulators include GSK-2831781.
CD29 modulators include PF-06687234.
CD3 antagonists include NI-0401.
CD4 antagonists include IT-1208.
CD40 ligand inhibitors include SAR-441344, and letolizumab.
CD40 gene inhibitors include NJA-730.
CD40 ligand receptor antagonists include FFP-104, BI-655064.
Chemokine CXC ligand inhibitors include LY-3041658.
CHST15 gene inhibitors include STNM-01.
Collagen modulators include ECCS-50 (DCCT-10).
COT protein kinase inhibitors include GS-4875.
CSF-1 antagonists include JNJ-40346527 (PRV-6527), and SNDX-6352.
CX3CR1 chemokine modulators include E-6130.
Ecobiotics include SER-287.
Eotaxin ligand inhibitors include bertilimumab.
EP4 prostanoid receptor agonists include KAG-308.
F1F0 ATP synthase modulators include LYC-30937 EC.
Fractalkine ligand inhibitors include E-6011.
Free fatty acid receptor 2 antagonists include GLPG-0974.
GATA 3 transcription factor inhibitors include SB-012.

Glucagon-like peptide 2 agonists include teduglutide.
Glucocorticoid agonists include budesonide, beclomethasone dipropionate, and dexamethasone sodium phosphate.
Glucocorticoid receptor modulators/TNF ligand inhibitors include ABBV-3373.
Guanylate cyclase receptor agonists include dolcanatide.
HIF prolyl hydroxylase inhibitors include DS-1093, and AKB-4924.
HIF prolyl hydroxylase-2 inhibitors/hypoxia inducible factor-1 stimulators include GB-004.
Histone deacetylase inhibitors include givinostat.
Histone deacetylase-6 inhibitors include CKD-506.
HLA class II antigen modulators include HLA class II protein modulators.
ICAM1 gene inhibitors include alicaforsen.
IL-12 antagonists include ustekinumab (IL12/IL23).
IL-13 antagonists include tralokinumab.
IL-18 antagonists include GSK-1070806
IL-22 agonists include RG-7880.
IL-23 antagonists include tildrakizumab, risankizumab (BI-655066), mirikizumab (LY-3074828), brazikumab (AMG-139), and PTG-200.
IL-23A inhibitors include guselkumab.
IL-6 antagonists include olokizumab.
IL-7 receptor antagonists include OSE-127.
IL-8 receptor antagonists include clotrimazole.
Integrin alpha-4/beta-1 antagonists include natalizumab.
Integrin alpha-4/beta-7 antagonists include etrolizumab (a4b7/aEb7), vedolizumab, carotegast methyl, TRK-170 (a4b7/a4b1), PN-10943, and PTG-100.
Integrin antagonists include E-6007.
Interleukin ligand inhibitors include bimekizumab (IL-17A/L-17F).
Interleukin receptor 17A antagonists include brodalumab.
Interleukin-1 beta ligands include K(D)PT.
Interleukin 1 like receptor 2 inhibitors include BI-655130.
IL-6 receptor modulators include olamkicept.
JAK tyrosine kinase inhibitors include tofacitinib (1/3), peficitinib (1/3), TD-3504, an TD-1473. Jak1 tyrosine kinase inhibitors include a compound disclosed in WO2008/109943. Examples of other JAK inhibitors include, but are not limited to, AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), XL019, upadacitinib (ABT-494), filgotinib, GLPG-0555, SHR-0302, and PF-06700841 (JAK1/Tyk2).
Jak3 tyrosine kinase inhibitors include PF-06651600.
Lactoferrin stimulators include recombinant human lactoferrin (VEN-100).
LanC like protein 2 modulators include BT-11.
Leukocyte elastase inhibitors/Leukocyte proteinase-3 inhibitors include tiprelestat.
MAdCAM inhibitors include SHP-647 (PF-547659).
Melanin concentrating hormone (MCH-1) antagonists include CSTI-100.
Melanocortin agonists include ASP-3291, and PL-8177.
Metalloprotease-9 inhibitors include GS-5745.
Natriuretic peptide receptor C agonists include plecanatide.
Neuregulin-4 ligands include NRG-4.
NKG2 D activating NK receptor antagonists include JNJ-4500.
NLPR3 inhibitors include dapansutrile, BMS-986299, SB-414, MCC-950, IFM-514, JT-194, PELA-167, and NBC-6.

NR1H4 receptor (FXR) agonists or modulators include tropifexor, and GS-9674.

Nuclear factor kappa B inhibitors include Thetanix.

Opioid receptor antagonists include naltrexone, and IRT-103.

OX40 ligand inhibitors include KHK-4083.

Oxidoreductase inhibitors include olsalazine.

Pellino homolog 1 inhibitors include BBT-401.

P2X7 purinoceptor modulators include SGM-1019.

PDE 4 inhibitors include apremilast.

PPAR alpha/delta agonists include elafibranor (GFT-1007).

PPAR gamma agonists include GED-0507-34-Levo.

Protein fimH inhibitors include EB-8018.

P-selectin glycoprotein ligand-1 inhibitors include SEL-K2, AbGn-168H, and neihulizumab.

Ret tyrosine kinase receptor inhibitors include GSK-3179106.

RIP-1 kinase inhibitors include GSK-2982772.

RIP-2 kinase inhibitors include GSK-2983559.

Sphingosine 1 phosphate phosphatase 1 stimulators include etrasimod.

Sphingosine-1-phosphate receptor-1 agonists include mocravimod (KRP-203), and BMS-986166.

Sphingosine-1-phosphate receptor-1 agonists/Sphingosine-1-phosphate receptor-5 agonists include ozanimod.

Sphingosine-1-phosphate receptor-1 antagonists include amiselimod (MT-1303).

Sphingosine-1-phosphate receptor-1 modulators include OPL-002.

Stem cell antigen-1 inhibitors include Ampion (DMI-9523).

Superoxide dismutase modulators include midismase.

Syk inhibitors include GS-9876.

TLR-3 antagonists include PRV-300.

TLR-4 antagonists include JKB-122.

Toll-like receptor 8 (TLR8) inhibitors include E-6887, IMO-4200, IMO-8400, IMO-9200, MCT-465, MEDI-9197, motolimod, resiquimod, VTX-1463, and VTX-763.

TLR-9 agonists include cobitolimod, IMO-2055, IMO-2125, lefitolimod, litenimod, MGN-1601, and PUL-042.

TNF alpha ligand inhibitors include adalimumab, certolizumab pegol, infliximab, golimumab, DLX-105, Debio-0512, HMPL-004, CYT-020-TNFQb, Hemay-007. and V-565.

TNF antagonists include AVX-470, tulinercept, and etanercept.

TPL-2 inhibitors include GS-4875.

Tumor necrosis factor 14 ligand modulators include AEVI-002.

Tumor necrosis factor 15 ligand inhibitors include PF-06480605.

Tyk2 tyrosine kinase inhibitors include PF-06826647, and BMS-986165.

Type I IL-1 receptor antagonists include anakinra.

Zonulin inhibitors include larazotide acetate.

Included herein are methods of treatment in which a compound described herein is administered in combination with an anti-inflammatory agent. Anti-inflammatory agents include but are not limited to NSAIDs, non-specific and COX-2 specific cycloxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, the anti-inflammatory compound is an anti-C5 monoclonal antibody (such as eculizumab or pexelizumab), a TNF antagonist, such as entanercept, or infliximab, which is an anti-TNF alpha monoclonal antibody.

Included herein are methods of treatment in which a compound described herein, is administered in combination with an immunosuppressant. In some embodiments, the immunosuppressant is methotrexate, leflunomide, cyclosporine, tacrolimus, azathioprine, or mycophenolate mofetil.

Included herein are methods of treatment in which a compound described herein, is administered in combination with a class of agent for treatment of IBD. Examples of classes of agents for treatment of IBD that can be used in combination with a compound described herein include ASK1 inhibitors, beta adrenoceptor antagonists, BTK inhibitors, beta-glucuronidase inhibitors, bradykinin receptor modulators, calcineurin inhibitors, calcium channel inhibitors, cathepsin S inhibitors, CCR3 chemokine antagonists, CD40 ligand receptor antagonists, chemokine CXC ligand inhibitors, CHST15 gene inhibitors, collagen modulators, CSF-1 antagonists, cyclooxygenase inhibitors, cytochrome P450 3A4 inhibitors, eotaxin ligand inhibitors, EP4 prostanoid receptor agonists, fractalkine ligand inhibitors, free fatty acid receptor 2 antagonists, GATA 3 transcription factor inhibitors, glucagon-like peptide 2 agonists, glucocorticoid agonists, guanylate cyclase receptor agonists, histone deacetylase inhibitors, HLA class II antigen modulators, IL-12 antagonists, IL-13 antagonists, IL-23 antagonists, IL-6 antagonists, IL-6 receptor modulators, interleukin-7 receptor modulators, IL-7 antagonists, IL-8 antagonists, integrin alpha-4/beta-1 antagonists, integrin alpha-4/beta-7 antagonists, integrin alpha-E antagonists, integrin antagonists, integrin beta-7 antagonists, interleukin ligand inhibitors, interleukin receptor 17A antagonists, interleukin-1 beta ligands, interleukin-1 beta ligand modulators, IRAK4 inhibitors, JAK tyrosine kinase inhibitors, Jak1 tyrosine kinase inhibitors, Jak3 tyrosine kinase inhibitors, LanC like protein 2 modulators, lipoxygenase modulators, MAdCAM inhibitors, matrix metalloprotease inhibitors, melanocortin agonists, metalloprotease-9 inhibitors, natriuretic peptide receptor C agonists, neuregulin-4 ligands, NKG2 D activating NK receptor antagonists, opioid receptor antagonists, opioid receptor delta antagonists, oxidoreductase inhibitors, P2X7 purinoceptor agonists, PDE 4 inhibitors, phagocytosis stimulating peptide modulators, potassium channel inhibitors, PPAR alpha agonists, PPAR delta agonists, PPAR gamma agonists, protein fimH inhibitors, P-selectin glycoprotein ligand-1 inhibitors, RNA polymerase inhibitors, sphingosine 1 phosphate phosphatase 1 stimulators, sphingosine 1 phosphate phosphatase modulators, sphingosine-1-phosphate receptor-1 agonists, sphingosine-1-phosphate receptor-1 antagonists, sphingosine-1-phosphate receptor-1 modulators, sphingosine-1-phosphate receptor-5 modulators, STAT3 gene inhibitors, stem cell antigen-1 inhibitors, superoxide dismutase modulators, superoxide dismutase stimulators, SYK inhibitors, TGF beta 1 iligand inhibitors, thymulin agonists, TLR antagonists, TLR agonists, TNF alpha ligand inhibitors, TNF antagonists, tumor necrosis factor 14 ligand modulators, type II TNF receptor modulators, Tpl 2 inhibitors, and Zonulin inhibitors.

Included herein are methods of treatment in which a compound described herein is administered in combination with an agent for treatment of IBD. Examples of agents for treatment of IBD that can be used in combination with a compound described herein, or a pharmaceutically acceptable salt, stereoisomer, mixture of stereoisomers, tautomer, or deuterated analog thereof, include those provided herein for the treatment of an inflammatory disease or condition, and ABX-464, adalimumab; alicaforsen, ALLO-ASC-CD, AMG-966, anakinra, apremilast; Alequel; AMG-139; amiselimod, ASD-003, ASP-3291, AX-1505, BBT-401, balsalazide; beclomethasone dipropionate; BI-655130, BMS-986184; budesonide; CEQ-508; certolizumab; *Clostridium butyricum*; ChAdOx2-HAV, dexamethasone sodium phosphate, DNVX-078, etanercept; ETX-201, golimumab; GS-4997, GS-9876, GS-4875, GS-4059, infliximab; mesalazine, HLD-400, LYC-30937 EC; IONIS-JB11-2.5Rx, JNJ-64304500, JNJ-4447, naltrexone; natalizumab; neihulizumab, olsalazine; PH-46-A, propionyl-L-carnitine; PTG-100; remestemcel-L; tacrolimus; teduglutide; tofacitinib; ASP-1002; ustekinumab; vedolizumab; AVX-470; INN-108; SGM-1019; PF-06480605; PF-06651600; PF-06687234; RBX-8225, SER-287; Thetanix; TOP-1288; VBY-129; 99mTc-annexin V-128; bertilimumab; DLX-105; dolcanatide; E-6011; FFP-104; filgotinib; foralumab; GED-0507-34-Levo; givinostat; GLPG-0974; iberogast; JNJ-40346527; K(D)PT; KAG-308; KHK-4083; KRP-203; larazotide acetate; LY-3074828, midismase; olokizumab; OvaSave; P-28-GST; PF-547659; prednisolone; QBECO; RBX-2660, JKB-122; SB-012; STNM-01; Debio-0512; TRK-170; zucapsaicin; ABT-494; Ampion; BI-655066; carotegast methyl; cobitolimod; elafibranor; etrolizumab; GS-5745; HMPL-004; LP-02, ozanimod; peficitinib; RHB-104; rifaximin; tildrakizumab; tralokinumab; brodalumab; laquinimod; plecanatide; vidofludimus; and AZD-058.

Included herein are methods of treatment in which a compound described herein is administered in combination with an agent for treatment of graft versus host disease. Examples of agents for treatment of graft versus host disease that can be used in combination with a compound described herein include those provided herein for the treatment of an inflammatory disease or condition, and [18F]F-AraG, AM-01, AAT-IV, Allocetra, AMG-592, arsenic trioxide, ATIR-101, basiliximab, belatacept, belimumab, bortezomib, brentuximab vedotin, brimonidine, brimonidine tartrate, cannabidiol, CE-1145, ciclosporin, clazakizumab, CSL-964, CYP-001, defibrotide, dilanubicel, dornase alfa, DSM-9843, eculizumab, EDP-1066, everolimus, Furestem, GSK-1070806, ibrutinib, IMSUT-CORD, IRX-4204, KD-025, MaaT-013, milatuzumab, mizoribine, mycophenolate mofetil, MSCTC-0010, nalotimagene carmaleucel, MET-2, nilotinib, OMS-721, pacritinib, PF-05285401, PLX-1, Pro-Tmune, QPI-1002, remestemcel-L, RGI-2001, rivogenlecleucel, saratin, SCM-CGH, sirolimus, T-allo10, telmisartan, T-Guard, TOP-1288, TZ-101, voclosporin; CCR5 chemokine antagonist: PRO-140; CD40 ligand receptor antagonist: iscalimab; Complement C1s subcomponent inhibitor: sutimlimab, Cinryze, BIVV-009; B-lymphocyte antigen CD20 inhibitor: obinutuzumab; CASP9 gene stimulator: rivogenlecleucel; CD3 antagonist or CD7 inhibitor: T-Guard; Complement C5a factor inhibitor: olendalizumab; Dipeptidyl peptidase IV inhibitor: begelomab; JAK1/2 tyrosine kinase inhibitor: ruxolitinib; Jak1 tyrosine kinase inhibitor: itacitinib; Interleukin-2 ligand: aldesleukin; Interleukin 22 ligand: F-652; IL-2 receptor alpha subunit inhibitor: inolimomab; IL-6 receptor agonist: PLX-1; IL-6 receptor antagonist: clazakizumab; OX40 ligand inhibitor: KY-1005; An example of such OX40 inhibitor is a compound disclosed in U.S. Pat. No. 8,450,460, the entire contents of which are incorporated herein by reference; Signal transducer CD24 modulator: CD24-IgFc; Somatostatin receptor agonist: Thymoglobulin; and sphingosine-1-phosphate receptor-1 agonist: ponesimod.

Included herein are methods of treatment in which a compound described herein is administered in combination with an agent for treatment of primary sclerosing cholangitis. Examples of agents for treatment of primary sclerosing cholangitis that can be used in combination with compounds described herein include those provided herein for the treatment of an inflammatory disease or condition, and BTT-1023, CM-101, Doconexent, GRI-0124, HTD-1801, HTD-2802, hymecromone, IDN-7314, NGM-282, norursodeoxycholic acid, ORBCEL-C, SCT-5-27, STP-705, farnesoid X receptor agonist: obeticholic acid, GS-9674, and MET-409; liver X receptor antagonist: DUR-928; and CCR5/CCR2 chemokine antagonist: cenicriviroc.

In some embodiments, the one or more additional therapeutic agents is selected from the group consisting of: combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (P3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In some embodiments, the one or more additional therapeutic agents is selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In some embodiments, the one or more additional therapeutic agent is an immune modulating agent, e.g., an immunostimulant or an immunosuppressant. In certain other embodiments, an immune modulating agent is an agent capable of altering the function of immune checkpoints, including the CTLA-4, LAG-3, B7-H3, B7-H4, Tim3, BTLA, KIR, A2aR, CD200 and/or PD-1 pathways. In other embodiments, the immune modulating agent is immune checkpoint modulating agents. Exemplary immune checkpoint modulating agents include anti-CTLA-4 antibody (e.g., ipilimumab), anti-LAG-3 antibody, anti-B7-H3 antibody, anti-B7-H4 antibody, anti-Tim3 antibody, anti-BTLA antibody, anti-KIR antibody, anti-A2aR antibody, anti CD200 antibody, anti-PD-1 antibody, anti-PD-L1 antibody, anti-CD28 antibody, anti-CD80 or -CD86 antibody, anti-B7RP1 antibody, anti-B7-H3 antibody, anti-HVEM antibody, anti-CD137 or -CD137L antibody, anti-OX40 or —OX40L antibody, anti-CD40 or -CD40L antibody, anti-GAL9 antibody, anti-IL-10 antibody and A2aR drug. For certain such immune pathway gene products, the use of either antagonists or agonists of such gene products is contemplated, as are small molecule modulators of such gene products. In some embodiments, immune modulating agents include those agents capable of altering the function of mediators in cytokine mediated signaling pathways.

In some embodiments, a compound as disclosed herein (e.g., a compound described herein) may be combined with one or more (e.g., one, two, three, four, one or two, one to three, or one to four) additional therapeutic agents in any dosage amount of the compound described herein (e.g., from 10 mg to 1000 mg of compound).

A compound described herein may be combined with the agents provided herein in any dosage amount of the compound (e.g., from 50 mg to 500 mg of compound) the same as if each combination of dosages were specifically and individually listed.

In some embodiments, provided are kits comprising a pharmaceutical composition comprising a compound described herein or a compound described herein and at least one additional therapeutic agent, or a pharmaceutically acceptable salt thereof, and at least one pharmaceutically acceptable carrier. In some embodiments, kits comprising a compound disclosed herein, or a pharmaceutically acceptable salt, stereoisomer, mixture of stereoisomers, tautomer, or deuterated analog thereof, in combination with one or more (e.g., one, two, three, four, one or two, or one to three, or one to four) additional therapeutic agents are provided. Any pharmaceutical composition provided in the present disclosure may be used in the kits, the same as if each and every composition were specifically and individually listed for use in a kit. In some embodiments, the kit comprises instructions for use in the treatment of an inflammatory disease or condition. In some embodiments, the instructions in the kit are directed to use of the pharmaceutical composition for the treatment of IBD.

List of Abbreviations and Acronyms

| Abbreviation | Meaning |
|---|---|
| % | Percent |
| ° C. | Degree Celsius |
| Ac | Acetyl |
| AcOH | Acetic acid |
| ACN/CH$_3$CN/MeCN | Acetonitrile |
| ADME | Absorption, distribution, metabolism and excretion |
| AIBN | 2,2'-Azobis(2-methylpropionitrile) |
| Aq. | Aqueous |
| ASK | Apoptosis signal-regulating kinase |
| Bicarb | Bicarbonate |
| Bn | Benzyl |
| BOC/Boc | Tert-butyloxycarbonyl |
| Bpin | Pinacolborane |
| br | Broad |
| CAS | Chemical Abstract Service |
| CNS | Central nervous system |
| COPD | Chronic obstructive pulmonary disease |
| CREST | Calcinosis, Raynaud's syndrome, esophageal |
| CVP | Cyclophosphamide, vincristine, prednisone |
| d | Doublet |
| D/d | Deuterium |
| DAST | Diethylaminosulfur trifluoride |
| DABCO ® | 1,4-Diazabicyclo[2.2.2]octane |
| DCC | N,N'-Dicyclohexylcarbodiimide |
| DCE | Dichloroethane |
| DCM | Dichloromethane/methylene chloride |
| dd | Doublet of doublets |
| DIEA | N,N-Diisopropylethylamine |
| DMA | N,N-Dimethylacetamide |
| DMAP | 4-Dimethylaminopyridine |
| DME | Dimethoxy ethane |
| DMF | Dimethylformamide |
| DMPK | Drug metabolism and pharmacokinetics |
| DMSO | Dimethylsulfoxide |
| DPPA | Diphenylphosphoryl azide |
| EC$_{50}$ | The half maximal effective concentration |
| equiv/eq | Equivalents |
| EA | Ethyl acetate |
| Et$_2$O | Diethyl ether |
| EtOAc/AcOEt | Ethyl acetate |
| EtOH | Ethanol |
| F | Fahrenheit |
| FBS | Fetal bovine serum |
| g | Grams |
| Gp | Glycoprotein |
| h/hr | Hours |
| HATU | (1-[Bis(dimethylamino)methylene]-1H-1,2,3-triazolo[4,5- |
| hex | Hexanes |
| HPLC | High pressure liquid chromatography |
| Hz | Hertz |
| IL | Interleukin |
| IUPAC | International Union of Pure and Applied Chemistry |
| J | Coupling constant (MHz) |
| JAK | Janus kinase |
| Kg/kg | Kilogram |
| L | Liter |
| LCMS/LC-MS | Liquid chromatography- |

| Abbreviation | Meaning |
|---|---|
| | mass spectrometry |
| LHMDS | Lithium hexamethyl disilazide |
| LiMg-TMP | 2,2,6,6-Tetramethylpiperidinyl-magnesium chloride |
| M | Molar |
| m | multiplet |
| M+ | Mass peak |
| M + H | Mass peak plus hydrogen |
| m-CPBA | Meta-Chloroperbenzoic acid |
| Me | Methyl |
| Me$_2$N | Dimethylamine |
| MeI | Methyl Iodide |
| MeOH | Methanol |
| MeOTs | Methyl Tosylate |
| mg | Milligram |
| MHz | Megahertz |
| min/m | Minute |
| ml/mL | Milliliter |
| mM | Millimolar |
| mmol | Millimole |
| mol | Mole |
| MS | Mass spectroscopy |
| MS | Multiple sclerosis |
| MsCl | Methanesulfonyl chloride |
| MTBE | Methyl tert-Butyl ether |
| M/Z | Mass/Charge |
| N | Normal |
| NADH | Nicotinamide adenine dinucleotide in reduced form |
| NaOH | Sodium hydroxide |
| NBS | N-Bromosuccinimide |
| ng | Nanograms |
| NIS | N-Iodosuccinimide |
| nM | Nanomolar |
| NMR | Nuclear magnetic resonance |
| ON | Overnight |
| PEG | Polyethylene glycol |
| PET | Positron emission tomography |
| Ph | Phenyl |
| PhMe | Toluene |
| PhNO$_2$ | Nitrobenzene |
| PhNTf$_2$ | N-Phenyl triflamide |
| pH | Expressing the acidity or alkalinity of a solution |
| prep | Preparative |
| RA | Rheumatoid arthritis |
| Rf | Retention factor |
| RPM | Revolutions per minute |
| RT/r | Room temperature |
| s | Second |
| s | Singlet |
| sat. | Saturated |
| SFC | Super-critical fluid chromatography |
| SLE | Systemic lupus erythematosus |
| SPECT | Single-photon emission computed tomography |
| SYK | Spleen tyrosine kinase |
| t | Triplet |
| TBACl | Tetrabutylammonium chloride |
| TBS / TBDMS | Tert-butyldimethylsilyl |
| tBuOH | Tert-butanol |
| TCA | Trichloroacetic acid |
| TEA/NEt$_3$ | Triethylamine |
| temp. | Temperature |
| TES | Triethylsilane |
| TFA | Trifluoroacetic acid |
| TFAA | Trifluoroacetic acid anhydride |
| THF | Tetrahydrofuran |
| TLC | Thin-layer chromatography |
| TMP | Tetramethyl piperidine |
| TMS | Trimethylsilyl |
| Tol | Toluene |
| TPL2 | Tumor Progression Locus 2 Kinase |
| Trityl | Triphenylmethyl |
| Vac | Vacuum |
| w/v | Weight/volume |
| w/w | Weight/weight |

| Abbreviation | Meaning |
|---|---|
| δ | Chemical shift (ppm) |
| μg | Microgram |
| μL/μl | Microliter |
| μM | Micromolar |
| μm | Micrometer |
| μmol | Micromole |

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of formula (I), e.g., compounds having structures described by one or more of formula (I), or other formulas or compounds disclosed herein, or a pharmaceutically acceptable salt, stereoisomer, mixture of stereoisomers, tautomer, or deuterated analog thereof, may be accomplished as described in the following examples.

General Schemes

Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

General Scheme 1

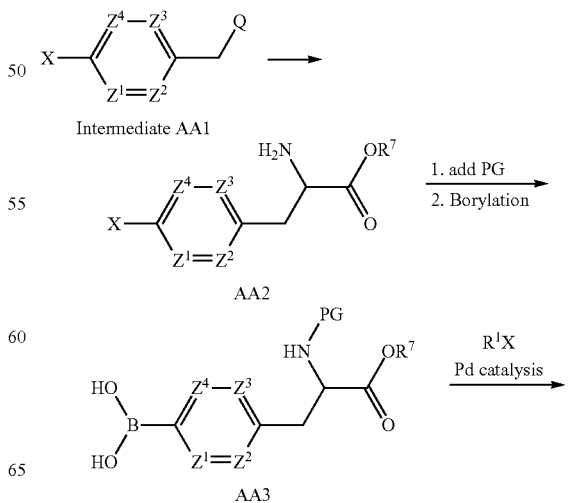

47
-continued

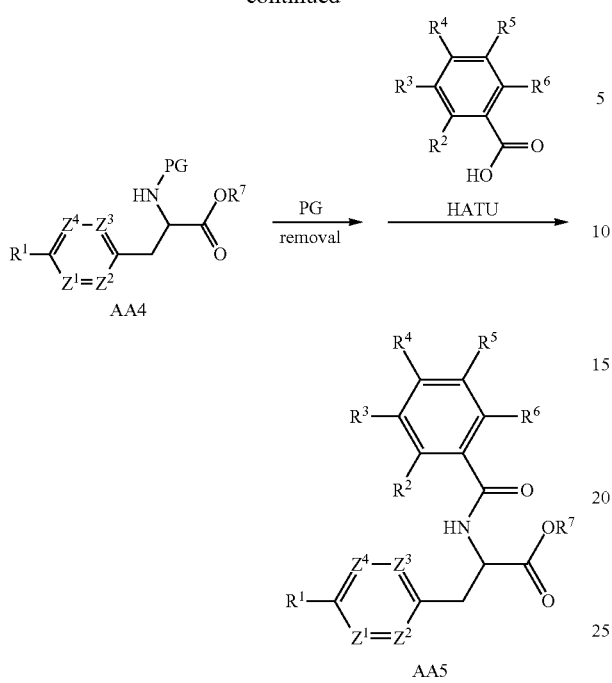

General Scheme 1 describes a general route that was used to prepare compounds of Formula (I). From Intermediate AA that has hydroxyl or halogen group as Q, and halogen group as X, amino acid esters (AA2) can be prepared under a variety of conditions (eg. Schollkopf, Maruoka, etc). After appropriate protection of the free amine with protecting groups (PG), eg. Trityl, Boc, etc., AA2 was converted to a boronic acid or boronic ester (AA3) under standard conditions (eg. Miyaura). $R^1$ was introduced under a variety of cross coupling conditions to give AA4. After removal of the amine protecting group (PG) under appropriate conditions, the amine was coupled with acids to provide AA5.

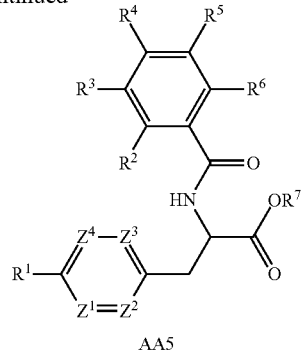

48
-continued

In some embodiments, AA4 is prepared as outlined in General Scheme 2 which describes another general route to prepare compounds of Formula (I). From Intermediate AA6 that has a halogen group as Q, and an amino group, several chemical steps such as urea formation and ring closure can prepare the $R^1$ group on AA7. Amino acid esters (AA4) can be prepared from AA7 under a variety of conditions (eg. Schollkopf, Maruoka, etc). After appropriate removal of the amine protecting group (PG) under appropriate conditions, the amine was coupled with acids to provide heterocyclic compounds AA5.

Intermediate A

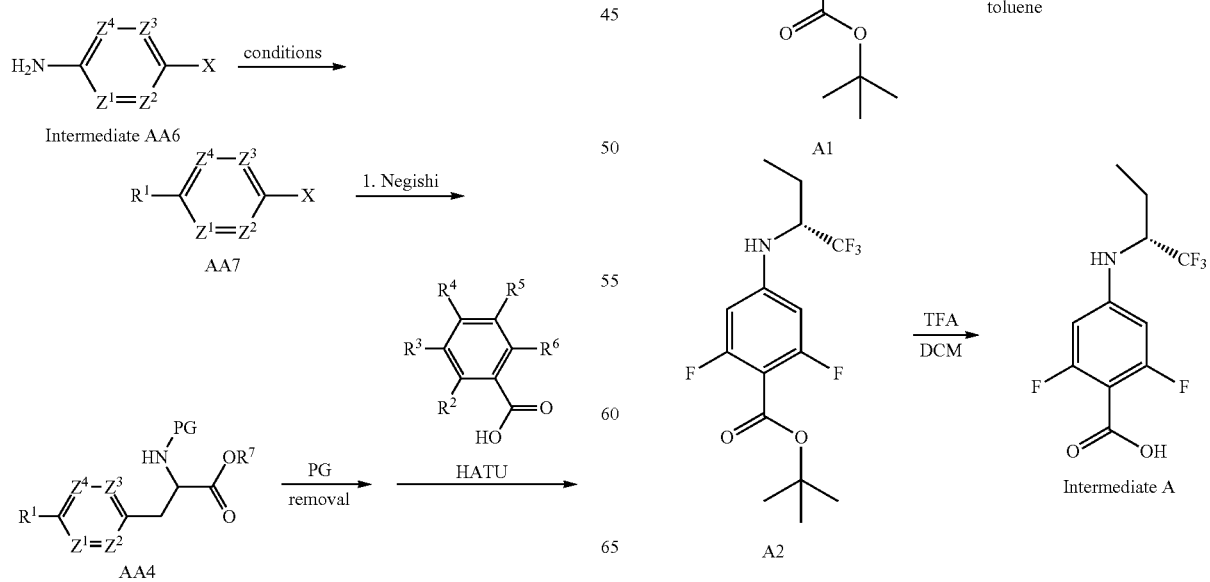

Synthesis of tert-butyl 4-bromo-2,6-difluorobenzoate (A1): To a stirred solution of 4-bromo-2,6-difluorobenzoic acid (5 g, 21.1 mmol) in DCM (50 mL) and tert-butyl alcohol (50 mL) was added di-tert-butyl dicarbonate (9.2 g, 42.2 mol) followed by 4-dimethylaminopyridine (0.8 g, 6.3 mmol). The reaction mixture was allowed to stir at RT for 12 h. The reaction mixture was concentrated under reduced pressure, dissolved in EA (100 mL) and washed with a 10% aqueous solution of citric acid (100 mL). The organic layer was washed with brine, dried over anhydrous $Na_2SO_4$, and concentrated under reduced pressure to afford crude material. This material was suspended in hexanes, the solid was filtered off and the filtrate was evaporated under reduced pressure to afford compound A1.

Synthesis of tert-butyl (R)-2,6-difluoro-4-((1,1,1-trifluorobutan-2-yl)amino)benzoate (A2): To a stirred suspension of A1 (250 mg, 0.55 mmol), (R)-1,1,1-trifluorobutan-2-amine (85 mg, 0.67 mmol), and cesium carbonate (904 mg, 2.8 mmol) in toluene (5 mL) was added XPhos Pd G3 (42 mg, 0.06 mmol). The reaction mixture was sparged with nitrogen and then heated to 90° C. for 12 h. The mixture was cooled to RT and diluted with EA (50 mL). The resultant suspension was filtered through a pad of celite, and the filtrate was evaporated under reduced pressure to afford compound A2.

Synthesis of (R)-2,6-difluoro-4-((1,1,1-trifluorobutan-2-yl)amino)benzoic acid (A): To a stirred solution of A2 (188 mg, 0.55 mmol) in DCM (1 mL) was added TFA (1 mL). The reaction mixture was allowed to stir at RT for 20 mins. The reaction mixture was concentrated under reduced pressure to afford crude material. This material was purified by silica gel column chromatography and eluted EA in hexane to afford intermediate A. MS (m/z) 284.1 $[M+H]^+$.

Intermediate B

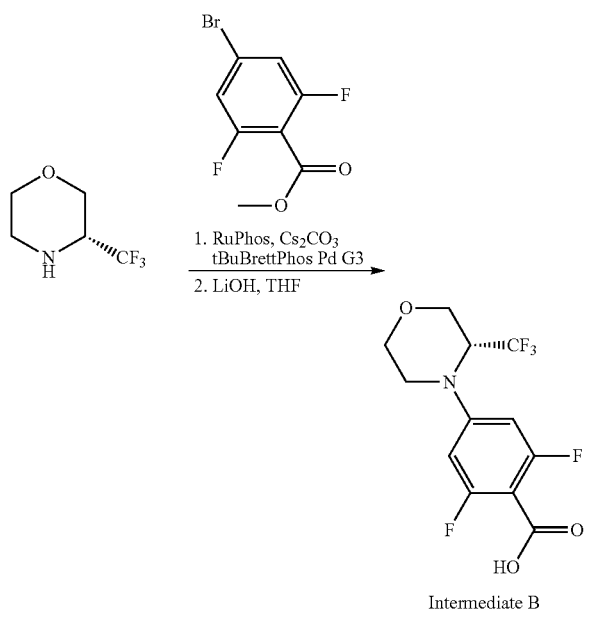

Intermediate B

Synthesis of (R)-2,6-difluoro-4-(3-(trifluoromethyl)morpholino)benzoic acid (B): To a 150 mL pressure vessel containing a stir bar was added methyl 4-bromo-2,6-difluorobenzoate (700 mg, 1.8 mmol), RuPhos (169 mg, 0.36 mmol), tBuBrettPhos Pd G3 (155 mg, 0.18 mmol), $Cs_2CO_3$ (2.95 g, 9.1 mmol), (R)-3-(trifluoromethyl)morpholine (416 mg, 2.7 mmol) and toluene (18 mL). The reaction vessel was then sealed and heated at 90° C. overnight. The reaction mixture was cooled to RT and filtered over a pad of Celite, rinsed with EA and the filtrate was evaporated to dryness under reduced pressure. The material was purified by silica gel chromatography using EA in Hexane as eluent. To this material was added THF (6 mL) and aqueous LiOH (6.2 mL, 1.0 M). The reaction mixture was stirred at 60° C. for 20 hrs. The reaction mixture was cooled to RT and acidified with 1.0 M HCl before extracting with EA. Organic layers were combined and dried over $Na_2SO_4$. The solvent was removed under reduced pressure to afford intermediate B.

Intermediate C

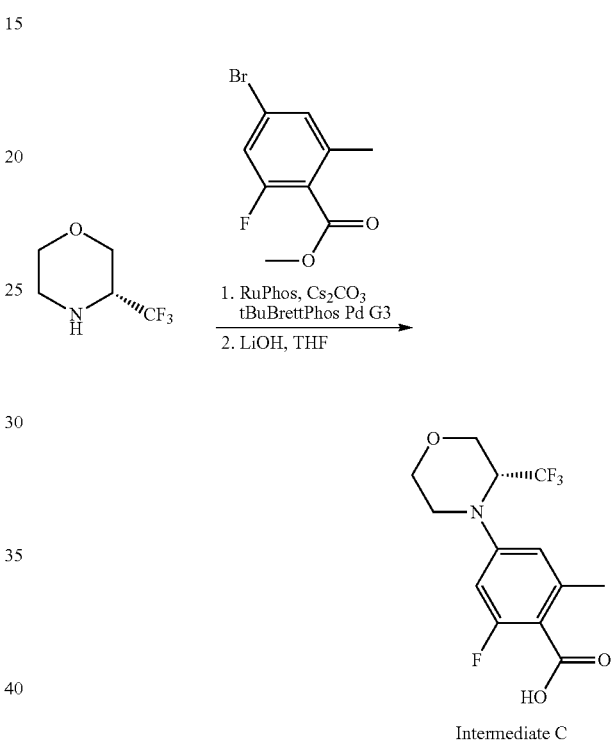

Intermediate C

Synthesis of (R)-2-fluoro-6-methyl-4-(3-(trifluoromethyl)morpholino)benzoic acid (C): The title compound was prepared according to the method presented for the synthesis of intermediate B starting with methyl 4-bromo-2-fluoro-6-methylbenzoate.

Intermediate D

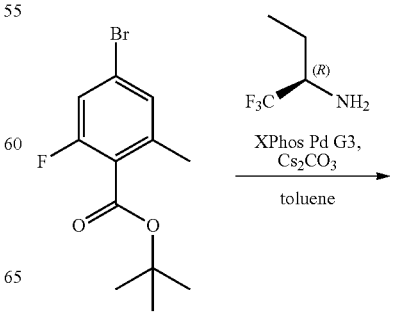

-continued

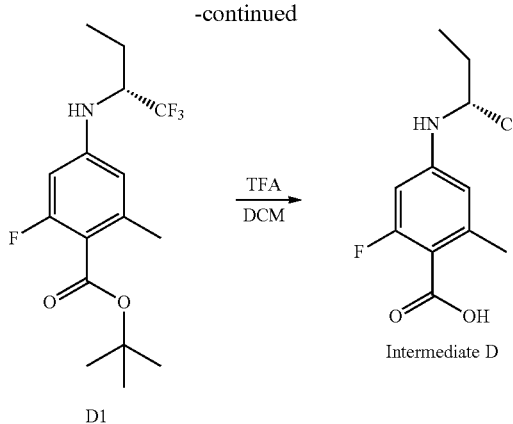

Synthesis of (R)-2-fluoro-6-methyl-4-((1,1,1-trifluorobutan-2-yl)amino)benzoic acid (D): The title compound was prepared according to the method presented for the synthesis of intermediate A starting with tert-butyl 4-bromo-2-fluoro-6-methylbenzoate.

Intermediate E

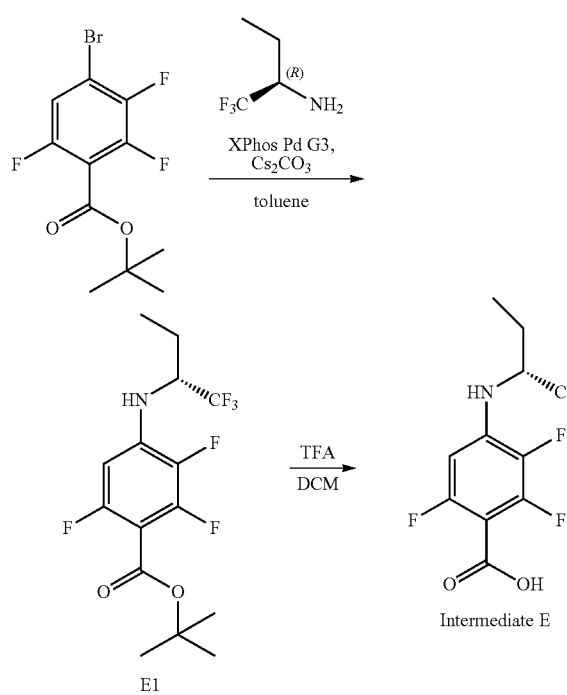

Synthesis of tert-butyl (R)-2,3,6-trifluoro-4-((1,1,1-trifluorobutan-2-yl)amino)benzoate (E1): To a stirred suspension of tert-butyl 4-bromo-2,3,6-trifluorobenzoate (250 mg, 0.55 mmol), (R)-1,1,1-trifluorobutan-2-amine (85 mg, 0.67 mmol), and cesium carbonate (904 mg, 2.8 mmol) in toluene (5 mL) was added XPhos Pd G3 (42 mg, 0.06 mmol). The reaction mixture was sparged with nitrogen and then heated to 90° C. for 2 h. The mixture was cooled to RT and diluted with EA (50 mL). The resultant suspension was filtered through a pad of celite, and the filtrate was evaporated under reduced pressure to afford compound E1.

Synthesis of (R)-2,3,6-trifluoro-4-((1,1,1-trifluorobutan-2-yl)amino)benzoic acid (E): To a stirred solution of E1 (188 mg, 0.55 mmol) in DCM (1 mL) was added TFA (1 mL). The reaction mixture was allowed to stir at RT for 20 mins. The reaction mixture was concentrated under reduced pressure to afford crude material. This material was purified by silica gel column chromatography and eluted EA in hexane to afford intermediate E.

Intermediate F

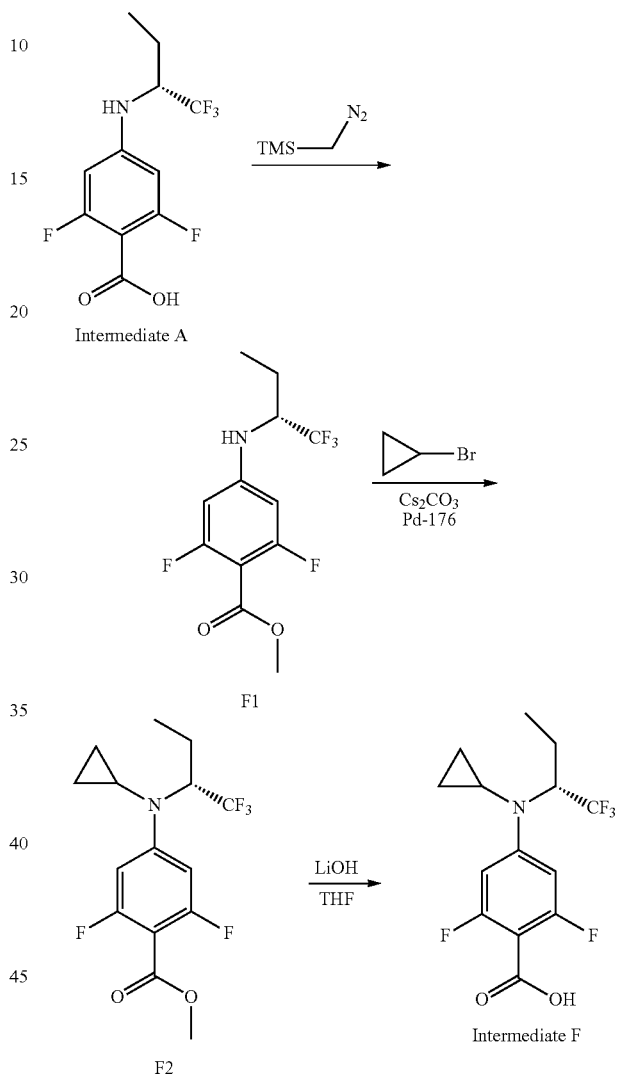

Synthesis of methyl (R)-2,6-difluoro-4-((1,1,1-trifluorobutan-2-yl)amino)benzoate (F1): To a solution of intermediate A (300 mg, 1.06 mmol) in MeOH (3 mL) and DCM (5 mL) was added TMS diazomethane (1.06 mL, 2.12 mmol). The reaction mixture was allowed to stir for 45 min at RT. Water was added and the organic layer was washed with brine, dried over $Na_2SO_4$, and concentrated in vacuo to provide F1 without further purification.

Synthesis of methyl (R)-4-(cyclopropyl(1,1,1-trifluorobutan-2-yl)amino)-2,6-difluorobenzoate (F2): To F1 (307 mg, 0.67 mmol) in dioxane was added $Cs_2CO_3$ (656 mg, 2 mmol) and Pd-176 (56 mg, 0.067 mmol). The reaction mixture was purged with $N_2$, and then cyclopropyl bromide (406 mg, 3.36 mmol) was added. The reaction was heated to 95° C. ON. The reaction mixture was filtered through celite, concentrated in vacuo, and purified by silica gel chromatography eluting with Hex/EA 0-60% to give F2.

Synthesis of (R)-4-(cyclopropyl(1,1,1-trifluorobutan-2-yl)amino)-2,6-difluorobenzoic acid (F): To F2 (360 mg, 1.07 mmol) in THF was added 1.0 M LiOH (5 mL). The reaction was allowed to stir ON at 40° C. 2.0 M HCl was added (20 mL) and extracted 3 times w/EA. Combined organics were washed with brine and concentrated in vacuo to give intermediate F without further purification.

Intermediate G

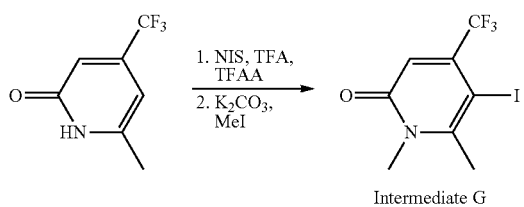

Intermediate G

Synthesis of 5-iodo-1,6-dimethyl-4-(trifluoromethyl)pyridin-2(1H)-one (G): A solution of 6-methyl-4-(trifluoromethyl)pyridin-2(1H)-one (1.26 g, 7.11 mmol), TFA (16.0 g, 140 mmol), and TFAA (3.2 g, 15 mmol) in DME (3.80 mL) was heated at 60° C. for 5 min, followed by the addition of NIS (2.04 g, 9.0 mmol). The mixture was then heated at 60° C. for an additional 12 h, after which the solvent was removed under reduced pressure and the residue was dissolved in EA, washed with water, and washed with sat. aq. NaHCO$_3$. The organic layer was concentrated under reduced pressure and the crude product was suspended in DME (3.80 mL). To this mixture was added K$_2$CO$_3$ (0.98 g, 7.0 mmol) and MeI (1.0 g, 7.0 mmol) and the mixture was heated at 95° C. for 2 h. Upon completion, the reaction was diluted with EA, and the solid was filtered off and washed with EA. The filtrate was concentrated under reduced pressure and the crude product was purified using flash chromatography eluting with EA in hexanes (25% to 100%) to afford intermediate G.

Intermediate H

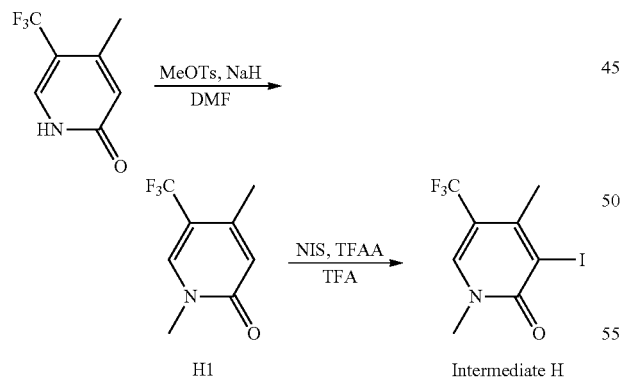

H1      Intermediate H

Synthesis of 1,4-dimethyl-5-(trifluoromethyl)pyridin-2(1H)-one (H1): To a stirred solution of 4-methyl-5-(trifluoromethyl)pyridin-2(1H)-one (100 mg, 0.056 mmol) in DMF was added NaH (25 mg, 0.62 mmol) and the reaction mixture was allowed to stir for 30 min at which time the bubbling ceased. The reaction mixture was cooled to 0° C. and methyl p-toluenesulfonate (116 mg, 0.062 mmol) was added dropwise. After 4 hrs the reaction mixture was allowed to warm to RT, concentrated under reduced pressure, and purified on silica gel chromatography eluting with Hex/EA 0-100% to afford the title compound.

Synthesis of 3-iodo-1,4-dimethyl-5-(trifluoromethyl)pyridin-2(1H)-one (H): To a stirred solution of H1 (0.72 g, 4 mmol) in neat TFA (16 mL) was added TFAA (1.6 g, 8 mmol). The reaction mixture was heated to 100° C. for 5 min in a sealed vial, followed by the addition of NIS (1.08 g, 5 mmol) and further heating at 60° C. for 3 hrs. The reaction mixture was cooled and the TFA removed under reduced pressure. The residue was dissolved in EA and washed with sat. sodium bicarbonate then brine. The organic layer was filtered then concentrated to give intermediate G without further purification.

Intermediate I

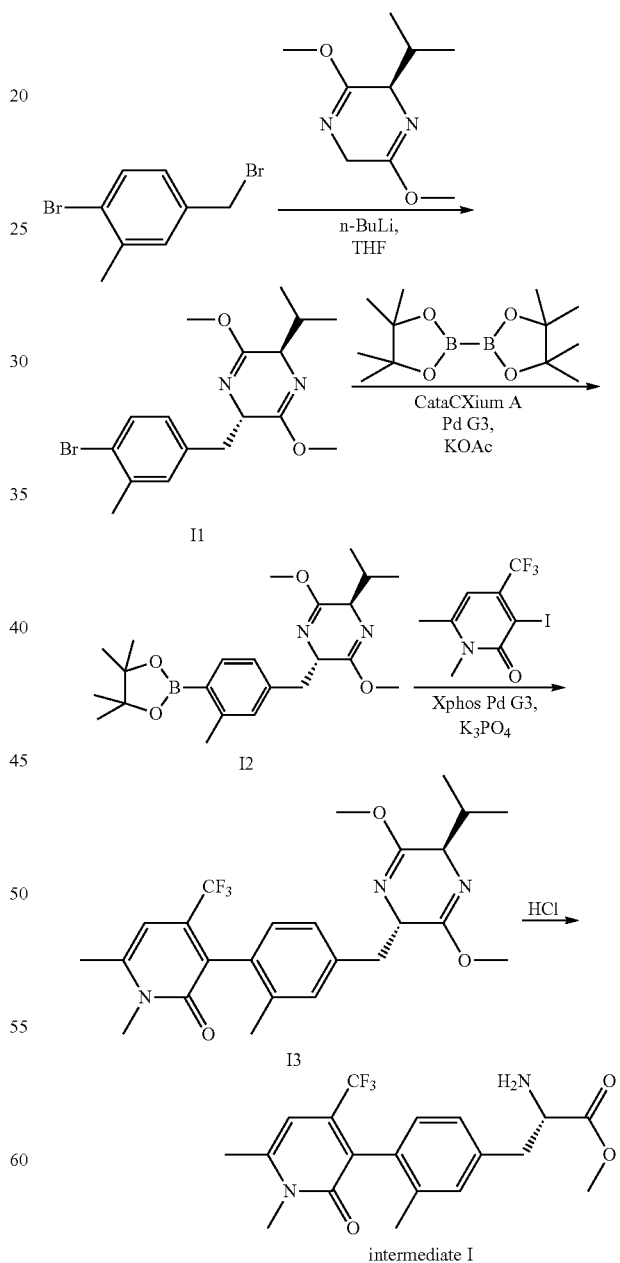

intermediate I

Synthesis of (2S,5R)-2-(4-bromo-3-methylbenzyl)-5-isopropyl-3,6-dimethoxy-2,5-dihydropyrazine (I1): To a solution of (R)-2-isopropyl-3,6-dimethoxy-2,5-dihydropyrazine (1.36 g, 7.39 mmol) in THF (28.0 mL) at −78° C. was added a solution of n-BuLi in hexanes (4.62 g, 7.96 mmol). The mixture was stirred at −78° C. for 20 min, followed by the drop-wise addition of a solution of 1-bromo-4-(bromomethyl)-2-methylbenzene (1.5 g, 5.68 mmol) in THF (37 mL). The reaction was stirred for 40 min at −78° C., and quenched with water (10 mL). The cold bath was removed and the reaction was allowed to warm to RT, and extracted with EA, washed with brine, dried over Na₂SO₄ and concentrated under reduced pressure to afford the crude material. The crude product was purified using flash chromatography eluting with EA in hexanes (10% to 100%) to afford compound 11.

Synthesis of (2S,5S)-2-isopropyl-3,6-dimethoxy-5-(3-methyl-4-(4,4,5,5-tetramethyl-1,3,2-dioxaborolan-2-yl)benzyl)-2,5-dihydropyrazine (12): To a solution of compound 11 (297 mg, 0.809 mmol) in DMA (5.40 mL) was added bis(pinacolato)diboron (262 mg, 1.03 mmol) and KOAc (238 mg, 2.42 mmol) and the mixture was purged with nitrogen gas for 6 min. CataCXium A Pd G3 (29.5 mg, 0.04 mmol) was added and the mixture was heated at 90° C. for 1 h. Upon completion, the reaction was quenched with water, extracted with EA, washed with brine, dried over Na₂SO₄, and concentrated under concentrated under reduced pressure to afford compound 12 which was used without further purification.

Synthesis of 3-(4-(((2S,5R)-5-isopropyl-3,6-dimethoxy-2,5-dihydropyrazin-2-yl)methyl)-2-methylphenyl)-1,6-dimethyl-4-(trifluoromethyl)pyridin-2(1H)-one (13): To a solution of compound 12 (130 mg, 0.157 mmol), 3-iodo-1,6-dimethyl-4-(trifluoromethyl)pyridin-2(1H)-one (65.0 mg, 0.204 mmol) in DME (1.50 mL) was added a 1 M aqueous solution of K₃PO4 (117 mg, 0.550 mmol) and the mixture was purged with nitrogen gas for 6 min. XPhos Pd G3 (13.0 mg, 0.016 mmol) was then added and the mixture was purged with nitrogen gas for an additional 3 min and heated thermally at 77° C. for 45 min. The solvent was then removed under reduced pressure, and the mixture was dissolved in EA, washed with H₂O, dried over Na₂SO₄ and concentrated under reduced pressure to afford the crude material. The crude material was purified using flash chromatography eluting with EA in hexanes (20% to 100%) and then MeOH in EA (0% to 35%) to afford 13.

Synthesis of methyl (S)-2-amino-3-(4-(1,6-dimethyl-2-oxo-4-(trifluoromethyl)-1,2-dihydropyridin-3-yl)-3-methylphenyl)propanoate (1): To a solution of compound 13 (185 mg, 0.387 mmol) in ACN (13 mL) was added an aqueous solution of 2 M HCl (67.6 mg, 1.16 mmol) and the mixture was stirred at rt for 3 h. Upon completion, the solvent was removed under reduced pressure and the crude material was purified using flash chromatography eluting with EA in hexanes (0% to 100%), then MeOH in DCM (0% to 35%) to afford intermediate I.

Intermediate J

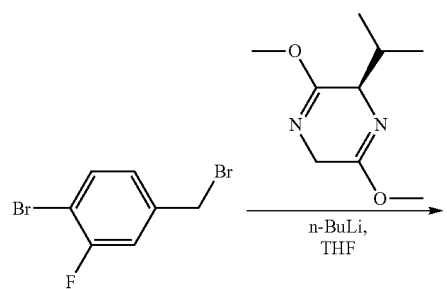

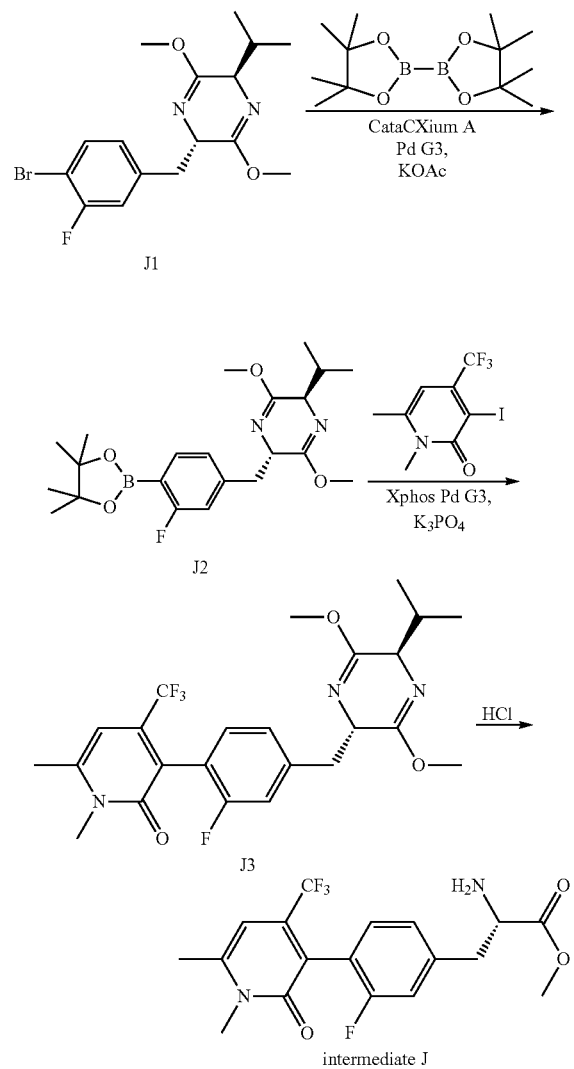

Synthesis of (2S,5R)-2-(4-bromo-3-fluorobenzyl)-5-isopropyl-3,6-dimethoxy-2,5-dihydropyrazine (J1): The title compound was prepared according to the method presented for the synthesis of intermediate I1 starting with 1-bromo-4-(bromomethyl)-2-fluorobenzene.

Synthesis of (2S,5R)-2-(3-fluoro-4-(4,4,5,5-tetramethyl-1,3,2-dioxaborolan-2-yl)benzyl)-5-isopropyl-3,6-dimethoxy-2,5-dihydropyrazine (J2): The title compound was prepared according to the method presented for the synthesis of intermediate I2 starting with J1.

Synthesis of 3-(2-fluoro-4-(((2S,5R)-5-isopropyl-3,6-dimethoxy-2,5-dihydropyrazin-2-yl)methyl)phenyl)-1,6-dimethyl-4-(trifluoromethyl)pyridin-2(1H)-one (J3): The title compound was prepared according to the method presented for the synthesis of I3 starting with compound J2.

Synthesis of methyl (S)-2-amino-3-(4-(1,6-dimethyl-2-oxo-4-(trifluoromethyl)-1,2-dihydropyridin-3-yl)-3-fluorophenyl)propanoate (J): The title compound was prepared according to the method presented for the synthesis of intermediate I starting with compound J3.

Intermediate K

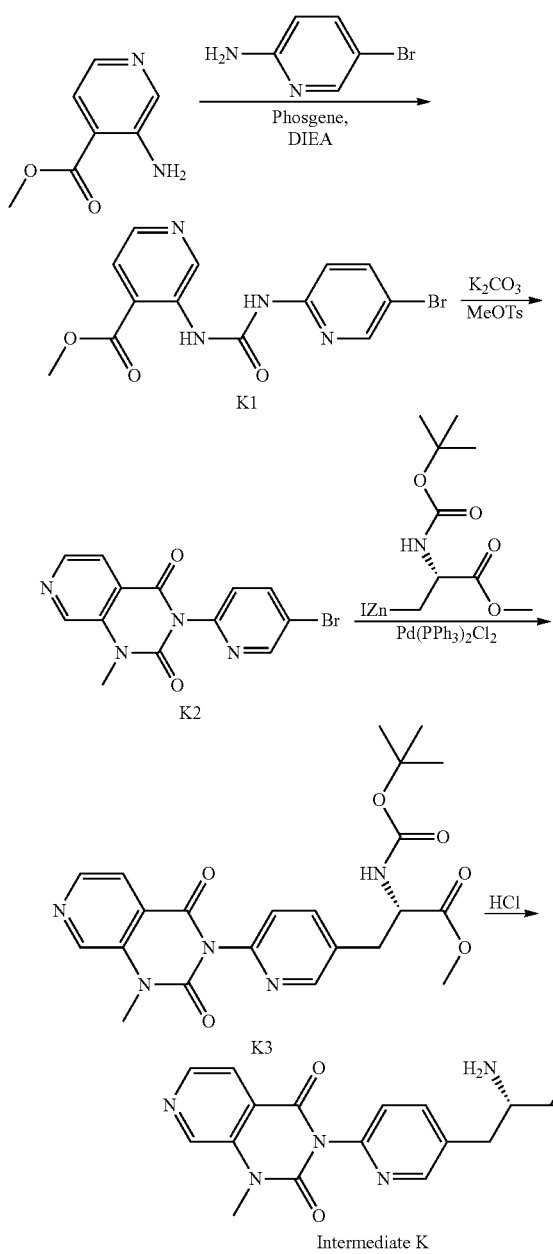

Synthesis of methyl 3-(3-(5-bromopyridin-2-yl)ureido)isonicotinate (K1): To methyl 3-aminoisonicotinate (21.5 g, 141 mmol, 1.00 eq) in DCM (430.0 mL) was added DIEA (36.5 g, 282 mmol, 49.2 mL, 2.00 eq). The mixture was degassed and purge with N₂ three times, then cooled 0° C. Triphosgene (14.69 g, 49.5 mmol, 0.35 eq) dissolved in DCM (90.0 mL) at 0° C. was added slowly. The mixture was allowed to stir for 2 h at 0° C. then concentrated in vacuo. MeCN (150.0 mL) and 5-bromopyridin-2-amine (24.4 g, 141 mmol, 1.00 eq) were added to the mixture and it was allowed to stir for 2 h at 65° C. After cooling to RT, the solids were filtered off and collected to give K1.

Synthesis of 3-(5-bromopyridin-2-yl)-1-methylpyrido[3,4-d]pyrimidine-2,4(1H,3H)-dione (K2): K1, without further purification, was dissolved in MeCN (430 mL) and allowed to stir for 16 h at 65° C. K₂CO₃ was added (19.5 g, 141.4 mmol, 1.00 eq), followed by MeOTs (39.4 g, 211.7 mmol, 1.5 eq). The resulting mixture was allowed to stir for 8 h at 65° C. EA (500 mL) and water (500 mL) were added. The organic layer was removed and the aqueous phase extracted with additional EA (500 mL). The combined organic layer was washed with brine (500 mL), dried over Na₂SO₄, and concentrated in vacuo. TBME was added to create a slurry and the resulting solids were collected on filter paper to give K2.

Synthesis of methyl (S)-2-((tert-butoxycarbonyl)amino)-3-(6-(1-methyl-2,4-dioxo-1,4-dihydropyrido[3,4-d]pyrimidin-3(2H)-yl)pyridin-3-yl)propanoate (K3): Zn (7.85 g, 120.0 mmol, 4.00 eq) was added to a round bottom flask and heated with a heat-gun at 110° C. for 10 minutes under vacuum. After cooling to RT, DMA (130 mL) and TMSCl (1.63 g, 15.0 mmol, 1.90 mL, 0.50 eq) was added and allowed to stir at 70° C. for 1 h. Methyl (R)-2-((tert-butoxycarbonyl)amino)-3-iodopropanoate (19.7 g, 60.0 mmol, 2.00 eq) dissolved in DMA (40 mL) was added and allowed to stir at 50° C. for 1 h. After cooling to 30° C., the zinc reagent was added dropwise to a previously degassed mixture of K2 (10.0 g, 30.0 mmol, 1.00 eq) and Pd(PPhs)₂C2 (6.32 g, 9.01 mmol, 0.30 eq) in DMA (130.0 mL). The reaction mixture was allowed to stir at 80° C. for 3 h. After cooling to RT, EA (200 mL) and water (500 mL) was added. The organic layer was separated and the aqueous layer washed with EA (200 mL). The combined organic layers were washed with brine (200 mL), dried over Na₂SO₄, and concentrated in vacuo. The material was purified by silica gel column chromatography using EA/hexanes to give K3.

Synthesis of methyl (S)-2-amino-3-(6-(1-methyl-2,4-dioxo-1,4-dihydropyrido[3,4-d]pyrimidin-3(2H)-yl)pyridin-3-yl)propanoate (K): The title compound was prepared according to the method presented for the synthesis of intermediate I starting with compound K3.

Intermediate L

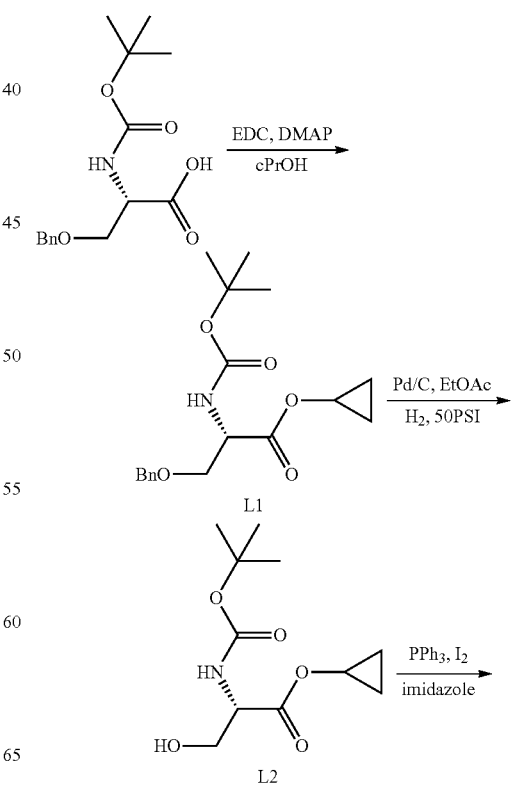

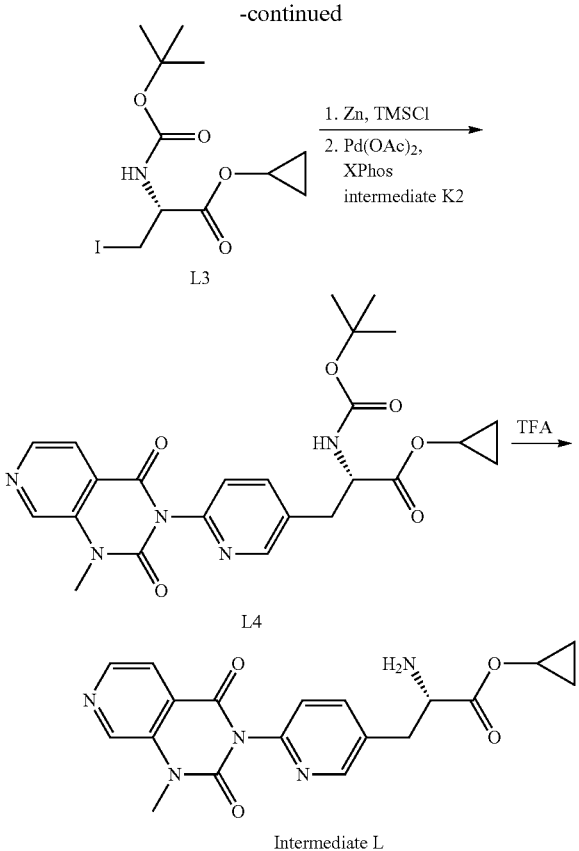

L3

L4

Intermediate L

Synthesis of cyclopropyl O-benzyl-N-(tert-butoxycarbonyl)-L-serinate (L1): To O-benzyl-N-(tert-butoxycarbonyl)-L-serine (20 g, 68 mmol) in DCM (135 mL) was added DMAP (8.27 g, 68 mmol), EDCl (25.96 g, 135 mmol) and cyclopropanol (39 g, 677 mmol). The mixture was stirred for 4 h, diluted with EA (500 mL) and washed with water (500 mL) and 0.5 N citric acid (2×500 mL). The organic layer was evaporated and the residue chromatographed silica gel eluting with 50% EA in hexanes to provide L1.

Synthesis of cyclopropyl (tert-butoxycarbonyl)-L-serinate (L2): To L1 (5.5 g, 16 mmol) in EA (10 mL) was added palladium on charcoal (3.5 g, 5% Pd). The contents were agitated on a Parr shaker under 50 PSI of hydrogen gas for 3 hours at RT. The mixture was filtered, washed with EA and solvents were evaporated providing L2, which was used in the next step without further purification.

Synthesis of cyclopropyl (R)-2-((tert-butoxycarbonyl)amino)-3-iodopropanoate (L3): To L2 (2.8 g 11.4 mmol) in DCM was added iodine (3.2 g 13 mmol, 1.1 eq), imidazole (0.855 g, 13 mmol, 1.1 eq), and PPh₃ (2.96 g, 12 mmol 1.05 eq) and the mixture allowed to stir for 2 h. Solvents were removed in vacuo and the residue was chromatographed on silica gel eluting with EA in hexanes (0-20%) to provide L3.

Synthesis of cyclopropyl (S)-2-((tert-butoxycarbonyl)amino)-3-(6-(1-methyl-2,4-dioxo-1,4-dihydropyrido[3,4-d]pyrimidin-3(2H)-yl)pyridin-3-yl)propanoate (L4): Zinc (1.27 g, 19.5 mmol, 20-30 mesh granular) was added to a flame dried round bottom flask vial containing a stir bar. DMF (4.2 mL) and TMSCl (0.49 mL, 3.8 mmol) were added and the mixture was stirred for 30 minutes. A syringe was used to decant the supernatant and the activated zinc was further washed with DMF (2×1.3 mL). L3 (2.985 g, 8.4 mmol, 2 eq) was then added in DMF (4.9 mL) dropwise at a rate so as to keep the resultant exotherm below 50° C. and then stirred for 30 minutes. The iodozinc reagent was then taken up via syringe and added to a second flask containing intermediate K2 (1.4 g, 4.2 mmol, 1 eq), palladium acetate (0.094 g, 0.42 mmol, 0.1 eq), Xphos (0.24 g, 0.5 mmol, 0.12 eq) and DMF (7.8 mL) and the reaction mixture was allowed to stir at 45° C. for 3 days. The mixture was diluted with EA, filtered through celite, solvents were removed in vacuo and chromatographed on silica gel eluting with methanol in DCM (0-10% methanol) to provide L4.

Synthesis of cyclopropyl (S)-2-amino-3-(6-(1-methyl-2,4-dioxo-1,4-dihydropyrido[3,4-d]pyrimidin-3(2H)-yl)pyridin-3-yl)propanoate (L): To L4 (1.8 g, 3.7 mmol) was added DCM (12 mL) and TFA (12 mL). The reaction was allowed to stir for 2 hours, and then concentrated in vacuo to give intermediate L.

Intermediate M

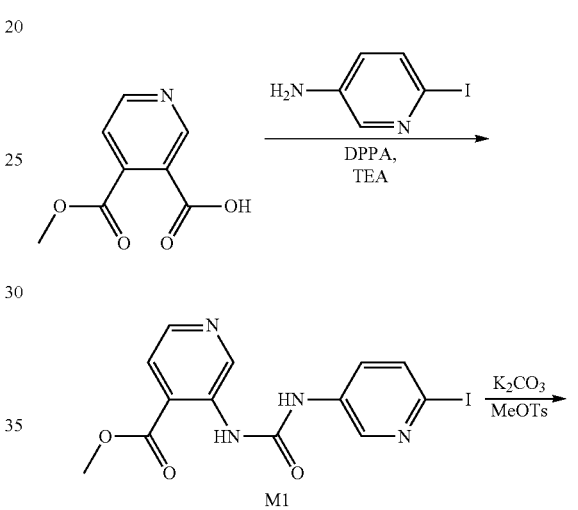

M1

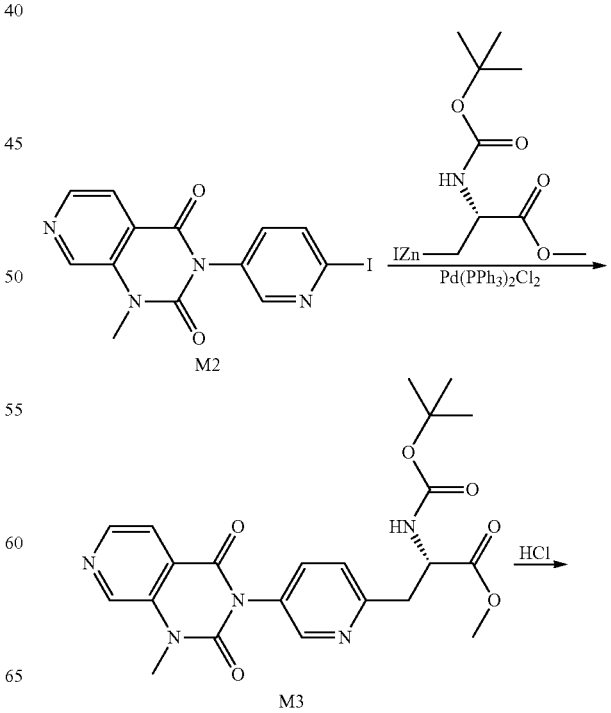

M2

M3

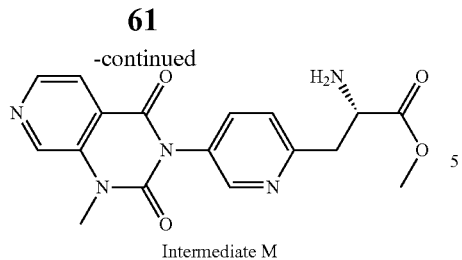

Intermediate M

Synthesis of methyl 3-(3-(6-iodopyridin-3-yl)ureido) isonicotinate (M1): To a 500 mL RB flask was added 6-iodopyridin-3-amine (5.0 g, 22.7 mmol, 1 eq.), 4-(methoxycarbonyl)nicotinic acid (4.57 g, 29.5 mmol, 1.3 eq.), (trifluoromethyl)benzene (46.0 mL) and triethylamine (4.76 mL, 34.1 mmol, 1.5 eq.). The reaction mixture was heated to 50° C. for 10 mins. After which time, diphenylphosphoryl azide (6.37 mL, 29.5 mmol, 1.3 eq.) was added dropwise to the reaction mixture. The reaction was allowed to stir for 60 min. The reaction mixture was cooled to RT and partitioned between ethyl acetate and water (200 ml each). Organics were separated and washed with brine (100 mL), dried over sodium sulfate, filtered and concentrated under vacuum. Crude purified by column chromatography on silica gel using methanol in DCM 0-20% as the eluant to afford the title compound (M1).

Synthesis of 3-(6-iodopyridin-3-yl)-1-methylpyrido[3,4-d]pyrimidine-2,4(1H,3H)-dione (M2): The title compound was prepared according to the method presented for the synthesis of intermediate K2 starting with M1.

Synthesis of methyl (S)-2-((tert-butoxycarbonyl)amino)-3-(5-(1-methyl-2,4-dioxo-1,4-dihydropyrido[3,4-d]pyrimidin-3(2H)-yl)pyridin-2-yl)propanoate (M3): The title compound was prepared according to the method presented for the synthesis of intermediate K3 starting with M2.

Synthesis of methyl (S)-2-amino-3-(5-(1-methyl-2,4-dioxo-1,4-dihydropyrido[3,4-d]pyrimidin-3(2H)-yl)pyridin-2-yl)propanoate (M): The title compound was prepared according to the method presented for the synthesis of intermediate K starting with M3.

Intermediate N

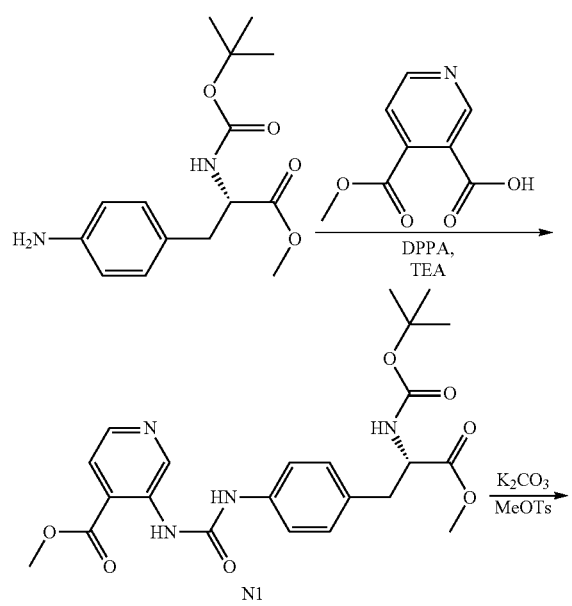

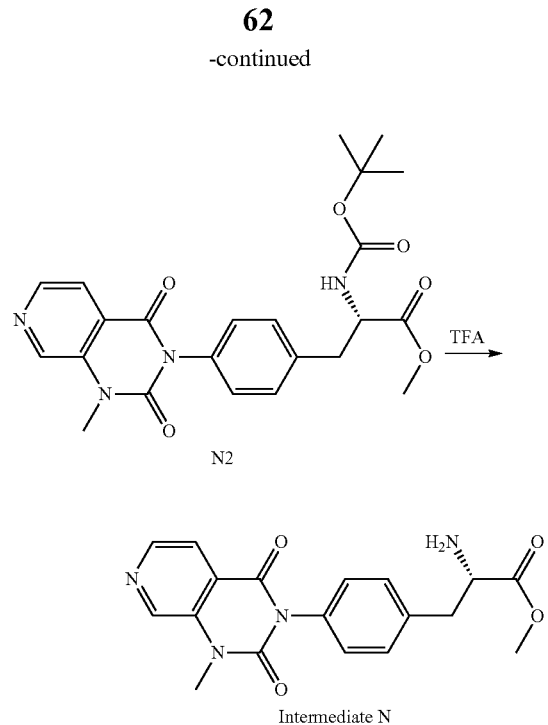

Intermediate N

Synthesis of methyl (S)-3-(3-(4-(2-((tert-butoxycarbonyl)amino)-3-methoxy-3-oxopropyl)phenyl)ureido)isonicotinate (N1): The title compound was prepared according to the method presented for the synthesis of intermediate M1 starting with methyl (S)-3-(4-aminophenyl)-2-((tert-butoxycarbonyl)amino)propanoate.

Synthesis of methyl (S)-2-((tert-butoxycarbonyl)amino)-3-(4-(1-methyl-2,4-dioxo-1,4-dihydropyrido[3,4-d]pyrimidin-3(2H)-yl)phenyl)propanoate (N2): The title compound was prepared according to the method presented for the synthesis of intermediate M2 starting with N1.

Synthesis of methyl (S)-2-amino-3-(4-(1-methyl-2,4-dioxo-1,4-dihydropyrido[3,4-d]pyrimidin-3(2H)-yl)phenyl)propanoate (N): The title compound was prepared according to the method presented for the synthesis of intermediate L starting with N2.

Intermediate O

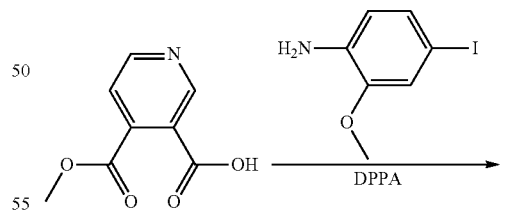

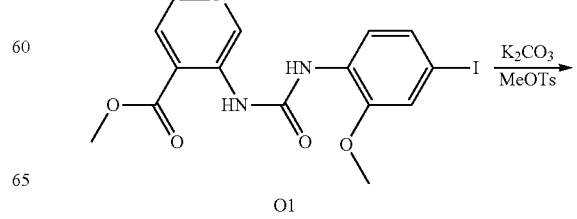

O1

Intermediate P

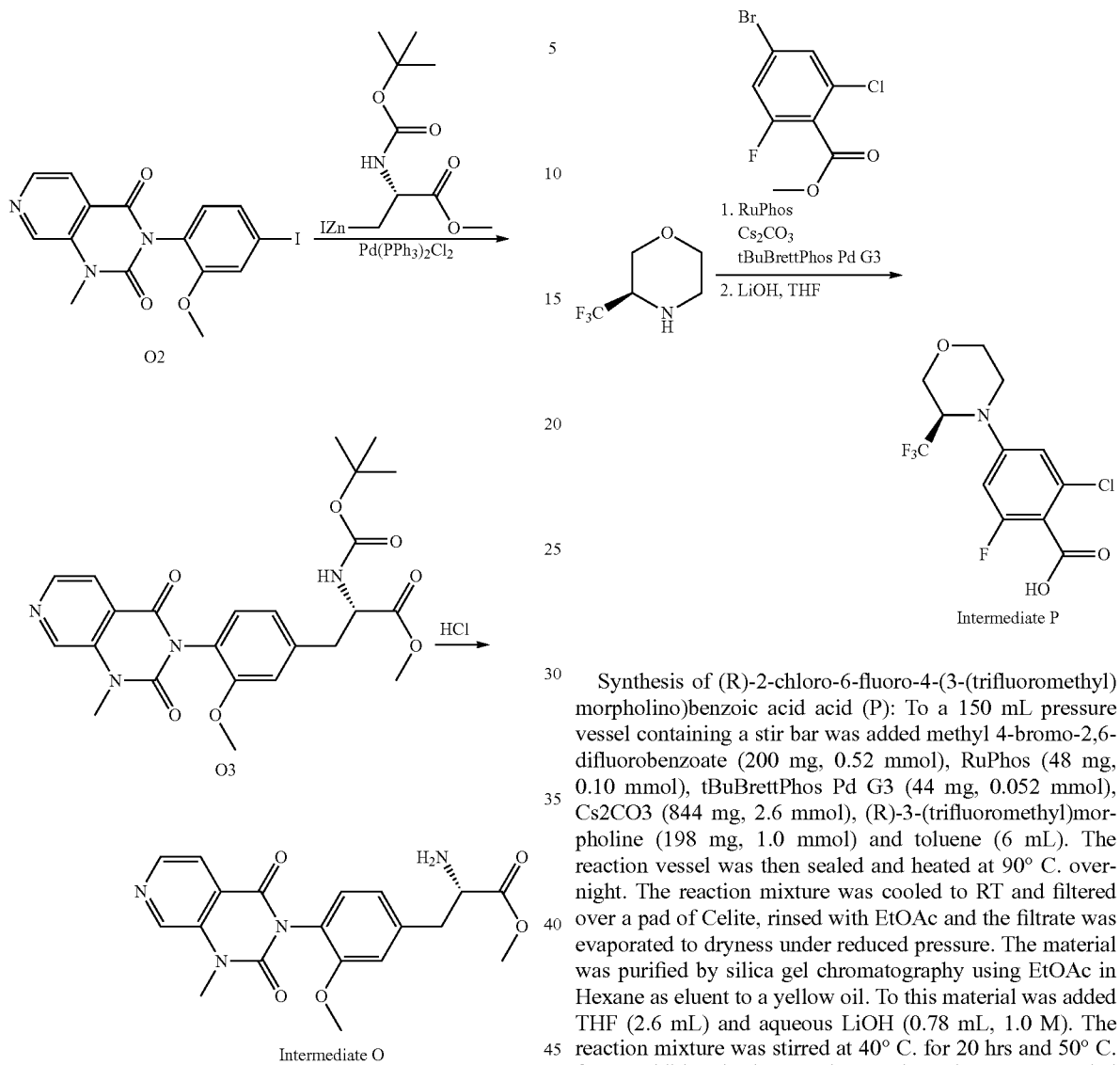

Synthesis of (R)-2-chloro-6-fluoro-4-(3-(trifluoromethyl)morpholino)benzoic acid acid (P): To a 150 mL pressure vessel containing a stir bar was added methyl 4-bromo-2,6-difluorobenzoate (200 mg, 0.52 mmol), RuPhos (48 mg, 0.10 mmol), tBuBrettPhos Pd G3 (44 mg, 0.052 mmol), Cs2CO3 (844 mg, 2.6 mmol), (R)-3-(trifluoromethyl)morpholine (198 mg, 1.0 mmol) and toluene (6 mL). The reaction vessel was then sealed and heated at 90° C. overnight. The reaction mixture was cooled to RT and filtered over a pad of Celite, rinsed with EtOAc and the filtrate was evaporated to dryness under reduced pressure. The material was purified by silica gel chromatography using EtOAc in Hexane as eluent to a yellow oil. To this material was added THF (2.6 mL) and aqueous LiOH (0.78 mL, 1.0 M). The reaction mixture was stirred at 40° C. for 20 hrs and 50° C. for an additional 4 hours. The reaction mixture was cooled to RT and acidified with 1.0 M HCl before extracting with EtOAc. Organic layers were combined and dried over Na2SO4. The solvent was removed under reduced pressure to afford P.

Synthesis of methyl 3-(3-(4-iodo-2-methoxyphenyl)ureido)isonicotinate (O1): The title compound was prepared according to the method presented for the synthesis of intermediate M1 starting with 4-iodo-2-methoxyaniline.

Synthesis of 3-(4-iodo-2-methoxyphenyl)-1-methylpyrido[3,4-d]pyrimidine-2,4(1H,3H)-dione (O2): The title compound was prepared according to the method presented for the synthesis of intermediate M2 starting with O1.

Synthesis of methyl (S)-2-((tert-butoxycarbonyl)amino)-3-(3-methoxy-4-(1-methyl-2,4-dioxo-1,4-dihydropyrido[3,4-d]pyrimidin-3(2H)-yl)phenyl)propanoate (O3): The title compound was prepared according to the method presented for the synthesis of M3 starting with O2.

Synthesis of methyl (S)-2-amino-3-(3-methoxy-4-(1-methyl-2,4-dioxo-1,4-dihydropyrido[3,4-d]pyrimidin-3(2H)-yl)phenyl)propanoate (O): The title compound was prepared according to the method presented for the synthesis of intermediate M starting with O3.

Intermediate Q

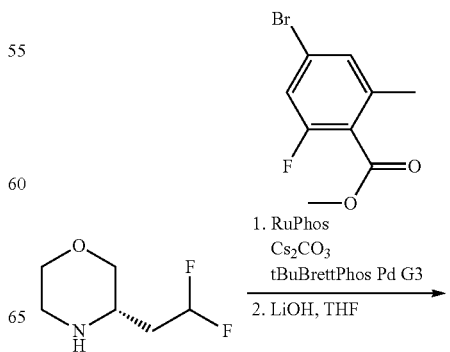

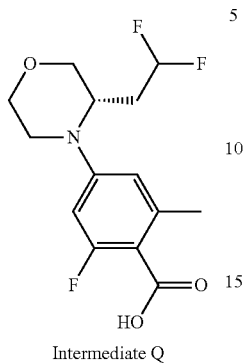

Intermediate Q

Synthesis of (S)-4-(3-(2,2-difluoroethyl)morpholino)-2-fluoro-6-methylbenzoic acid (Q): To a 150 mL pressure vessel containing a stir bar was added methyl 4-bromo-2-fluoro-6-methylbenzoate (700 mg, 1.8 mmol), RuPhos (169 mg, 0.36 mmol), tBuBrettPhos Pd G3 (155 mg, 0.18 mmol), Cs2CO3 (2.95 g, 9.1 mmol), (S)-3-(2,2-difluoroethyl)morpholine (416 mg, 2.7 mmol) and toluene (18 mL). The reaction vessel was then sealed and heated at 90° C. overnight. The reaction mixture was cooled to RT and filtered over a pad of Celite, rinsed with EA and the filtrate was evaporated to dryness under reduced pressure. The material was purified by silica gel chromatography using EA in Hexane as eluent. To this material was added THF (6 mL) and aqueous LiOH (6.2 mL, 1.0 M). The reaction mixture was stirred at 60° C. for 20 hrs. The reaction mixture was cooled to RT and acidified with 1.0 M HCl before extracting with EA. Organic layers were combined and dried over $Na_2SO_4$. The solvent was removed under reduced pressure to afford Q.

Intermediate R

Synthesis of methyl (S)-4-(3-(4-(2-((tert-butoxycarbonyl)amino)-3-methoxy-3-oxopropyl)phenyl)ureido)-5,6-dihydro-2H-pyran-3-carboxylate (R1): To a solution of methyl 4-amino-5,6-dihydro-2H-pyran-3-carboxylate (114 mg, 0.725 mmol) in dichloromethane (4 mL) was added 20% phosgene in toluene (0.352 mL, 0.67 mmol), and the reaction was allowed to stir at room temperature for 30 minutes. It was cooled to 0° C., then Hunig's base (0.237 mL, 1.36 mmol) was added, followed by methyl (S)-3-(4-aminophenyl)-2-((tert-butoxycarbonyl)amino)propanoate (100 mg, 0.34 mmol). The reaction was allowed to warm to room temperature and stir for 16 hours. It was diluted with ethyl acetate and was washed with 10% citric acid, saturated sodium bicarbonate, and saturated sodium chloride solutions. It was dried over anhydrous sodium sulfate, filtered, and concentrated. It was purified via flash chromatrography (5-100% linear gradient of ethyl acetate/hexanes) to yield R1.

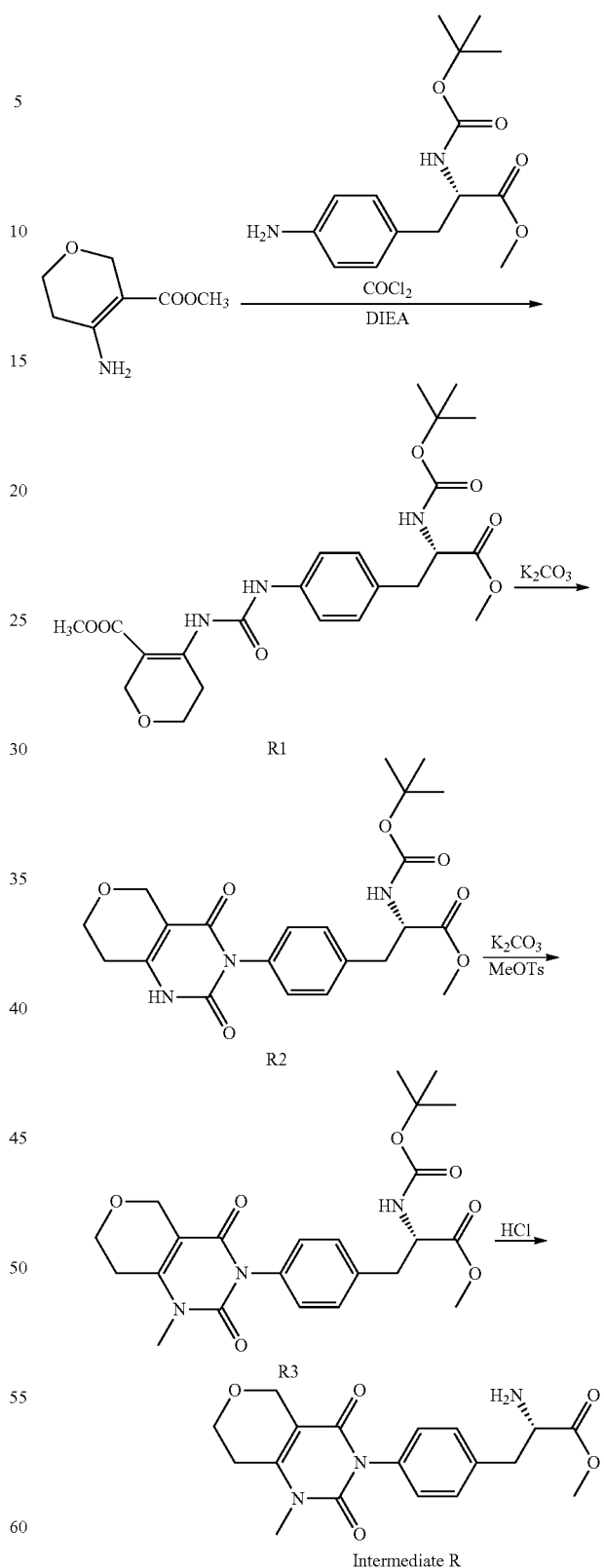

Intermediate R

Synthesis of methyl (S)-2-((tert-butoxycarbonyl)amino)-3-(4-(2,4-dioxo-1,5,7,8-tetrahydro-2H-pyrano[4,3-d]pyrimidin-3(4H)-yl)phenyl)propanoate (R2): To a solution of R1 (107 mg, 0.224 mmol) in anhydrous methanol (2.8 mL)

was added anhydrous potassium carbonate (155 mg, 1.12 mmol), and the reaction was allowed to stir for 20 minutes. It was quenched by the addition of 10% citric acid in water. Additional water was added to precipitate the product, which was collected via filtration to yield R2.

Synthesis of methyl (S)-2-((tert-butoxycarbonyl)amino)-3-(4-(1-methyl-2,4-dioxo-1,5,7,8-tetrahydro-2H-pyrano[4,3-d]pyrimidin-3(4H)-yl)phenyl)propanoate (R3): To a solution of R2 (47 mg, 0.11 mmol) in N,N-dimethylformamide (0.36 mL) was added anhydrous potassium carbonate (15 mg, 0.11 mmol) and methyl tosylate (16 μL, 0.11 mmol), and the reaction was allowed to stir for 4 hours. Water was added to precipitate the product, and the solids were collected to yield R3.

Synthesis of methyl (S)-2-amino-3-(4-(1-methyl-2,4-dioxo-1,5,7,8-tetrahydro-2H-pyrano[4,3-d]pyrimidin-3(4H)-yl)phenyl)propanoate (R): To R3 (37 mg, 0.08 mmol) in ethyl acetate (0.7 mL) was added 4M hydrogen chloride in dioxane (0.2 mL, 0.8 mmol), and the reaction was allowed to stir for 16 hours. It was concentrated to yield R.

Intermediate S

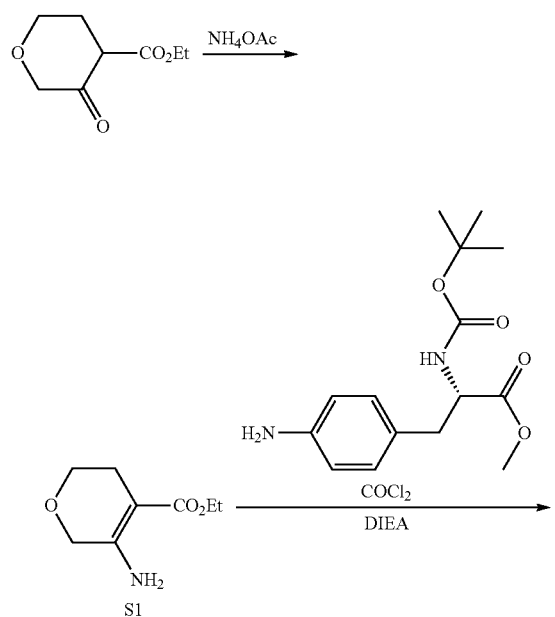

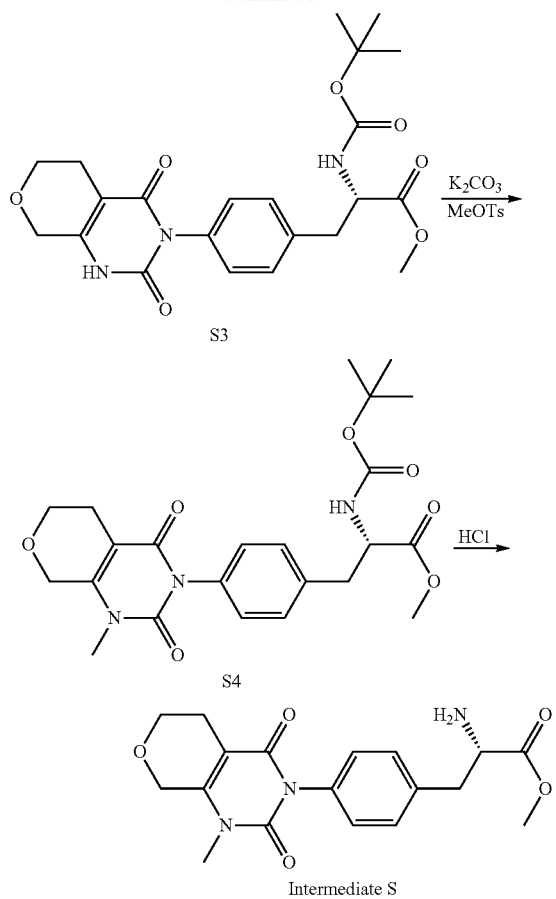

Synthesis of ethyl 5-amino-3,6-dihydro-2H-pyran-4-carboxylate (S1): To a solution of ethyl 3-oxotetrahydro-2H-pyran-4-carboxylate (2.0 g, 12 mmol) in methanol (71 mL) was added ammonium acetate (4.57 g, 59 mmol), and the reaction was stirred at room temperature for 3 hours. It was concentrated, dissolved in dichloromethane, and washed with water and saturated sodium chloride. It was dried over anhydrous sodium sulfate, filtered, and concentrated to yield S1.

Synthesis of methyl (S)-2-amino-3-(4-(1-methyl-2,4-dioxo-1,2,4,5,6,8-hexahydro-3H-pyrano[3,4-d]pyrimidin-3-yl)phenyl)propanoate (S): The title compound was prepared according to the method presented for the synthesis of intermediate R starting with S1.

Intermediate T

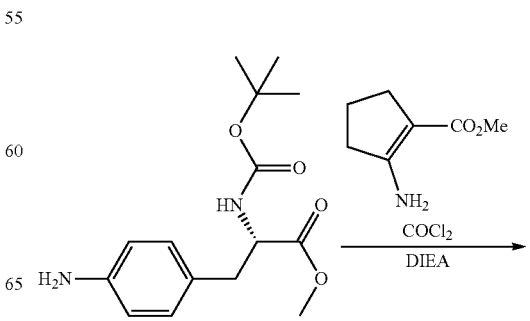

Intermediate U

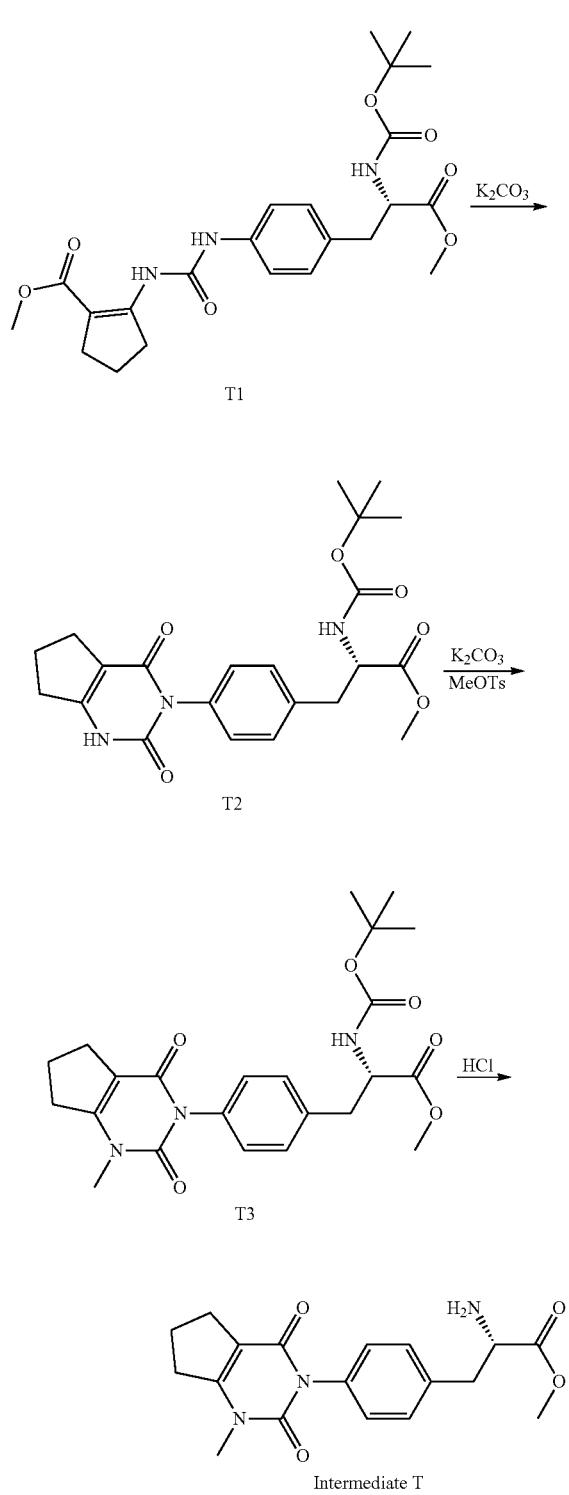

Synthesis of methyl (S)-2-amino-3-(4-(1-methyl-2,4-dioxo-1,2,4,5,6,7-hexahydro-3H-cyclopenta[d]pyrimidin-3-yl)phenyl)propanoate (T): The title compound was prepared according to the method presented for the synthesis of intermediate R starting with methyl 2-aminocyclopent-1-ene-1-carboxylate.

Synthesis of methyl (S)-2-amino-3-(4-(1-methyl-2,4-dioxo-1,2,5,7-tetrahydrofuro[3,4-d]pyrimidin-3(4H)-yl)phenyl)propanoate (U): The title compound was prepared according to the method presented for the synthesis of intermediate R starting with methyl 4-amino-2,5-dihydrofuran-3-carboxylate.

Intermediate V

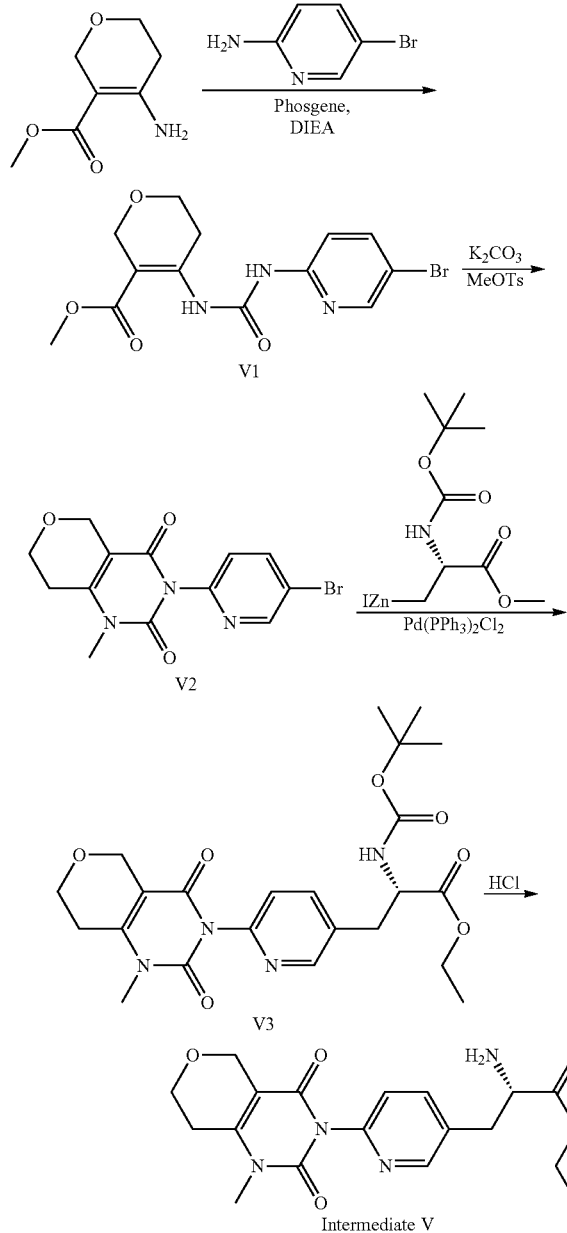

Synthesis of ethyl (S)-2-amino-3-(6-(1-methyl-2,4-dioxo-1,5,7,8-tetrahydro-2H-pyrano[4,3-d]pyrimidin-3(4H)-yl)pyridin-3-yl)propanoate (V): The title compound was prepared according to the method presented for the synthesis of intermediate R starting with methyl 4-amino-5,6-dihydro-2H-pyran-3-carboxylate.

Intermediate W

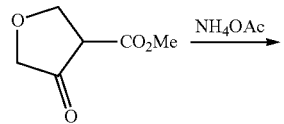

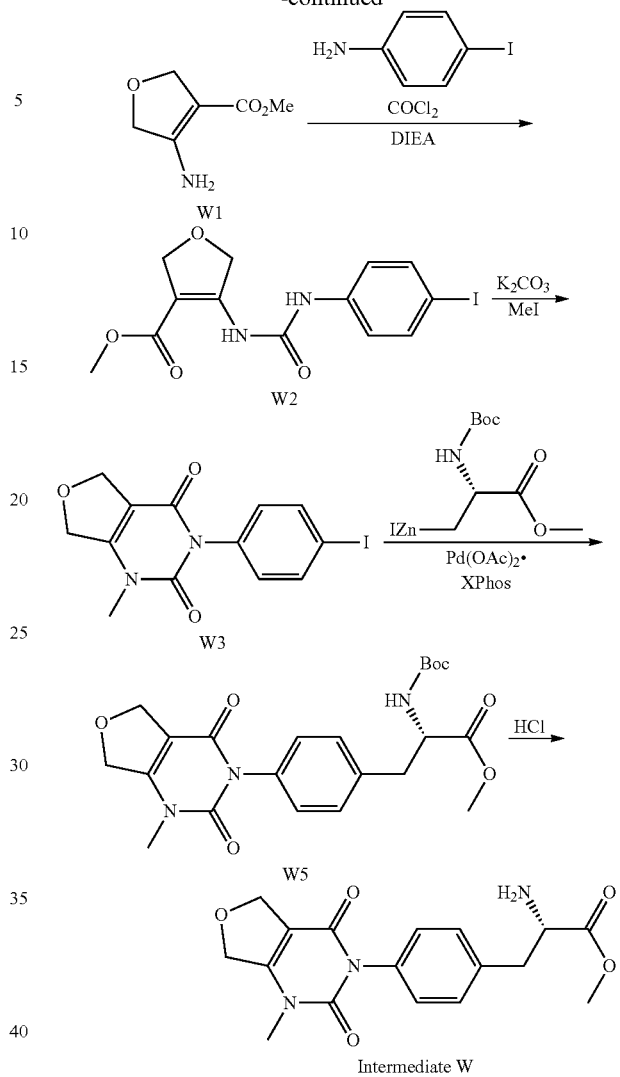

Synthesis of methyl 4-amino-2,5-dihydrofuran-3-carboxylate (W1): The title compound was prepared according to the method presented for the synthesis of intermediate S1 starting with methyl 4-oxotetrahydrofuran-3-carboxylate.

Synthesis of methyl 4-(3-(4-iodophenyl)ureido)-2,5-dihydrofuran-3-carboxylate (W2): The title compound was prepared according to the method presented for the synthesis of intermediate S2 starting with W1.

Synthesis of methyl (S)-2-amino-3-(4-(1-methyl-2,4-dioxo-1,2,5,7-tetrahydrofuro[3,4-d]pyrimidin-3(4H)-yl)phenyl)propanoate (W): The title compound was prepared according to the method presented for the synthesis of intermediate O starting with W2 in place of O1.

Example 1

Synthesis of methyl (S)-2-((tert-butoxycarbonyl)amino)-3-(4-(1,6-dimethyl-2-oxo-4-(trifluoromethyl)-1,2-dihydropyridin-3-yl)phenyl)propanoate (1A): A solution of (S)-(4-(2-((tert-butoxycarbonyl)amino)-3-methoxy-3-oxopropyl)phenyl)boronic acid (100 mg, 0.310 mmol) and 3-iodo-1,6-dimethyl-4-(trifluoromethyl)pyridin-2(1H)-one (124 mg, 0.390 mmol) in DME (1.6 mL) was purged with nitrogen gas for 5 min. To this mixture was added XPhos Pd G3 (26.0 mg, 0.031 mmol) and a 1 M aqueous solution of K₃PO4 (230 mg, 1.00 mmol), and the reaction was purged with nitrogen gas for an addition 5 min. The mixture was then heated at 77° C. for 7 min under stirring. Upon completion, the solvent was removed under reduced pressure and the mixture was dissolved in EA, washed with water, dried over Na₂SO₄, and concentrated under reduced pressure to afford the crude material. The crude product was purified using flash chromatography eluting with EA in hexanes (20% to 80%) to afford compound 1A.

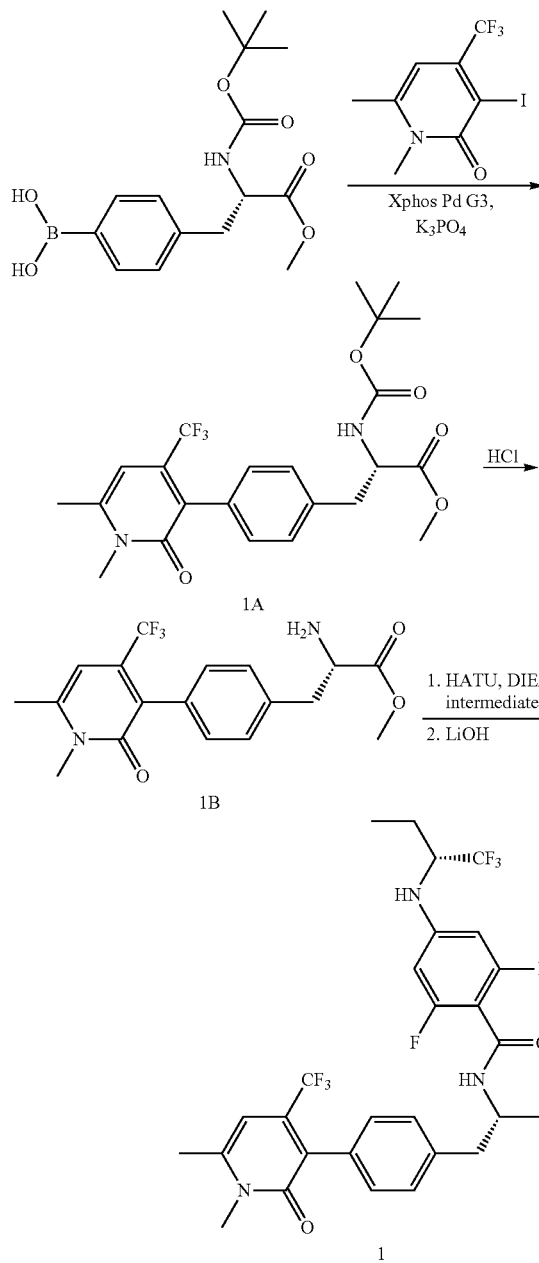

Synthesis of methyl (S)-2-amino-3-(4-(1,6-dimethyl-2-oxo-4-(trifluoromethyl)-1,2-dihydropyridin-3-yl)phenyl)propanoate (1B): To a solution of compound 1A (98.0 mg, 0.210 mmol) in EA (1.1 mL) was added a 4M solution of HCl in dioxane (76.2 mg, 2.10 mmol) and the mixture was stirred at rt for 2 h. Upon completion, the solvent was removed under reduced pressure and the crude product 1B was used in the next step without further purification.

Synthesis of (S)-2-(2,6-difluoro-4-(((R)-1,1,1-trifluorobutan-2-yl)amino)benzamido)-3-(4-(1,6-dimethyl-2-oxo-4-(trifluoromethyl)-1,2-dihydropyridin-3-yl)phenyl)propanoic acid (1): To a solution of compound 1B (85.0 mg, 0.210 mmol), intermediate A (65.0 mg, 0.231 mmol), and DIEA (163 mg, 1.26 mmol) in DMF (2.1 mL) was added HATU (96.0 mg, 0.252 mmol) and the mixture was stirred at rt for 2 h. Upon completion, the mixture was diluted with EA, washed with water, dried over Na₂SO₄, and concentrated under reduced pressure to afford the crude material. The crude product was purified using flash chromatography eluting with EA in hexanes (12% to 100%) to afford the ester. To a solution of the ester (91.0 mg, 0.144 mmol) in THF (4.80 mL) was added a 1 M aqueous solution of LiOH (10.0 mg, 0.432 mmol), and the mixture was stirred at rt for 40 min. Upon completion, the mixture was acidified with TFA, and the volatiles were removed under reduced pressure. The crude material was dissolved in DMSO and chromatographed on C-18 modified silica gel eluting with acetonitrile in water (0.4% TFA) to afford compound 1. MS (m/z) 620.1 [M+H]+. 1H NMR (400 MHz, DMSO-d6) δ 8.68 (d, J=7.7 Hz, 1H), 7.28 (d, J=8.1 Hz, 2H), 7.06 (d, J=8.2 Hz, 2H), 6.76 (d, J=10.4 Hz, 1H), 6.50 (s, 1H), 6.45 (d, J=11.4 Hz, 2H), 4.58-4.50 (m, 1H), 4.37-4.26 (m, 1H), 3.48 (s, 3H), 3.13 (dd, J=14.1, 5.8 Hz, 1H), 2.97 (dd, J=13.7, 10.1 Hz, 1H), 2.47 (s, 3H), 1.81-1.74 (m, 1H), 1.59-1.48 (m, 1H), 0.93 (t, J=7.5 Hz, 3H).

Example 2

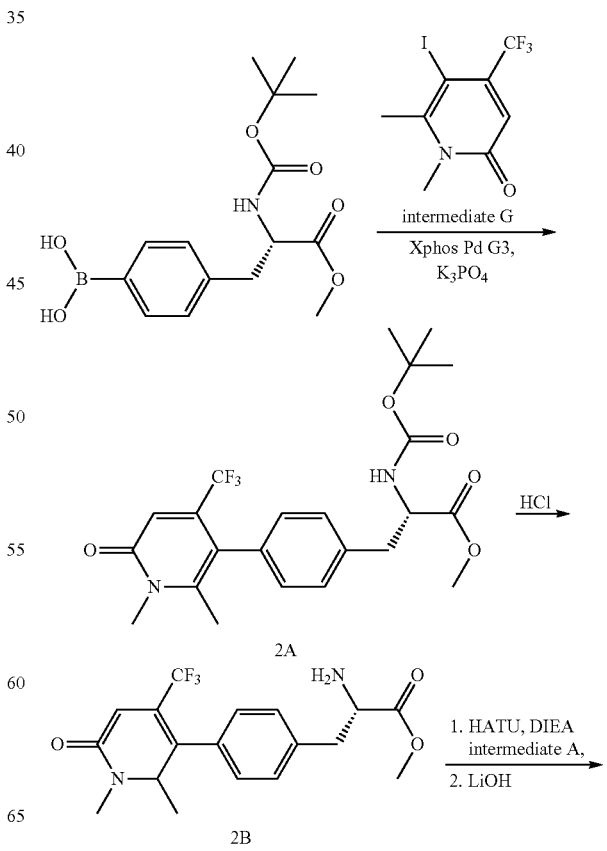

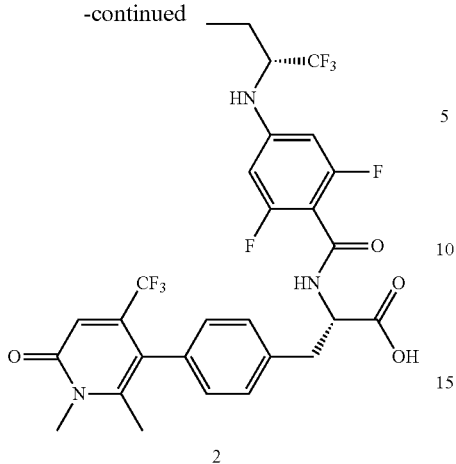

2

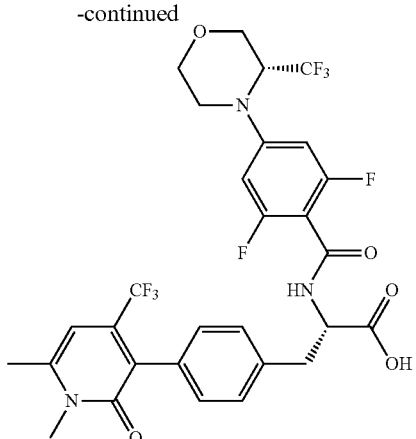

3

Synthesis of methyl (S)-2-((tert-butoxycarbonyl)amino)-3-(4-(1,2-dimethyl-6-oxo-4-(trifluoromethyl)-1,6-dihydropyridin-3-yl)phenyl)propanoate (2A): A solution of (S)-(4-(2-((tert-butoxycarbonyl)amino)-3-methoxy-3-oxopropyl)phenyl)boronic acid (200 mg, 0.619 mmol) and intermediate G (247 mg, 0.780 mmol) in DME (3.0 mL) was purged with nitrogen gas for 5 min. To this mixture was added XPhos Pd G3 (52.0 mg, 0.062 mmol) and a 1 M aqueous solution of K$_3$PO$_4$ (460 mg, 2.0 mmol), and the reaction was purged with nitrogen gas for an additional 5 min. The mixture was then heated at 90° C. for 10 min while stirring, after which the solvent was removed under reduced pressure. The mixture was dissolved in EA, washed with water, dried over Na$_2$SO$_4$, and concentrated under reduced pressure to afford the crude material. The crude product was purified using flash chromatography eluting with EA in hexanes (20% to 80%) to afford compound 2A.

Synthesis of methyl (S)-2-amino-3-(4-(1,2-dimethyl-6-oxo-4-(trifluoromethyl)-1,6-dihydropyridin-3-yl)phenyl)propanoate (2B): The title compound was prepared according to the method presented for the synthesis of 1B starting with 2A.

Synthesis of (S)-2-(2,6-difluoro-4-(((R)-1,1,1-trifluorobutan-2-yl)amino)benzamido)-3-(4-(1,2-dimethyl-6-oxo-4-(trifluoromethyl)-1,6-dihydropyridin-3-yl)phenyl)propanoic acid (2): The title compound was prepared according to the method presented for the synthesis of 1 starting with 2B and intermediate A. MS (m/z) 620.1 [M+H]+. 1H NMR (400 MHz, DMSO-d6) δ 8.65 (d, J=8.1 Hz, 1H), 7.35-7.30 (m, 2H), 7.09 (t, J=7.4 Hz, 2H), 6.74 (d, J=10.9 Hz, 1H), 6.73 (s, 1H), 6.43 (d, J=11.3 Hz, 2H), 4.66-4.57 (m, 1H), 4.37-4.24 (m, 1H), 3.54 (s, 3H), 3.18 (dd, J=14.1, 4.4 Hz, 1H), 2.94 (dd, J=14.3, 10.2 Hz, 1H), 2.03 (s, 3H), 1.80 (s, 1H), 1.58-1.47 (m, 1H), 0.93 (t, J=7.2 Hz, 3H).

Example 3

Synthesis of (S)-2-(2,6-difluoro-4-((R)-3-(trifluoromethyl)morpholino)benzamido)-3-(4-(1,6-dimethyl-2-oxo-4-(trifluoromethyl)-1,2-dihydropyridin-3-yl)phenyl)propanoic acid (3): The title compound was prepared according to the method presented for the synthesis of 1 using intermediate 1B and intermediate B. MS (m/z) 648.3 [M+H]+. 1H NMR (400 MHz, DMSO-d6) δ 8.84 (d, J=7.9 Hz, 1H), 7.29 (d, J=8.1 Hz, 2H), 7.06 (d, J=8.0 Hz, 2H), 6.76 (d, J=11.6 Hz, 2H), 6.49 (s, 2H), 4.91 (m, 1H), 4.57 (m, 1H), 4.16 (d, J=12.7 Hz, 1H), 3.96 (dd, J=11.5, 3.8 Hz, 1H), 3.78-3.70 (m, 1H), 3.56 (td, J=11.6, 2.9 Hz, 1H), 3.48 (s, 3H), 3.43 (d, J=12.9 Hz, 1H), 3.24 (t, J=12.2 Hz, 1H), 3.15 (dd, J=14.2, 4.7 Hz, 1H), 2.99 (dd, J=14.1, 9.8 Hz, 1H), 2.47 (s, 3H).

Example 4

Synthesis of methyl (S)-2-((tert-butoxycarbonyl)amino)-3-(4-(1,4-dimethyl-2-oxo-5-(trifluoromethyl)-1,2-dihydropyridin-3-yl)phenyl)propanoate (4A): A solution of (S)-(4-(2-((tert-butoxycarbonyl)amino)-3-methoxy-3-oxopropyl)phenyl)boronic acid (100 mg, 0.310 mmol) and intermediate H (124 mg, 0.390 mmol) in DME (1.6 mL) was purged with nitrogen gas for 5 min. To this mixture was added XPhos Pd G3 (26.0 mg, 0.031 mmol) and a 1 M aqueous solution of K$_3$PO$_4$ (230 mg, 1.00 mmol), and the reaction was purged with nitrogen gas for an additional 5 min. The mixture was then heated at 77° C. for 7 min under stirring. Upon completion, the solvent was removed under reduced pressure and the mixture was dissolved in EA, washed with water, dried over Na$_2$SO$_4$, and concentrated under reduced pressure to afford the crude material. The crude product was purified using flash chromatography eluting with EA in hexanes (20% to 100%) to afford compound 4A.

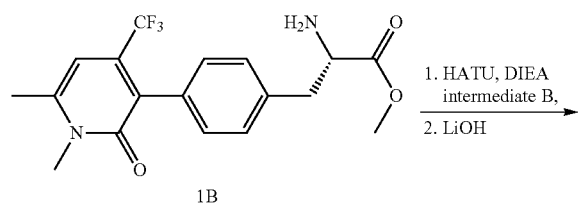

1B

1. HATU, DIEA intermediate B,
2. LiOH

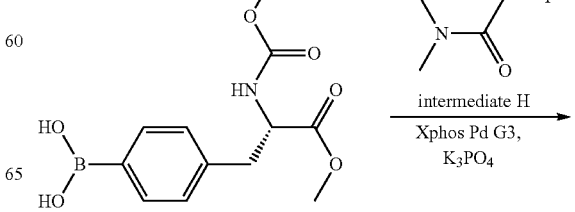

intermediate H
Xphos Pd G3,
K$_3$PO$_4$

Example 5

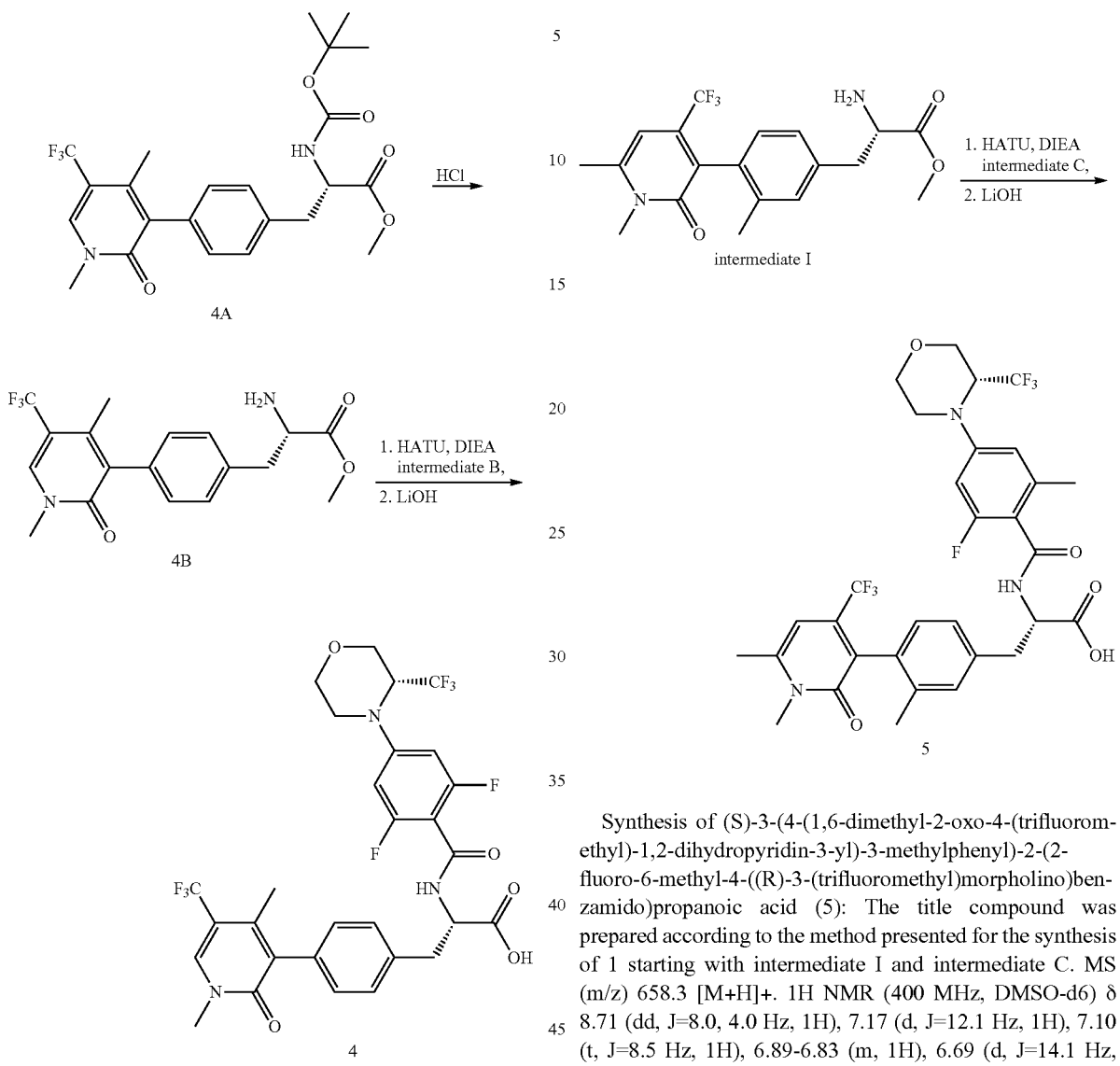

Synthesis of methyl (S)-2-amino-3-(4-(1,4-dimethyl-2-oxo-5-(trifluoromethyl)-1,2-dihydropyridin-3-yl)phenyl)propanoate (4B): The title compound was prepared according to the method presented for the synthesis of 1B starting with compound 4A.

Synthesis of (S)-2-(2,6-difluoro-4-((R)-3-(trifluoromethyl)morpholino)benzamido)-3-(4-(1,4-dimethyl-2-oxo-5-(trifluoromethyl)-1,2-dihydropyridin-3-yl)phenyl)propanoic acid (4): The title compound was prepared according to the method presented for the synthesis of 1 starting with compound 4B and intermediate B. MS (m/z) 648.3 [M+H]+. 1H NMR (400 MHz, DMSO-d6) δ 8.82 (d, J=8.0 Hz, 1H), 8.30 (s, 1H), 7.32 (d, J=8.1 Hz, 2H), 7.09 (d, J=8.2 Hz, 2H), 6.76 (d, J=11.6 Hz, 2H), 4.90 (td, J=8.5, 3.2 Hz, 1H), 4.62-4.55 (m, 1H), 4.16 (d, J=12.7 Hz, 1H), 3.98-3.91 (m, 1H), 3.76-3.71 (m, 1H), 3.59-3.52 (m, 1H), 3.49 (s, 3H), 3.42 (d, J=12.3 Hz, 1H), 3.29-3.23 (m, 1H), 3.17 (dd, J=14.0, 4.6 Hz, 1H), 2.98 (dd, J=13.9, 10.1 Hz, 1H), 2.00 (s, 3H).

Synthesis of (S)-3-(4-(1,6-dimethyl-2-oxo-4-(trifluoromethyl)-1,2-dihydropyridin-3-yl)-3-methylphenyl)-2-(2-fluoro-6-methyl-4-((R)-3-(trifluoromethyl)morpholino)benzamido)propanoic acid (5): The title compound was prepared according to the method presented for the synthesis of 1 starting with intermediate I and intermediate C. MS (m/z) 658.3 [M+H]+. 1H NMR (400 MHz, DMSO-d6) δ 8.71 (dd, J=8.0, 4.0 Hz, 1H), 7.17 (d, J=12.1 Hz, 1H), 7.10 (t, J=8.5 Hz, 1H), 6.89-6.83 (m, 1H), 6.69 (d, J=14.1 Hz, 1H), 6.65 (s, 1H), 6.51 (s, 1H), 4.90-4.79 (m, 1H), 4.68-4.55 (m, 1H), 4.14 (d, J=12.6 Hz, 1H), 3.94 (dd, J=11.2, 3.2 Hz, 1H), 3.73 (d, J=11.9 Hz, 1H), 3.59-3.51 (m, 1H), 3.50 (s, 3H), 3.35 (d, J=11.5 Hz, 1H), 3.27 (d, J=12.8 Hz, 1H), 3.13 (dd, J=14.2, 3.9 Hz, 1H), 2.97-2.89 (m, 1H), 2.49 (s, 3H), 2.04 (d, J=1.6 Hz, 3H), 1.97 (d, J=4.0 Hz, 3H).

Example 6

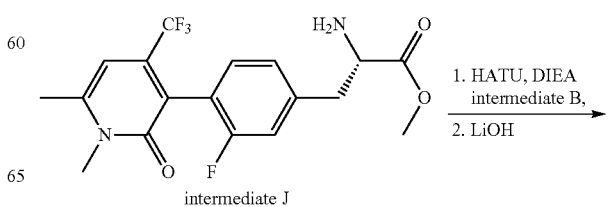

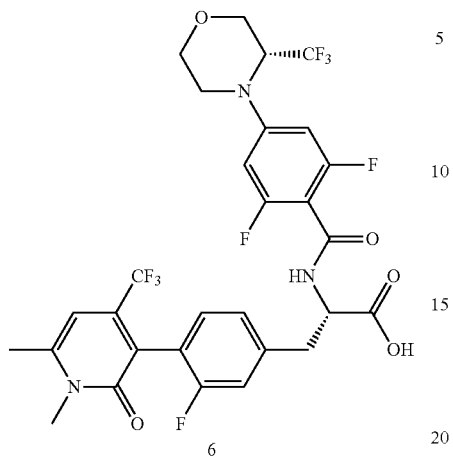

Synthesis of (S)-2-(2,6-difluoro-4-((R)-3-(trifluoromethyl)morpholino)benzamido)-3-(4-(1,6-dimethyl-2-oxo-4-(trifluoromethyl)-1,2-dihydropyridin-3-yl)-3-fluorophenyl)propanoic acid (6): The title compound was prepared according to the method presented for the synthesis of 1 starting with intermediate J and intermediate B. MS (m/z) 666.1 [M+H]+. 1H NMR (400 MHz, DMSO-d6) δ 8.87 (dd, J=7.9, 2.4 Hz, 1H), 7.19-7.03 (m, 2H), 6.77 (d, J=8.1 Hz, 2H), 6.54 (s, 1H), 4.97-4.86 (m, 1H), 4.63-4.54 (m, 1H), 4.16 (d, J=12.7 Hz, 1H), 3.95 (dd, J=11.3, 3.5 Hz, 1H), 3.74 (d, J=14.9 Hz, 1H), 3.56 (td, J=11.9, 2.8 Hz, 1H), 3.50 (s, 3H), 3.43 (d, J=13.9 Hz, 1H), 3.22 (ddd, J=31.6, 12.8, 4.0 Hz, 2H), 3.00 (t, J=13.3 Hz, 1H).

Example 7

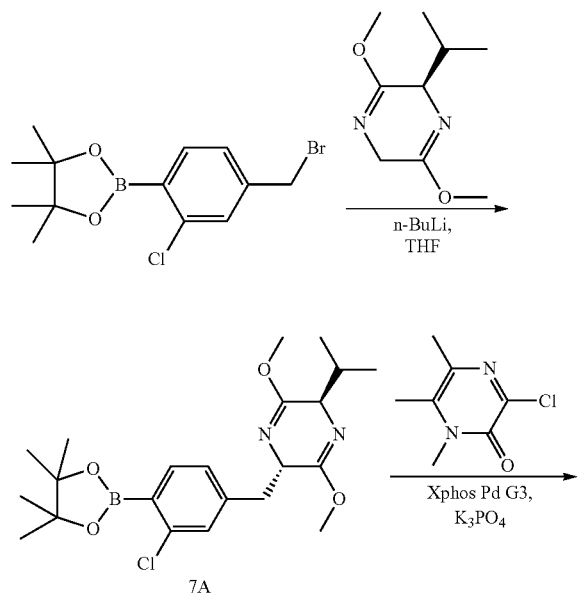

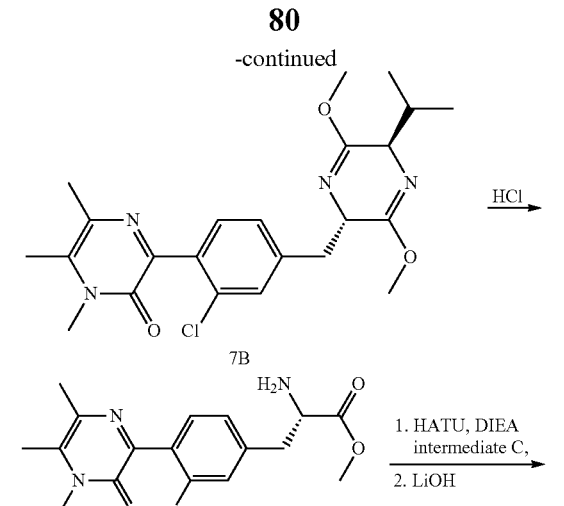

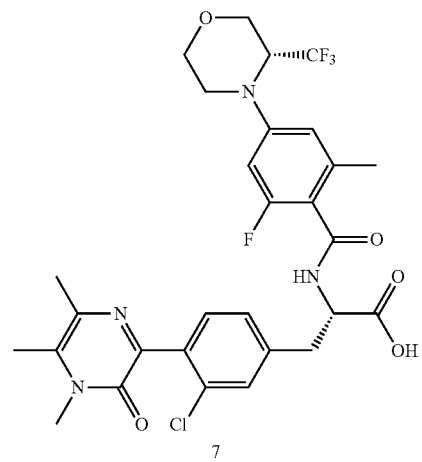

Synthesis of (2S,5R)-2-(3-chloro-4-(4,4,5,5-tetramethyl-1,3,2-dioxaborolan-2-yl)benzyl)-5-isopropyl-3,6-dimethoxy-2,5-dihydropyrazine (7A): To a solution of (R)-2-isopropyl-3,6-dimethoxy-2,5-dihydropyrazine (361 mg, 1.96 mmol) in THF (9.80 mL) at −78° C. was added a solution of n-BuLi in hexanes (2.11 g, 2.11 mmol). The mixture was stirred at −78° C. for 20 min, followed by the drop-wise addition of a solution of 2-(4-(bromomethyl)-2-chlorophenyl)-4,4,5,5-tetramethyl-1,3,2-dioxaborolane (500 mg, 1.51 mmol) in THF (7.50 mL). The reaction was stirred for 40 min at −78° C., and quenched with water. The cold bath was removed and the reaction was allowed to warm to rt, and extracted with EA, washed with brine, dried over Na2SO4 and concentrated under reduced pressure to afford compound 7A which was used without further purification.

Synthesis of 3-(2-chloro-4-(((2S,5R)-5-isopropyl-3,6-dimethoxy-2,5-dihydropyrazin-2-yl)methyl)phenyl)-1,5,6-trimethylpyrazin-2(1H)-one (7B): To a solution of compound 7A (200 mg, 0.276 mmol), 3-chloro-1,5,6-trimethylpyrazin-2(1H)-one (47.6 mg, 0.276 mmol) in DME (2.3 mL) was added a 1 M aqueous solution of K3PO4 (342 mg, 0.1.61 mmol) and the mixture was purged with nitrogen gas for 6 min. XPhos Pd G3 (11.7 mg, 0.014 mmol) was then added and the mixture was purged with nitrogen gas for an additional 4 min and heated at 90° C. for 30 min. The solvent was then removed under reduced pressure, and the mixture was dissolved in EA, washed with water, dried over Na2SO4 and concentrated under reduced pressure to afford the crude material. The crude product was purified using flash chromatography eluting with EA in hexanes (20% to 100%) and then MeOH in EA (0% to 25%) to afford compound 7B.

Synthesis of methyl (S)-2-amino-3-(3-chloro-4-(4,5,6-trimethyl-3-oxo-3,4-dihydropyrazin-2-yl)phenyl)propanoate (7C): The title compound was prepared according to the method presented for the synthesis of intermediate J starting with compound 7B.

Synthesis of (S)-3-(3-chloro-4-(4,5,6-trimethyl-3-oxo-3,4-dihydropyrazin-2-yl)phenyl)-2-(2-fluoro-6-methyl-4-((R)-3-(trifluoromethyl)morpholino)benzamido)propanoic acid (7): The title compound was prepared according to the method presented for the synthesis of 1 using 7C and intermediate C. MS (m/z) 625.2 [M+H]+. 1H NMR (400 MHz, DMSO-d6) δ 8.73 (d, J=7.8 Hz, 1H), 7.42 (s, 1H), 7.29 (s, 2H), 6.73-6.63 (m, 2H), 4.90-4.79 (m, 1H), 4.64-4.56 (m, 1H), 4.14 (d, J=7.9 Hz, 1H), 3.95 (d, J=11.7 Hz, 1H), 3.73 (d, J=13.9 Hz, 1H), 3.56 (d, J=12.2 Hz, 1H), 3.52 (s, 3H), 3.36 (d, J=11.3 Hz, 1H), 3.27 (d, J=11.9 Hz, 1H), 3.18 (d, J=11.2 Hz, 1H), 3.03-2.93 (m, 1H), 2.37 (s, 3H), 2.30 (s, 3H), 2.09 (s, 3H).

Example 8

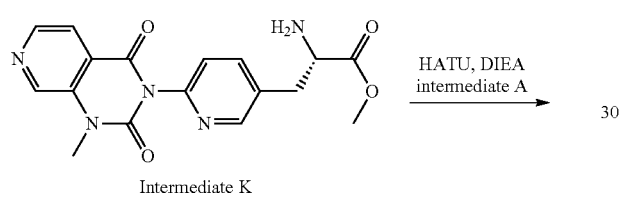

Intermediate K

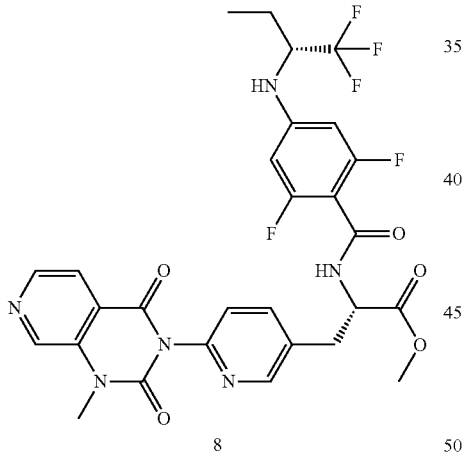

8

Synthesis of methyl (S)-2-(2,6-difluoro-4-(((R)-1,1,1-trifluorobutan-2-yl)amino)benzamido)-3-(6-(1-methyl-2,4-dioxo-1,4-dihydropyrido[3,4-d]pyrimidin-3(2H)-yl)pyridin-3-yl)propanoate (8): The title compound was prepared according to the method presented for the synthesis of 1 using intermediate K and intermediate A. MS (m/z) 621.1 [M+H]+. 1H NMR (400 MHz, DMSO-d6) δ 8.99 (s, 1H), 8.93 (d, J=7.6 Hz, 1H), 8.56 (d, J=5.0 Hz, 1H), 8.47 (d, J=2.3 Hz, 1H), 7.96-7.85 (m, 2H), 7.40 (d, J=8.1 Hz, 1H), 6.81 (d, J=9.4 Hz, 1H), 6.46 (d, J=11.6 Hz, 2H), 4.72-4.56 (m, 1H), 4.31 (d, J=10.0 Hz, 1H), 3.20 (dd, J=14.2, 5.1 Hz, 1H), 3.16-2.99 (m, 2H), 2.67 (d, J=0.7 Hz, 2H), 1.76 (ddd, J=13.7, 7.3, 3.3 Hz, 1H), 1.52 (ddd, J=13.8, 10.5, 7.2 Hz, 1H), 1.32-1.21 (m, 6H), 1.09 (d, J=0.7 Hz, 2H), 0.91 (t, J=7.3 Hz, 3H).

Example 9

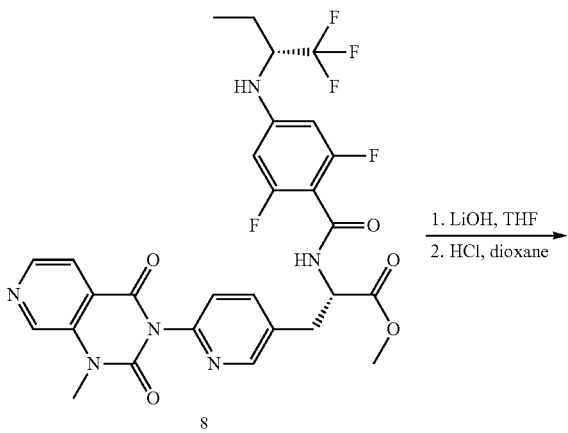

8

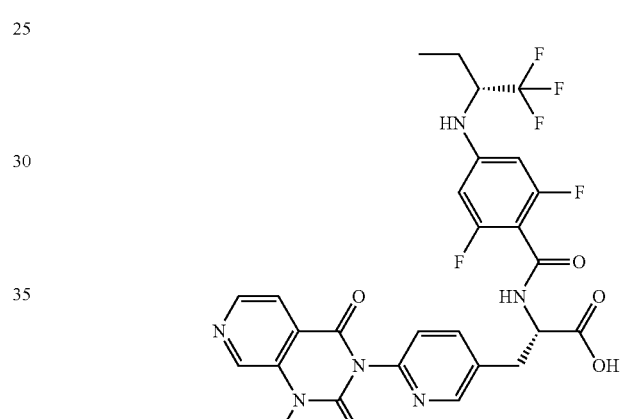

9

Synthesis of (S)-2-(2,6-difluoro-4-(((R)-1,1,1-trifluorobutan-2-yl)amino)benzamido)-3-(6-(1-methyl-2,4-dioxo-1,4-dihydropyrido[3,4-d]pyrimidin-3(2H)-yl)pyridin-3-yl)propanoic acid (9): To 8 (12.5 mg, 0.02 mmol) dissolved in THF was added 1.0 M LiOH (0.04 mL, 0.04 mmol) and the mixture was allowed to stir for 1 hr at RT. 4.0 M HCl in dioxane (0.1 mL, 0.4 mmol) was then added and the mixture was allowed to stir ON. The reaction mixture was concentrated, filtered, and purified via reverse phase HPLC (MeCN/H2O) to afford 9.

Example 10

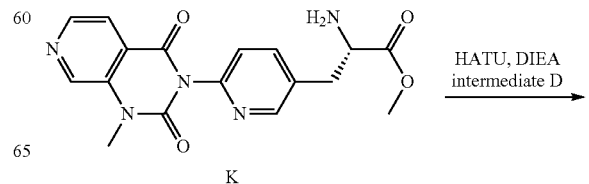

K

-continued

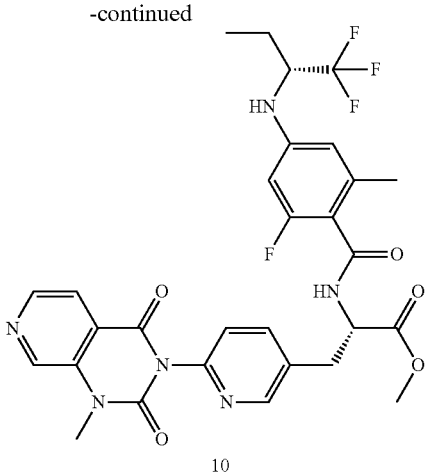

10

Synthesis of methyl (S)-2-(2-fluoro-6-methyl-4-(((R)-1, 1,1-trifluorobutan-2-yl)amino) benzamido)-3-(6-(1-methyl-2,4-dioxo-1,4-dihydropyrido[3,4-d]pyrimidin-3(2H)-yl) pyridin-3-yl)propanoate (10): The title compound was prepared according to the method presented for the synthesis of 1 using intermediate K and intermediate D. MS (m/z) 617.3 [M+H]+. 1H NMR (400 MHz, DMSO-d6) δ 9.00 (s, 1H), 8.81 (d, J=7.8 Hz, 1H), 8.57 (dd, J=5.1, 1.8 Hz, 1H), 8.49 (s, 1H), 8.16 (s, 2H), 7.92 (dd, J=12.9, 6.5 Hz, 2H), 7.42 (d, J=8.1 Hz, 1H), 6.40 (d, J=7.4 Hz, 2H), 6.32 (d, J=9.3 Hz, 1H), 4.72 (d, J=6.2 Hz, 1H), 4.20 (s, 1H), 3.68 (d, J=2.0 Hz, 3H), 3.32 (d, J=1.9 Hz, 4H), 3.24 (dd, J=14.9, 4.6 Hz, 1H), 3.19-3.01 (m, 4H), 2.00 (s, 3H), 1.75 (d, J=10.1 Hz, 1H), 1.55 (d, J=15.8 Hz, 1H), 0.93 (t, J=7.3 Hz, 3H).

Example 11

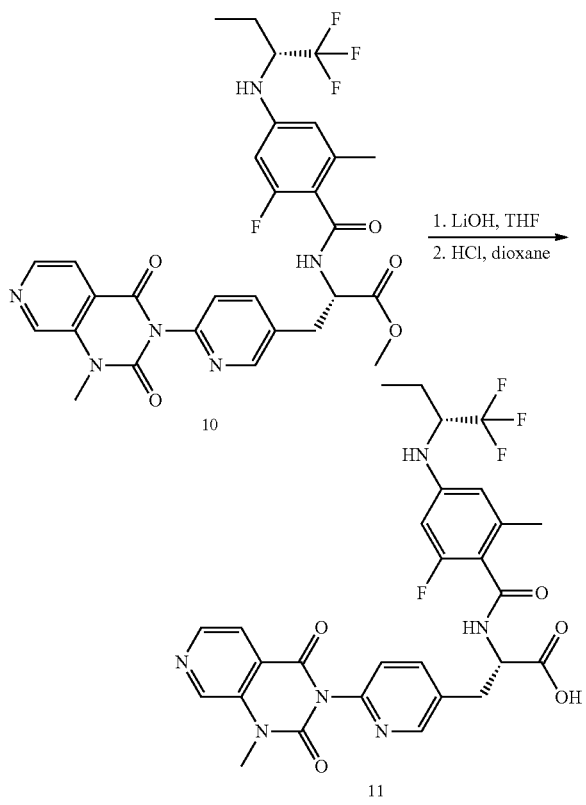

Synthesis of (S)-2-(2-fluoro-6-methyl-4-(((R)-1,1,1-trifluorobutan-2-yl)amino) benzamido)-3-(6-(1-methyl-2,4-dioxo-1,4-dihydropyrido[3,4-d]pyrimidin-3(2H)-yl)pyridin-3-yl)propanoic acid (11): The title compound was prepared according to the method presented for the synthesis of Example 9 starting with 10. MS (m/z) 603.2 [M+H]+. 1H NMR (400 MHz, DMSO-d6) δ 9.00 (d, J=1.9 Hz, 1H), 8.67 (d, J=8.1 Hz, 1H), 8.62-8.52 (m, 1H), 8.50 (s, 1H), 8.02-7.80 (m, 2H), 7.41 (dd, J=8.2, 2.0 Hz, 1H), 6.53-6.34 (m, 3H), 6.30 (d, J=9.2 Hz, 1H), 5.76 (d, J=1.8 Hz, 1H), 4.65 (d, J=11.1 Hz, 1H), 4.03 (d, J=7.0 Hz, 1H), 3.61 (s, 3H), 3.26 (d, J=13.9 Hz, 1H), 3.03 (t, J=12.6 Hz, 1H), 2.00 (d, J=2.3 Hz, 4H), 1.89-1.63 (m, 2H), 1.52 (dd, J=14.8, 8.1 Hz, 1H), 0.93 (t, J=7.4 Hz, 3H).

Example 12

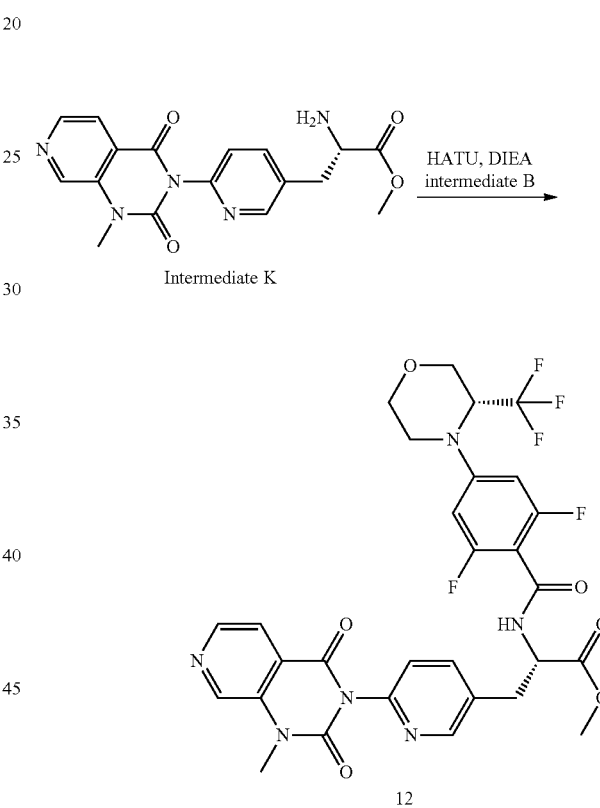

Synthesis of methyl (S)-2-(2,6-difluoro-4-((R)-3-(trifluoromethyl)morpholino) benzamido)-3-(6-(1-methyl-2,4-dioxo-1,4-dihydropyrido[3,4-d]pyrimidin-3(2H)-yl)pyridin-3-yl)propanoate (12): The title compound was prepared according to the method presented for the synthesis of 1 using intermediate K and intermediate B. MS (m/z) 649.5 [M+H]+. 1H NMR (400 MHz, DMSO-d6) δ 9.09 (d, J=7.6 Hz, 1H), 9.00 (s, 1H), 8.57 (dd, J=5.0, 1.5 Hz, 1H), 8.50 (d, J=2.0 Hz, 1H), 8.01-7.80 (m, 2H), 7.42 (d, J=8.0 Hz, 1H), 6.79 (d, J=11.8 Hz, 2H), 5.09-4.81 (m, 1H), 4.70 (td, J=9.0, 5.7 Hz, 1H), 4.17 (d, J=12.7 Hz, 1H), 4.07-3.88 (m, 1H), 3.75 (d, J=12.9 Hz, 1H), 3.67 (d, J=1.6 Hz, 3H), 3.61 (d, J=1.6 Hz, 3H), 3.58-3.51 (m, 1H), 3.44 (d, J=12.7 Hz, 1H), 3.29-3.19 (m, 2H), 3.12 (dd, J=14.2, 9.9 Hz, 1H).

Example 13

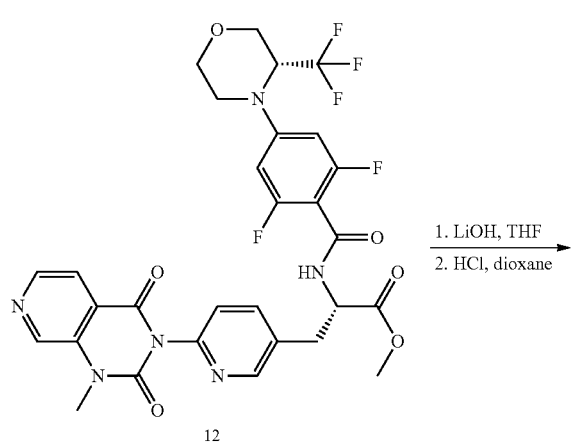

Synthesis of (S)-2-(2,6-difluoro-4-((R)-3-(trifluoromethyl)morpholino)benzamido)-3-(6-(1-methyl-2,4-dioxo-1,4-dihydropyrido[3,4-d]pyrimidin-3(2H)-yl)pyridin-3-yl)propanoic acid (13): The title compound was prepared according to the method presented for the synthesis of Example 9 starting with 12. MS (m/z) 635.2 [M+H]+. 1H NMR (400 MHz, DMSO-d6) δ 9.00 (s, 1H), 8.95 (d, J=7.9 Hz, 1H), 8.57 (d, J=5.0 Hz, 1H), 8.50 (d, J=2.3 Hz, 1H), 7.96-7.85 (m, 2H), 7.41 (d, J=8.1 Hz, 1H), 6.78 (d, J=11.6 Hz, 2H), 4.92 (s, 1H), 4.70-4.55 (m, 1H), 4.16 (d, J=12.7 Hz, 1H), 3.96 (dd, J=11.3, 3.9 Hz, 1H), 3.74 (d, J=12.6 Hz, 1H), 3.61 (s, 3H), 3.55 (d, J=10.6 Hz, 1H), 3.44 (d, J=12.5 Hz, 1H), 3.25 (dd, J=14.3, 4.6 Hz, 2H), 3.08 (dd, J=14.3, 10.0 Hz, 1H).

Example 14

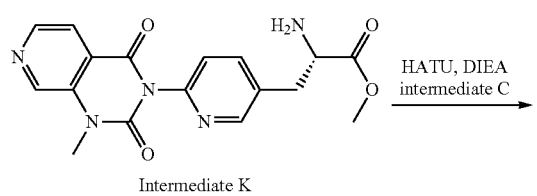

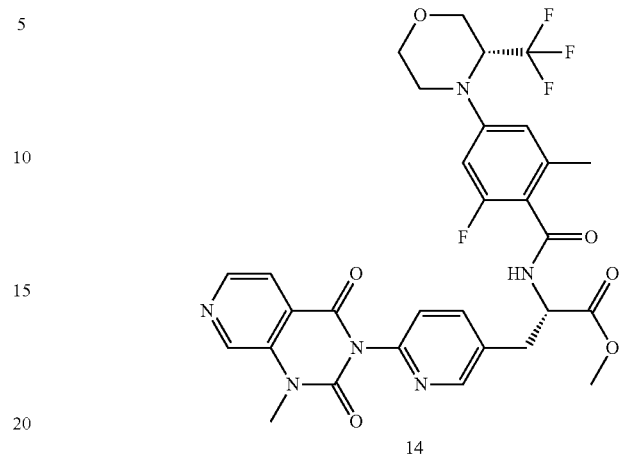

Synthesis of methyl (S)-2-(2-fluoro-6-methyl-4-((R)-3-(trifluoromethyl)morpholino) benzamido)-3-(6-(1-methyl-2,4-dioxo-1,4-dihydropyrido[3,4-d]pyrimidin-3(2H)-yl)pyridin-3-yl)propanoate (14): The title compound was prepared according to the method presented for the synthesis of 1 using intermediate K and intermediate C. MS (m/z) 644.8 [M+H]+. 1H NMR (400 MHz, DMSO-d6) δ 9.00 (s, 1H), 8.93 (d, J=7.9 Hz, 1H), 8.57 (dd, J=5.0, 1.6 Hz, 1H), 8.50 (s, 1H), 7.93 (dd, J=16.9, 6.6 Hz, 2H), 7.42 (d, J=8.1 Hz, 1H), 6.87-6.48 (m, 2H), 4.93-4.69 (m, 2H), 4.15 (d, J=12.7 Hz, 2H), 3.97 (s, 12H), 3.77-3.71 (m, 1H), 3.69 (d, J=1.7 Hz, 3H), 3.61 (d, J=1.7 Hz, 3H), 3.59-3.48 (m, 1H), 3.36 (d, J=12.4 Hz, 1H), 3.26 (dd, J=14.1, 4.9 Hz, 2H), 3.14-3.01 (m, 1H), 2.06 (s, 3H).

Example 15

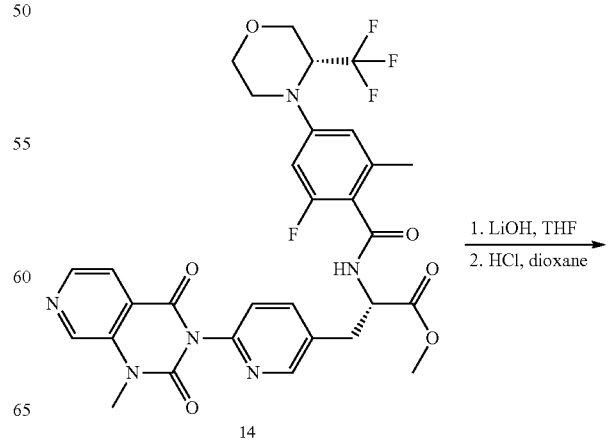

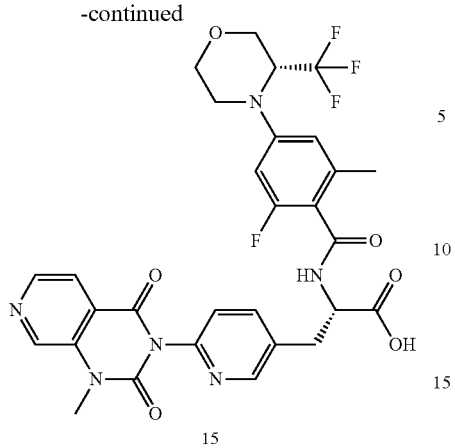

15

Synthesis of (S)-2-(2-fluoro-6-methyl-4-((R)-3-(trifluoromethyl)morpholino)benzamido)-3-(6-(1-methyl-2,4-dioxo-1,4-dihydropyrido[3,4-d]pyrimidin-3(2H)-yl)pyridin-3-yl)propanoic acid (15): The title compound was prepared according to the method presented for the synthesis of Example 9 starting with 14. MS (m/z) 631.2 [M+H]+. 1H NMR (400 MHz, DMSO-d6) δ 9.00 (s, 1H), 8.79 (d, J=8.1 Hz, 1H), 8.57 (d, J=5.0 Hz, 1H), 8.50 (s, 1H), 7.95 (d, J=8.3 Hz, 1H), 7.90 (d, J=5.1 Hz, 1H), 7.42 (d, J=8.0 Hz, 1H), 6.75-6.61 (m, 2H), 4.85 (d, J=9.6 Hz, 1H), 4.69 (d, J=8.4 Hz, 1H), 4.15 (d, J=12.6 Hz, 1H), 4.07-3.90 (m, 1H), 3.73 (d, J=12.6 Hz, 1H), 3.61 (s, 3H), 3.59-3.49 (m, 1H), 3.43-3.19 (m, 3H), 3.13-2.95 (m, 1H), 2.04 (s, 3H).

Example 16

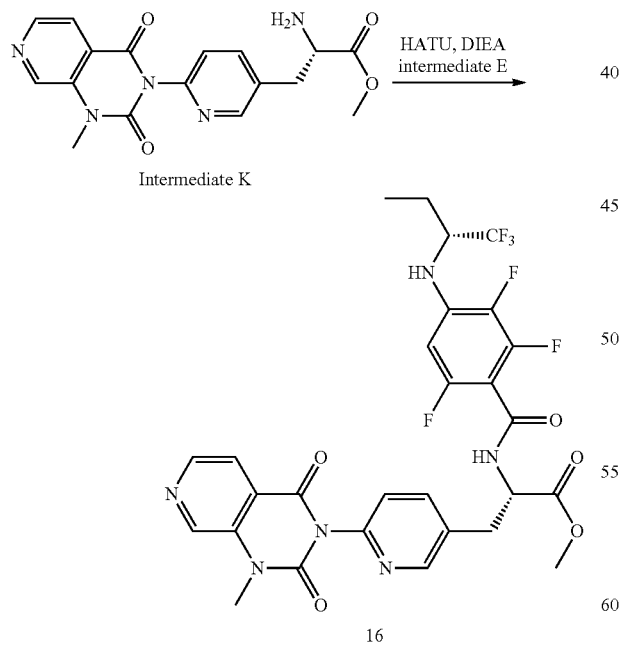

Synthesis of methyl (S)-3-(6-(1-methyl-2,4-dioxo-1,4-dihydropyrido[3,4-d]pyrimidin-3(2H)-yl)pyridin-3-yl)-2-(2,3,6-trifluoro-4-(((R)-1,1,1-trifluorobutan-2-yl)amino)benzamido) propanoate (16): The title compound was prepared according to the method presented for the synthesis of 1 using intermediate K and intermediate E. MS (m/z) 639.2 [M+H]+. 1H NMR (400 MHz, DMSO-d6) δ 9.10 (d, J=7.8 Hz, 1H), 9.00 (s, 1H), 8.60-8.54 (m, 1H), 8.49 (s, 1H), 7.92 (d, J=8.3 Hz, 2H), 7.48-7.35 (m, 1H), 6.99-6.78 (m, 1H), 6.73 (d, J=9.3 Hz, 1H), 4.77-4.66 (m, 1H), 4.44-4.34 (m, 1H), 3.67 (s, 3H), 3.61 (s, 3H), 3.29-3.19 (m, 1H), 3.16-3.04 (m, 1H), 1.77 (q, J=7.3 Hz, 2H), 0.93 (t, J=6.8 Hz, 3H).

Example 17

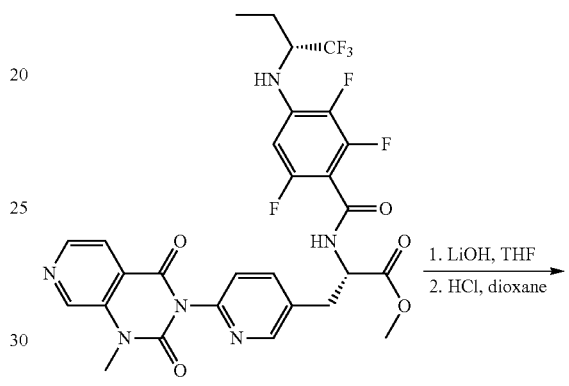

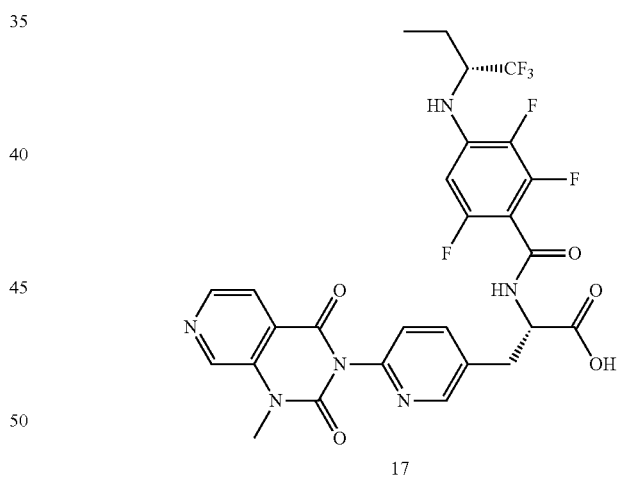

Synthesis of (S)-3-(6-(1-methyl-2,4-dioxo-1,4-dihydropyrido[3,4-d]pyrimidin-3(2H)-yl)pyridin-3-yl)-2-(2,3,6-trifluoro-4-(((R)-1,1,1-trifluorobutan-2-yl)amino)benzamido) propanoic acid (17): The title compound was prepared according to the method presented for the synthesis of Example 9 starting with 16. MS (m/z) 625.2 [M+H]+. 1H NMR (400 MHz, DMSO-d6) δ 9.02-8.91 (m, 2H), 8.57 (d, J=5.4 Hz, 1H), 8.49 (s, 1H), 7.98-7.87 (m, 2H), 7.44-7.36 (m, 1H), 6.94-6.80 (m, 1H), 6.71 (d, J=9.2 Hz, 1H), 4.64 (s, 1H), 3.61 (s, 3H), 3.26 (d, J=14.1 Hz, 1H), 3.15-2.95 (m, 1H), 1.77 (d, J=8.4 Hz, 2H), 0.93 (t, J=7.1 Hz, 3H).

Example 18

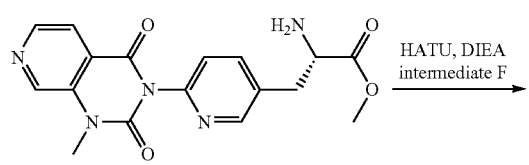

Intermediate K

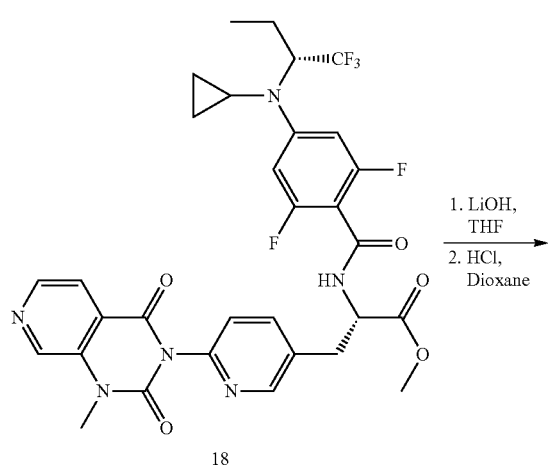

18

Synthesis of methyl (S)-2-(4-(cyclopropyl((R)-1,1,1-trifluorobutan-2-yl)amino)-2,6-difluorobenzamido)-3-(6-(1-methyl-2,4-dioxo-1,4-dihydropyrido[3,4-d]pyrimidin-3(2H)-yl)pyridin-3-yl)propanoate (18): The title compound was prepared according to the method presented for the synthesis of 1 using intermediate K and intermediate F. MS (m/z) 661.3 [M+H]+. 1H NMR (400 MHz, DMSO-d6) δ 9.05 (d, J=7.6 Hz, 1H), 9.00 (s, 1H), 8.57 (d, J=5.0 Hz, 1H), 8.52-8.45 (m, 1H), 7.96-7.87 (m, 2H), 7.42 (dd, J=8.1, 0.7 Hz, 1H), 6.68 (d, J=12.1 Hz, 2H), 5.68 (ddd, J=22.3, 10.1, 4.9 Hz, 1H), 5.25-5.15 (m, 2H), 4.81 (s, 1H), 4.69 (ddd, J=10.1, 7.6, 5.1 Hz, 1H), 4.01 (s, 2H), 3.67 (s, 3H), 3.61 (s, 3H), 3.23 (dd, J=14.2, 5.1 Hz, 1H), 3.09 (dd, J=14.2, 10.0 Hz, 1H), 1.92 (ddd, J=14.3, 10.4, 7.1 Hz, 1H), 1.78 (dtd, J=13.8, 7.0, 3.8 Hz, 1H), 0.87 (t, J=7.3 Hz, 3H).

Example 19

18

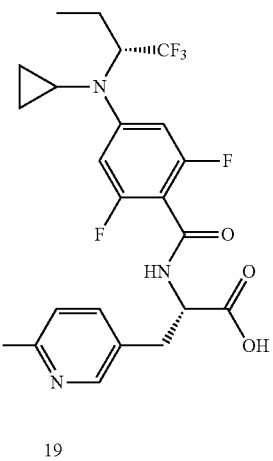

19

Synthesis of (S)-2-(4-(cyclopropyl((R)-1,1,1-trifluorobutan-2-yl)amino)-2,6-difluorobenzamido)-3-(6-(1-methyl-2,4-dioxo-1,4-dihydropyrido[3,4-d]pyrimidin-3(2H)-yl)pyridin-3-yl)propanoic acid (19): The title compound was prepared according to the method presented for the synthesis of Example 9 starting with 18. MS (m/z) 647.2 [M+H]+. 1H NMR (400 MHz, DMSO-d6) δ 13.23-12.44 (s, 1H), 9.00 (s, 1H), 8.91 (d, J=7.9 Hz, 1H), 8.57 (d, J=4.9 Hz, 1H), 8.50 (d, J=2.3 Hz, 1H), 7.97-7.86 (m, 2H), 7.45-7.38 (m, 1H), 6.67 (d, J=12.0 Hz, 2H), 5.78-5.59 (m, 1H), 5.28-5.12 (m, 2H), 4.81 (s, 1H), 4.61 (ddd, J=10.1, 7.8, 4.5 Hz, 1H), 4.01 (s, 2H), 3.61 (s, 3H), 3.24 (dd, J=14.2, 4.5 Hz, 1H), 3.06 (dd, J=14.2, 10.2 Hz, 1H), 1.99-1.85 (m, 1H), 1.85-1.73 (m, 1H), 0.86 (t, J=7.3 Hz, 3H).

Example 20

Synthesis of cyclopropyl (S)-2-(2-fluoro-6-methyl-4-((R)-3-(trifluoromethyl)morpholino) benzamido)-3-(6-(1-methyl-2,4-dioxo-1,4-dihydropyrido[3,4-d]pyrimidin-3(2H)-yl)pyridin-3-yl)propanoate (20): The title compound was prepared according to the method presented for the synthesis of 1 using intermediate L and intermediate C. MS (m/z) 671.2 [M+H]+. 1H NMR (400 MHz, DMSO-d6) δ 9.00 (s, 1H), 8.92 (d, J=7.7 Hz, 1H), 8.57 (d, J=4.9 Hz, 1H), 8.49 (d, J=2.3 Hz, 1H), 8.00-7.86 (m, 2H), 7.42 (d, J=8.1 Hz, 1H), 6.82-6.60 (m, 2H), 4.85 (d, J=9.7 Hz, 1H), 4.71 (ddd, J=10.3, 7.6, 5.2 Hz, 1H), 4.14 (ddd, J=9.3, 4.7, 2.3 Hz, 2H), 3.99-3.92 (m, 1H), 3.61 (s, 3H), 3.36 (d, J=12.4 Hz, 1H), 3.23 (dd, J=14.2, 5.3 Hz, 1H), 3.08 (dd, J=14.2, 10.3 Hz, 1H), 2.06 (s, 3H), 0.77-0.52 (m, 3H).

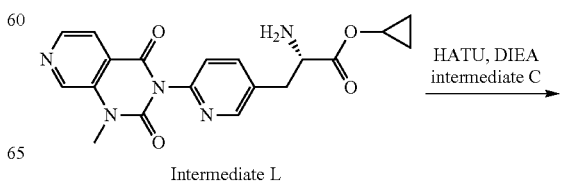

Intermediate L (13 mL) was added DIAD (1.15 mL, 8.0 mmol), EtOH (0.47 mL, 8.0 mmol) and PPh₃ (1.27 g, 4.83 mmol) and the mixture was allowed to stir for 10 min. The reaction mixture was concentrated in vacuo and then was purified by column chromatography on silica gel eluting with EA in hexanes 0-100% to afford 21. MS (m/z) 659.2 [M+H]+. 1H NMR (400 MHz, DMSO-d6) δ 9.00 (s, 1H), 8.92 (d, J=7.7 Hz, 1H), 8.57 (d, J=4.9 Hz, 1H), 8.50 (d, J=2.3 Hz, 1H), 7.95 (dd, J=8.2, 2.4 Hz, 1H), 7.91 (dd, J=5.0, 0.8 Hz, 1H), 7.47-7.35 (m, 1H), 6.77-6.59 (m, 2H), 4.85 (dd, J=8.8, 3.5 Hz, 1H), 4.74 (ddd, J=10.4, 7.8, 5.2 Hz, 1H), 4.20-4.08 (m, 3H), 3.95 (dd, J=11.4, 3.6 Hz, 1H), 3.79-3.72 (m, 1H), 3.61 (s, 3H), 3.58-3.50 (m, 1H), 3.43 (s, 1H), 3.35 (s, 1H), 3.31-3.21 (m, 2H), 3.09 (dd, J=14.2, 10.4 Hz, 1H), 2.07 (s, 3H), 1.20 (t, J=7.1 Hz, 3H).

Example 22

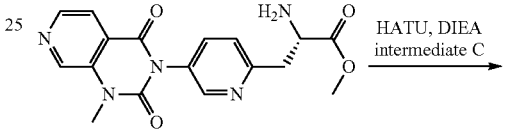

Intermediate M

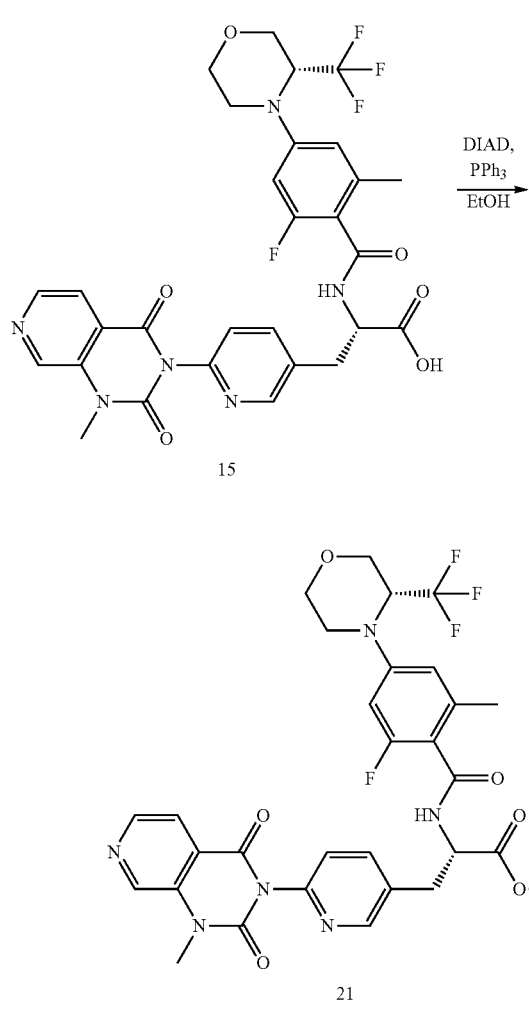

Synthesis of methyl (S)-2-(2-fluoro-6-methyl-4-((R)-3-(trifluoromethyl)morpholino) benzamido)-3-(5-(1-methyl-2,4-dioxo-1,4-dihydropyrido[3,4-d]pyrimidin-3(2H)-yl)pyridin-2-yl)propanoate (22): The title compound was prepared according to the method presented for the synthesis of 1 using intermediate M and intermediate C. MS (m/z) 645.2 [M+H]+. 1H NMR (400 MHz, DMSO-d6) δ 9.00 (s, 1H), 8.86 (d, J=7.7 Hz, 1H), 8.58 (d, J=5.0 Hz, 1H), 8.48 (d, J=2.5 Hz, 1H), 7.92 (d, J=4.9 Hz, 1H), 7.74 (dd, J=8.2, 2.5 Hz, 1H), 7.48 (d, J=8.3 Hz, 1H), 6.77-6.61 (m, 2H), 4.97 (ddd, J=9.8, 7.7, 5.2 Hz, 1H), 4.85 (dd, J=8.9, 3.6 Hz, 1H), 4.15 (d, J=12.6 Hz, 1H), 3.95 (dd, J=11.5, 3.6 Hz, 1H), 3.74 (d, J=12.7 Hz, 1H), 3.67 (s, 3H), 3.62 (s, 3H), 3.59-3.47 (m, 1H), 3.41-3.29 (m, 2H), 3.23 (dd, J=14.3, 9.8 Hz, 2H), 2.06 (s, 3H).

Example 21

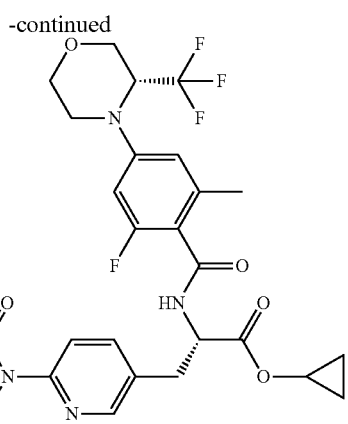

Synthesis of ethyl (S)-2-(2-fluoro-6-methyl-4-((R)-3-(trifluoromethyl)morpholino) benzamido)-3-(6-(1-methyl-2,4-dioxo-1,4-dihydropyrido[3,4-d]pyrimidin-3(2H)-yl)pyridin-3-yl)propanoate (21): To 15 (600 mg, 0.8 mmol) in DCM

Example 23

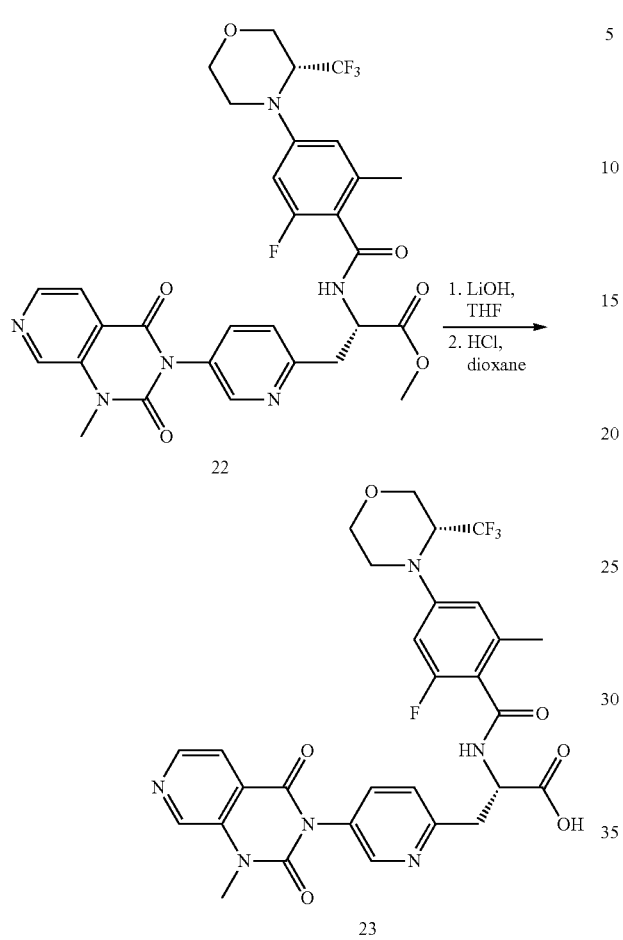

Synthesis of (S)-2-(2-fluoro-6-methyl-4-((R)-3-(trifluoromethyl)morpholino)benzamido)-3-(5-(1-methyl-2,4-dioxo-1,4-dihydropyrido[3,4-d]pyrimidin-3(2H)-yl)pyridin-2-yl)propanoic acid (23): The title compound was prepared according to the method presented for the synthesis of Example 9 starting with 22. MS (m/z) 631.2 [M+H]+. 1H NMR (400 MHz, DMSO-d6) δ 9.00 (s, 1H), 8.71 (d, J=8.0 Hz, 1H), 8.58 (d, J=4.9 Hz, 1H), 8.48 (d, J=2.5 Hz, 1H), 7.92 (d, J=4.9 Hz, 1H), 7.74 (dd, J=8.2, 2.5 Hz, 1H), 7.47 (d, J=8.3 Hz, 1H), 6.74-6.61 (m, 2H), 4.98-4.78 (m, 2H), 4.14 (d, J=12.6 Hz, 1H), 3.95 (dd, J=11.6, 3.6 Hz, 1H), 3.73 (d, J=12.8 Hz, 1H), 3.62 (s, 3H), 3.60-3.49 (m, 1H), 3.42-3.29 (m, 2H), 3.31-3.09 (m, 2H), 2.05 (s, 3H).

Example 24

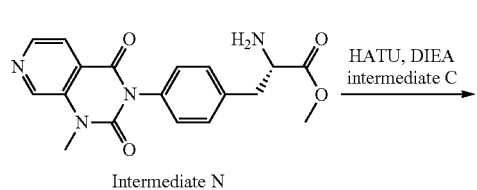

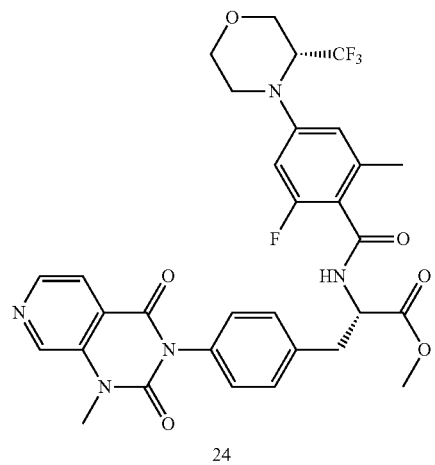

Synthesis of methyl (S)-2-(2-fluoro-6-methyl-4-((R)-3-(trifluoromethyl)morpholino)benzamido)-3-(4-(1-methyl-2,4-dioxo-1,4-dihydropyrido[3,4-d]pyrimidin-3(2H)-yl)phenyl)propanoate (24): The title compound was prepared according to the method presented for the synthesis of 1 using intermediate N and intermediate C. MS (m/z) 644.2 [M+H]+. 1H NMR (400 MHz, DMSO-d6) δ 8.98 (s, 1H), 8.89 (d, J=7.7 Hz, 1H), 8.55 (d, J=5.0 Hz, 1H), 7.90 (d, J=5.0 Hz, 1H), 7.39 (d, J=8.1 Hz, 2H), 7.23 (d, J=8.2 Hz, 2H), 6.70 (dd, J=12.9, 2.3 Hz, 1H), 6.67 (d, J=2.3 Hz, 1H), 4.84 (dt, J=9.8, 5.1 Hz, 1H), 4.70 (ddd, J=10.4, 7.7, 4.8 Hz, 1H), 4.15 (d, J=12.6 Hz, 1H), 3.95 (dd, J=11.5, 3.7 Hz, 1H), 3.74 (dd, J=12.1, 3.4 Hz, 1H), 3.67 (s, 3H), 3.60 (s, 3H), 3.59-3.50 (m, 1H), 3.36 (d, J=11.8 Hz, 1H), 3.27 (d, J=12.2 Hz, 1H), 3.19 (dd, J=14.2, 5.0 Hz, 1H), 3.05 (dd, J=14.1, 10.4 Hz, 1H), 2.07 (s, 3H).

Example 25

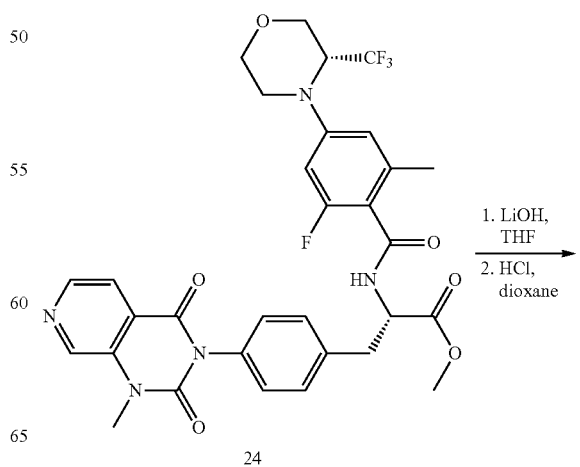

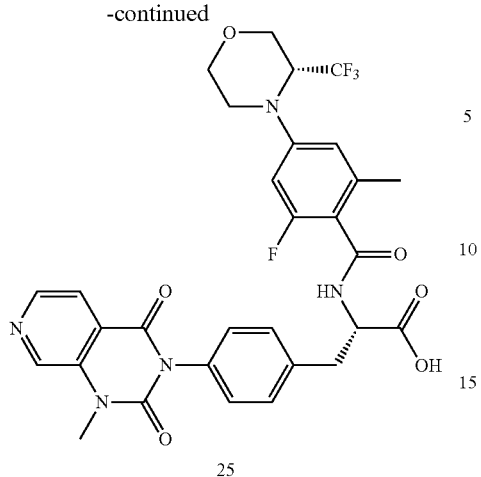

25

Synthesis of (S)-2-(2-fluoro-6-methyl-4-((R)-3-(trifluoromethyl)morpholino)benzamido)-3-(4-(1-methyl-2,4-dioxo-1,4-dihydropyrido[3,4-d]pyrimidin-3(2H)-yl)phenyl)propanoic acid (25): The title compound was prepared according to the method presented for the synthesis of Example 9 starting with 24. MS (m/z) 630.2 [M+H]+. 1H NMR (400 MHz, DMSO-d6) δ 8.97 (s, 1H), 8.74 (d, J=8.0 Hz, 1H), 8.55 (d, J=5.0 Hz, 1H), 7.90 (d, J=5.0 Hz, 1H), 7.40 (d, J=8.3 Hz, 2H), 7.22 (d, J=8.3 Hz, 2H), 6.69 (dd, J=13.0, 2.2 Hz, 1H), 6.65 (d, J=2.3 Hz, 1H), 4.90-4.78 (m, 1H), 4.65 (tt, J=8.0, 4.3 Hz, 1H), 4.15 (d, J=12.5 Hz, 1H), 3.95 (dd, J=11.5, 3.6 Hz, 1H), 3.73 (d, J=12.6 Hz, 1H), 3.60 (s, 3H), 3.55 (td, J=11.8, 11.3, 3.0 Hz, 1H), 3.36 (d, J=11.5 Hz, 1H), 3.27 (d, J=12.4 Hz, 1H), 3.21 (dd, J=14.1, 4.2 Hz, 1H), 3.01 (dd, J=14.2, 10.7 Hz, 1H), 2.05 (s, 3H).

Example 26

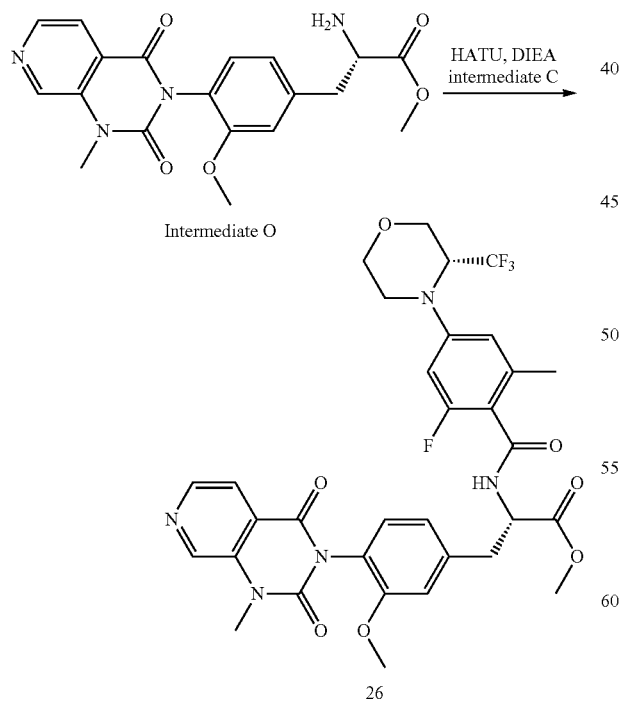

Synthesis of methyl (S)-2-(2-fluoro-6-methyl-4-((R)-3-(trifluoromethyl)morpholino) benzamido)-3-(3-methoxy-4-(1-methyl-2,4-dioxo-1,4-dihydropyrido[3,4-d]pyrimidin-3(2H)-yl)phenyl)propanoate (26): The title compound was prepared according to the method presented for the synthesis of 1 using intermediate O and intermediate C. MS (m/z) 674.2 [M+H]+. 1H NMR (400 MHz, DMSO-d6) δ 8.97 (s, 1H), 8.91 (d, J=7.7 Hz, 1H), 8.56 (d, J=4.9 Hz, 1H), 7.94-7.84 (m, 1H), 7.21-7.09 (m, 2H), 6.96 (dd, J=8.0, 1.7 Hz, 1H), 6.77-6.63 (m, 2H), 4.84 (td, J=8.8, 3.5 Hz, 1H), 4.72 (ddd, J=10.6, 7.7, 4.7 Hz, 1H), 4.15 (d, J=12.6 Hz, 1H), 3.95 (dd, J=11.4, 3.6 Hz, 1H), 3.84-3.72 (m, 1H), 3.69 (d, J=3.9 Hz, 6H), 3.64-3.58 (m, 4H), 3.31-3.00 (m, 6H), 2.09 (s, 3H).

Example 27

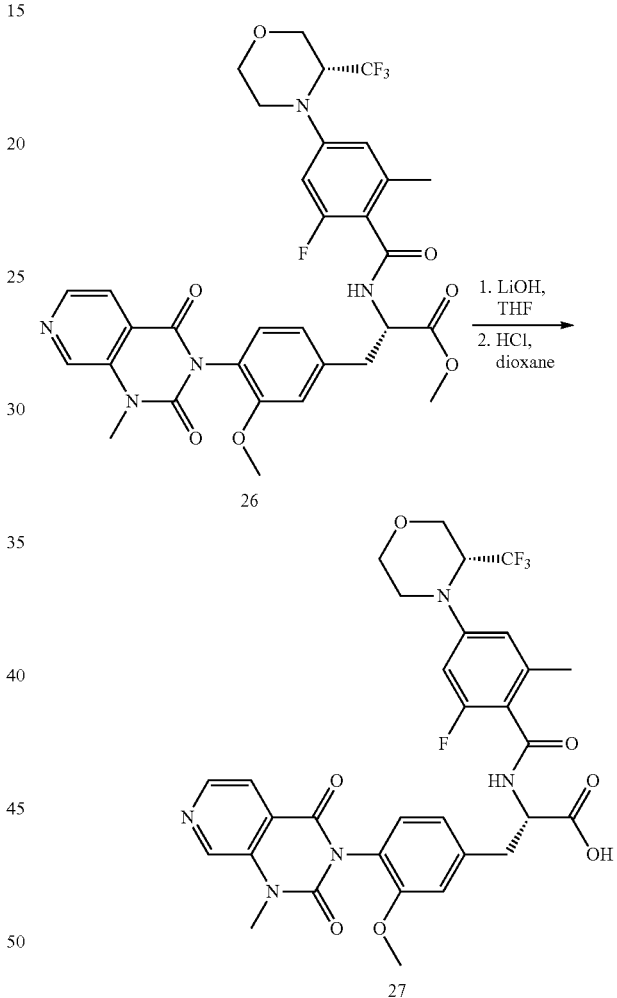

Synthesis of (S)-2-(2-fluoro-6-methyl-4-((R)-3-(trifluoromethyl)morpholino)benzamido)-3-(3-methoxy-4-(1-methyl-2,4-dioxo-1,4-dihydropyrido[3,4-d]pyrimidin-3(2H)-yl)phenyl)propanoic acid (27): The title compound was prepared according to the method presented for the synthesis of Example 9 starting with 26. MS (m/z) 660.2 [M+H]+. 1H NMR (400 MHz, DMSO-d6) δ 8.97 (s, 1H), 8.76 (d, J=8.0 Hz, 1H), 8.56 (d, J=5.0 Hz, 1H), 7.89 (dd, J=5.0, 1.4 Hz, 1H), 7.20-7.12 (m, 2H), 6.97 (dd, J=8.0, 1.6 Hz, 1H), 6.74-6.61 (m, 2H), 4.84 (dd, J=8.9, 3.5 Hz, 1H), 4.67 (ddd, J=11.6, 7.9, 4.1 Hz, 1H), 4.15 (d, J=12.6 Hz, 1H), 3.95 (dd, J=11.5, 3.7 Hz, 1H), 3.71 (s, 5H), 3.69 (s, 3H), 3.40-3.31 (m, 1H), 3.31-3.17 (m, 2H), 3.01 (dd, J=14.2, 10.8 Hz, 1H), 2.08 (s, 3H).

Example 54

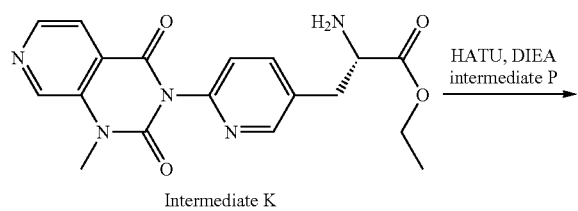

Intermediate K
(ethyl ester)

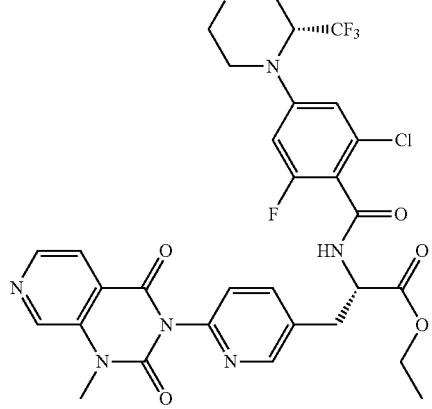

54

Synthesis of ethyl (S)-2-(2-chloro-6-fluoro-4-((R)-3-(trifluoromethyl)morpholino) benzamido)-3-(6-(1-methyl-2,4-dioxo-1,4-dihydropyrido[3,4-d]pyrimidin-3(2H)-yl)pyridin-3-yl)propanoate (54): The title compound was prepared according to the method presented for the synthesis of 8 using the ethyl ester of intermediate K and intermediate P. MS (m/z) 679.2 [M+H]+. 1H NMR (400 MHz, DMSO-d6) δ 9.16 (d, J=7.9 Hz, 1H), 9.00 (s, 1H), 8.57 (d, J=5.0 Hz, 1H), 8.50 (d, J=2.3 Hz, 1H), 7.94 (dd, J=8.1, 2.4 Hz, 1H), 7.90 (d, J=5.0 Hz, 1H), 7.41 (d, J=8.1 Hz, 1H), 6.98-6.88 (m, 2H), 4.93 (dd, J=8.9, 3.5 Hz, 1H), 4.74 (ddd, J=10.3, 7.9, 5.1 Hz, 1H), 4.20-4.08 (m, 3H), 3.95 (dd, J=11.6, 3.7 Hz, 1H), 3.74 (d, J=12.7 Hz, 1H), 3.61 (s, 3H), 3.54 (t, J=9.14 Hz, 1H), 3.41 (d, J=12.5 Hz, 1H), 3.25 (m, 2H), 3.09 (dd, J=14.2, 10.2 Hz, 1H), 1.20 (t, J=7.1 Hz, 3H).

Example 55

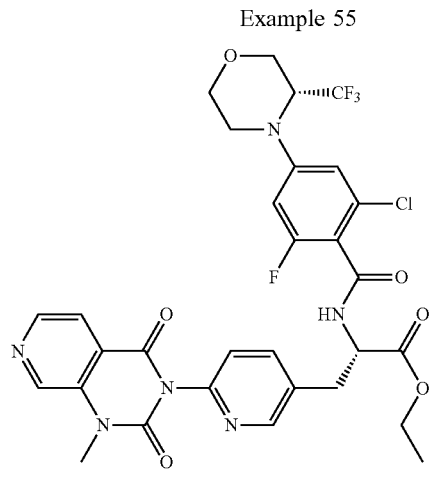

54

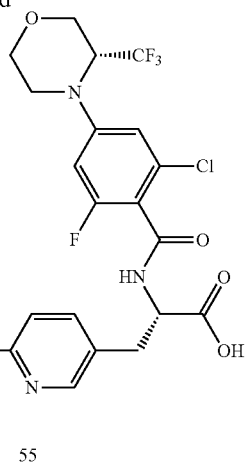

55

Synthesis of (S)-2-(2-chloro-6-fluoro-4-((R)-3-(trifluoromethyl)morpholino)benzamido)-3-(6-(1-methyl-2,4-dioxo-1,4-dihydropyrido[3,4-d]pyrimidin-3(2H)-yl)pyridin-3-yl)propanoic acid (55): The title compound was prepared according to the method presented for the synthesis of Example 9 starting with 54. MS (m/z) 651.1 [M+H]+. 1H NMR (400 MHz, DMSO-d6) δ 13.32-12.45 (s, 1H), 9.04 (d, J=8.2 Hz, 1H), 9.00 (s, 1H), 8.57 (d, J=5.0 Hz, 1H), 8.50 (d, J=2.3 Hz, 1H), 7.94 (dd, J=8.1, 2.4 Hz, 1H), 7.90 (d, J=5.0 Hz, 1H), 7.41 (d, J=8.1 Hz, 1H), 6.96-6.87 (m, 2H), 5.00-4.84 (m, 1H), 4.76-4.63 (m, 1H), 4.15 (d, J=12.7 Hz, 1H), 3.95 (dd, J=11.5, 3.7 Hz, 1H), 3.74 (d, J=12.7 Hz, 1H), 3.61 (s, 3H), 3.60-3.49 (m, 1H), 3.40 (d, J=12.7 Hz, 1H), 3.27 (m, 2H), 3.04 (dd, J=14.3, 10.6 Hz, 1H).

Example 56

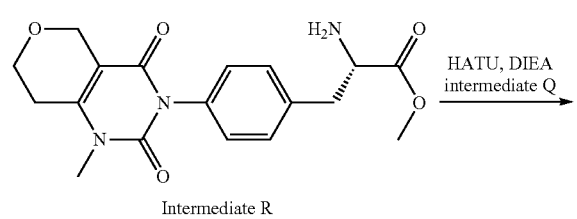

Intermediate R

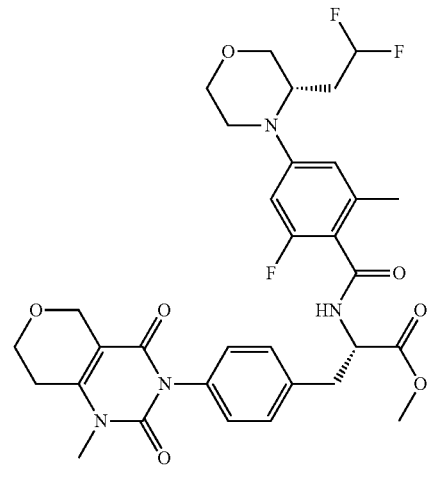

56

Synthesis of methyl (S)-2-(4-((S)-3-(2,2-difluoroethyl) morpholino)-2-fluoro-6-methylbenzamido)-3-(4-(1-methyl-2,4-dioxo-1,5,7,8-tetrahydro-2H-pyrano[4,3-d]pyrimidin-3(4H)-yl)phenyl)propanoate (56): The title compound was prepared according to the method presented for the synthesis of 8 using the ethyl ester of intermediate R and intermediate Q. MS (m/z) 645.4 [M+H]+. 1H NMR (400 MHz, DMSO-d6) δ 8.83 (d, J=7.7 Hz, 1H), 7.40-7.29 (m, 2H), 7.14-7.05 (m, 2H), 6.61-6.48 (m, 2H), 6.36-5.97 (m, 1H), 4.67 (ddd, J=10.4, 7.7, 4.9 Hz, 1H), 4.28 (d, J=1.8 Hz, 2H), 4.02 (d, J=9.3 Hz, 1H), 3.93-3.80 (m, 4H), 3.66 (s, 3H), 3.63 (s, 1H), 3.52 (td, J=11.7, 3.2 Hz, 1H), 3.34 (s, 1H), 3.16 (dd, J=14.1, 4.9 Hz, 1H), 3.09-2.95 (m, 2H), 2.72 (d, J=5.8 Hz, 2H), 2.37 (d, J=14.0 Hz, 1H), 2.05 (s, 3H), 1.77 (q, J=17.5 Hz, 1H).

Example 57

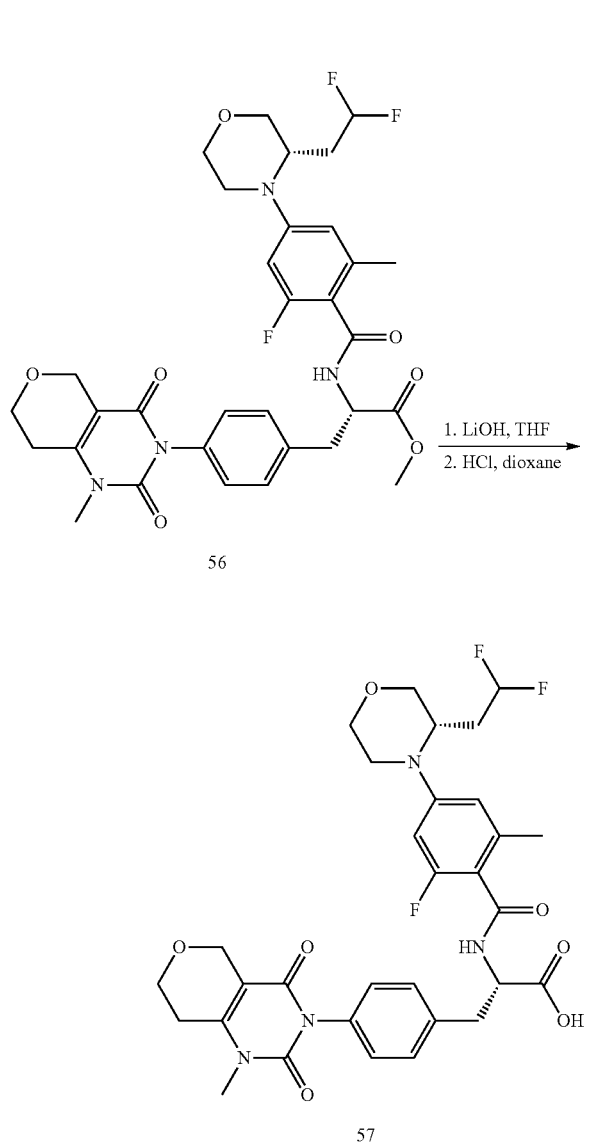 [SMILES: COC(=O)[C@H](Cc1ccc(-n2c(=O)c3c(n(C)c2=O)CCOC3)cc1)NC(=O)c1c(C)cc(N2CCOC[C@@H]2CC(F)F)cc1F ; Cc1cc(N2CCOC[C@@H]2CC(F)F)cc(F)c1C(=O)N[C@@H](Cc1ccc(-n2c(=O)c3c(n(C)c2=O)CCOC3)cc1)C(=O)O]

Synthesis of (S)-2-(4-((S)-3-(2,2-difluoroethyl)morpholino)-2-fluoro-6-methylbenzamido)-3-(4-(1-methyl-2,4-dioxo-1,5,7,8-tetrahydro-2H-pyrano[4,3-d]pyrimidin-3(4H)-yl)phenyl)propanoic acid (57): The title compound was prepared according to the method presented for the synthesis of Example 9 starting with 56. MS (m/z) 631.4 [M+H]+. 1H NMR (400 MHz, DMSO-d6) δ 12.87-12.58 (s, 1H), 8.68 (d, J=8.1 Hz, 1H), 7.36 (d, J=8.2 Hz, 2H), 7.10 (d, J=8.2 Hz, 2H), 6.53 (d, J=8.7 Hz, 2H), 6.34-5.94 (m, 1H), 4.70-4.54 (m, 1H), 4.28 (s, 2H), 4.01 (s, 1H), 3.94-3.79 (m, 4H), 3.64 (d, J=11.2 Hz, 1H), 3.52 (d, J=3.3 Hz, 1H), 3.33 (s, 1H), 3.31 (s, 3H), 3.22-3.14 (m, 1H), 3.09-2.93 (m, 2H), 2.71 (s, 2H), 2.43-2.34 (m, 1H), 2.04 (s, 3H), 1.79 (s, 1H).

Example 58

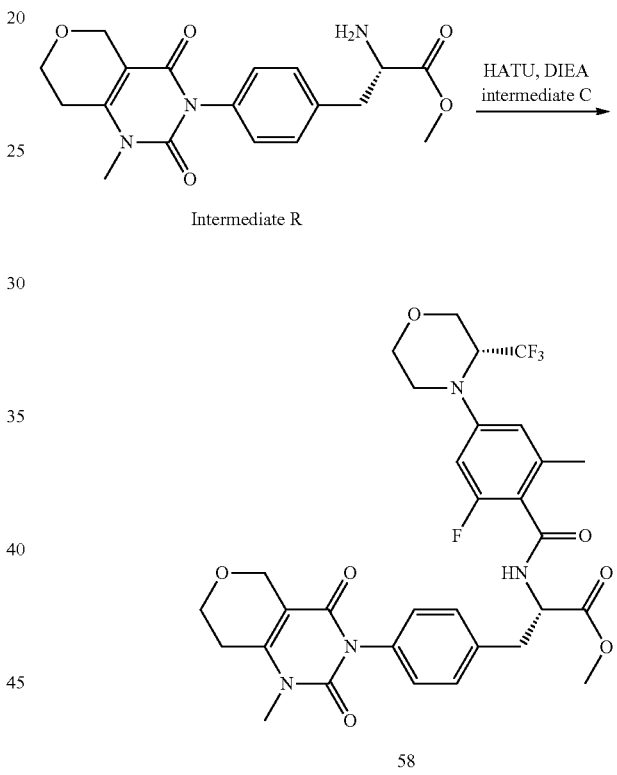

Synthesis of methyl (S)-2-(2-fluoro-6-methyl-4-((R)-3-(trifluoromethyl)morpholino) benzamido)-3-(4-(1-methyl-2,4-dioxo-1,5,7,8-tetrahydro-2H-pyrano[4,3-d]pyrimidin-3(4H)-yl)phenyl)propanoate (58): The title compound was prepared according to the method presented for the synthesis of 8 using the ethyl ester of intermediate R and intermediate C. MS (m/z) 649.2 [M+H]+. 1H NMR (400 MHz, DMSO-d6) δ 8.87 (d, J=7.7 Hz, 1H), 7.35 (d, J=8.3 Hz, 2H), 7.14-7.07 (m, 2H), 6.69 (d, J=13.5 Hz, 1H), 6.66 (d, J=2.3 Hz, 1H), 4.84 (d, J=9.0 Hz, 1H), 4.68 (ddd, J=12.4, 7.8, 4.9 Hz, 1H), 4.29 (s, 2H), 4.15 (d, J=12.6 Hz, 1H), 4.00-3.92 (m, 1H), 3.88 (t, J=5.6 Hz, 2H), 3.73 (d, J=12.6 Hz, 1H), 3.66 (s, 3H), 3.54 (t, J=10.2 Hz, 1H), 3.35 (d, J=13.3 Hz, 2H), 3.31 (s, 2H), 3.16 (dd, J=14.2, 5.0 Hz, 1H), 3.02 (dd, J=14.1, 10.2 Hz, 1H), 2.71 (m, 2H), 2.05 (s, 3H).

Example 59

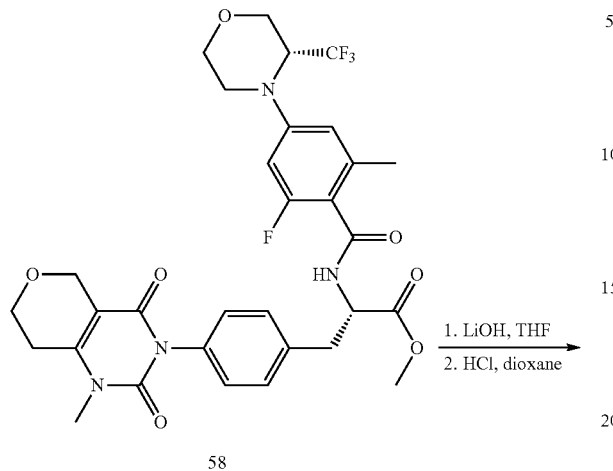

Synthesis of (S)-2-(2-fluoro-6-methyl-4-((R)-3-(trifluoromethyl)morpholino)benzamido)-3-(4-(1-methyl-2,4-dioxo-1,5,7,8-tetrahydro-2H-pyrano[4,3-d]pyrimidin-3(4H)-yl)phenyl)propanoic acid (59): The title compound was prepared according to the method presented for the synthesis of Example 9 starting with 58. MS (m/z) 635.2 [M+H]+. 1H NMR (400 MHz, DMSO-d6) δ 8.72 (d, J=8.0 Hz, 1H), 7.41-7.30 (m, 2H), 7.13-7.05 (m, 2H), 6.68 (dd, J=12.9, 2.3 Hz, 1H), 6.64 (d, J=2.4 Hz, 1H), 4.84 (dd, J=8.9, 3.5 Hz, 1H), 4.63 (ddd, J=12.0, 8.0, 4.4 Hz, 1H), 4.28 (d, J=1.8 Hz, 2H), 4.14 (d, J=12.6 Hz, 1H), 3.95 (dd, J=11.3, 3.7 Hz, 1H), 3.88 (t, J=5.6 Hz, 2H), 3.73 (d, J=12.7 Hz, 1H), 3.62-3.49 (m, 1H), 3.31 (s, 5H), 3.18 (dd, J=14.2, 4.3 Hz, 1H), 2.99 (dd, J=14.2, 10.6 Hz, 1H), 2.71 (s, 1H), 2.04 (s, 3H).

Example 60

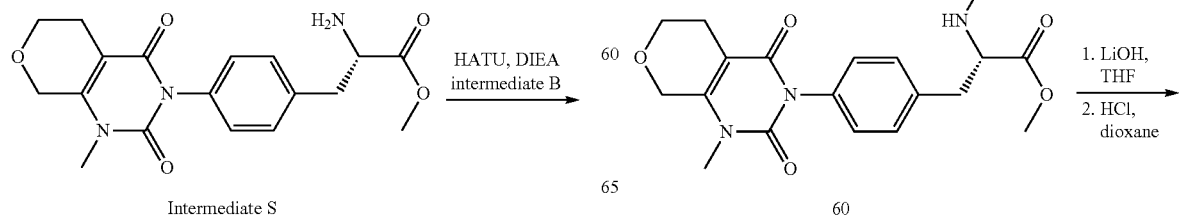

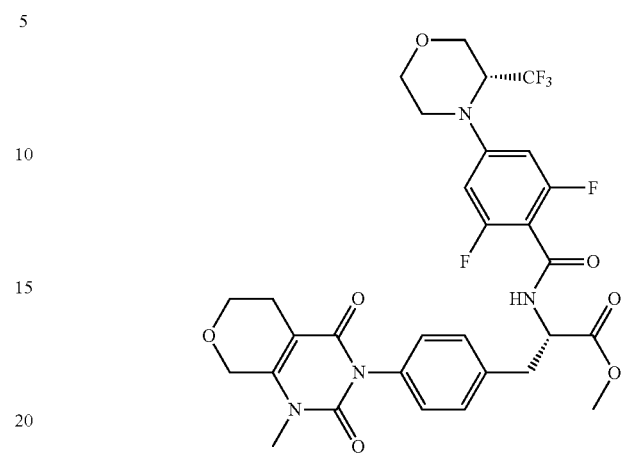

Synthesis of methyl (S)-2-(2,6-difluoro-4-((R)-3-(trifluoromethyl)morpholino) benzamido)-3-(4-(1-methyl-2,4-dioxo-1,2,4,5,6,8-hexahydro-3H-pyrano[3,4-d]pyrimidin-3-yl)phenyl)propanoate (60): The title compound was prepared according to the method presented for the synthesis of 8 using the ethyl ester of intermediate S and intermediate B. MS (m/z) 653.2 [M+H]+. 1H NMR (400 MHz, DMSO-d6) δ 9.03 (d, J=7.5 Hz, 1H), 7.34 (d, J=8.4 Hz, 2H), 7.11 (d, J=8.3 Hz, 2H), 6.79 (d, J=11.6 Hz, 2H), 4.91 (dt, J=12.0, 6.0 Hz, 1H), 4.68-4.56 (m, 3H), 4.17 (d, J=12.7 Hz, 1H), 3.96 (dd, J=11.4, 3.8 Hz, 1H), 3.84-3.70 (m, 3H), 3.64 (s, 3H), 3.61-3.51 (m, 1H), 3.44 (d, J=12.7 Hz, 1H), 3.26 (d, J=13.2 Hz, 1H), 3.21 (s, 3H), 3.17 (d, J=5.3 Hz, 1H), 3.15-3.01 (m, 2H), 2.39-2.24 (m, 2H).

Example 61

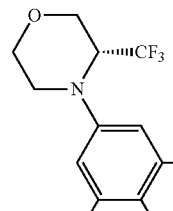

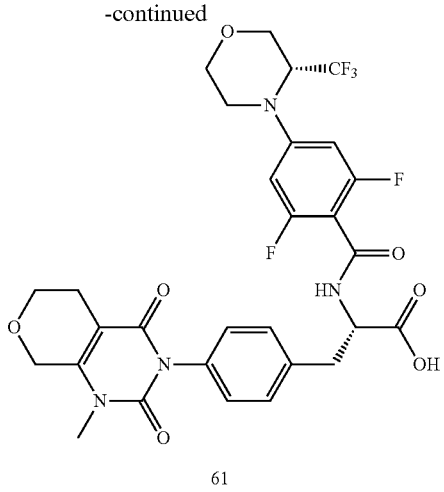

61

Synthesis of (S)-2-(2,6-difluoro-4-((R)-3-(trifluoromethyl)morpholino)benzamido)-3-(4-(1-methyl-2,4-dioxo-1,2,4,5,6,8-hexahydro-3H-pyrano[3,4-d]pyrimidin-3-yl)phenyl)propanoic acid (61): The title compound was prepared according to the method presented for the synthesis of Example 9 starting with 60. MS (m/z) 639.2 [M+H]+. 1H NMR (400 MHz, DMSO-d6) δ 8.88 (d, J=7.8 Hz, 1H), 7.35 (dd, J=8.5, 2.0 Hz, 2H), 7.16-7.00 (m, 2H), 6.78 (d, J=11.6 Hz, 2H), 5.04-4.82 (m, 1H), 4.64-4.49 (m, 3H), 4.16 (d, J=12.7 Hz, 1H), 3.96 (dd, J=11.5, 3.7 Hz, 1H), 3.83-3.70 (m, 3H), 3.62-3.49 (m, 1H), 3.43 (d, J=12.7 Hz, 1H), 3.26 (d, J=12.5 Hz, 1H), 3.21 (s, 3H), 3.16 (dd, J=14.2, 4.8 Hz, 1H), 3.02 (dd, J=14.2, 9.7 Hz, 1H), 2.33 (qd, J=4.3, 3.0, 2.4 Hz, 2H).

Example 62

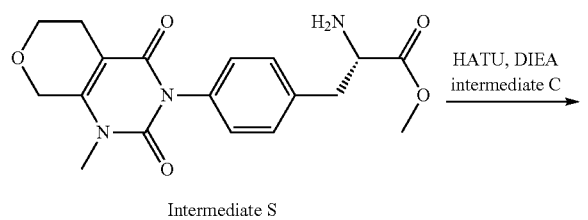

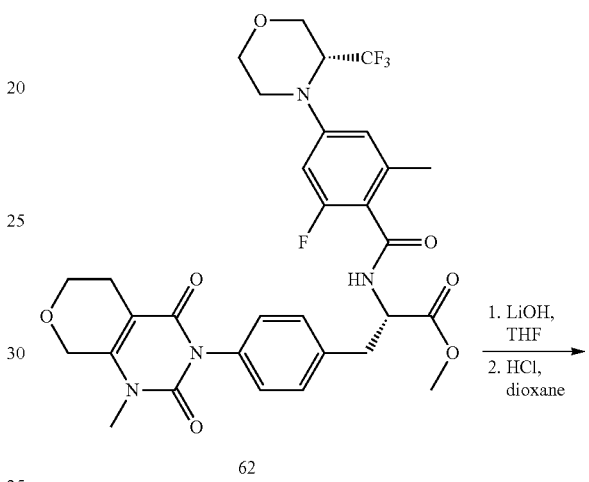

62

Synthesis of methyl (S)-2-(2-fluoro-6-methyl-4-((R)-3-(trifluoromethyl)morpholino) benzamido)-3-(4-(1-methyl-2,4-dioxo-1,2,4,5,6,8-hexahydro-3H-pyrano[3,4-d]pyrimidin-3-yl)phenyl)propanoate (62): The title compound was prepared according to the method presented for the synthesis of 8 using the ethyl ester of intermediate S and intermediate C. MS (m/z) 671.2 [M+Na]. 1H NMR (400 MHz, DMSO-d6) δ 8.87 (d, J=7.7 Hz, 1H), 7.35 (d, J=8.2 Hz, 2H), 7.10 (d, J=8.2 Hz, 2H), 6.70 (d, J=13.5 Hz, 1H), 6.66 (s, 1H), 4.84 (d, J=7.7 Hz, 1H), 4.76-4.64 (m, 1H), 4.60 (s, 2H), 4.15 (d, J=12.6 Hz, 1H), 4.03-3.90 (m, 1H), 3.86-3.70 (m, 3H), 3.66 (s, 3H), 3.55 (t, J=10.7 Hz, 1H), 3.21 (s, 4H), 3.03 (dd, J=14.1, 10.3 Hz, 1H), 2.33 (d, J=2.5 Hz, 3H), 2.06 (s, 3H).

Example 63

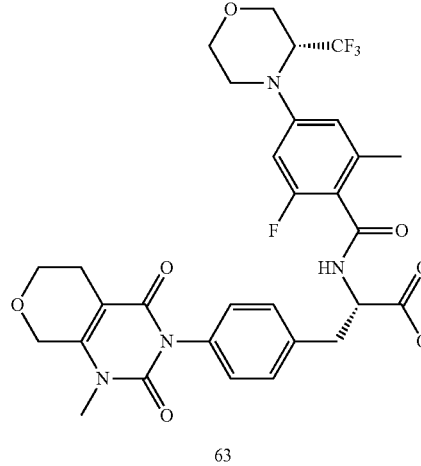

63

Synthesis of (S)-2-(2-fluoro-6-methyl-4-((R)-3-(trifluoromethyl)morpholino)benzamido)-3-(4-(1-methyl-2,4-dioxo-1,2,4,5,6,8-hexahydro-3H-pyrano[3,4-d]pyrimidin-3-yl)phenyl)propanoic acid (63): The title compound was prepared according to the method presented for the synthesis of Example 9 starting with 62. MS (m/z) 635.2 [M+H]+. 1H NMR (400 MHz, DMSO-d6) δ 8.72 (d, J=8.0 Hz, 1H), 7.41-7.33 (m, 2H), 7.15-7.03 (m, 2H), 6.68 (dd, J=12.9, 2.3 Hz, 1H), 6.64 (d, J=2.3 Hz, 1H), 4.84 (dd, J=9.0, 3.6 Hz, 1H), 4.69-4.56 (m, 3H), 4.14 (d, J=12.6 Hz, 1H), 3.95 (dd, J=11.4, 3.6 Hz, 1H), 3.79 (t, J=5.5 Hz, 2H), 3.76-3.68 (m, 1H), 3.61-3.49 (m, 1H), 3.35 (d, J=12.3 Hz, 1H), 3.27 (d, J=12.5 Hz, 1H), 3.21 (s, 4H), 2.99 (dd, J=14.2, 10.6 Hz, 1H), 2.40-2.25 (m, 2H), 2.04 (s, 3H).

Example 64

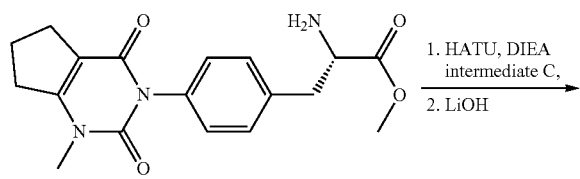

Intermediate T

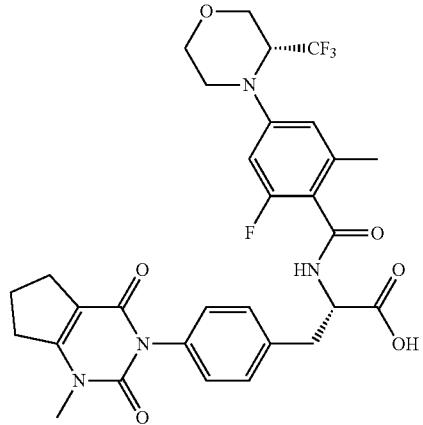

64

Synthesis of (S)-2-(2-fluoro-6-methyl-4-((R)-3-(trifluoromethyl)morpholino)benzamido)-3-(4-(1-methyl-2,4-dioxo-1,2,4,5,6,7-hexahydro-3H-cyclopenta[d]pyrimidin-3-yl)phenyl)propanoic acid (64): The title compound was prepared according to the method presented for the synthesis of 1 using the ethyl ester of intermediate T and intermediate C. MS (m/z) 619.2 [M+H]+. 1H NMR (400 MHz, DMSO-d6) δ 8.72 (d, J=8.0 Hz, 1H), 7.35 (dd, J=8.5, 2.0 Hz, 2H), 7.11-7.00 (m, 2H), 6.68 (dd, J=12.9, 2.4 Hz, 1H), 6.64 (d, J=2.4 Hz, 1H), 4.84 (dd, J=8.8, 3.5 Hz, 1H), 4.63 (ddd, J=10.6, 8.0, 4.2 Hz, 1H), 4.14 (d, J=12.6 Hz, 1H), 3.94 (dd, J=11.4, 3.6 Hz, 1H), 3.73 (d, J=12.7 Hz, 1H), 3.54 (td, J=11.7, 3.5 Hz, 1H), 3.35 (d, J=12.2 Hz, 1H), 3.29 (s, 3H), 3.18 (dd, J=14.3, 4.3 Hz, 1H), 3.05-2.89 (m, 3H), 2.61 (t, J=7.4 Hz, 2H), 2.04 (s, 3H).

Example 65

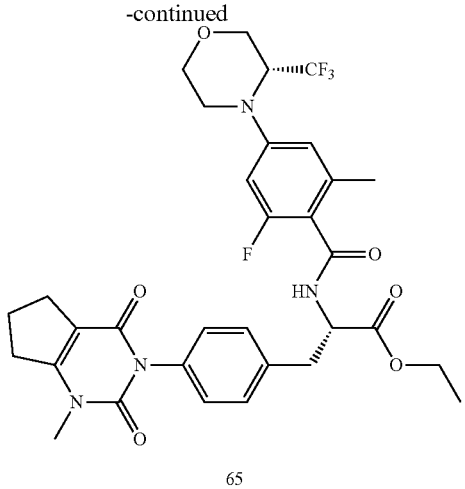

64

DIAD, TPP
DCM, EtOH

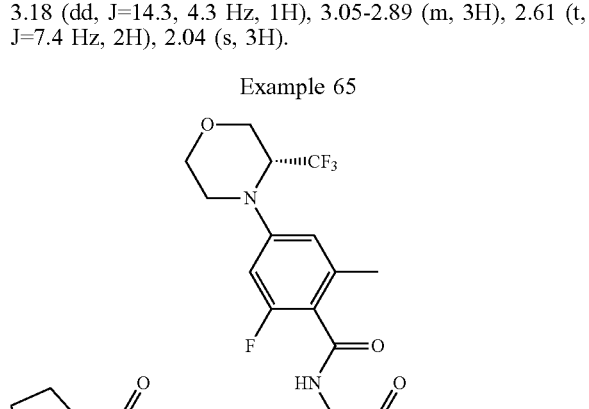

65

Synthesis of ethyl (S)-2-(2-fluoro-6-methyl-4-((R)-3-(trifluoromethyl)morpholino) benzamido)-3-(4-(1-methyl-2,4-dioxo-1,2,4,5,6,7-hexahydro-3H-cyclopenta[d]pyrimidin-3-yl)phenyl)propanoate (65): To 64 (30 mg, 0.05 mmol), TPP (38 mg, 0.145 mmol) and EtOH (0.03 mL, 0.48 mmol) in DCM was added DIAD (0.05 mL, 0.24 mmol). The mixture was allowed to stir for 60 min at RT. Upon completion, the mixture was acidified with TFA, and the volatiles were removed under reduced pressure. The crude material was dissolved in DMSO and chromatographed on C-18 modified silica gel eluting with acetonitrile in water (0.4% TFA) to afford compound 65. MS (m/z) 647.3 [M+H]+. 1H NMR (400 MHz, DMSO-d6) δ 8.86 (d, J=7.6 Hz, 1H), 7.39-7.28 (m, 2H), 7.12-7.01 (m, 2H), 6.75-6.67 (m, 1H), 6.66 (d, J=2.3 Hz, 1H), 4.92-4.76 (m, 1H), 4.65 (ddd, J=9.9, 7.6, 5.2 Hz, 1H), 4.19-4.06 (m, 3H), 3.95 (dd, J=11.4, 3.7 Hz, 1H), 3.73 (d, J=12.7 Hz, 1H), 3.62-3.43 (m, 1H), 3.36 (d, J=12.4 Hz, 1H), 3.29 (s, 4H), 3.15 (dd, J=14.1, 5.3 Hz, 1H), 3.10-3.00 (m, 1H), 2.97 (q, J=7.6, 6.6 Hz, 2H), 2.61 (t, J=7.5 Hz, 2H), 2.13-1.92 (m, 5H), 1.17 (t, J=7.1 Hz, 3H).

Example 66

Synthesis of (S)-2-(2-fluoro-6-methyl-4-((R)-3-(trifluoromethyl)morpholino)benzamido)-3-(4-(1-methyl-2,4-dioxo-1,2,5,7-tetrahydrofuro[3,4-d]pyrimidin-3(4H)-yl)phenyl)propanoic acid (66): The title compound was prepared according to the method presented for the synthesis of 1 using the ethyl ester of intermediate U and intermediate C. MS (m/z) 621.2 [M+H 1H NMR (400 MHz, DMSO-d6) δ 8.72 (d, J=8.0 Hz, 1H), 7.42-7.30 (m, 2H), 7.16-7.03 (m, 2H), 6.68 (dd, J=12.9, 2.3 Hz, 1H), 6.64 (d, J=2.3 Hz, 1H), 5.06 (t, J=3.6 Hz, 2H), 4.86 (t, J=3.6 Hz, 3H), 4.64 (ddd, J=10.7, 8.0, 4.2 Hz, 1H), 4.14 (d, J=12.6 Hz, 1H), 3.94 (dd, J=11.4, 3.6 Hz, 1H), 3.73 (d, J=12.5 Hz, 1H), 3.63-3.47 (m, 1H), 3.35 (d, J=12.2 Hz, 1H), 3.23 (s, 5H), 2.99 (dd, J=14.2, 10.7 Hz, 1H), 2.03 (s, 3H).

Intermediate U

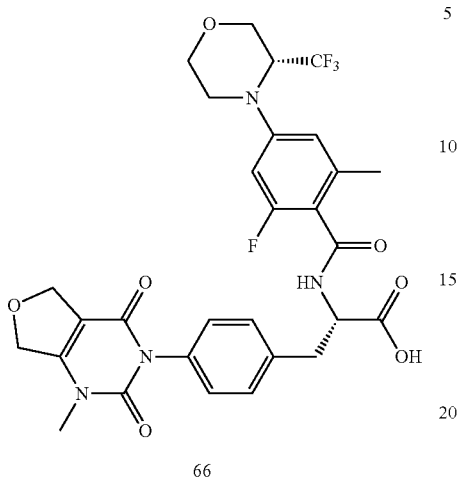

66

Example 67

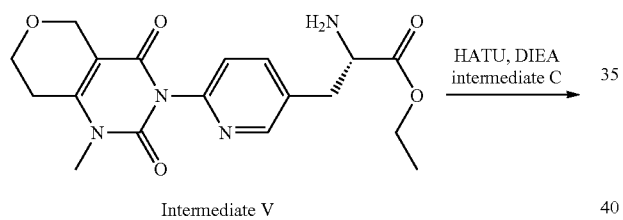

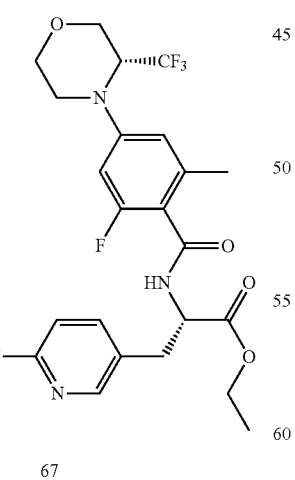

67

Synthesis of ethyl (S)-2-(2-fluoro-6-methyl-4-((R)-3-(trifluoromethyl)morpholino) benzamido)-3-(6-(1-methyl-2,4-dioxo-1,5,7,8-tetrahydro-2H-pyrano[4,3-d]pyrimidin-3(4H)-yl)pyridin-3-yl)propanoate (67): The title compound was prepared according to the method presented for the synthesis of 8 using the ethyl ester of intermediate V and intermediate C. MS (m/z) 664.0 [M+H]+. 1H NMR (400 MHz, DMSO-d6) δ 8.90 (d, J=7.7 Hz, 1H), 8.45 (d, J=2.3 Hz, 1H), 7.95 (s, 1H), 7.89 (dd, J=8.2, 2.4 Hz, 1H), 7.30 (dd, J=8.1, 0.7 Hz, 1H), 6.75-6.64 (m, 2H), 4.84 (dd, J=8.8, 3.5 Hz, 1H), 4.71 (ddd, J=10.4, 7.8, 5.2 Hz, 1H), 4.29 (s, 2H), 4.19-4.06 (m, 3H), 3.99-3.84 (m, 3H), 3.73 (d, J=12.5 Hz, 1H), 3.59-3.49 (m, 1H), 3.31 (s, 4H), 3.28-3.16 (m, 2H), 3.07 (dd, J=14.3, 10.3 Hz, 1H), 2.89 (s, 2H), 2.77-2.66 (m, 4H), 2.06 (s, 3H), 1.18 (t, J=7.1 Hz, 3H).

Example 68

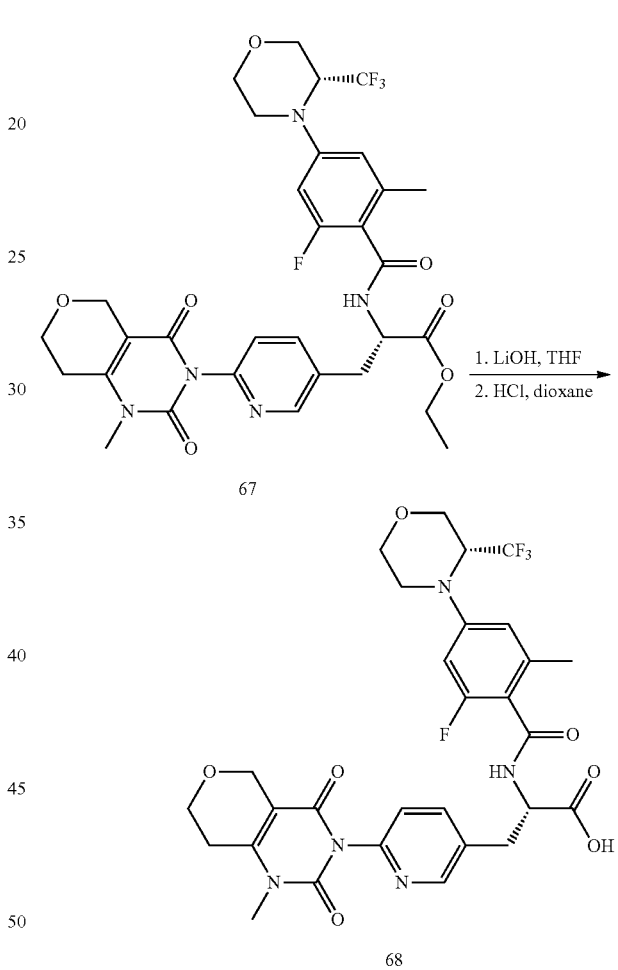

Synthesis of (S)-2-(2-fluoro-6-methyl-4-((R)-3-(trifluoromethyl)morpholino)benzamido)-3-(6-(1-methyl-2,4-dioxo-1,5,7,8-tetrahydro-2H-pyrano[4,3-d]pyrimidin-3(4H)-yl)pyridin-3-yl)propanoic acid (68): The title compound was prepared according to the method presented for the synthesis of Example 9 starting with 67. MS (m/z) 636.3 [M+H]+. 1H NMR (400 MHz, DMSO-d6) δ 8.77 (d, J=8.1 Hz, 1H), 8.46 (d, J=2.3 Hz, 1H), 7.88 (dd, J=8.2, 2.4 Hz, 1H), 7.33-7.26 (m, 1H), 6.73-6.62 (m, 2H), 4.84 (dd, J=8.8, 3.6 Hz, 1H), 4.67 (ddd, J=11.9, 8.0, 4.2 Hz, 1H), 4.29 (s, 2H), 4.14 (d, J=12.6 Hz, 1H), 3.95 (dd, J=11.4, 3.6 Hz, 1H), 3.88 (d, J=11.0 Hz, 1H), 3.73 (d, J=11.8 Hz, 1H), 3.59-3.48 (m, 1H), 3.35 (d, J=12.3 Hz, 1H), 3.31 (s, 5H), 3.02 (dd, J=14.3, 10.9 Hz, 1H), 2.73 (s, 2H), 2.03 (s, 3H).

Example 69

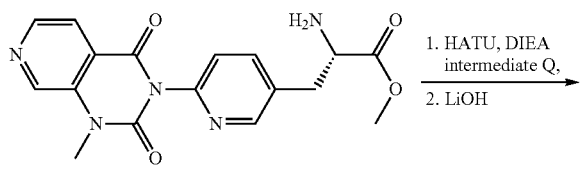

Intermediate K

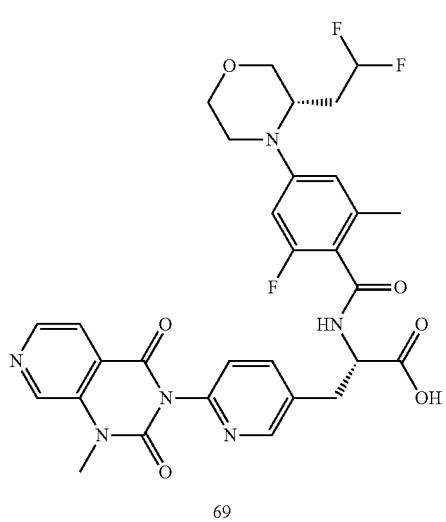

69

Synthesis of (S)-2-(4-((S)-3-(2,2-difluoroethyl)morpholino)-2-fluoro-6-methylbenzamido)-3-(6-(1-methyl-2,4-dioxo-1,4-dihydropyrido[3,4-d]pyrimidin-3(2H)-yl)pyridin-3-yl)propanoic acid (69): The title compound was prepared according to the method presented for the synthesis of 1 using the ethyl ester of intermediate K and intermediate Q. MS (m/z) 627.1 [M+H]+. 1H NMR (400 MHz, DMSO-d6) δ 9.00 (s, 1H), 8.75 (d, J=8.2 Hz, 1H), 8.57 (d, J=5.0 Hz, 1H), 8.50 (d, J=2.4 Hz, 1H), 7.94 (dd, J=8.3, 2.4 Hz, 1H), 7.92-7.89 (m, 1H), 7.42 (d, J=8.0 Hz, 1H), 6.53 (t, J=6.1 Hz, 2H), 6.36-5.96 (m, 1H), 4.75-4.61 (m, 1H), 4.03 (m, 1H), 3.90 (d, J=9.1 Hz, 1H), 3.84 (d, J=11.8 Hz, 1H), 3.61 (s, 3H), 3.58-3.46 (m, 1H), 3.35-3.13 (m, 2H), 3.04 (dd, J=14.4, 10.9 Hz, 2H), 2.03 (s, 3H).

Example 70

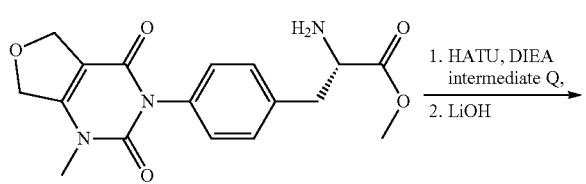

Intermediate W

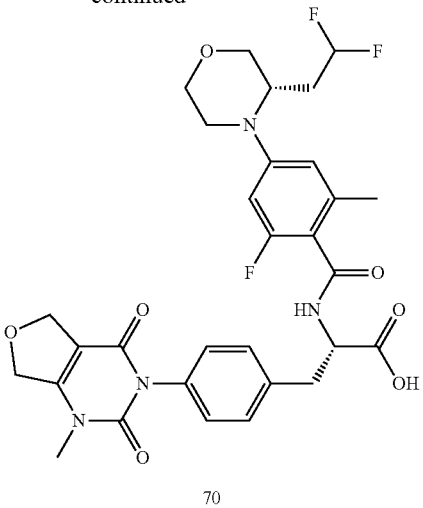

70

Synthesis of (S)-2-(4-((S)-3-(2,2-difluoroethyl)morpholino)-2-fluoro-6-methylbenzamido)-3-(4-(1-methyl-2,4-dioxo-1,2,5,7-tetrahydrofuro[3,4-d]pyrimidin-3(4H)-yl)phenyl)propanoic acid (70): The title compound was prepared according to the method presented for the synthesis of 1 using the ethyl ester of intermediate W and intermediate Q. MS (m/z) 617.2 [M+H]+. 1H NMR (400 MHz, DMSO-d6) δ 8.68 (d, J=8.0 Hz, 1H), 7.42-7.30 (m, 2H), 7.16-7.04 (m, 2H), 6.61-6.44 (m, 2H), 6.16 (tt, J=56.3, 4.5 Hz, 1H), 5.06 (t, J=3.6 Hz, 2H), 4.86 (t, J=3.6 Hz, 2H), 4.64 (ddd, J=11.9, 8.1, 4.2 Hz, 1H), 4.01 (d, J=9.3 Hz, 1H), 3.89 (dd, J=11.2, 3.5 Hz, 1H), 3.84 (d, J=11.6 Hz, 1H), 3.69-3.58 (m, 1H), 3.52 (td, J=11.6, 3.1 Hz, 1H), 3.31 (d, J=12.6 Hz, 1H), 3.23 (s, 3H), 3.19 (dd, J=14.3, 4.3 Hz, 1H), 3.08-2.85 (m, 2H), 2.43-2.25 (m, 1H), 2.03 (s, 3H), 1.75 (dd, J=19.1, 14.8 Hz, 1H).

α4β7 Integrin Cell Capture Assay

The potency of inhibitors in preventing α4β7 integrin interaction with MadCAM-1 was measured by monitoring the capture of α4β7 integrin expressing cells on a recombinant MadCAM-1 extracellular domain-coated plate.

384-well plates (Corning 3702) were coated with MadCAM-1 extracellular domain by dispensing 20 μL of MAdCAM-1 at 1.0 μg/mL per well and incubating overnight at 4° C. The plates were then washed with PBS and blocked with 3% BSA for 2 hours before being washed again.

RPM18866 cells were spun down and re-suspended in assay medium (DMEM+0.5% FBS+0.5 mM $MnCl_2$) at a density of $0.5 \times 10^6$ cells/mL. The cells were then dispensed (60 μL/well) to a 384-well plate (Greiner 781280) that was previously spotted with 60 nL of test compound per well. The plates were incubated at 37° C. for 1 hour. 50 μL of cells were transferred to the blocked, MadCAM-1-coated plates and incubated for 30 minutes at 37° C. 10 μL of 12% glutaraldehyde containing Hoechst 33342 (0.06 mg/mL) was added to the cells (2% glutaraldehyde and 0.01 mg/mL final concentrations). The plates were incubated for 90 minutes at room temperature. The plates were then washed 3 times with 70 μL of PBS per well and imaged on a Cellomics ArrayScan instrument. The cells that were bound to the plate were counted and plotted against the compound concentration to determine the $EC_{50}$ of the test compounds. Results are presented in Tables 1 and 2.

α4β1 Cell Capture Assay

The potency of inhibitors in preventing α4β1 integrin interaction with VCAM-1 was measured by monitoring the capture of α4β1 expressing cells to a recombinant VCAM-1 extracellular domain-coated plate.

384-well plates (Corning 3702) were coated with VCAM-1 extracellular domain by dispensing 20 μL of VCAM-1 at 0.5 μg/ml per well and incubating overnight at 4° C. The plates were then washed with PBS and blocked with 3% BSA for 2 hours before being washed again.

Jurkat cells were spun down and re-suspended in assay medium (DMEM+0.5% FBS+0.5 mM $MnCl_2$) at a density of $0.5 \times 10^6$ cells/ml. The cells were then dispensed (60 μL/well) to a 384-well plate (Greiner 781280) that was previously spotted with 60 nL of test compound per well. The plates were incubated at 37° C. for 1 hour. 50 μL of cells were transferred to the blocked, VCAM-1-coated plates and incubated for 30 minutes at 37° C. 10 μl of 12% glutaraldehyde containing Hoechst 33342 (0.06 mg/mL) was added to the cells (2% glutaraldehyde and 0.01 mg/ml Hoechst 33342 final concentrations). The plates were incubated for 90 minutes at room temperature. The plates were then washed 3 times with 70 μL of PBS per well and imaged on a Cellomics ArrayScan instrument. The cells that were bound to the plate were counted and plotted against the compound concentration to determine the $EC_{50}$ of the test compounds. Results are presented in Tables 1 and 2.

TABLE 1

| Example # | α4β7 EC50 (nM) | α4β1 EC50 (nM) |
|---|---|---|
| 1 | 1.4 | 10.3 |
| 2 | 13.6 | 905 |
| 3 | 0.5 | 18.5 |
| 4 | 1.2 | 63.7 |
| 5 | 0.2 | 16.6 |
| 6 | 0.3 | 9.9 |
| 7 | 0.5 | 15.3 |
| 9 | 1.6 | 117 |
| 11 | 0.5 | 30.1 |
| 13 | 0.8 | 38.9 |
| 15 | 0.21 | 10.6 |
| 17 | 0.7 | 58.9 |
| 19 | 2.0 | 127 |
| 23 | 0.2 | 9.8 |
| 25 | 0.1 | 3.4 |
| 27 | 0.1 | 8.6 |
| 55 | 0.1 | 3.4 |
| 57 | 0.2 | 2.8 |
| 59 | 0.1 | 2.9 |
| 61 | 0.4 | 11.5 |
| 63 | 0.1 | 3.7 |
| 64 | 0.1 | 1.8 |
| 66 | 0.1 | 4.8 |
| 68 | 0.3 | 14.9 |
| 69 | 0.2 | 20.8 |
| 70 | 3.9 | 2.4 |

TABLE 2

| Ex # | Structure | 1H-NMR | M/Z [M + H]+ | α4β7 EC50 (nM) | α4β1 EC50 (nM) |
|---|---|---|---|---|---|
| 28 | 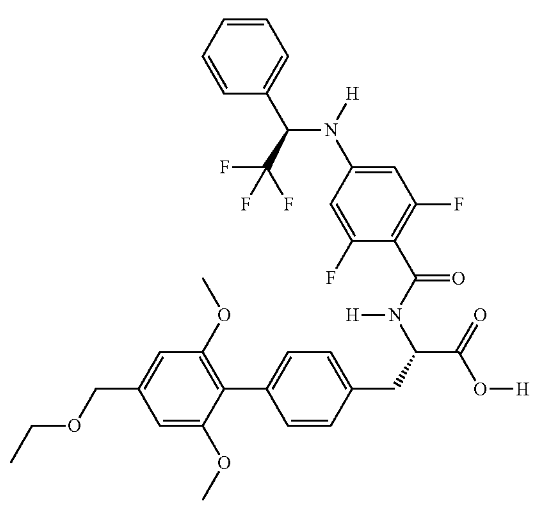 [SMILES: CCOCc1cc(OC)c(-c2ccc(C[C@H](NC(=O)c3c(F)cc(N[C@H](c4ccccc4)C(F)(F)F)cc3F)C(=O)O)cc2)c(OC)c1] | $^1$H NMR (400 MHz, DMSO-$d_6$) δ 12.69 (s, 1H), 8.66 (s, 1H), 7.62-7.55 (m, 2H), 7.52 (d, J = 10.2 Hz, 1H), 7.46-7.34 (m, 3H), 7.25-7.17 (m, 2H), 7.14-7.05 (m, 2H), 6.68 (s, 2H), 6.57 (d, J = 11.3 Hz, 2H), 5.70 (p, J = 8.4 Hz, 1H), 4.47 (s, 3H), 3.64 (s, 6H), 3.53 (q, J = 7.0 Hz, 2H), 3.09 (dd, J = 14.0, 4.7 Hz, 1H), 2.93 (dd, J = 14.1, 9.5 Hz, 1H), 1.19 (t, J = 7.0 Hz, 3H). | 673.5 | 7.2 | 70.7 |

TABLE 2-continued

| Ex # | Structure | 1H-NMR | M/Z [M + H]+ | α4β7 EC50 (nM) | α4β1 EC50 (nM) |
|---|---|---|---|---|---|
| 29 | 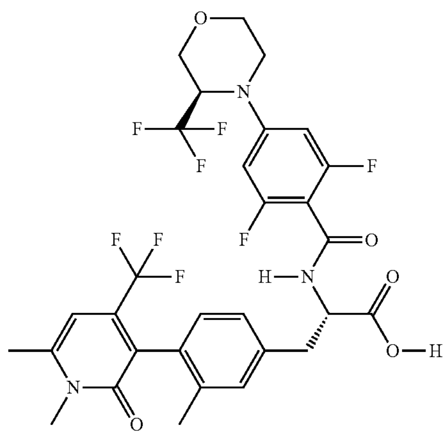 [SMILES: Cc1cc(C[C@H](NC(=O)c2c(F)cc(N3CCOC[C@@H]3C(F)(F)F)cc2F)C(=O)O)ccc1-c1c(C(F)(F)F)cc(C)n(C)c1=O] | 1H MR (400 MHz, DMSO-d$_6$) δ 8.85 (dd, J = 7.8, 2.9 Hz, 1H), 7.16 (d, J = 9.3 Hz, 1H), 7.12-7.05 (m, 1H), 6.86 (d, J = 7.7 Hz, 1H), 6.77 (d, J = 12.0 Hz, 2H), 6.51 (s, 1H), 4.92 (d, J = 11.6 Hz, 1H), 4.58-4.49 (m, 1H), 4.16 (d, J = 12.6 Hz, 1H), 3.95 (dd, J = 11.3, 3.4 Hz, 1H), 3.74 (d, J = 14.3 Hz, 1H), 3.56 (m, 1H), 3.50 (s, 3H), 3.43 (d, J = 12.8 Hz, 1H), 3.24 (t, J = 14.8 Hz, 1H), 3.10 (dd, J = 14.3, 4.6 Hz, 1H), 3.04-2.90 (m, 1H), 2.49 (s, 3H), 1.97 (s, 3H). | 662.2 | 0.6 | 29.0 |
| 30 | 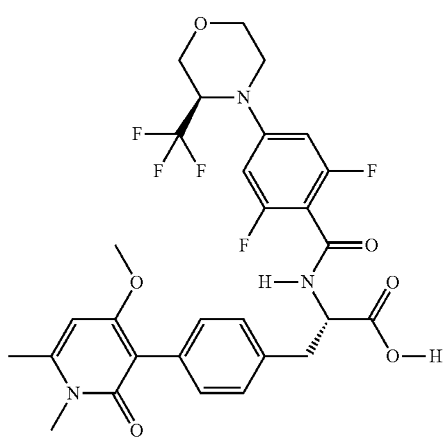 [SMILES: COc1cc(C)n(C)c(=O)c1-c1ccc(C[C@H](NC(=O)c2c(F)cc(N3CCOC[C@@H]3C(F)(F)F)cc2F)C(=O)O)cc1] | 1H NMR (400 MHz, DMSO-d6) δ 8.83 (d, J = 7.8 Hz, 1H), 7.20 (s, 4H), 6.78 (d, J = 11.7 Hz, 2H), 6.31 (s, 1H), 4.91 (tt, J = 8.7, 5.4 Hz, 1H), 4.52 (ddd, J = 9.2, 7.8, 4.9 Hz, 1H), 4.17 (d, J = 12.7 Hz, 1H), 3.96 (dd, J = 11.5, 3.8 Hz, 1H), 3.73 (m, 1H), 3.72 (s, 3H), 3.56 (td, J = 11.9, 3.4 Hz, 1H), 3.47-3.43 (m, 1H), 3.41 (s, 3H), 3.25 (t, J = 12.3 Hz, 1H), 3.09 (dd, J = 14.0, 4.9 Hz, 1H), 3.01-2.88 (m, 1H), 2.41 (s, 3H). | 610.3 | 0.5 | 10.1 |
| 31 | 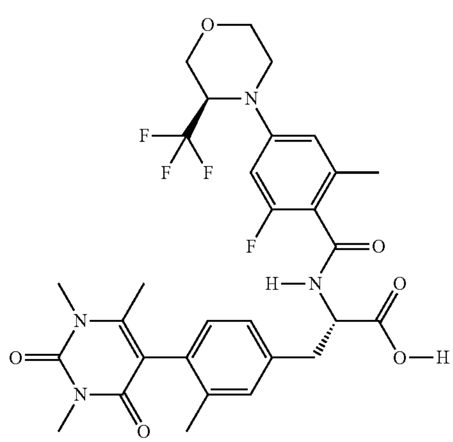 [SMILES: Cc1cc(C[C@H](NC(=O)c2c(C)cc(N3CCOC[C@@H]3C(F)(F)F)cc2F)C(=O)O)ccc1-c1c(C)n(C)c(=O)n(C)c1=O] | 1H NMR (400 MHz, DMSO-d6) δ 8.68 (d, J = 8.1 Hz, 1H), 7.19 (d, J = 11.5 Hz, 1H), 7.12 (t, J = 8.7 Hz, 1H), 6.92 (m, 1H), 6.68 (d, J = 13.9 Hz, 1H), 6.64 (s, 1H), 4.89-4.78 (m, 1H), 4.61 (m, 1H), 4.14 (d, J = 12.7 Hz, 1H), 3.94 (d, J = 11.7 Hz, 1H), 3.73 (d, J = 14.6 Hz, 1H), 3.52 (m, 1H), 3.41 (s, 3H), 3.35 (d, J = 15.3 Hz, 1H), 3.26 (d, J = 13.2 Hz, 1H), 3.21 (s, 3H), 3.13 (dd, J = 13.8, 3.7 Hz, 1H), 2.95-2.86 (m, 1H), 2.02 (s, 6H), 1.97 (s, 3H). | 621.2 | 0.2 | 11.6 |

TABLE 2-continued

| Ex # | Structure | 1H-NMR | M/Z [M + H]+ | α4β7 EC50 (nM) | α4β1 EC50 (nM) |
|---|---|---|---|---|---|
| 32 | 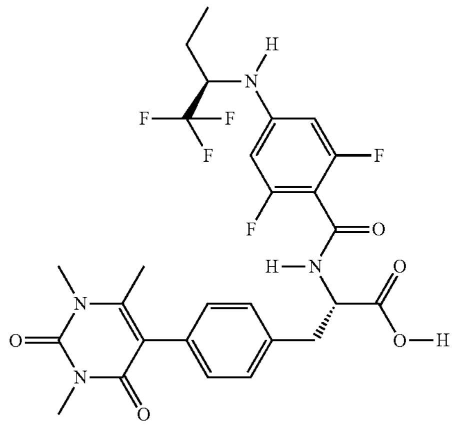 [SMILES: CC[C@@H](Nc1cc(F)c(C(=O)N[C@@H](Cc2ccc(-c3c(C)n(C)c(=O)n(C)c3=O)cc2)C(=O)O)c(F)c1)C(F)(F)F] | 1H NMR (400 MHz, DMSO-d6) δ 8.67 (d, J = 8.0 Hz, 1H), 7.28 (d, J = 8.1 Hz, 2H), 7.08 (d, J = 8.1 Hz, 2H), 6.76 (d, J = 10.0 Hz, 1H), 6.44 (d, J = 11.3 Hz, 2H), 4.58-4.52 (m, 1H), 4.34-4.28 (m, 1H), 3.41 (s, 2H), 3.21 (s, 3H), 3.13 (dd, J = 13.9, 4.6 Hz, 1H), 2.95 (dd, J = 14.0, 10.0 Hz, 1H), 2.10 (s, 3H), 1.82-1.72 (m, 1H), 1.59-1.47 (m, 1H), 0.93 (t, J = 7.3 Hz, 3H). | 583.2 | 1.2 | 14.4 |
| 33 | 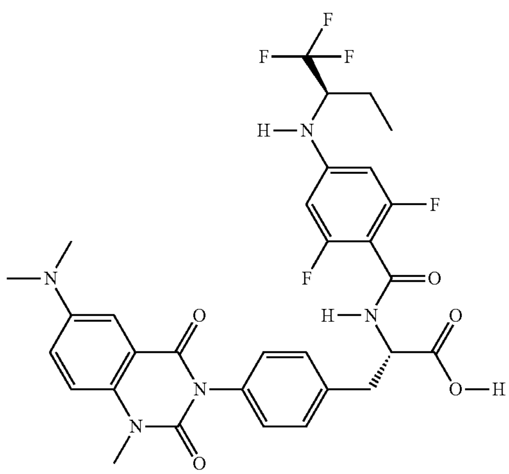 [SMILES: CC[C@@H](Nc1cc(F)c(C(=O)N[C@@H](Cc2ccc(-n3c(=O)c4cc(N(C)C)ccc4n(C)c3=O)cc2)C(=O)O)c(F)c1)C(F)(F)F] | 1H NMR (400 MHz, DMSO-d6) δ 8.73 (d, J = 7.8 Hz, 1H), 7.37 (dd, J = 14.4, 8.7 Hz, 4H), 7.26 (d, J = 2.9 Hz, 1H), 7.16 (d, J = 8.3 Hz, 2H), 6.76 (d, J = 9.5 Hz, 1H), 6.45 (d, J = 11.6 Hz, 2H), 4.58-4.47 (m, 1H), 4.30 (d, J = 10.1 Hz, 1H), 3.48 (s, 3H), 3.14 (dd, J = 14.2, 4.6 Hz, 1H), 3.00 (dd, J = 14.2, 9.8 Hz, 1H), 2.93 (s, 6H), 1.76 (ddd, J = 13.5, 7.3, 3.2 Hz, 1H), 1.52 (ddd, J = 13.6, 10.4, 7.1 Hz, 1H), 0.92 (t, J = 7.3 Hz, 3H). | 648.3 | 2.5 | 104.9 |
| 34 | 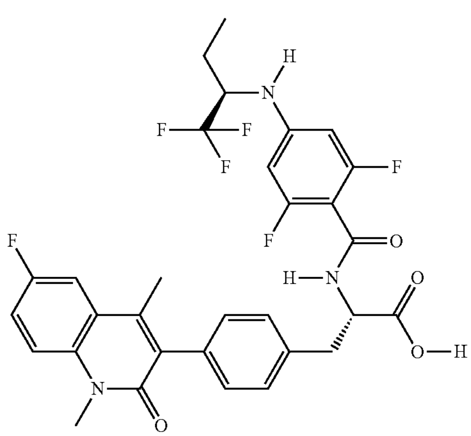 [SMILES: CC[C@@H](Nc1cc(F)c(C(=O)N[C@@H](Cc2ccc(-c3c(C)c4cc(F)ccc4n(C)c3=O)cc2)C(=O)O)c(F)c1)C(F)(F)F] | 1H NMR (400 MHz, DMSO-d6) δ 8.70 (d, J = 8.0 Hz, 1H), 7.68 (dd, J = 10.1, 2.8 Hz, 1H), 7.60 (dd, J = 9.4, 4.9 Hz, 1H), 7.58-7.49 (m, 1H), 7.33 (d, J = 8.1 Hz, 2H), 7.14 (d, J = 8.1 Hz, 2H), 6.77 (d, J = 9.5 Hz, 1H), 6.46 (d, J = 11.4 Hz, 2H), 4.63-4.53 (m, 1H), 4.38-4.25 (m, 1H), 3.66 (s, 3H), 3.17 (d, J = 13.8, 4.6 Hz, 1H), 2.99 (dd, J = 13.9, 10.1 Hz, 1H), 2.23 (s, 3H), 1.85-1.70 (m, 1H), 1.61-1.45 (m, 1H), 0.93 (t, J = 7.3 Hz, 3H). | 620.2 | 3.2 | 61.4 |

TABLE 2-continued

| Ex # | Structure | 1H-NMR | M/Z [M + H]+ | α4β7 EC50 (nM) | α4β1 EC50 (nM) |
|---|---|---|---|---|---|
| 35 | 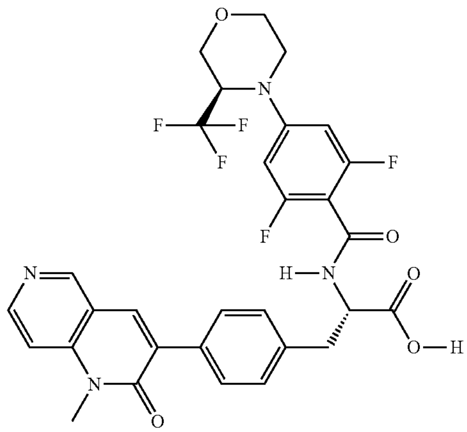 [SMILES: Cn1c(=O)c(-c2ccc(C[C@H](NC(=O)c3c(F)cc(N4CCOC[C@@H]4C(F)(F)F)cc3F)C(=O)O)cc2)cc2cnccc21] | 1H NMR (400 MHz, DMSO-d6) δ 9.10 (s, 1H), 8.85 (d, J = 7.9 Hz, 1H), 8.71 (s, 1H), 8.27 (s, 1H), 7.74 (d, J = 6.0 Hz, 1H), 7.67 (d, J = 8.0 Hz, 2H), 7.39 (d, J = 8.0 Hz, 2H), 6.77 (d, J = 11.6 Hz, 2H), 4.96-4.86 (m, 1H), 4.63-4.55 (m, 1H), 4.17 (d, J = 12.7 Hz, 1H), 3.96 (dd, J = 11.4, 3.2 Hz, 1H), 3.74 (d, J = 14.0 Hz, 1H), 3.71 (s, 3H), 3.62-3.50 (m, 1H), 3.43 (d, J = 12.7 Hz, 1H), 3.26 (d, J = 16.6 Hz, 1H), 3.18 (dd, J = 13.8, 4.7 Hz, 1H), 3.02 (dd, J = 13.6, 10.0 Hz, 1H). | 617.2 | 1.1 | 34.1 |
| 36 | 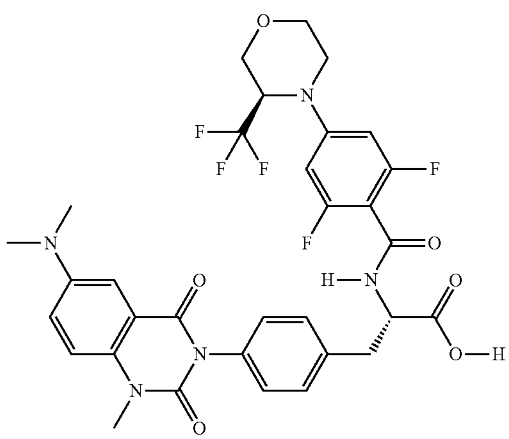 [SMILES: CN(C)c1ccc2c(c1)c(=O)n(-c1ccc(C[C@H](NC(=O)c3c(F)cc(N4CCOC[C@@H]4C(F)(F)F)cc3F)C(=O)O)cc1)c(=O)n2C] | 1H NMR (400 MHz, DMSO-d6) δ 8.90 (d, J = 7.8 Hz, 1H), 7.42-7.29 (m, 4H), 7.26 (d, J = 2.8 Hz, 1H), 71.6 (d, J = 8.2 Hz, 2H), 6.77 (d, J = 11.6 Hz, 2H), 4.91 (dd, J = 8.6, 3.6 Hz, 1H), 4.61-4.50 (m, 1H), 4.15 (d, J = 12.7 Hz, 1H), 3.94 (dd, J = 11.5, 3.8 Hz, 1H), 3.73 (d, J = 12.6 Hz, 1H), 3.60-3.49 (m, 1H), 3.49-3.45 (m, 3H), 3.42 (d, J = 12.5 Hz, 1H), 3.24 (d, J = 10.9 Hz, 1H), 3.16 (dd, J = 14.3, 4.7 Hz, 1H), 3.02 (dd, J = 14.2, 9.8 Hz, 1H), 2.93 (s, 6H). | 676.3 | 1.2 | 27.3 |
| 37 | 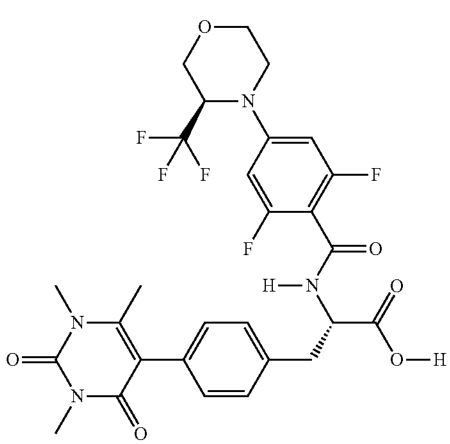 [SMILES: Cc1c(-c2ccc(C[C@H](NC(=O)c3c(F)cc(N4CCOC[C@@H]4C(F)(F)F)cc3F)C(=O)O)cc2)c(=O)n(C)c(=O)n1C] | 1H NMR (400 MHz, DMSO-d6) δ 8.83 (d, J = 8.1 Hz, 1H), 7.29 (d, J = 7.9 Hz, 2H), 7.08 (d, J = 8.0 Hz, 2H), 6.76 (d, J = 11.7 Hz, 2H), 4.96-4.87 (m, 1H), 4.61-4.54 (m, 1H), 4.16 (d, J = 13.0 Hz, 1H), 3.98-3.93 (m, 1H), 3.73 (d, J = 16.2 Hz, 1H), 3.61-3.54 (m, 3H), 3.41 (s, 3H), 3.26-3.22 (m, 1H), 3.21 (s, 3H), 3.17-3.12 (m, 1H), 2.99-2.91 (m, 1H), 2.10 (s, 3H). | 611.2 | 0.4 | 9.8 |

TABLE 2-continued

| Ex # | Structure | 1H-NMR | M/Z [M + H]+ | α4β7 EC50 (nM) | α4β1 EC50 (nM) |
|---|---|---|---|---|---|
| 38 | 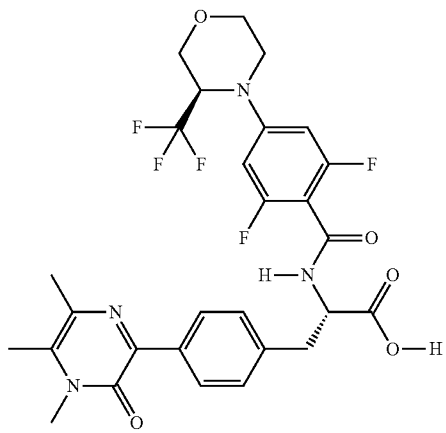 [SMILES: Cc1nc(-c2ccc(C[C@H](NC(=O)c3c(F)cc(N4CCOC[C@@H]4C(F)(F)F)cc3F)C(=O)O)cc2)c(=O)n(C)c1C] | 1H NMR (400 MHz, DMSO-d6) δ 8.81 (d, J = 7.9 Hz, 1H), 8.24 (d, J = 8.4 Hz, 2H), 7.31 (d, J = 8.4 Hz, 2H), 6.77 (d, J = 11.7 Hz, 2H), 4.90 (qd, J = 8.6, 3.3 Hz, 1H), 4.56 (ddd, J = 9.7, 8.0, 4.7 Hz, 1H), 4.16 (d, J = 12.7 Hz, 1H), 3.95 (dd, J = 11.5, 3.8 Hz, 1H), 3.74 (d, J = 12.9 Hz, 1H), 3.58 (m, 1H), 3.54 (s, 3H), 3.43 (d, J = 13.4 Hz, 1H), 3.29-3.18 (m, 1H), 3.15 (dd, J = 13.9, 4.7 Hz, 1H), 2.98 (dd, J = 13.9, 9.8 Hz, 1H), 2.37 (s, 3H), 2.35 (s, 3H). | 595.2 | 4.9 | 86.1 |
| 39 | 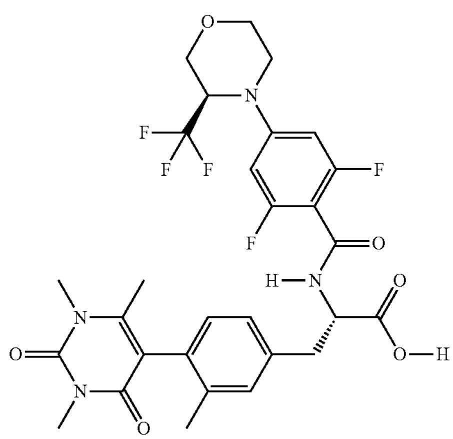 [SMILES: Cc1cc(C[C@H](NC(=O)c2c(F)cc(N3CCOC[C@@H]3C(F)(F)F)cc2F)C(=O)O)ccc1-c1c(C)n(C)c(=O)n(C)c1=O] | 1H NMR (400 MHz, DMSO-d6) δ 8.82 (d, J = 7.7 Hz, 1H), 7.17 (d, J = 8.8 Hz, 1H), 7.10 (t, J = 7.3 Hz, 1H), 6.92 (t, J = 6.1 Hz, 1H), 6.76 (d, J = 11.5 Hz, 2H), 4.96-4.86 (m, 1H), 4.60-4.50 (m, 1H), 4.16 (d, J = 12.8 Hz, 1H), 3.96 (d, J = 10.9 Hz, 1H), 3.74 (d, J = 12.6 Hz, 1H), 3.56 (t, J = 11.8 Hz, 1H), 3.46-3.42 (m, 1H), 3.40 (s, J = 2.2 Hz, 3H), 3.25 (d, J = 13.0 Hz, 1H), 3.21 (s, J = 2.1 Hz, 3H), 3.14-3.07 (m, 1H), 2.98-2.89 (m, 1H), 2.03 (s, J = 2.6 Hz, 3H), 1.97 (s, 3H). | 625.2 | 0.4 | 12.8 |
| 40 | 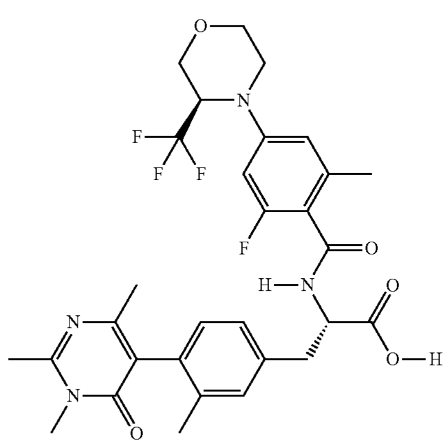 [SMILES: Cc1cc(C[C@H](NC(=O)c2c(C)cc(N3CCOC[C@@H]3C(F)(F)F)cc2F)C(=O)O)ccc1-c1c(C)nc(C)n(C)c1=O] | 1H NMR (400 MHz, DMSO-d6) δ 8.69 (d, J = 8.3 Hz, 1H), 7.21 (d, J = 11.7 Hz, 1H), 7.14 (t, J = 8.8 Hz, 1H), 6.93 (t, J = 7.0 Hz, 1H), 6.67 (d, J = 18.0 Hz, 1H), 6.64 (s, 1H), 4.93-4.74 (m, 1H), 4.68-4.56 (m, 1H), 4.14 (d, J = 11.0 Hz, 1H), 3.94 (d, J = 11.0 Hz, 1H), 3.73 (d, J = 11.0 Hz, 1H), 3.58-3.49 (m, 1H), 3.47 (s, 3H), 3.35 (d, J = 12.9 Hz, 1H), 3.27 (d, J = 16.7 Hz, 1H), 3.16-3.11 (m, 1H), 2.96-2.87 (m, 1H), 2.57 (s, 3H), 2.03 (d, J = 2.0 Hz, 3H), 2.01 (d, J = 4.0 Hz, 3H), 1.92 (s, 3H). | 605.2 | 0.3 | 7.7 |

TABLE 2-continued

| Ex # | Structure | 1H-NMR | M/Z [M + H]+ | α4β7 EC50 (nM) | α4β1 EC50 (nM) |
|---|---|---|---|---|---|
| 41 | 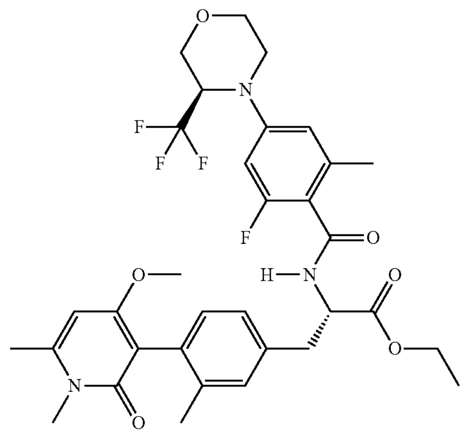 [SMILES: CCOC(=O)[C@H](Cc1ccc(-c2c(OC)cc(C)n(C)c2=O)c(C)c1)NC(=O)c1c(C)cc(N2CCOC[C@@H]2C(F)(F)F)cc1F] | 1H NMR (400 MHz, DMSO-d6) δ 8.70 (d, J = 7.9 Hz, 1H), 7.10 (s, 1H), 7.03 (d, J = 8.0 Hz, 1H), 6.90-6.84 (m, 1H), 6.69 (d, J = 13.1 Hz, 1H), 6.66 (s, 1H), 6.30 (s, 1H), 4.88-4.78 (m, 1H), 4.62-4.54 (m, 1H), 4.15 (d, J =12.5 Hz, 1H), 3.95 (d, J = 14.1 Hz, 1H), 3.73 (d, J = 16.1 Hz, 1H), 3.68 (s, 3H), 3.55 (t, J = 12.8 Hz, 1H), 3.41 (s, 3H), 3.35 (d, J = 11.5 Hz, 1H), 3.27 (d, J = 10.9 Hz, 1H), 3.09 (dd, J = 14.1, 4.0 Hz, 1H), 2.91 (dd, J = 13.9, 10.6 Hz, 1H), 2.42 (s, 3H), 2.08 (s, 3H), 1.98 (d, J = 2.2 Hz, 3H). | 620.2 | 0.3 | 8.3 |
| 42 | 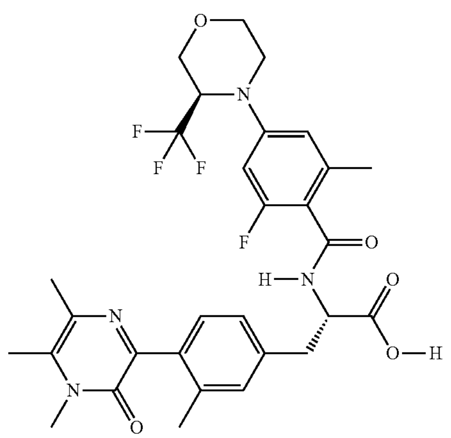 [SMILES: Cc1cc(C[C@H](NC(=O)c2c(C)cc(N3CCOC[C@@H]3C(F)(F)F)cc2F)C(=O)O)ccc1-c1nc(C)c(C)n(C)c1=O] | 1H NMR (400 MHz, DMSO-d6) δ 8.69 (d, J = 8.0 Hz, 1H), 7.19 (d, J = 7.7 Hz, 1H), 7.15-7.10 (m, 2H), 6.73-6.64 (m, 2H), 4.89-4.78 (m, 1H), 4.59-4.53 (m, 1H), 4.14 (d, J = 12.7 Hz, 1H), 3.94 (d, J = 11.9 Hz, 1H), 3.73 (d, J = 10.5 Hz, 1H), 3.56 (d, J = 12.8 Hz, 1H), 3.51 (s, 3H), 3.35 (d, J = 11.5 Hz, 1H), 3.27 (d, J = 12.1 Hz, 1H), 3.11 (dd, J = 14.1, 4.4 Hz, 1H), 2.95 (dd, J = 13.6, 10.4 Hz, 1H), 2.36 (s, 3H), 2.30 (s, 3H), 2.15 (s, 3H), 2.10 (s, 3H). | 605.2 | 0.3 | 5.8 |
| 43 | 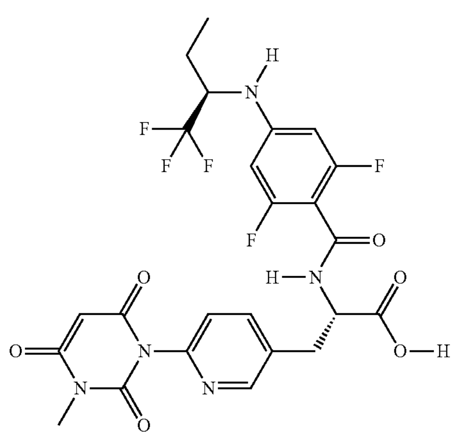 | 1H NMR (400 MHz, DMSO-d6) δ 8.78 (d, J = 7.8 Hz, 1H), 8.44 (d, J = 2.3 Hz, 1H), 7.84 (dd, J = 8.2, 2.4 Hz, 1H), 7.26 (d, J = 8.1 Hz, 1H), 6.78 (d, J = 9.4 Hz, 1H), 6.46 (d, J = 11.6 Hz, 2H), 5.73 (s, 1H), 4.62-4.42 (m, 1H), 4.31 (d, J = 8.9 Hz, 1H), 3.32 (s, 3H), 3.26-2.93 (m, 2H), 2.32 (s, 3H), 1.78 (ddd, J = 13.9, 7.3, 3.2 Hz, 1H), 1.54 (dd, J = 6.9, 3.4 Hz, 1H), 0.92 (d, J = 7.4 Hz, 2H). | 570.2 | 15.9 | 661.3 |

TABLE 2-continued

| Ex # | Structure | 1H-NMR | M/Z [M + H]+ | α4β7 EC50 (nM) | α4β1 EC50 (nM) |
| --- | --- | --- | --- | --- | --- |
| 44 | 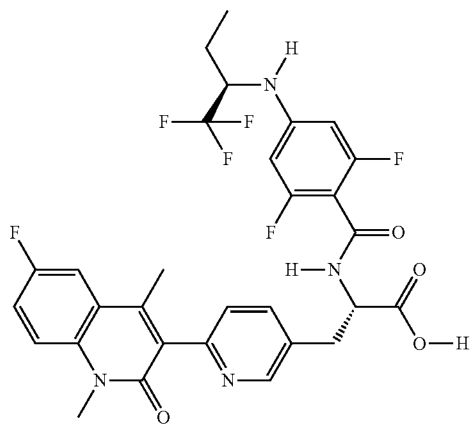 [SMILES: CC[C@@H](Nc1cc(F)c(C(=O)N[C@@H](Cc2ccc(-c3c(C)c4cc(F)ccc4n(C)c3=O)nc2)C(=O)O)c(F)c1)C(F)(F)F] | 1H NMR (400 MHz, DMSO-d6) δ 8.78 (d, J = 8.5 Hz, 1H), 8.73 (s, 1H), 8.19-8.11 (m, 1H), 7.79 (dd, J = 10.0, 2.6 Hz, 1H), 7.71-7.61 (m, 3H), 6.79 (d, J = 9.5 Hz, 1H), 6.45 (d, J = 11.5 Hz, 2H), 4.77-4.69 (m, 1H), 4.37-4.26 (m, 1H), 3.69 (s, 3H), 3.38-3.30 (m, 1H), 3.08 (dd, J = 14.2, 10.8 Hz, 1H), 2.24 (s, 3H), 1.83-1.72 (m, 1H), 1.59-1.47 (m, 1H), 0.93 (t, J = 7.4 Hz, 3H). | 621.2 | 2.9 | 37.6 |
| 45 | 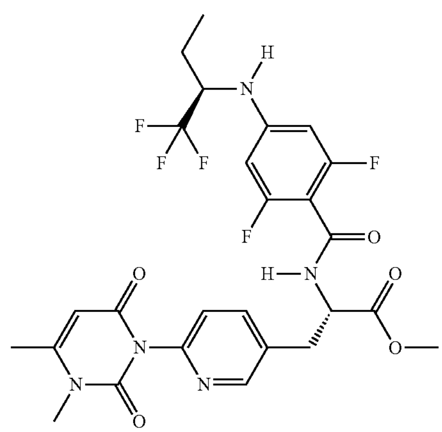 | 1H NMR (400 MHz, DMSO-d6) δ 8.92 (d, J = 7.6 Hz, 1H), 8.44 (d, J = 2.3 Hz, 1H), 7.85 (dd, J = 8.1, 2.4 Hz, 1H), 7.26 (d, J = 8.1 Hz, 1H), 6.80 (d, J = 9.4 Hz, 1H), 6.47 (d, J = 11.6 Hz, 2H), 5.73 (s, 1H), 4.64 (ddd, J = 9.8, 7.5, 5.1 Hz, 1H), 4.32 (d, J = 8.7 Hz, 1H), 3.65 (s, 3H), 3.32 (s, 3H), 3.27-2.97 (m, 2H), 2.32 (s, 3H), 1.78 (ddd, J = 13.9, 7.4, 3.3 Hz, 1H), 1.53 (ddd, J = 13.8, 10.4, 7.1 Hz, 1H), 0.93 (t, J = 7.3 Hz, 3H). | 584.2 | NA | NA |
| 46 | 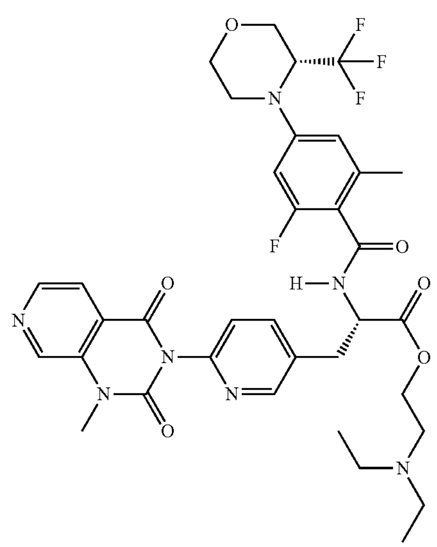 [SMILES: CCN(CC)CCOC(=O)[C@H](Cc1ccc(-n2c(=O)c3ccncc3n(C)c2=O)nc1)NC(=O)c1c(C)cc(N2CCOC[C@@H]2C(F)(F)F)cc1F] | 1H NMR (400 MHz, DMSO-d6) δ 9.28 (s, 1H), 9.05-8.93 (m, 2H), 8.58 (d, J = 4.9 Hz, 1H), 8.51 (d, J = 2.3 Hz, 1H), 7.96 (dd, J = 8.2, 2.4 Hz, 1H), 7.90 (dd, J = 5.0, 0.7 Hz, 1H), 7.51-7.41 (m, 1H), 6.79-6.64 (m, 2H), 4.83 (ddd, J = 10.1, 7.6, 5.5 Hz, 1H), 4.50-4.30 (m, 2H), 4.16 (d, J = 12.6 Hz, 1H), 4.01-3.90 (m, 1H), 3.76 (d, 2H), 3.61 (s, 3H), 3.59-3.50 (m, 1H), 3.45-3.32 (m, 3H), 3.32-3.05 (m, 7H), 2.08 (s, 3H), 1.22 (td, J = 7.2, 2.1 Hz, 7H) | 730.3 | NA | NA |

TABLE 2-continued

| Ex # | Structure | 1H-NMR | M/Z [M + H]+ | α4β7 EC50 (nM) | α4β1 EC50 (nM) |
|---|---|---|---|---|---|
| 47 | 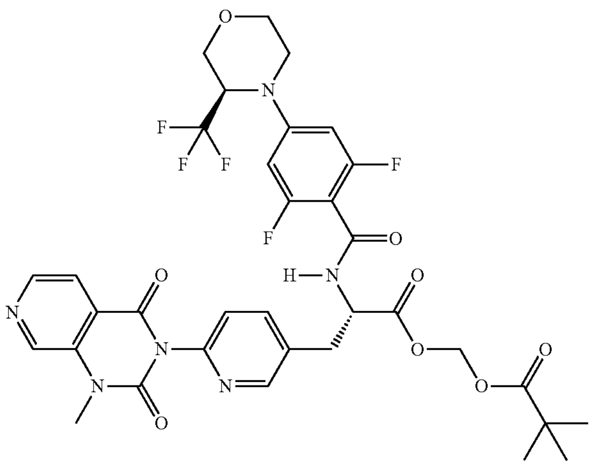 [SMILES: Cn1c(=O)n(-c2ccc(C[C@H](NC(=O)c3c(F)cc(N4CCOC[C@@H]4C(F)(F)F)cc3F)C(=O)OCOC(=O)C(C)(C)C)cn2)c(=O)c2ccncc21] | 1H NMR (400 MHz, DMSO-d6) δ 9.13 (d, J = 7.6 Hz, 1H), 9.00 (s, 1H), 8.57 (d, J = 5.0 Hz, 1H), 8.51 (d, J = 2.2 Hz, 1H), 7.98-7.86 (m, 2H), 7.42 (d, J = 8.1 Hz, 1H), 6.79 (d, J = 11.7 Hz, 2H), 5.83-5.74 (m, 2H), 4.99-4.87 (m, 1H), 4.77-4.67 (m, 1H), 4.16 (d, J = 12.7 Hz, 1H), 3.96 (dd, J = 11.4, 3.7 Hz, 1H), 3.74 (d, J = 12.8 Hz, 1H), 3.61 (s, 3H), 3.54 (d, J = 10.6 Hz, 1H), 3.44 (d, J = 12.6 Hz, 1H), 3.24 (dd, J = 14.3, 5.4 Hz, 2H), 3.12 (dd, J = 14.3, 10.3 Hz, 1H), 1.16 (s, 9H). | 749.7 | NA | NA |
| 48 | 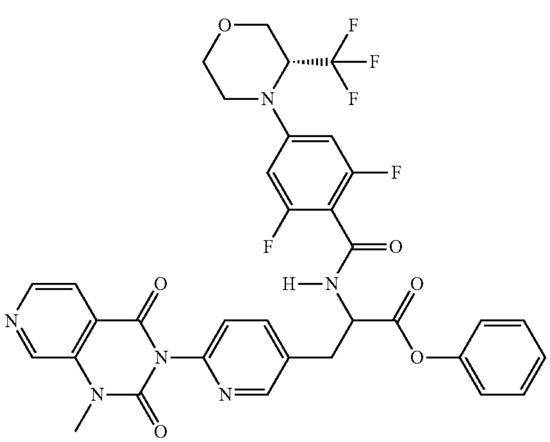 [SMILES: Cc1cc(N2CCOC[C@@H]2C(F)(F)F)cc(F)c1C(=O)NC(Cc1ccc(-n2c(=O)c3ccncc3n(C)c2=O)nc1)C(=O)Oc1ccccc1] | 1H NMR (400 MHz, DMSO-d6) δ 9.34 (dd, J = 6.9, 3.3 Hz, 1H), 9.01 (s, 1H), 8.58 (d, J = 4.9 Hz, 2H), 8.03 (dd, J = 8.4, 2.2 Hz, 1H), 7.92 (d, J = 4.9 Hz, 1H), 7.50-7.41 (m, 3H), 7.28 (t, J = 7.4 Hz, 1H), 7.04 (d, J = 7.9 Hz, 2H), 6.82 (d, J = 11.7 Hz, 2H), 4.93 (s, 1H), 4.92-4.84 (m, 1H), 4.17 (d, J = 12.7 Hz, 1H), 3.96 (dd, J = 11.4, 3.7 Hz, 1H), 3.75 (d, J = 13.0 Hz, 1H), 3.62 (s, 3H), 3.60-3.53 (m, 1H), 3.45 (d, J = 12.2 Hz, 1H), 3.37 (d, J = 7.9 Hz, 1H), 3.34-3.30 (m, 1H), 3.29-3.21 (m, 1H). | 710.9 | NA | NA |

TABLE 2-continued
| Ex # | Structure | 1H-NMR | M/Z [M + H]+ | α4β7 EC50 (nM) | α4β1 EC50 (nM) |
|---|---|---|---|---|---|
| 49 | 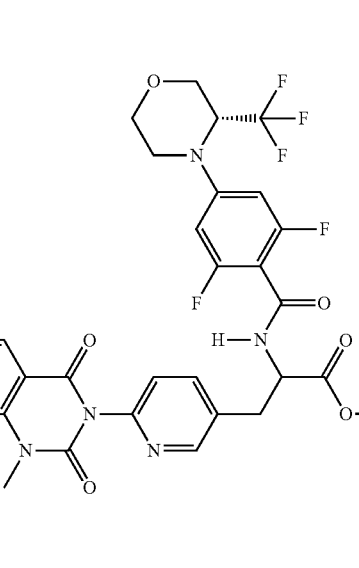 | 1H NMR (400 MHz, DMSO-d6) δ 9.17 (d, J = 7.3 Hz, 1H), 9.01 (s, 1H), 8.58 (d, J = 5.0 Hz, 1H), 8.51 (d, J = 2.2 Hz, 1H), 7.94 (d, J = 8.5 Hz, 1H), 7.90 (d, J = 5.0 Hz, 1H), 7.45 (d, J = 8.1 Hz, 1H), 6.81 (d, J = 11.8 Hz, 2H), 4.93 (d, J = 10.2 Hz, 1H), 4.75 (q, J = 7.4 Hz, 1H), 4.47-4.27 (m, 2H), 4.18 (d, J = 12.8 Hz, 1H), 4.01-3.92 (m, 1H), 3.75 (d, J = 12.8 Hz, 1H), 3.61 (s, 3H), 3.55 (t, J = 11.9 Hz, 1H), 3.45 (d, J = 12.7 Hz, 1H), 3.37 (s, 2H), 3.26 (dd, J = 14.2, 5.7 Hz, 1H), 3.20 (s, 1H), 3.18 (m, 5H), 1.20 (td, J = 7.2, 2.2 Hz, 6H). | 734.4 | NA | NA |
| 50 | 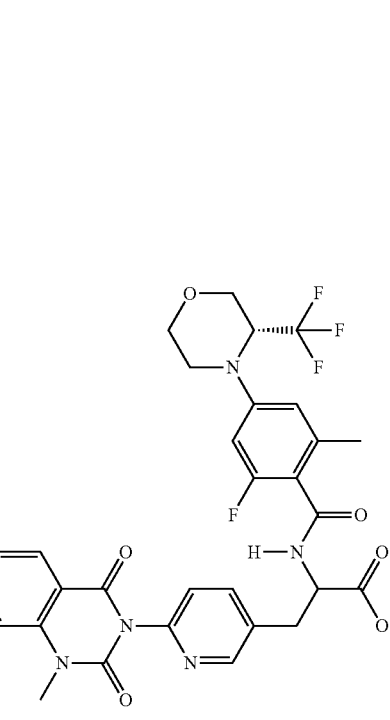 | 1H NMR (400 MHz, DMSO-d6) δ 9.18 (d, J = 7.1 Hz, 1H), 9.01 (s, 1H), 8.58 (d, J = 5.0 Hz, 2H), 8.04 (dd, J = 8.1, 2.3 Hz, 1H), 7.92 (d, J = 5.0 Hz, 1H), 7.50-7.39 (m, 3H), 7.29 (t, J = 7.4 Hz, 1H), 7.13-6.97 (m, 2H), 6.84-6.61 (m, 2H), 5.21-4.67 (m, 2H), 4.15 (d, J = 12.7 Hz, 1H), 4.03 (q, J = 7.1 Hz, 1H), 3.99-3.90 (m, 1H), 3.74 (d, J = 12.9 Hz, 1H), 3.62 (s, 3H), 3.62-3.48 (m, 1H), 3.46-3.34 (m, 2H), 3.32 (s, 4H), 3.27 (d, J = 14.2 Hz, 1H), 3.22-3.05 (m, 1H), 2.69 (s, 2H), 2.11 (d, J = 2.3 Hz, 3H), 1.99 (s, 2H), 1.26 (dd, J = 6.6, 5.4 Hz, 6H), 1.17 (t, J = 7.1 Hz, 2H). | 707.2 | NA | NA |

TABLE 2-continued

| Ex # | Structure | 1H-NMR | M/Z [M + H]+ | α4β7 EC50 (nM) | α4β1 EC50 (nM) |
|---|---|---|---|---|---|
| 51 | 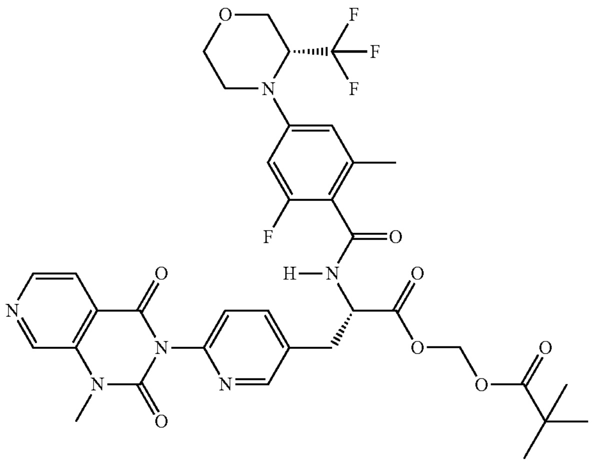 [SMILES: Cc1cc(N2CCOC[C@@H]2C(F)(F)F)cc(F)c1C(=O)N[C@@H](Cc1ccc(-n2c(=O)c3ccncc3n(C)c2=O)nc1)C(=O)OCOC(=O)C(C)(C)C] | 1H NMR (400 MHz, DMSO-d6) δ 9.08-8.92 (m, 2H), 8.57 (d, J = 5.0 Hz, 1H), 8.51 (d, J = 2.3 Hz, 1H), 7.96 (dd, J = 8.1, 2.4 Hz, 1H), 7.94-7.86 (m, 1H), 7.42 (d, J = 8.1 Hz, 1H), 6.78-6.62 (m, 2H), 5.81 (q, J = 5.8 Hz, 2H), 4.81 (dd, J = 7.5, 4.2 Hz, 1H), 4.15 (d, J = 12.6 Hz, 2H), 3.95 (dd, J = 11.4, 3.7 Hz, 1H), 3.75 (s, 1H), 3.61 (s, 3H), 3.60-3.44 (m, 1H), 3.36 (d, J = 12.2 Hz, 1H), 3.26 (dd, J = 14.3, 4.5 Hz, 1H), 3.09 (dd, J = 14.3, 11.0 Hz, 1H), 2.04 (s, 3H), 1.17 (s, 9H). | 745.3 | NA | NA |
| 52 | 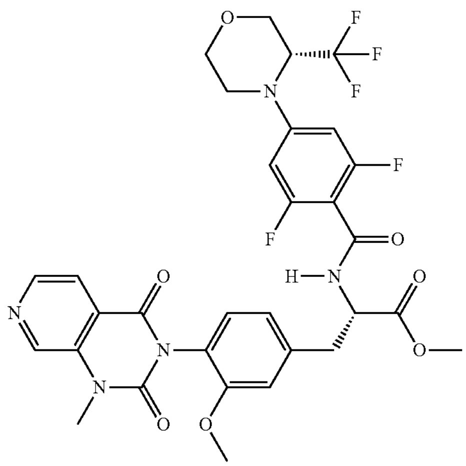 [SMILES: COC(=O)[C@H](Cc1ccc(-n2c(=O)c3ccncc3n(C)c2=O)c(OC)c1)NC(=O)c1c(F)cc(N2CCOC[C@@H]2C(F)(F)F)cc1F] | 1H NMR (400 MHz, DMSO-d6) δ 9.07 (d, J = 7.5 Hz, 1H), 9.00-8.89 (m, 1H), 8.56 (d, J = 5.0 Hz, 1H), 7.89 (dt, J = 5.0, 1.0 Hz, 1H), 7.17 (d, J = 7.9 Hz, 1H), 7.12 (d, J = 1.7 Hz, 1H), 6.95 (dd, J = 8.0, 1.7 Hz, 1H), 6.79 (d, J = 11.7 Hz, 2H), 4.91 (dd, J = 8.7, 3.7 Hz, 1H), 4.66 (ddd, J = 9.7, 7.5, 5.1 Hz, 1H), 4.17 (d, J = 12.7 Hz, 1H), 3.96 (dd, J = 11.5, 3.8 Hz, 1H), 3.90-3.72 (m, 2H), 3.70 (s, 3H), 3.67 (s, 3H), 3.61 (s, 1H), 3.55 (dd, J = 12.1, 3.6 Hz, 1H), 3.31-3.03 (m, 4H), 2.69 (s, 3H). | 678.2 | NA | NA |
| 53 | 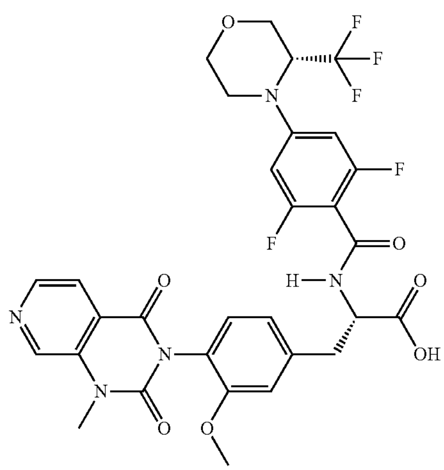 [SMILES: COc1cc(C[C@H](NC(=O)c2c(F)cc(N3CCOC[C@@H]3C(F)(F)F)cc2F)C(=O)O)ccc1-n1c(=O)c2ccncc2n(C)c1=O] | 1H NMR (400 MHz, DMSO-d6) δ 8.97 (s, 1H), 8.92 (d, J = 7.8 Hz, 1H), 8.56 (d, J = 5.0 Hz, 1H), 7.89 (dt, J = 5.0, 1.0 Hz, 1H), 7.16 (d, J = 7.9 Hz, 1H), 7.12 (d, J = 1.7 Hz, 1H), 6.96 (dd, J = 8.0, 1.7 Hz, 1H), 6.79 (d, J = 1.17 Hz, 2H), 4.92 (dd, J = 8.8, 3.5 Hz, 1H), 4.60 (ddd, J = 9.8, 7.8, 4.4 Hz, 1H), 4.16 (d, J = 12.7 Hz, 1H), 3.96 (dd, J = 11.5, 3.8 Hz, 1H), 3.74 (d, J = 13.6 Hz, 2H), 3.70 (s, 3H), 3.61 (d, J = 0.8 Hz, 3H), 3.42 (s, 1H), 3.31-3.15 (m, 2H), 3.05 (dd, J = 14.1, 9.9 Hz, 1H). | 664.2 | 0.2 | 18.6 |

TABLE 2-continued

| Ex # | Structure | 1H-NMR | M/Z [M + H]+ | α4β7 EC50 (nM) | α4β1 EC50 (nM) |
|---|---|---|---|---|---|
| 71 | 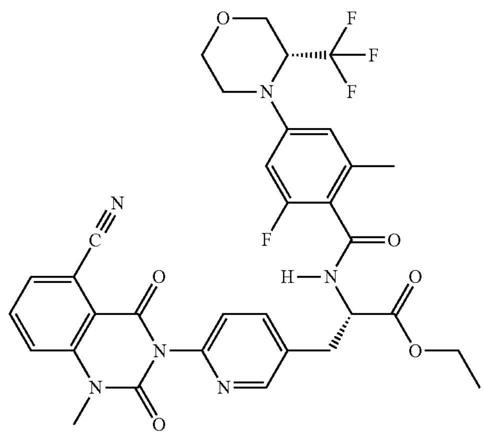 [SMILES: CCOC(=O)[C@H](Cc1ccc(-n2c(=O)c3c(C#N)cccc3n(C)c2=O)nc1)NC(=O)c1c(C)cc(N2CCOC[C@@H]2C(F)(F)F)cc1F] | 1H NMR (400 MHz, DMSO-d6) δ 8.93 (d, J = 7.7 Hz, 1H), 8.51 (d, J = 2.3 Hz, 1H), 8.01-7.93 (m, 2H), 7.88 (dd, J = 8.8, 1.0 Hz, 1H), 7.83 (dd, J = 7.4, 1.0 Hz, 1H), 7.43 (d, J = 8.1 Hz, 1H), 6.71 (d, J = 13.2 Hz, 1H), 6.67 (s, 1H), 4.91-4.79 (m, 1H), 4.72 (ddd, J = 10.4, 7.7, 5.1 Hz, 1H), 4.14 (m, 3H), 3.95 (dd, J = 11.3, 3.6 Hz, 1H), 3.74 (d, J = 12.2 Hz, 1H), 3.56 (s, 3H), 3.52 (m, 1H), 3.36 (d, J = 12.3 Hz, 1H), 3.25 (dd, J = 14.2, 5.3 Hz, 2H), 3.11 (dd, J = 14.2, 10.3 Hz, 1H), 2.10 (s, 3H), 1.20 (t, J = 7.1 Hz, 3H). | 683.2 | NA | NA |
| 72 | 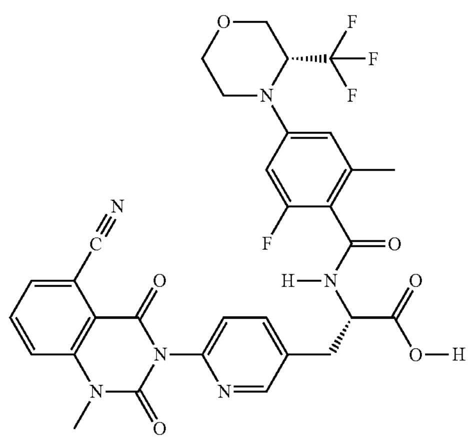 [SMILES: Cc1cc(N2CCOC[C@@H]2C(F)(F)F)cc(F)c1C(=O)N[C@@H](Cc1ccc(-n2c(=O)c3c(C#N)cccc3n(C)c2=O)nc1)C(=O)O] | 1H NMR (400 MHz, DMSO-d6) δ 12.93-12.73 (s, 1H), 8.80 (d, J = 8.0 Hz, 1H), 8.51 (s, 1H), 7.97 (q, J = 7.6, 6.9 Hz, 2H), 7.88 (d, J = 8.2 Hz, 1H), 7.83 (d, J = 7.4 Hz, 1H), 7.43 (d, J = 8.1 Hz, 1H), 6.70 (d, J = 13.3 Hz, 1H), 6.66 (s, 1H), 4.84 (s, 1H), 4.72-4.62 (m, 1H), 4.14 (d, J = 12.8 Hz, 2H), 3.95 (d, J = 11.1 Hz, 1H), 3.73 (d, J = 13.3 Hz, 1H), 3.56 (s, 3H), 3.55-3.50 (m, 1H), 3.47-3.45 (m, 1H), 3.26 (m, 1H), 3.07 (d, J = 25.1 Hz, 1H), 2.08 (s, 3H). | 655.2 | 0.18 | 4.0 |
| 73 | 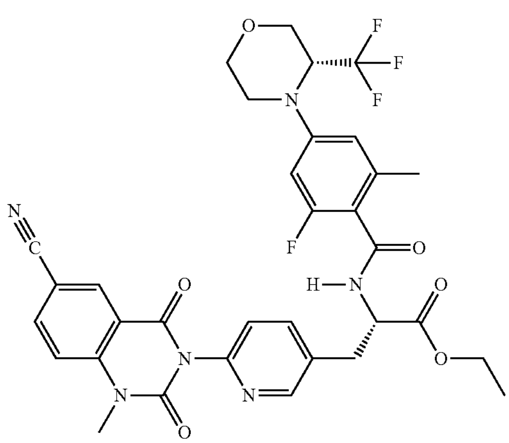 [SMILES: CCOC(=O)[C@H](Cc1ccc(-n2c(=O)c3cc(C#N)ccc3n(C)c2=O)nc1)NC(=O)c1c(C)cc(N2CCOC[C@@H]2C(F)(F)F)cc1F] | 1H NMR (400 MHz, DMSO-d6) δ 8.92 (d, J = 7.8 Hz, 1H), 8.50 (d, J = 2.3 Hz, 1H), 8.42 (d, J = 2.0 Hz, 1H), 8.25 (dd, J = 8.8, 2.1 Hz, 1H), 7.95 (dd, J = 8.1, 2.4 Hz, 1H), 7.71 (d, J = 8.8 Hz, 1H), 7.42 (dd, J = 8.1, 0.7 Hz, 1H), 6.71 (dd, J = 12.9, 2.3 Hz, 1H), 6.67 (d, J = 2.4 Hz, 1H), 4.84 (m, 1H), 4.73 (ddd, J = 10.4, 7.8, 5.2 Hz, 1H), 4.20-4.05 (m, 3H), 3.95 (dd, J = 11.4, 3.6 Hz, 1H), 3.74 (d, J = 12.6 Hz, 1H), 3.56 (s, 3H), 3.53 (m, 1H), 3.36 (d, J = 13.4 Hz, 1H), | 683.2 | NA | NA |

TABLE 2-continued

| Ex # | Structure | 1H-NMR | M/Z [M + H]+ | α4β7 EC50 (nM) | α4β1 EC50 (nM) |
|---|---|---|---|---|---|
| | | 3.31-3.19 (m, 2H), 3.10 (dd, J = 14.2, 10.4 Hz, 1H), 2.07 (s, 3H), 1.20 (t, J = 7.1 Hz, 3H). | | | |
| 74 | 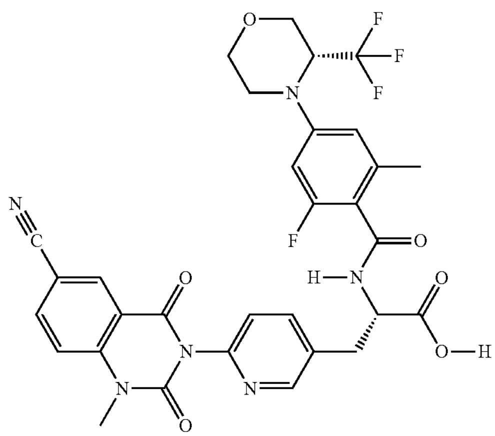 [SMILES: Cc1cc(N2CCOC[C@@H]2C(F)(F)F)cc(F)c1C(=O)N[C@@H](Cc1ccc(-n2c(=O)c3cc(C#N)ccc3n(C)c2=O)nc1)C(=O)O] | 1H NMR (400 MHz, DMSO-d6) δ 13.07-12.43 (s, 1H), 8.79 (d, J = 8.2 Hz, 1H), 8.54-8.46 (m, 1H), 8.41 (d, J = 2.1 Hz, 1H), 8.25 (dd, J = 8.8, 2.1 Hz, 1H), 7.94 (dd, J = 8.2, 2.4 Hz, 1H), 7.71 (d, J = 8.9 Hz, 1H), 7.41 (d, J = 8.0 Hz, 1H), 6.69 (d, J = 13.0 Hz, 1H), 6.66 (s, 1H), 4.84 (d, J = 9.5 Hz, 1H), 4.70 (ddd, J = 11.9, 8.0, 4.3 Hz, 1H), 4.15 (d, J = 12.6 Hz, 1H), 3.98-3.90 (m, 1H), 3.73 (d, J = 12.6 Hz, 1H), 3.56 (s, 3H), 3.52 (s, 1H), 3.35 (d, J = 12.4 Hz, 1H), 3.31-3.17 (m, 2H), 3.05 (dd, J = 14.2, 11.0 Hz, 1H), 2.05 (s, 3H). | 655.2 | 0.14 | 5.2 |
| 75 | 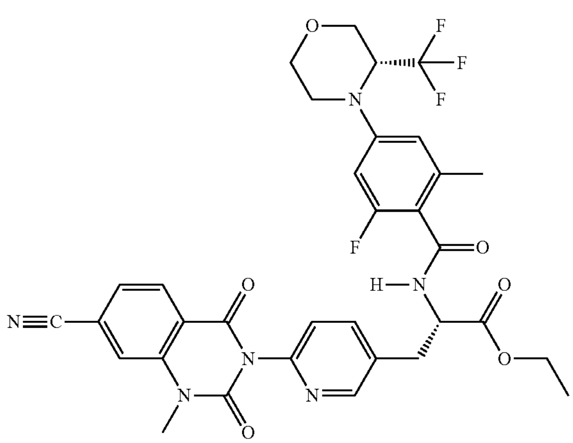 [SMILES: CCOC(=O)[C@H](Cc1ccc(-n2c(=O)c3ccc(C#N)cc3n(C)c2=O)nc1)NC(=O)c1c(C)cc(N2CCOC[C@@H]2C(F)(F)F)cc1F] | 1H NMR (400 MHz, DMSO-d6) δ 8.92 (d, J = 7.8 Hz, 1H), 8.49 (d, J = 2.3 Hz, 1H), 8.18 (d, J = 8.1 Hz, 1H), 8.11 (d, J = 1.3 Hz, 1H), 7.95 (dd, J = 8.1, 2.4 Hz, 1H), 7.75 (dd, J = 8.0, 1.3 Hz, 1H), 7.41 (dd, J = 8.1, 0.2 Hz, 1H), 6.71 (d, J = 13.0 Hz, 1H), 6.67 (s, 1H), 4.91-4.79 (m, 1H), 4.73 (ddd, J = 10.4, 7.8, 5.2 Hz, 1H), 4.18-4.10 (m, 3H), 3.95 (dd, J = 11.3, 3.6 Hz, 1H), 3.74 (d, J = 12.7 Hz, 1H), 3.56 (s, 3H), 3.52 (m, 1H), 3.36 (d, J = 12.0 Hz, 1H), 3.25 (dt, J = 14.2, 6.9 Hz, 2H), 3.09 (dd, J = 14.2, 10.4 Hz, 1H), 2.07 (s, 3H), 1.20 (t, J = 7.1 Hz, 3H). | 683.2 | NA | NA |

TABLE 2-continued

| Ex # | Structure | 1H-NMR | M/Z [M + H]+ | α4β7 EC50 (nM) | α4β1 EC50 (nM) |
|---|---|---|---|---|---|
| 76 | 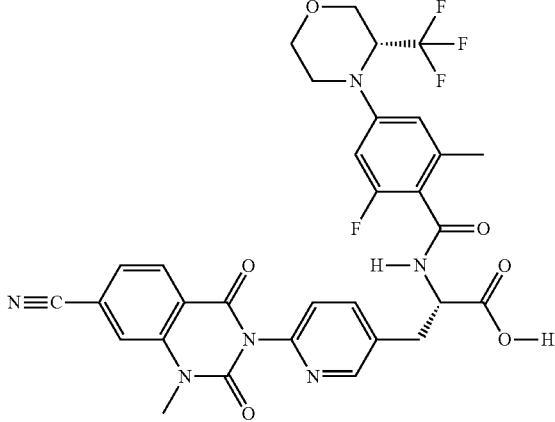 [SMILES: Cc1cc(N2CCOC[C@@H]2C(F)(F)F)cc(F)c1C(=O)N[C@@H](Cc1ccc(-n2c(=O)c3ccc(C#N)cc3n(C)c2=O)nc1)C(=O)O] | 1H NMR (400 MHz, DMSO-d6) δ 13.02-12.67 (s, 1H), 8.79 (d, J = 8.2 Hz, 1H), 8.50 (d, J = 2.4 Hz, 1H), 8.18 (d, J = 8.0 Hz, 1H), 8.11 (d, J = 1.3 Hz, 1H), 7.94 (dd, J = 8.1, 2.4 Hz, 1H), 7.75 (dd, J = 8.1, 1.3 Hz, 1H), 7.45-7.38 (m, 1H), 6.69 (d, J = 13.0 Hz, 1H), 6.66 (s, 1H), 4.90-4.77 (m, 1H), 4.69 (ddd, J = 11.9, 8.1, 4.2 Hz, 1H), 4.15 (d, J = 12.6 Hz, 1H), 3.95 (dd, J = 11.3, 3.7 Hz, 1H), 3.73 (d, J = 12.5 Hz, 1H), 3.56 (s, 3H), 3.52 (m, 1H), 3.36 (d, J = 12.4 Hz, 1H), 3.27 (dd, J = 14.1, 4.2 Hz, 2H), 3.05 (dd, J = 14.2, 10.9 Hz, 1H), 2.05 (s, 3H). | 655.2 | 0.16 | 4.9 |
| 77 | 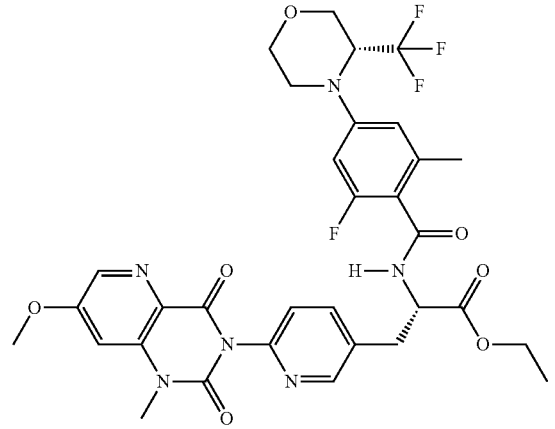 [SMILES: CCOC(=O)[C@H](Cc1ccc(-n2c(=O)c3ncc(OC)cc3n(C)c2=O)nc1)NC(=O)c1c(C)cc(N2CCOC[C@@H]2C(F)(F)F)cc1F] | 1H NMR (400 MHz, DMSO-d6) δ 8.92 (d, J = 7.8 Hz, 1H), 8.49 (d, J = 2.3 Hz, 1H), 8.30 (d, J = 2.3 Hz, 1H), 7.93 (dd, J = 8.1, 2.4 Hz, 1H), 7.45-7.36 (m, 2H), 6.78-6.68 (m, 1H), 6.67 (d, J = 2.3 Hz, 1H), 4.85 (d, J = 8.0 Hz, 1H), 4.73 (m, 1H), 4.14 (m, 3H), 4.04 (s, 3H), 3.95 (dd, J = 11.3, 3.6 Hz, 1H), 3.74 (d, J = 12.6 Hz, 1H), 3.55 (m, 4H), 3.36 (d, J = 12.3 Hz, 1H), 3.24 (dd, J = 14.1, 4.9 Hz, 2H), 3.09 (dd, J = 14.2, 10.4 Hz, 1H), 2.07 (s, 3H), 1.20 (t, J = 7.1 Hz, 3H). | 689.3 | NA | NA |
| 78 | 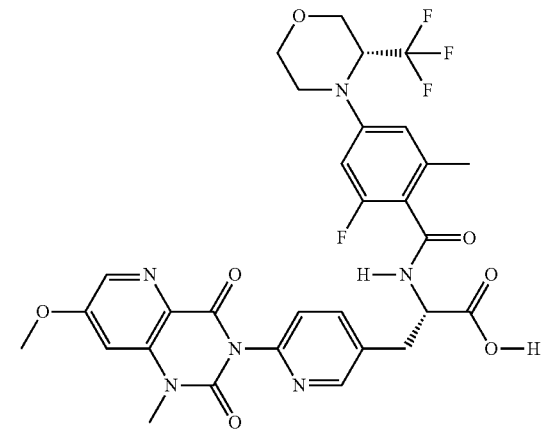 [SMILES: COc1cnc2c(=O)n(-c3ccc(C[C@H](NC(=O)c4c(C)cc(N5CCOC[C@@H]5C(F)(F)F)cc4F)C(=O)O)cn3)c(=O)n(C)c2c1] | 1H NMR (400 MHz, DMSO-d6) δ 13.03-12.58 (s, 1H), 8.79 (d, J = 8.2 Hz, 1H), 8.49 (d, J = 2.3 Hz, 1H), 8.30 (d, J = 2.3 Hz, 1H), 7.93 (dd, J = 8.2, 2.4 Hz, 1H), 7.42-7.35 (m, 2H), 6.69 (d, J = 13.5 Hz, 1H), 6.66 (s, 1H), 4.85 (m, 1H), 4.75-4.63 (m, 1H), 4.14 (d, J = 12.6 Hz, 1H), 4.04 (s, 3H), 3.97-3.90 (m, 1H), 3.73 (d, J = 12.4 Hz, 1H), 3.55 (m, 4H), 3.36 (d, J = 12.2 Hz, 1H), 3.27 (dd, J = 14.3, 4.1 Hz, 2H), 3.11-2.98 (m, 1H), 2.05 (s, 3H). | 661.2 | 0.16 | 3.4 |

TABLE 2-continued

| Ex # | Structure | 1H-NMR | M/Z [M + H]+ | α4β7 EC50 (nM) | α4β1 EC50 (nM) |
|---|---|---|---|---|---|
| 79 | 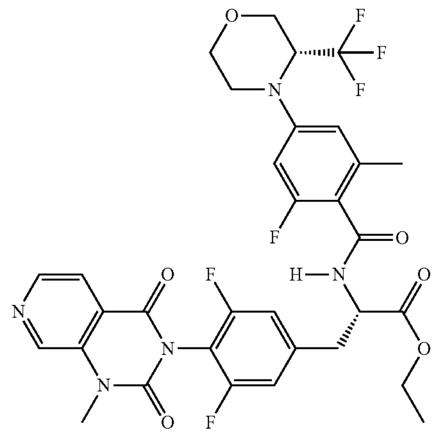 [SMILES: CCOC(=O)[C@H](Cc1cc(F)c(-n2c(=O)c3ccncc3n(C)c2=O)c(F)c1)NC(=O)c1c(C)cc(N2CCOC[C@@H]2C(F)(F)F)cc1F] | 1H NMR (400 MHz, DMSO-d6) δ 9.03 (s, 1H), 8.90 (d, J = 7.9 Hz, 1H), 8.61 (d, J = 5.0 Hz, 1H), 7.95 (d, J = 5.0 Hz, 1H), 7.31 (d, J = 9.5 Hz, 2H), 6.77-6.57 (m, 2H), 4.85 (tt, J = 8.7, 4.6 Hz, 1H), 4.76 (ddd, J = 10.8, 7.9, 4.8 Hz, 1H), 4.22-4.09 (m, 3H), 3.95 (dd, J = 11.4, 3.6 Hz, 1H), 3.74 (ddd, J = 12.7, 4.0, 2.1 Hz, 1H), 3.66 (s, 3H), 3.63-3.48 (m, 1H), 3.41-3.34 (m, 1H), 3.33 (s, 2H), 3.27 (dd, J = 14.2, 4.9 Hz, 1H), 3.08 (dd, J = 14.1, 10.8 Hz, 1H), 2.50 (p, J = 1.8 Hz, 2H), 2.10 (s, 3H), 1.21 (t, J = 7.1 Hz, 3H). | 694.2 | NA | NA |
| 80 | 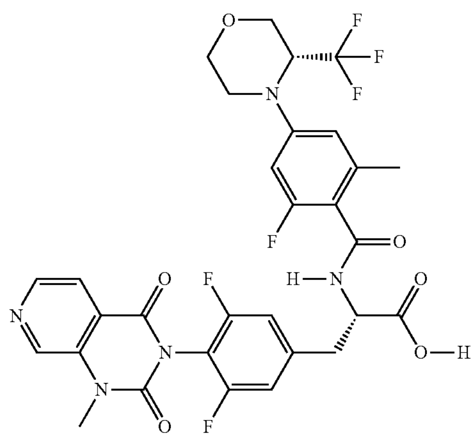 [SMILES: Cc1cc(N2CCOC[C@@H]2C(F)(F)F)cc(F)c1C(=O)N[C@@H](Cc1cc(F)c(-n2c(=O)c3ccncc3n(C)c2=O)c(F)c1)C(=O)O] | 1H NMR (400 MHz, DMSO-d6) δ 9.03 (s, 1H), 8.77 (d, J = 8.3 Hz, 1H), 8.61 (d, J = 5.0 Hz, 1H), 7.94 (d, J = 5.0 Hz, 1H), 7.29 (d, J = 9.7 Hz, 2H), 6.81-6.58 (m, 2H), 4.84 (m, 1H), 4.71 (m, 1H), 4.15 (d, J = 12.6 Hz, 1H), 3.95 (dd, J = 11.4, 3.7 Hz, 1H), 3.82-3.69 (m, 1H), 3.65 (s, 3H), 3.55 (td, J = 11.3, 3.3 Hz, 1H), 3.44-3.18 (m, 3H), 3.04 (dd, J = 14.2, 11.3 Hz, 1H), 2.07 (s, 3H). | 666.2 | 0.06 | 2.1 |
| 81 | 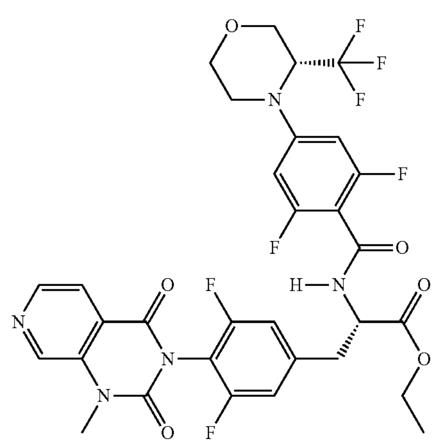 [SMILES: CCOC(=O)[C@H](Cc1cc(F)c(-n2c(=O)c3ccncc3n(C)c2=O)c(F)c1)NC(=O)c1c(F)cc(N2CCOC[C@@H]2C(F)(F)F)cc1F] | 1H NMR (400 MHz, DMSO-d6) δ 9.00 (s, 1H), 8.89 (d, J = 7.8 Hz, 1H), 8.58 (d, J = 5.0 Hz, 1H), 7.92 (dd, J = 4.9, 1.1 Hz, 1H), 7.45-7.33 (m, 2H), 7.26 (dd, J = 8.1, 1.7 Hz, 1H), 6.79-6.62 (m, 2H), 4.85 (qd, J = 8.8, 3.4 Hz, 1H), 4.72 ddd, J = 10.5, 7.7, 5.0 Hz, 1H), 4.14 (m, 3H), 3.95 (dd, J = 11.4, 3.6 Hz, 1H), 3.74 (m, 1H), 3.63 (s, 3H), 3.55 (d, J = 3.5 Hz, 1H), 3.41-3.17 (m, 6H), 3.07 (m1H), 2.58-2.45 (m, 1H), 2.09 (s, 3H), 1.20 (t, J = 7.1 Hz, 3H). | 698.2 | NA | NA |

TABLE 2-continued

| Ex # | Structure | 1H-NMR | M/Z [M + H]+ | α4β7 EC50 (nM) | α4β1 EC50 (nM) |
|---|---|---|---|---|---|
| 82 | 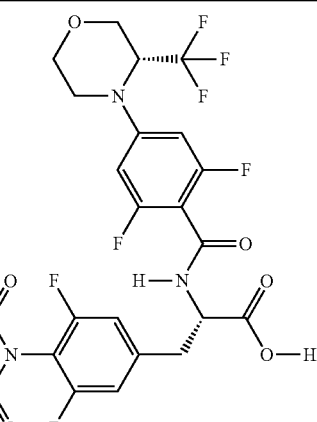 | 1H NMR (400 MHz, DMSO-d6) δ 9.03 (s, 1H), 8.94 (d, J = 8.1 Hz, 1H), 8.61 (d, J = 5.0 Hz, 1H), 7.94 (d, J = 5.0 Hz, 1H), 7.27 (d, J = 9.5 Hz, 2H), 6.79 (d, J = 11.7 Hz, 2H), 4.92 (dd, J = 8.7, 3.6 Hz, 1H), 4.64 (ddd, J = 10.5, 8.0, 4.3 Hz, 1H), 4.16 (d, J = 12.7 Hz, 1H), 3.96 (dd, J = 11.5, 3.8 Hz, 1H), 3.74 (ddd, J = 12.7, 4.0, 2.1 Hz, 1H), 3.65 (s, 3H), 3.56 (td, J = 11.9, 3.4 Hz, 1H), 3.50-3.39 (m, 1H), 3.27 (dd, J = 14.2, 4.2 Hz, 2H), 3.07 (dd, J = 14.1, 10.6 Hz, 1H). | 670.2 | 0.15 | 4.5 |
| 83 | 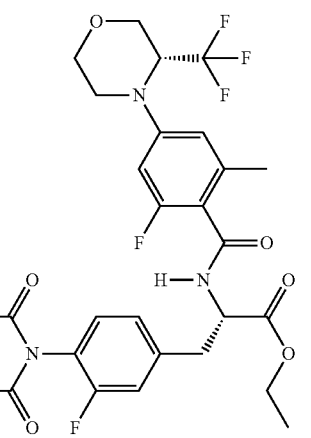 | 1H NMR (400 MHz, DMSO-d6) δ 9.07 (d, J = 7.6 Hz, 1H), 9.03 (s, 1H), 8.77 (dd, J = 4.4, 1.4 Hz, 1H), 8.61 (d, J = 5.0 Hz, 1H), 8.54 (dd, J = 8.4, 1.4 Hz, 1H), 7.95 (d, J = 5.0 Hz, 1H), 7.52 (dd, J = 8.4, 4.4 Hz, 1H), 7.29 (d, J = 9.4 Hz, 2H), 6.81 (d, J = 11.6 Hz, 2H), 4.92 (dt, J = 8.9, 4.5 Hz, 1H), 4.68 (ddd, J = 10.1, 7.6, 5.2 Hz, 1H), 4.24-4.08 (m, 3H), 3.96 (dd, J = 11.5, 3.8 Hz, 1H), 3.82-3.71 (m, 1H), 3.66 (s, 3H), 3.63-3.50 (m, 1H), 3.51-3.31 (m, 5H), 3.25 (m, 2H), 3.12 (m, 1H), 1.19 (t, J = 7.1 Hz, 3H). | 676.2 | NA | NA |
| 84 | 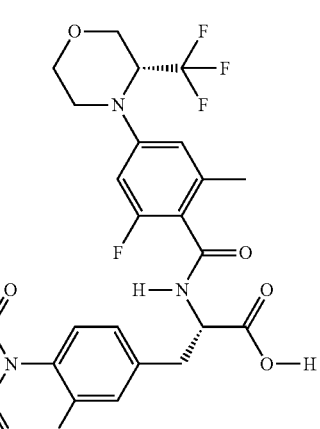 | 1H NMR (400 MHz, DMSO-d6) δ 9.00 (s, 1H), 8.76 (d, J = 8.2 Hz, 1H), 8.58 (d, J = 5.0 Hz, 1H), 7.92 (d, J = 4.9 Hz, 1H), 7.43-7.20 (m, 3H), 6.77-6.59 (m, 2H), 4.84 (dd, J = 8.8, 3.5 Hz, 1H), 4.68 (ddd, J = 11.8, 8.1, 4.1 Hz, 1H), 4.15 (d, J = 12.6 Hz, 1H), 3.95 (dd, J = 11.4, 3.7 Hz, 1H), 3.63 (s, 3H), 3.60-3.49 (m, 1H), 3.36 (d, J = 12.3 Hz, 1H), 3.30-3.17 (m, 2H), 3.02 (dd, J = 14.2, 11.1 Hz, 1H), 2.06 (s, 3H). | 648.2 | 0.05 | 1.7 |

TABLE 2-continued

| Ex # | Structure | 1H-NMR | M/Z [M + H]+ | α4β7 EC50 (nM) | α4β1 EC50 (nM) |
|---|---|---|---|---|---|
| 85 | 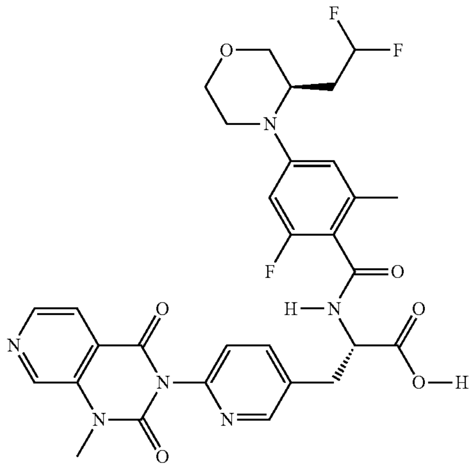 [SMILES: Cc1cc(N2CCOC[C@H]2CC(F)F)cc(F)c1C(=O)N[C@@H](Cc1ccc(-n2c(=O)c3ccncc3n(C)c2=O)nc1)C(=O)O] | 1H NMR (400 MHz, DMSO-d6) δ 9.00 (s, 1H), 8.76 (d, J = 8.1 Hz, 1H), 8.57 (d, J = 4.9 Hz, 1H), 8.51 (d, J = 2.4 Hz, 1H), 7.95 (dd, J = 8.1, 2.4 Hz, 1H), 7.90 (d, J = 4.9 Hz, 1H), 7.42 (d, J = 8.1 Hz, 1H), 6.54 (d, J = 8.4 Hz, 2H), 6.16 (t, J = 56.3 Hz, 1H), 4.67 (d, J = 12.2 Hz, 1H), 4.03 (m, 1H), 3.86 (dd, J = 22.5, 10.7 Hz, 2H), 3.61 (s, 4H), 3.53 (d, J = 11.9 Hz, 1H), 3.43-3.17 (m, 2H), 3.13-2.97 (m, 2H), 2.06 (s, 3H). | 627.2 | 3.9 | 17.9 |
| 86 | 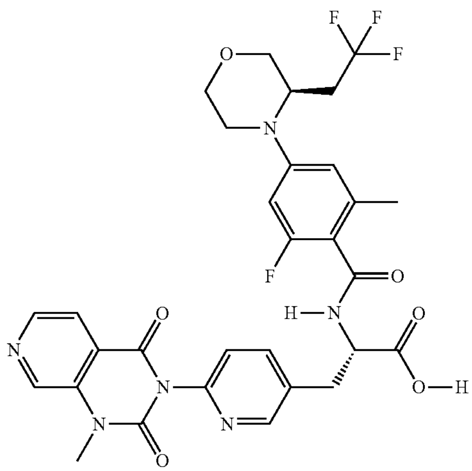 [SMILES: Cc1cc(N2CCOC[C@H]2CC(F)(F)F)cc(F)c1C(=O)N[C@@H](Cc1ccc(-n2c(=O)c3ccncc3n(C)c2=O)nc1)C(=O)O] | 1H NMR (400 MHz, DMSO-d6) δ 9.00 (s, 1H), 8.77 (d, J = 8.1 Hz, 1H), 8.57 (d, J = 5.0 Hz, 1H), 8.51 (d, J = 2.4 Hz, 1H), 7.95 (dd, J = 8.2, 2.4 Hz, 1H), 7.90 (dd, J = 4.9, 0.7 Hz, 1H), 7.42 (d, J = 8.0 Hz, 1H), 6.56 (d, J = 12.2 Hz, 2H), 4.69 (ddd, J = 11.8, 8.0, 4.2 Hz, 1H), 4.20 (d, J = 8.7 Hz, 1H), 3.90 (dd, J = 11.5, 3.5 Hz, 1H), 3.78 (d, J = 1.17 Hz, 1H), 3.68 (d, J = 11.4 Hz, 1H), 3.61 (s, 3H), 3.59-3.46 (m, 1H), 3.43-3.21 (m, 1H), 3.16-2.98 (m, 2H), 2.89-2.74 (m, 1H), 2.16 (q, J = 13.4, 12.6 Hz, 1H), 2.06 (s, 3H). | 645.2 | 4.2 | 46.1 |
| 87 | 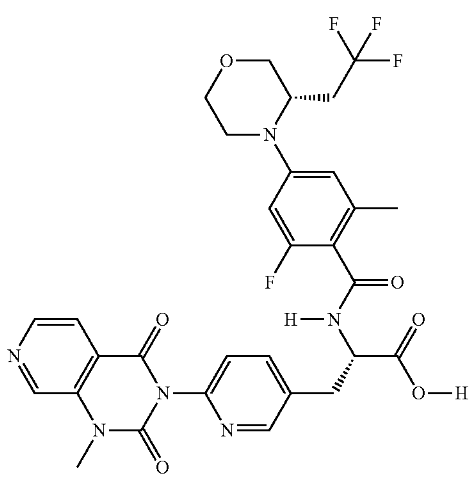 [SMILES: Cc1cc(N2CCOC[C@@H]2CC(F)(F)F)cc(F)c1C(=O)N[C@@H](Cc1ccc(-n2c(=O)c3ccncc3n(C)c2=O)nc1)C(=O)O] | 1H NMR (400 MHz, DMSO-d6) δ 9.00 (s, 1H), 8.77 (d, J = 8.2 Hz, 1H), 8.57 (d, J = 4.9 Hz, 1H), 8.50 (d, J = 2.4 Hz, 1H), 7.94 (dd, J = 8.2, 2.4 Hz, 1H), 7.90 (dd, J = 5.0, 0.7 Hz, 1H), 7.42 (d, J = 8.0 Hz, 1H), 6.56 (d, J = 9.6 Hz, 2H), 4.70 (ddd, J = 12.3, 8.2, 4.2 Hz, 1H), 4.20 (d, J = 8.9 Hz, 1H), 3.90 (d, J = 9.1 Hz, 1H), 3.78 (d, J = 11.7 Hz, 1H), 3.68 (d, J = 11.6 Hz, 1H), 3.61 (s, 3H), 3.59-3.46 (m, 1H), 3.37-3.17 (m, 2H), 3.11-2.96 (m, 2H), 2.86-2.73 (m, 1H), 2.14 (t, J = 12.3 Hz, 1H), 2.04 (s, 3H). | 645.2 | 0.9 | 19.7 |

TABLE 2-continued

| Ex # | Structure | 1H-NMR | M/Z [M + H]+ | α4β7 EC50 (nM) | α4β1 EC50 (nM) |
|---|---|---|---|---|---|
| 88 | 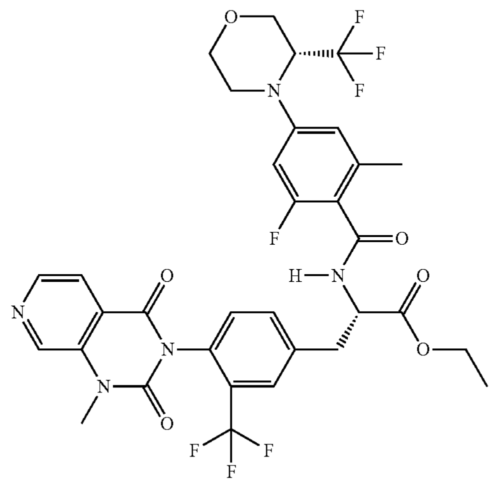 [SMILES: CCOC(=O)[C@H](Cc1ccc(-n2c(=O)c3ccncc3n(C)c2=O)c(C(F)(F)F)c1)NC(=O)c1c(C)cc(N2CCOC[C@@H]2C(F)(F)F)cc1F] | 1H NMR (400 MHz, DMSO-d6) δ 9.02 (s, 1H), 8.92 (d, J = 7.8 Hz, 1H), 8.59 (d, J = 5.0 Hz, 1H), 7.92 (dt, J = 5.0, 0.9 Hz, 1H), 7.82 (d, J = 1.9 Hz, 1H), 7.80-7.73 (m, 1H), 7.54 (d, J = 8.1 Hz, 1H), 6.75-6.62 (m, 2H), 4.85 (tt, J = 8.7, 4.9 Hz, 1H), 4.75 (ddd, J = 10.6, 7.8, 4.9 Hz, 1H), 4.21-4.07 (m, 3H), 3.95 (dd, J = 11.4, 3.7 Hz, 1H), 3.81-3.67 (m, 1H), 3.68-3.60 (m, 3H), 3.60-3.47 (m, 1H), 3.42-3.21 (m, 4H), 3.15 (dd, J = 14.1, 10.6 Hz, 1H), 2.06 (s, 3H), 1.20 (t, J = 7.1 Hz, 3H). | 726.2 | NA | NA |
| 89 | 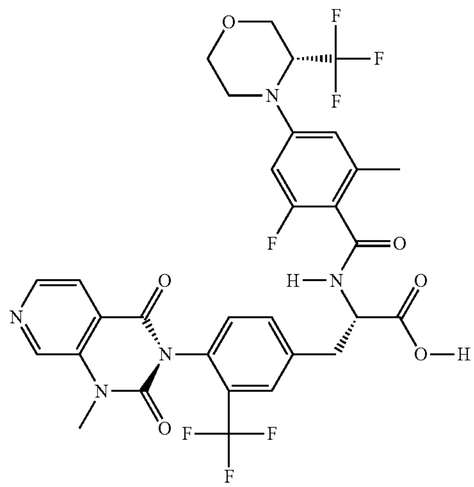 | 1H NMR (400 MHz, DMSO-d6) δ 9.02 (s, 1H), 8.79 (d, J = 8.2 Hz, 1H), 8.59 (d, J = 5.0 Hz, 1H), 7.92 (d, J = 4.9 Hz, 1H), 7.82 (d, J = 1.9 Hz, 1H), 7.77 (d, J = 8.4 Hz, 1H), 7.66-7.58 (m, 1H), 7.55 (t, J = 7.2 Hz, 2H), 6.75-6.56 (m, 2H), 4.85 (dd, J = 8.8, 3.6 Hz, 1H), 4.71 (ddd, J = 11.8, 8.1, 4.0 Hz, 1H), 4.14 (d, J = 12.6 Hz, 1H), 3.95 (dd, J = 11.4, 3.7 Hz, 1H), 3.73 (d, J = 13.0 Hz, 1H), 3.63 (s, 3H), 3.60-3.49 (m, 1H), 3.40-3.30 (m, 2H), 3.25 (t, J = 12.2 Hz, 1H), 3.10 (dd, J = 14.1, 11.2 Hz, 1H), 2.03 (s, 3H). | 698.2 | 0.6 | 2.3 |
| 90 | 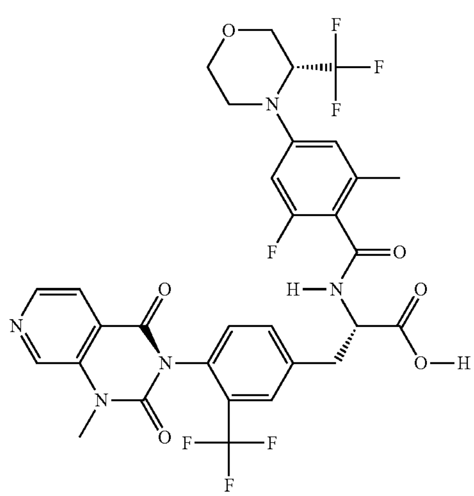 | 1H NMR (400 MHz, DMOS-d6) δ 9.02 (s, 1H), 8.79 (d, J = 8.2 Hz, 1H), 8.59 (d, J = 5.0 Hz, 1H), 7.92 (dd, J = 5.3, 1.5 Hz, 1H), 7.82 (s, 1H), 7.77 (d, J = 8.3 Hz, 1H), 7.55 (t, J = 7.1 Hz, 2H), 6.68 (d, J = 16.9 Hz, 2H), 4.91-4.78 (m, 1H), 4.78-4.62 (m, 1H), 4.14 (d, J = 12.6 Hz, 1H), 3.95 (dd, J = 11.4, 3.7 Hz, 1H), 3.73 (d, J = 12.6 Hz, 1H), 3.63 (s, 3H), 3.59-3.48 (m, 1H), 3.42-3.30 (m, 2H), 3.25 (t, J = 11.9 Hz, 1H), 3.16-3.04 (m, 1H), 2.03 (s, 3H). | 698.2 | 0.7 | 9.7 |

TABLE 2-continued

| Ex # | Structure | 1H-NMR | M/Z [M + H]+ | α4β7 EC50 (nM) | α4β1 EC50 (nM) |
|---|---|---|---|---|---|
| 91 | 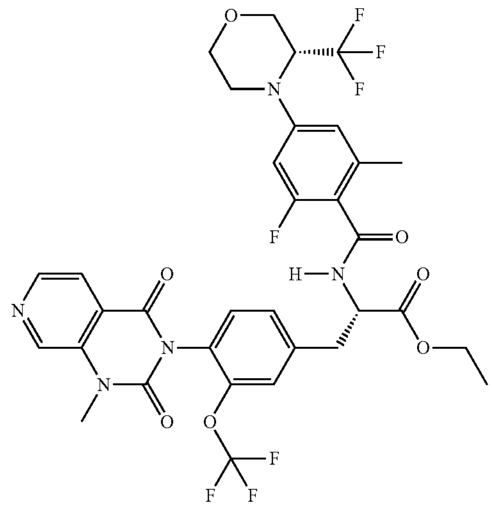 [SMILES: CCOC(=O)[C@H](Cc1ccc(-n2c(=O)c3ccncc3n(C)c2=O)c(OC(F)(F)F)c1)NC(=O)c1c(C)cc(N2CCOC[C@@H]2C(F)(F)F)cc1F] | 1H NMR (400 MHz, DMSO-d6) δ 9.01 (s, 1H), 8.90 (d, J = 7.7 Hz, 1H), 8.59 (d, J = 5.0 Hz, 1H), 7.93 (dt, J = 5.0, 0.9 Hz, 1H), 7.47 (td, J = 9.9, 8.9, 5.2 Hz, 3H), 6.74-6.62 (m, 2H), 4.85 (dd, J = 8.8, 3.6 Hz, 1H), 4.72 (dd, J = 15.0, 8.3 Hz, 1H), 4.13 (p, J = 7.0 Hz, 3H), 3.95 (dd, J = 11.4, 3.7 Hz, 1H), 3.74 (d, J = 12.7 Hz, 1H), 3.64 (s, 3H), 3.61-3.50 (m, 1H), 3.36 (d, J = 12.3 Hz, 1H), 3.25 (dd, J = 14.1, 5.3 Hz, 1H), 3.11 (dd, J = 14.1, 10.4 Hz, 1H), 2.08 (s, 3H), 1.19 (t, J = 7.1 Hz, 3H). | 742.2 | NA | NA |
| 92 | 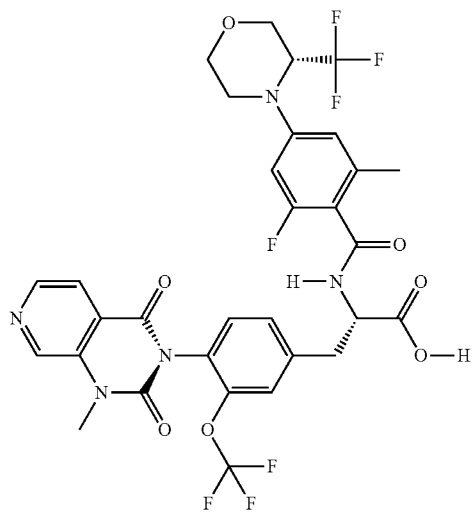 | 1H NMR (400 MHz, DMSO-d6) δ 9.01 (s, 1H), 8.76 (d, J = 8.2 Hz, 1H), 8.59 (d, J = 5.0 Hz, 1H), 7.93 (dt, J = 5.0, 0.9 Hz, 1H), 7.67-7.58 (m, 1H), 7.55 (ddd, J = 8.4, 6.5, 4.7 Hz, 1H), 7.52-7.41 (m, 3H), 6.72-6.62 (m, 2H), 4.85 (dd, J = 8.8, 3.6 Hz, 1H), 4.74-4.62 (m, 1H), 4.14 (d, J = 12.6 Hz, 1H), 3.95 (dd, J = 11.3, 3.7 Hz, 1H), 3.79-3.68 (m, 1H), 3.64 (s, 3H), 3.60-3.50 (m, 1H), 3.36 (d, J = 12.3 Hz, 1H), 3.33-3.20 (m, 2H), 3.06 (dd, J = 14.3, 11.0 Hz, 1H), 2.04 (d, J = 1.2 Hz, 3H). | 714.2 | 0.2 | 1.3 |
| 93 | 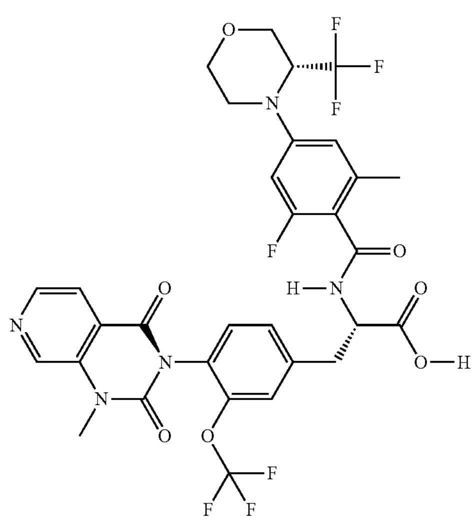 | 1H NMR (400 MHz, DMOS-d6) δ 9.01 (s, 1H), 8.76 (d, J = 8.1 Hz, 1H), 8.59 (d, J = 5.0 Hz, 1H), 7.95-7.89 (m, 1H), 7.51-7.38 (m, 3H), 6.73-6.59 (m, 2H), 4.84 (d, J = 9.1 Hz, 1H), 4.74-4.63 (m, 1H), 4.14 (d, J = 12.6 Hz, 1H), 3.95 (dd, J = 11.4, 3.6 Hz, 1H), 3.73 (d, J = 12.5 Hz, 1H), 3.64 (s, 3H), 3.60-3.48 (m, 1H), 3.42-3.16 (m, 3H), 3.06 (dd, J = 14.3, 11.1 Hz, 1H), 2.04 (d, J = 1.2 Hz, 3H). | 714.2 | 0.4 | 25.8 |

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

What is claimed is:

1. A compound of formula (IIc):

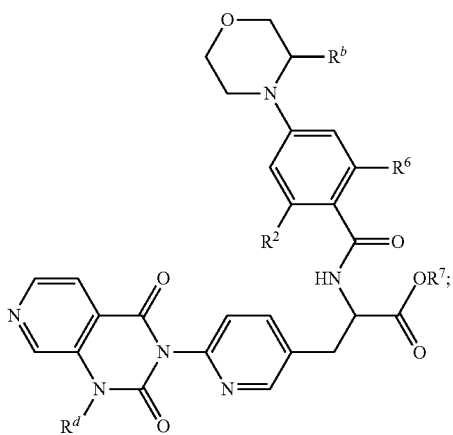

or a pharmaceutically acceptable salt thereof, wherein;
$R^b$ is $C_{1-4}$alkyl, or $C_{1-6}$haloalkyl;
$R^d$ is selected from the group consisting of H, $C_{1-4}$alkyl, and $C_{1-4}$haloalkyl;
each $R^2$ and $R^6$ is independently selected from the group consisting of H, halo, cyano, hydroxyl, —$NR^{a1}R^{a2}$, $C_{1-4}$alkyl, $C_{1-4}$alkoxyl, $C_{1-4}$haloalkyl, and $C_{1-4}$haloalkoxyl;
$R^7$ is selected from the group consisting of H, $C_{1-10}$alkyl, $C_{1-10}$haloalkyl, $C_{3-10}$cycloalkyl, 3-14 membered heterocyclyl, $C_{6-10}$aryl, 5-10 membered heteroaryl, —$C_{1-4}$alkylene-$NR^{a1}R^{a2}$, —$C_{1-4}$alkylene-C(O)$NR^{a1}R^{a2}$, $C_{1-4}$alkylene-$C_{3-10}$cycloalkyl, —$C_{1-4}$alkylene-3-14 membered heterocyclyl, —$C_{1-4}$alkylene-$C_{6-10}$aryl, —$C_{1-4}$alkylene-5-10 membered heteroaryl, and -$L^1$-$R^9$;
wherein $L^1$ is selected from the group consisting of —$C_{1-4}$alkylene-O—, —$C_{1-4}$alkylene-C(O)—, —$C_{1-4}$alkylene-O—C(O)—, —$C_{1-4}$alkylene-O—C(O)—$C_{1-4}$alkylene-, —$C_{1-4}$alkylene-C(O)—O—, —$C_{1-4}$alkylene-C(O)—O—$C_{1-4}$alkylene-, —$C_{1-4}$alkylene-O—C(O)—O—, —$C_{1-4}$alkylene-O—C(O)—O—$C_{1-4}$alkylene-, —$C_{1-4}$alkylene-$NR^{a1}$C(O)—O—, and —$C_{1-4}$alkylene-O—C(O)—$NR^{a1}$—;
$R^9$ is selected from the group consisting of $C_{1-6}$alkyl, $C_{1-6}$haloalkyl, $C_{3-10}$cycloalkyl, 3-14 membered heterocyclyl, $C_{6-10}$aryl, and 5-10 membered heteroaryl, wherein each $C_{3-10}$cycloalkyl, 3-14 membered heterocyclyl, $C_{6-10}$aryl, and 5-10 membered heteroaryl of $R^7$ and $R^9$ is optionally substituted with one to four members independently selected from the group consisting of halo, hydroxyl, $C_{1-4}$ alkyl, $C_{1-4}$alkoxyl, $C_{1-4}$haloalkyl, $C_{1-4}$haloalkoxyl, —$NR^{a1}R^{a2}$, and —$C_{1-4}$alkylene-$NR^{a1}R^{a2}$; and
each $R^{a1}$ and $R^{a2}$ is independently selected from the group consisting of H, $C_{1-6}$alkyl, $C_{1-6}$haloalkyl, and $C_{3-10}$cycloalkyl.

2. The compound of claim 1, or a pharmaceutically acceptable salt thereof, wherein the compound is of formula (IId):

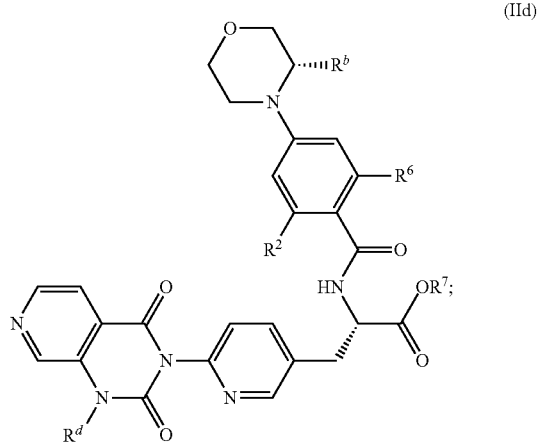

wherein
$R^d$ is $C_{1-4}$alkyl, or $C_{1-4}$haloalkyl; and
each $R^2$ and $R^6$ is independently selected from the group consisting of halo, $C_{1-4}$alkyl and $C_{1-4}$haloalkyl.

3. The compound of claim 1, or a pharmaceutically acceptable salt thereof, wherein $R^2$ is F, and $R^6$ is —$CH_3$.

4. The compound of claim 1, or a pharmaceutically acceptable salt thereof, $R^7$ is selected from the group consisting of H, methyl, ethyl, and cyclopropyl.

5. A pharmaceutical composition comprising a compound of claim 1, and at least one pharmaceutically acceptable carrier.

6. A compound of formula (TIN:

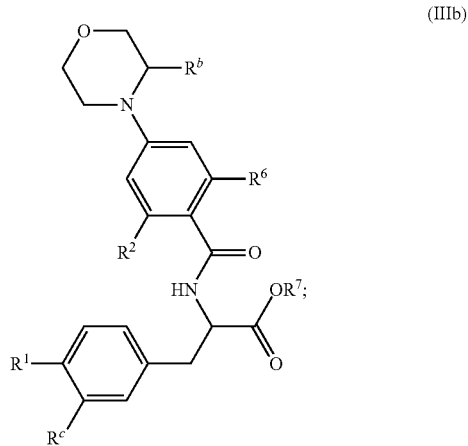

or a pharmaceutically acceptable salt thereof, wherein;
R¹ is 5-10 membered heteroaryl or 6-10 membered heterocyclyl;
  wherein each 5-10 membered heteroaryl and 6-10 membered heterocyclyl of R' contains one to four N and optionally one to three C(O) as a ring member(s); and
  wherein each 5-10 membered heteroaryl and 6-10 membered heterocyclyl of R' is optionally substituted with one to four $R^a$; and wherein each $R^a$ is independently selected from the group consisting of halo, cyano, hydroxyl, —$NR^{a1}R^{a2}$, $C_{1-4}$alkyl, $C_{1-4}$alkoxyl, $C_{1-4}$haloalkyl, $C_{1-4}$haloalkoxyl, —$C_{1-4}$alkylene-O—$C_{1-4}$alkyl, and $C_{3-10}$cycloalkyl;
each $R^2$, and $R^6$ is independently selected from the group consisting of H, halo, cyano, hydroxyl, —$NR^{a1}R^{a2}$, $C_{1-4}$alkyl, $C_{1-4}$alkoxyl, $C_{1-4}$haloalkyl, and $C_{1-4}$haloalkoxyl;
$R^b$ is $C_{1-4}$alkyl, or $C_{1-6}$haloaky;
$R^c$ is H, halo, cyano, hydroxyl, —$NR^{a1}R^{a2}$, $C_{1-4}$alkyl, $C_{1-4}$alkoxyl, $C_{1-4}$haloalkyl, and $C_{1-4}$haloalkoxyl; and
$R^7$ is selected from the group consisting of H, $C_{1-10}$alkyl, $C_{1-10}$haloalkyl, $C_{3-10}$cycloalkyl, 3-14 membered heterocyclyl, $C_{6-10}$aryl, 5-10 membered heteroaryl, —$C_{1-4}$alkylene-$NR^{a1}R^{a2}$, —$C_{1-4}$alkylene-C(O)$NR^{a1}R^{a2}$, $C_{1-4}$alkylene-$C_{3-10}$cycloalkyl, —$C_{1-4}$alkylene-3-14 membered heterocyclyl, —$C_{1-4}$alkylene-$C_{6-10}$aryl, —$C_{1-4}$alkylene-5-10 membered heteroaryl, and -$L^2$-$R^9$;
  wherein $L^1$ is selected from the group consisting of —$C_{1-4}$alkylene-O—, —$C_{1-4}$alkylene-C(O)—, —$C_{1-4}$alkylene-O—C(O)—, —$C_{1-4}$alkylene-O—C(O)—$C_{1-4}$alkylene-, —$C_{1-4}$alkylene-C(O)—O—, —$C_{1-4}$alkylene-C(O)—O—$C_{1-4}$alkylene-, —$C_{1-4}$alkylene-O—C(O)—O—, —$C_{1-4}$alkylene-O—C(O)—O—$C_{1-4}$alkylene-, —$C_{1-4}$alkylene-$NR^{a1}$C(O)—O—, and —$C_{1-4}$alkylene-O—C(O)—$NR^{a1}$—;
  $R^9$ is selected from the group consisting of $C_{1-6}$alkyl, $C_{1-6}$haloalkyl, $C_{3-10}$cycloalkyl, 3-14 membered heterocyclyl, $C_{6-10}$aryl, and 5-10 membered heteroaryl, wherein each $C_{3-10}$cycloalkyl, 3-14 membered heterocyclyl, $C_{6-10}$aryl, and 5-10 membered heteroaryl of $R^7$ and $R^9$ is optionally substituted with one to four groups independently selected from group consisting of halo, hydroxyl, $C_{1-4}$alkyl, $C_{1-4}$alkoxyl, $C_{1-4}$haloalkyl, $C_{1-4}$haloalkoxyl, —$NR^{a1}R^{a2}$, and —$C_{1-4}$alkylene-$NR^{a1}R^{a2}$; and
each $R^{a1}$ and $R^{a2}$ is independently selected from the group consisting of H, $C_{1-6}$alkyl, $C_{1-6}$haloalkyl, and $C_{3-10}$cycloalkyl.

7. The compound of claim 6, or a pharmaceutically acceptable salt thereof, wherein R¹ is

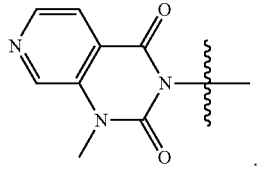

8. The compound of claim 6, or a pharmaceutically acceptable salt thereof, wherein R¹ is selected from the group consisting of

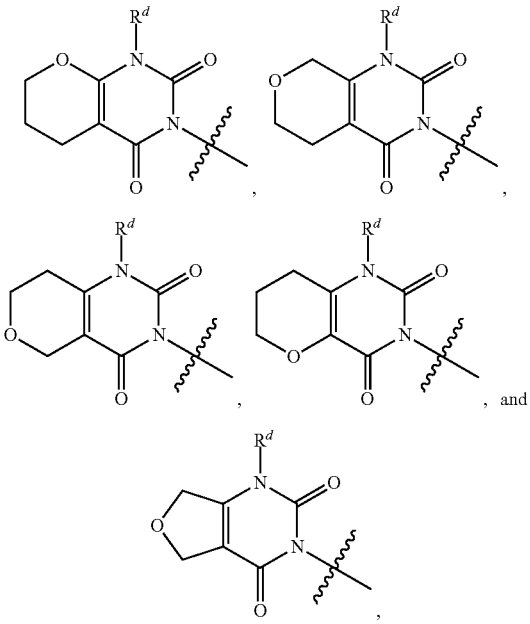

, and wherein $R^d$ is $C_{1-4}$alkyl, or $C_{1-4}$haloalkyl.

9. The compound of claim 6, or a pharmaceutically acceptable salt thereof, wherein R¹ is

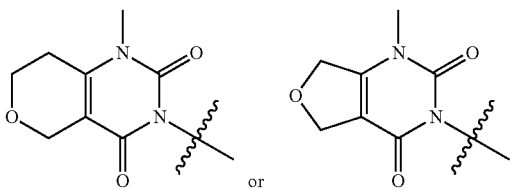 [SMILES: *n1c(=O)c2c(n(C)c1=O)CCOC2 ; *n1c(=O)c2c(n(C)c1=O)COC2]

10. A compound, or a pharmaceutically acceptable salt thereof, wherein the compound is selected from the group consisting of:

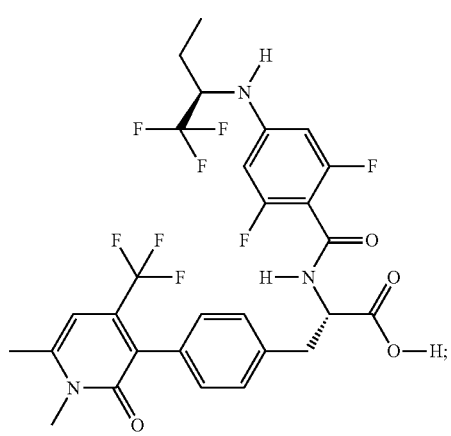

151
-continued
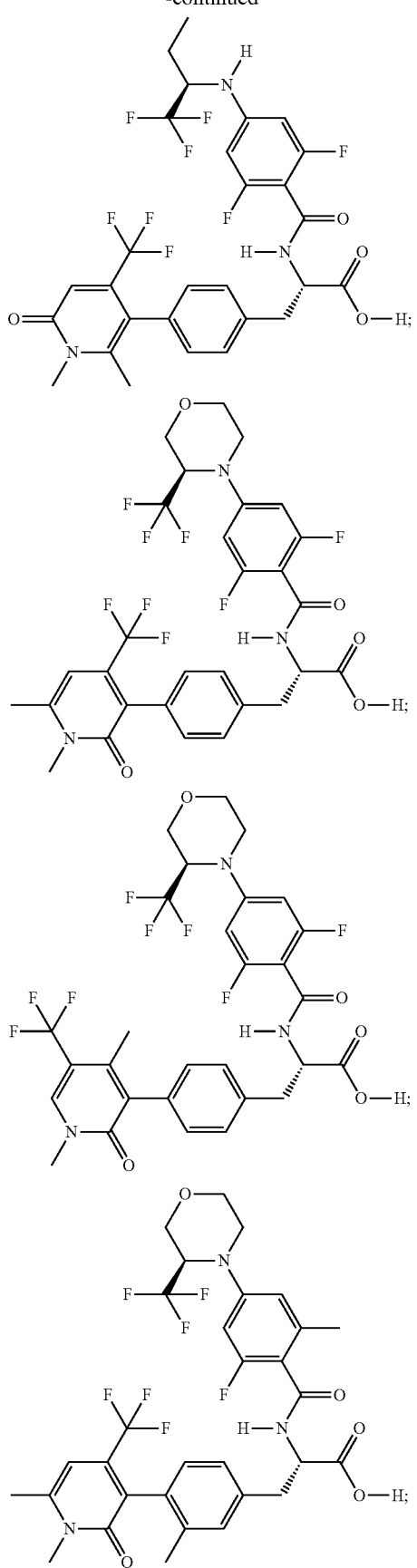
152
-continued
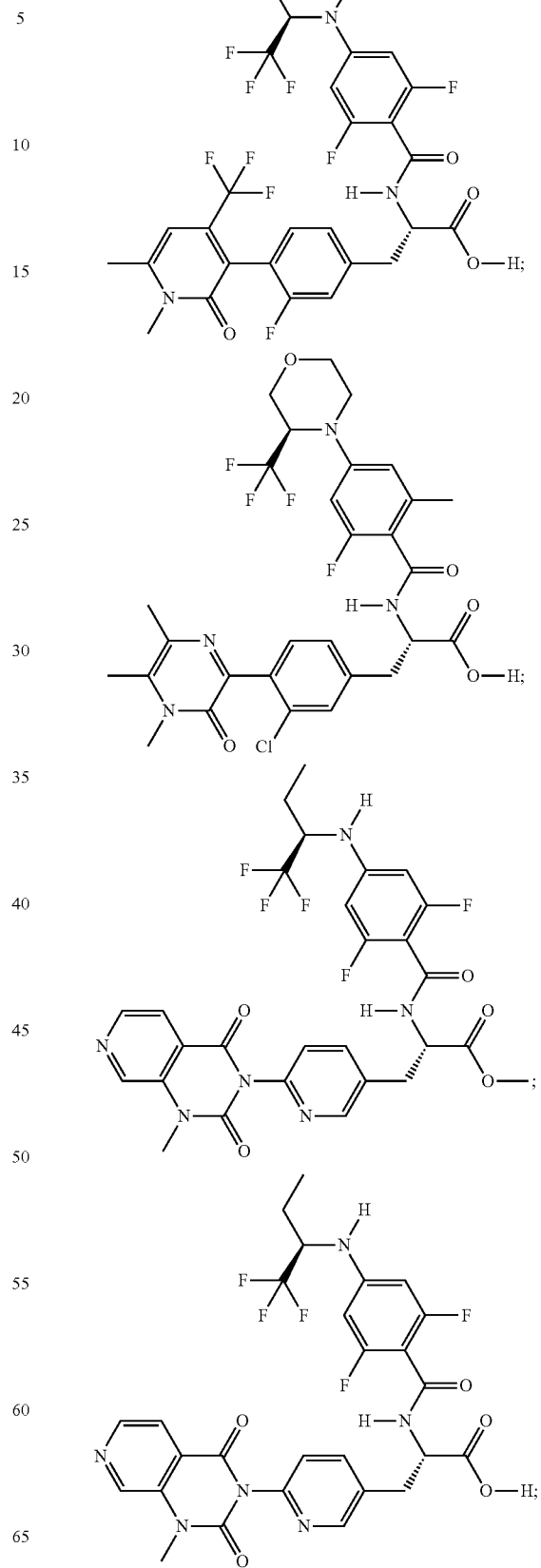

153
-continued
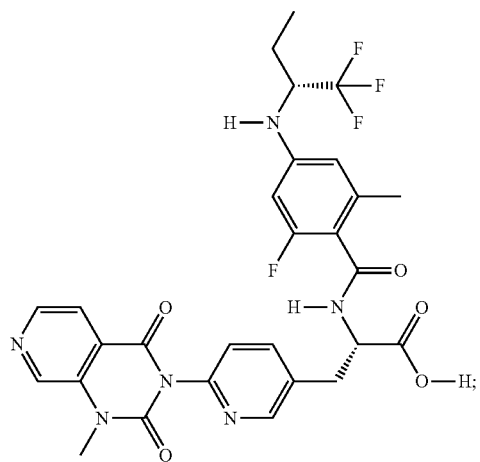
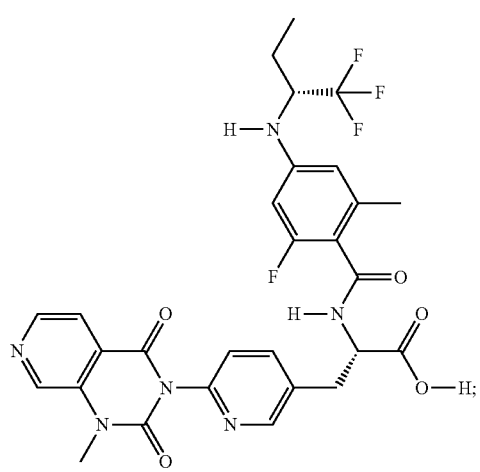
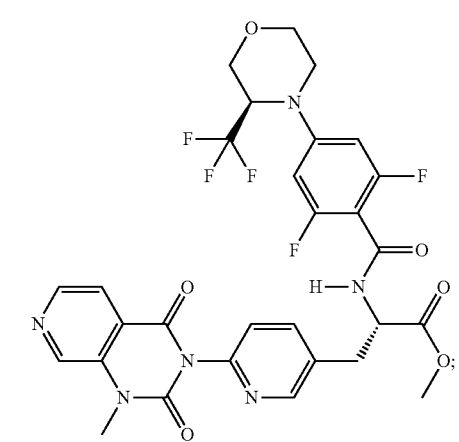
154
-continued
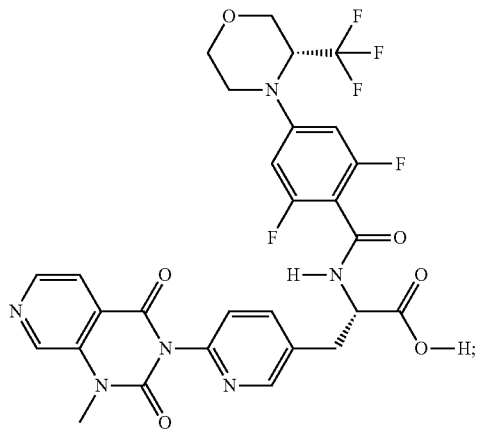
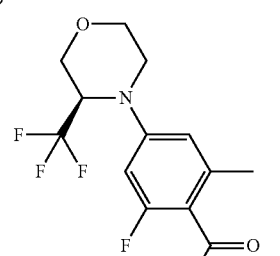
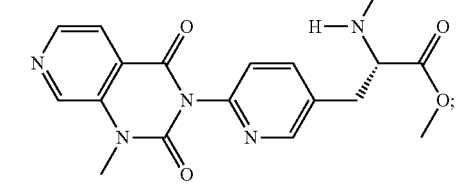
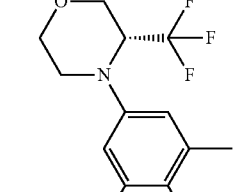
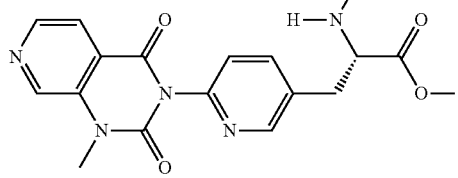
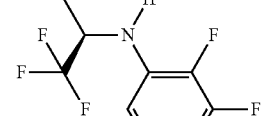
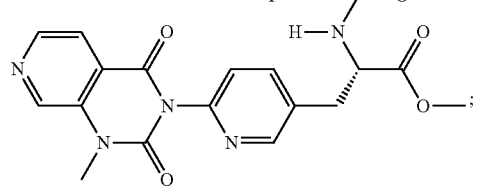

155
-continued
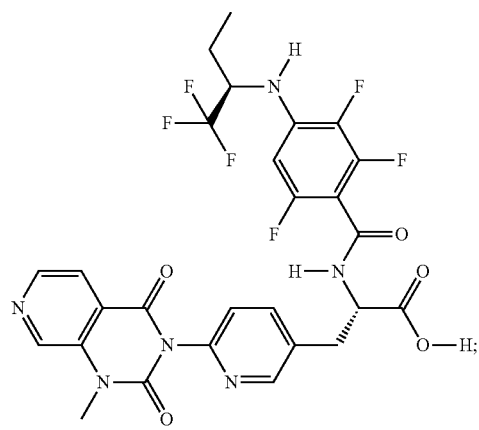
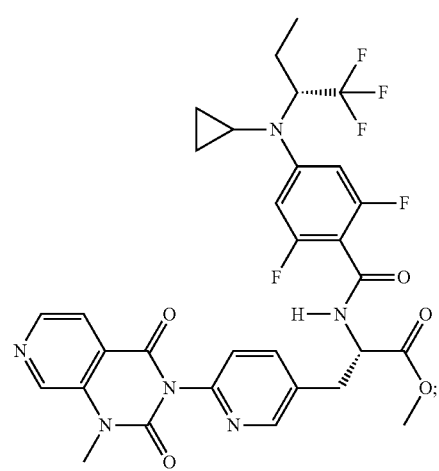
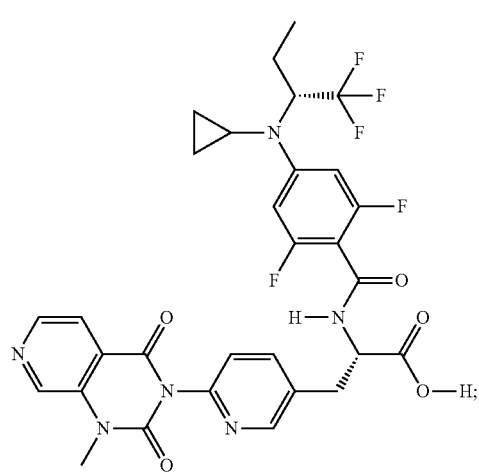
156
-continued
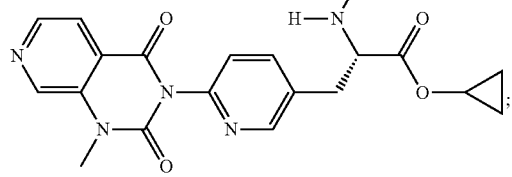
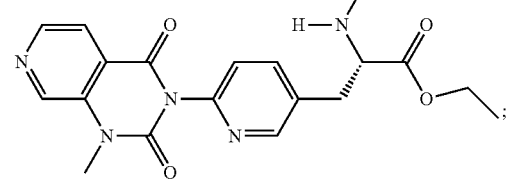
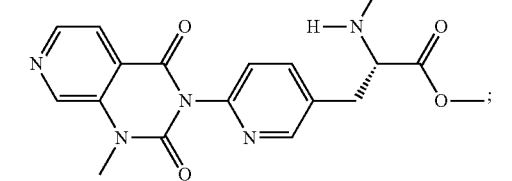
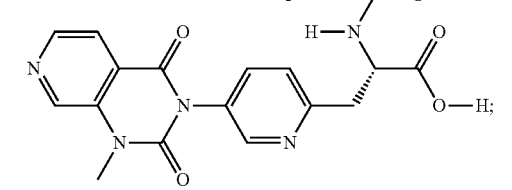

157
-continued
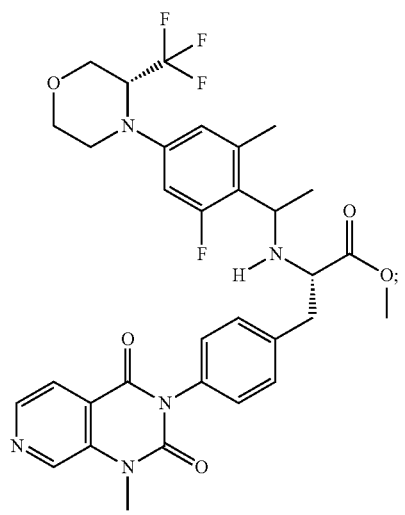
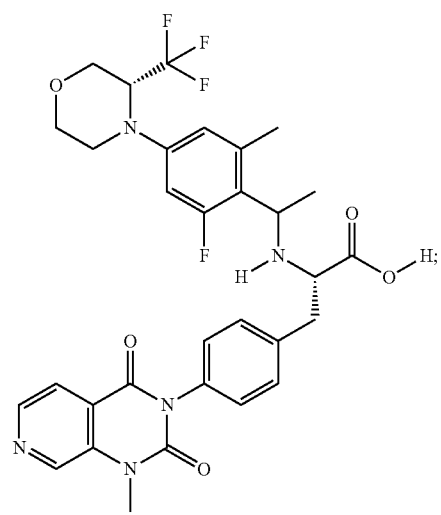
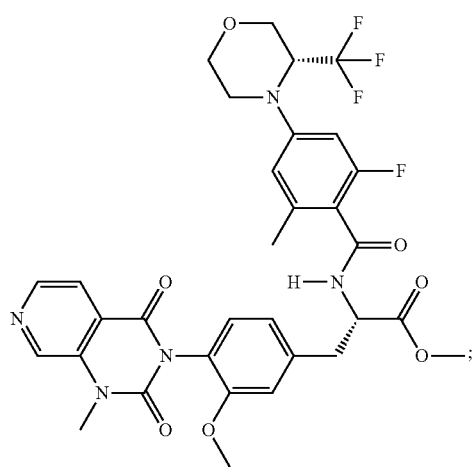
158
-continued
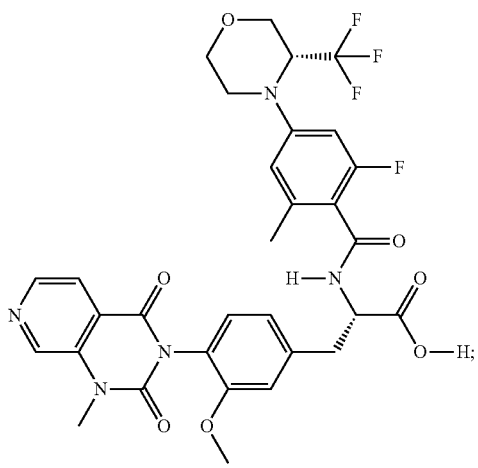
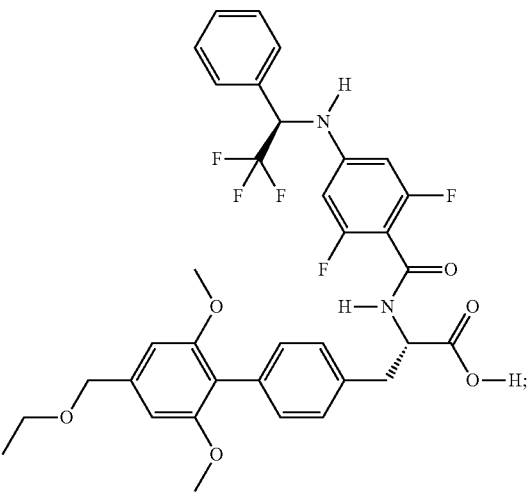

-continued
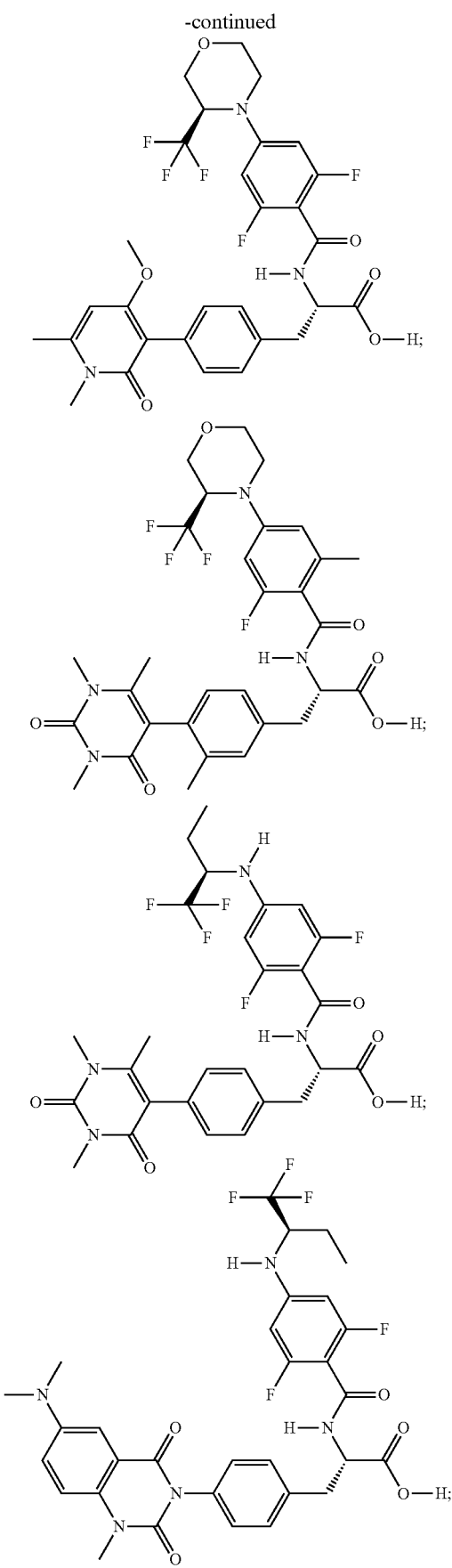
-continued
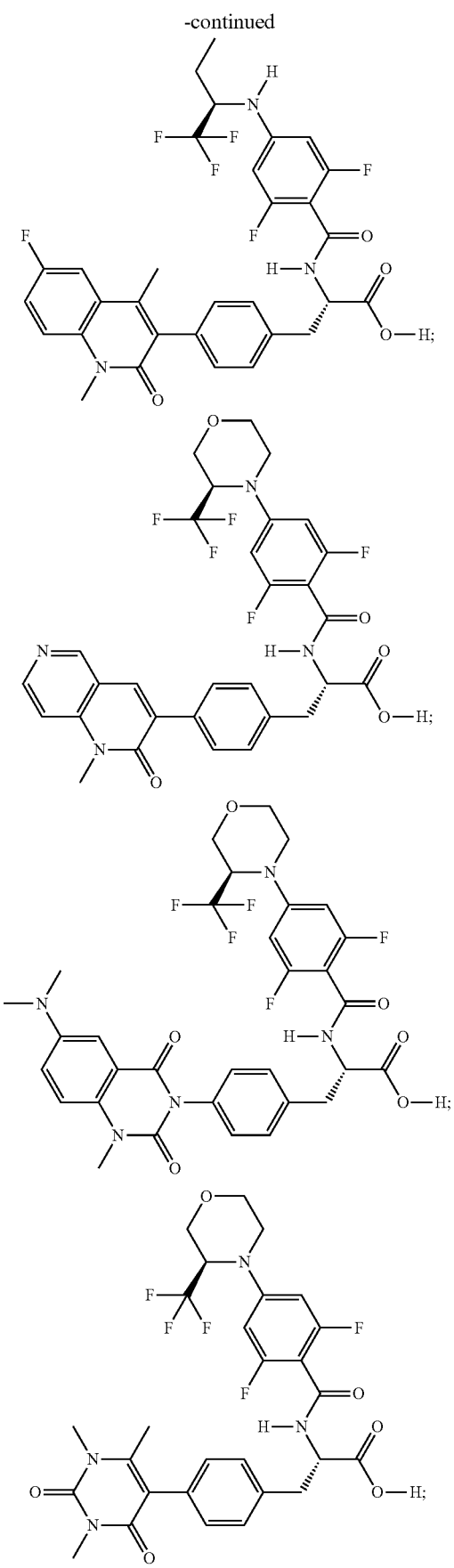

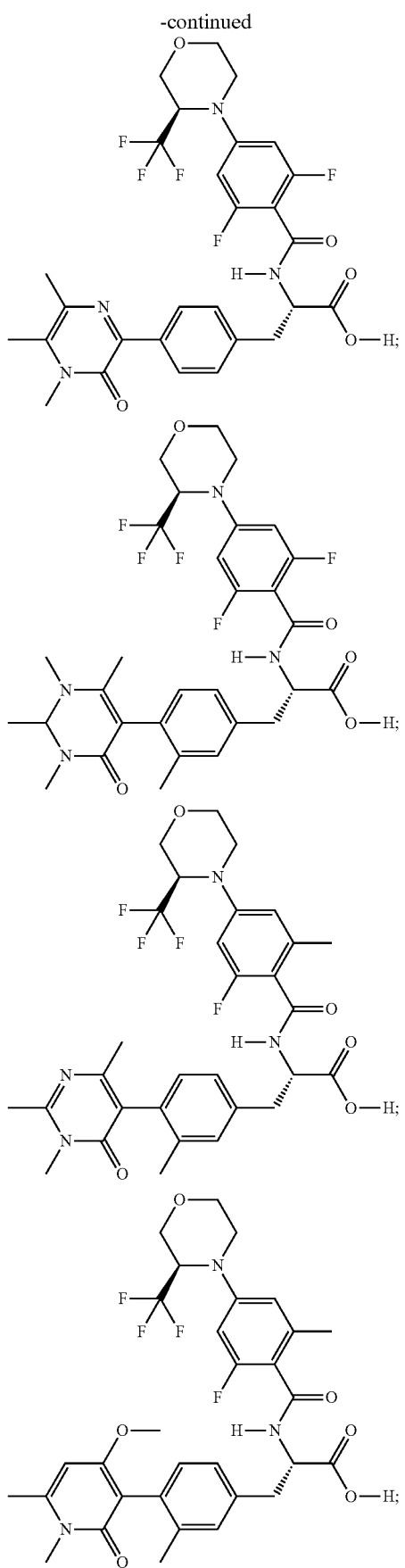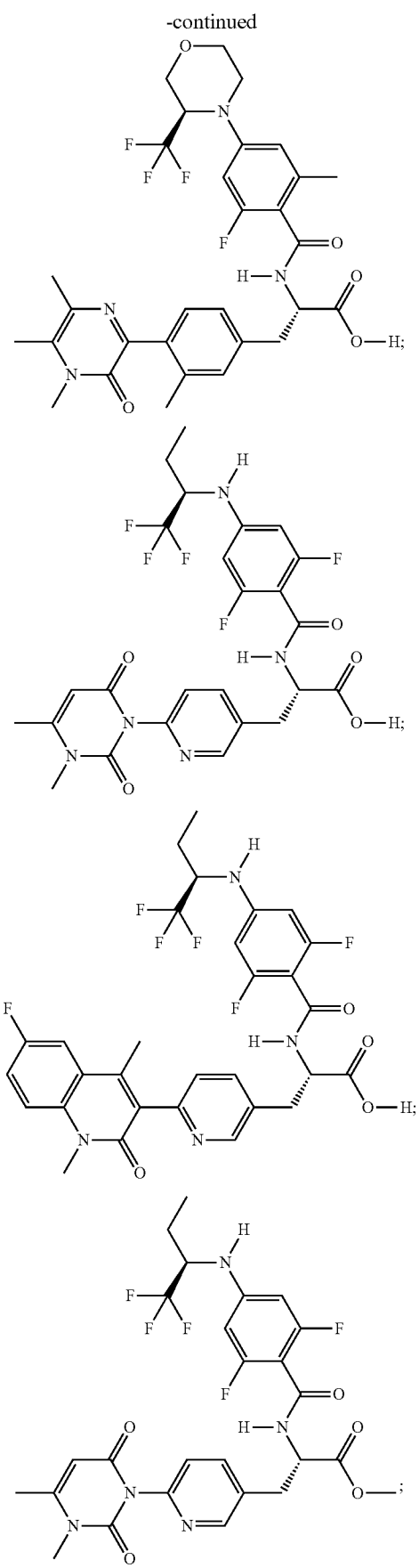

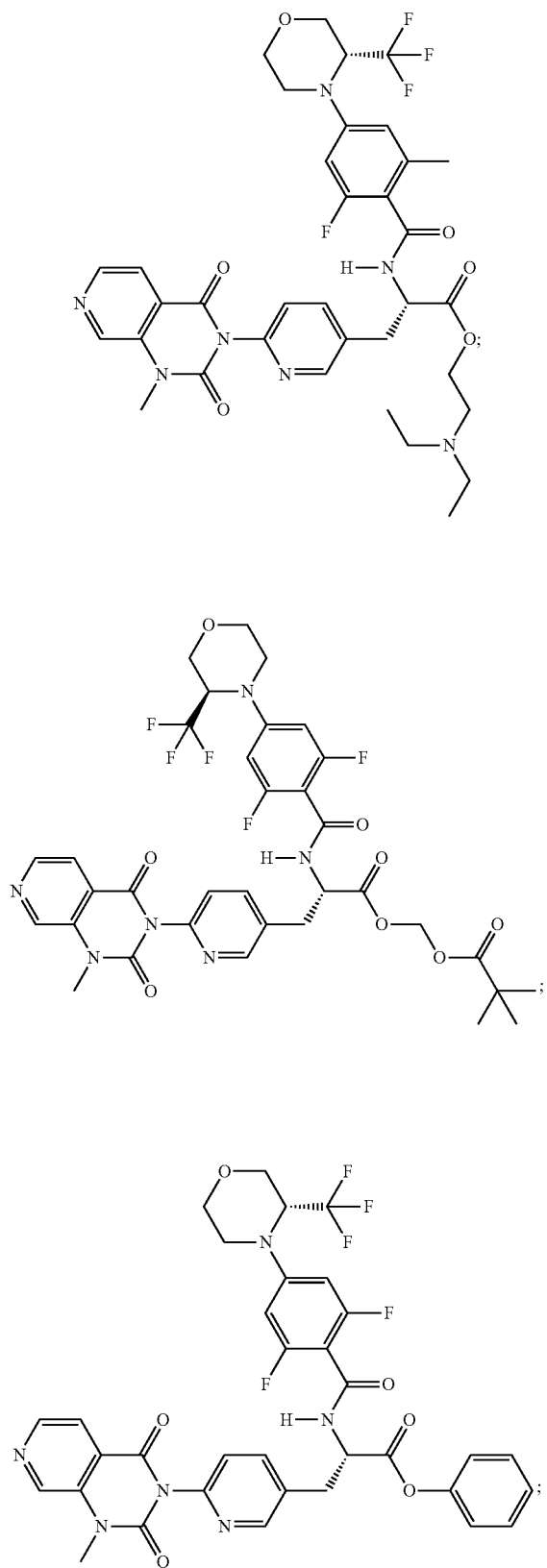
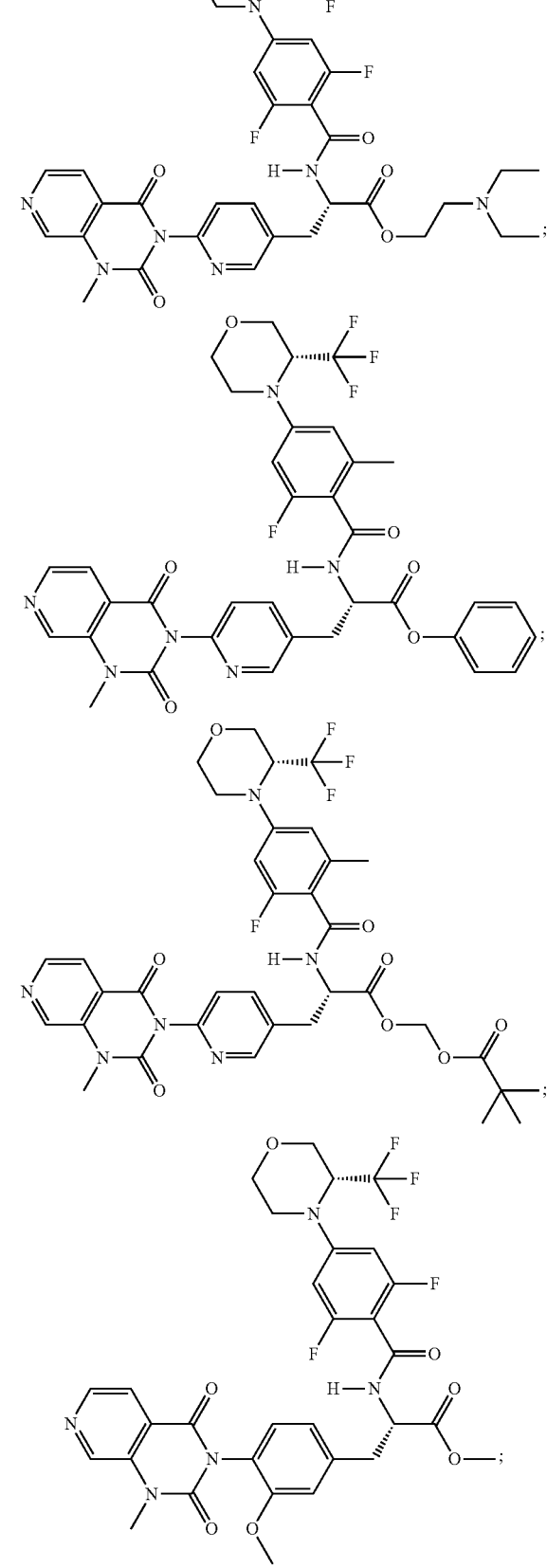

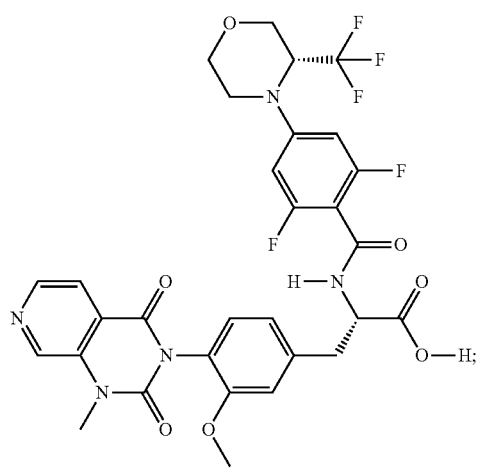
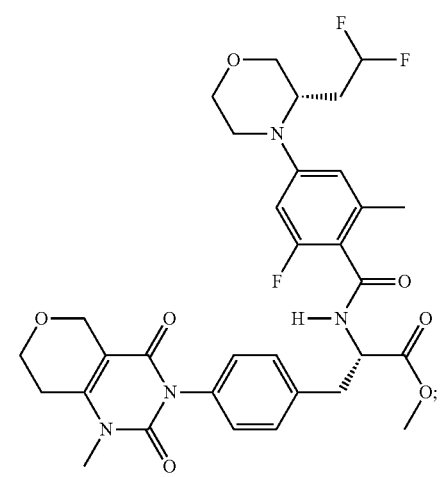
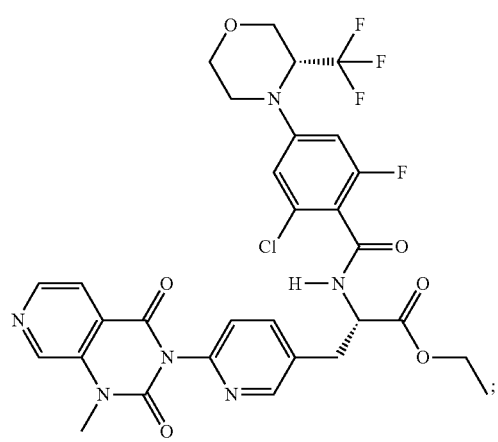
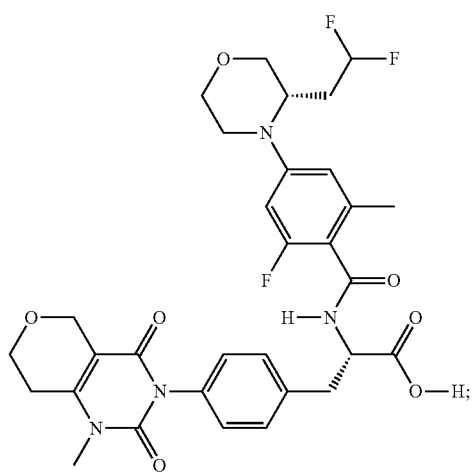
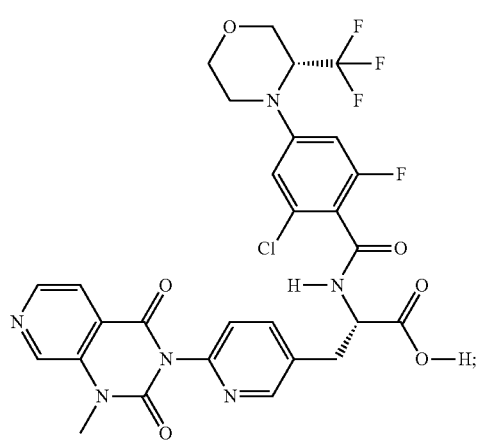
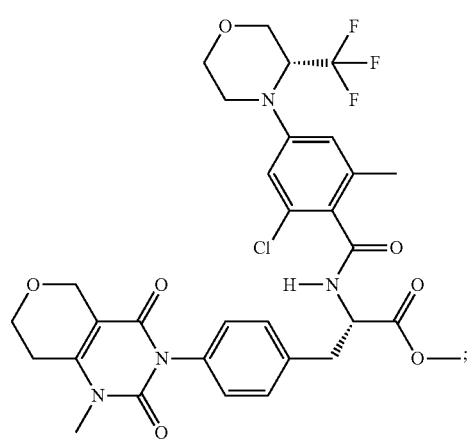

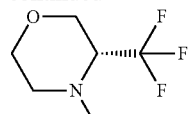
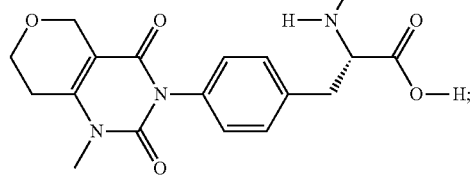
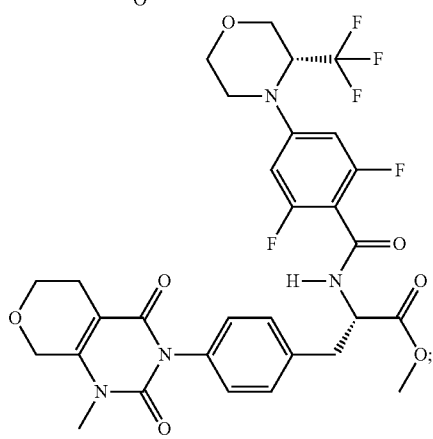
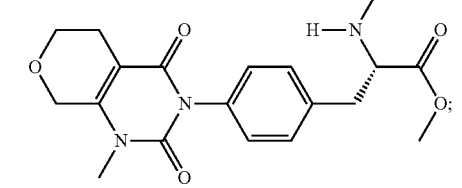
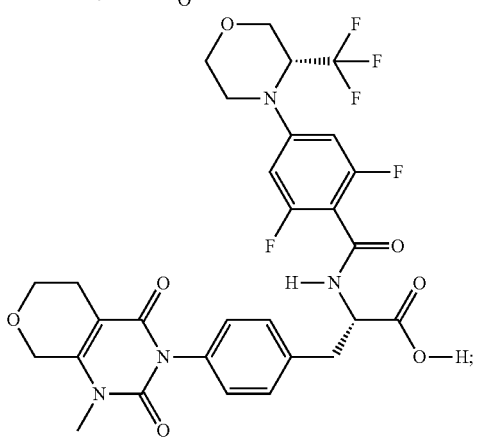
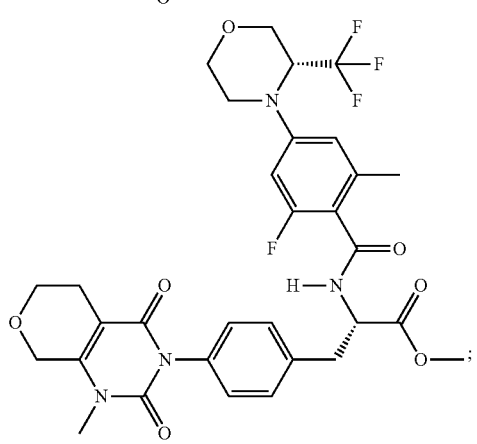
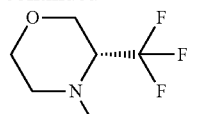
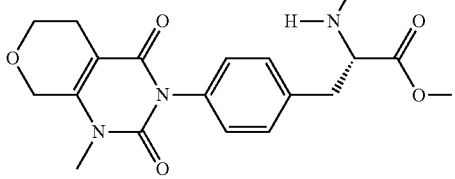
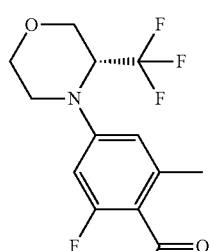
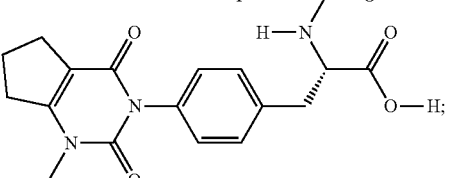
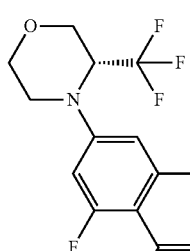
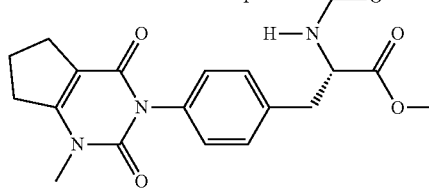
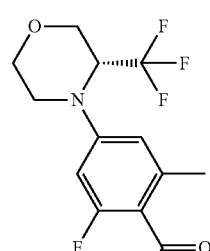
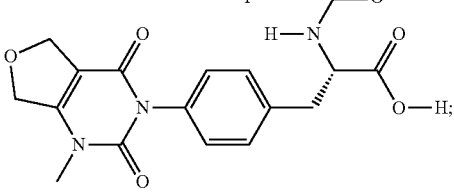

169
-continued
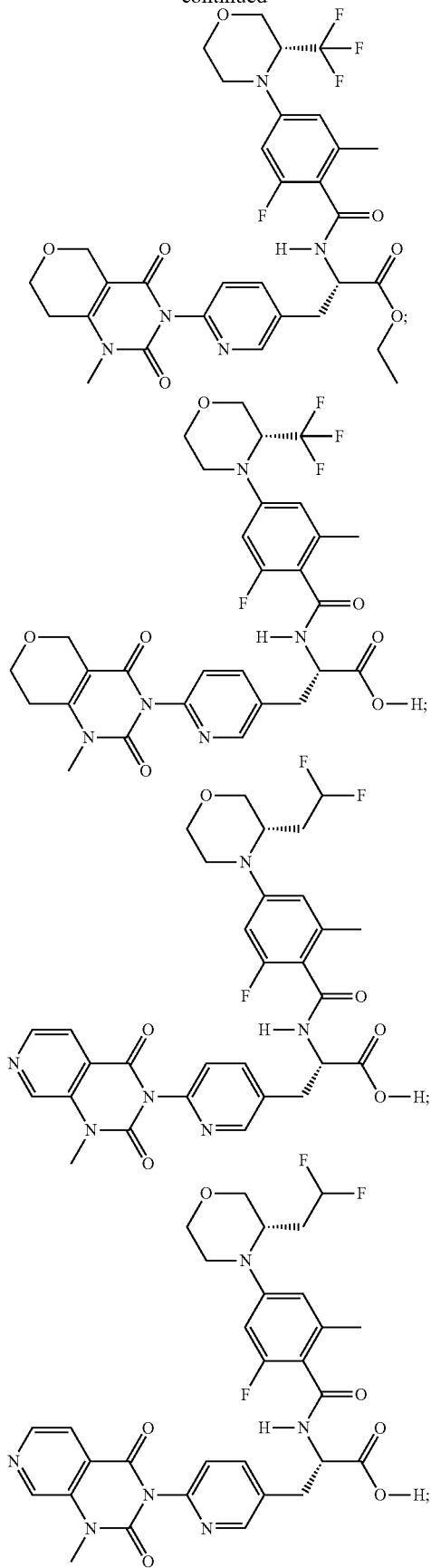
170
-continued
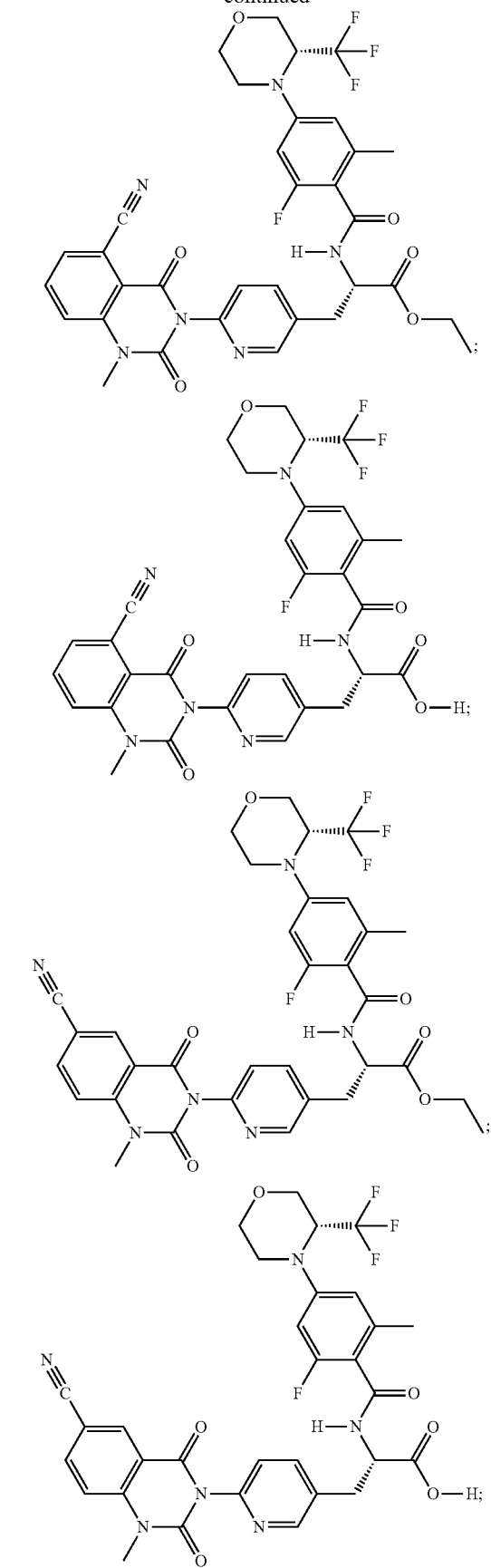

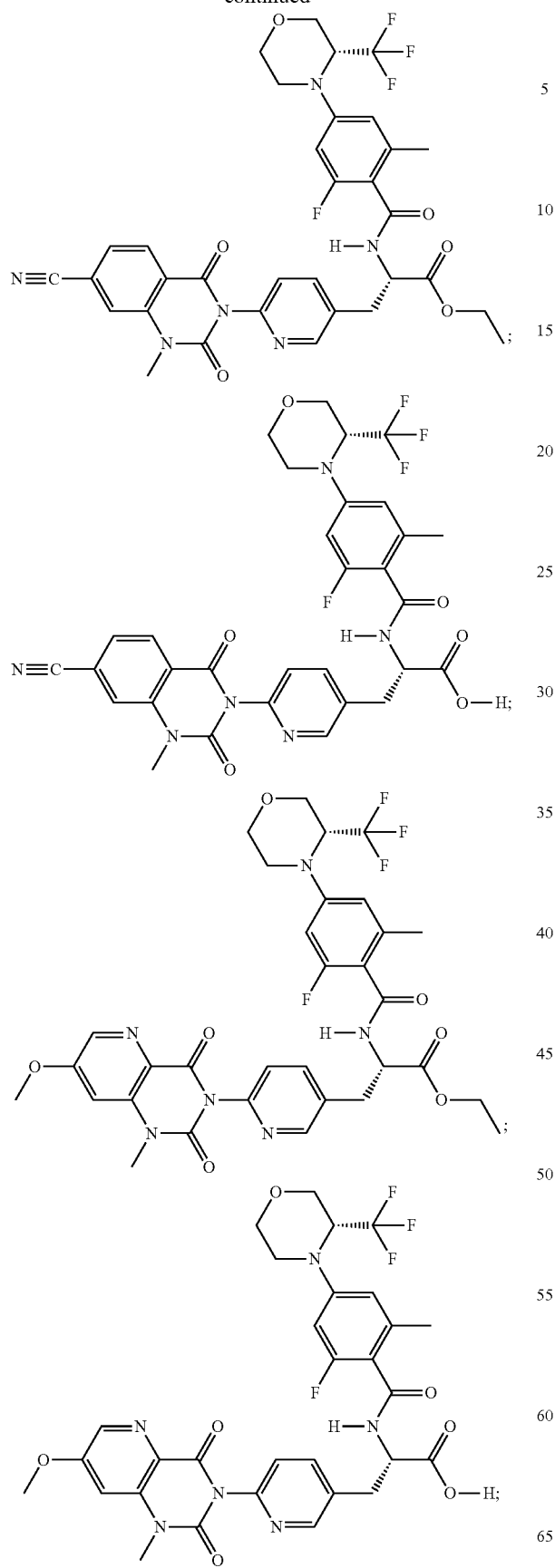
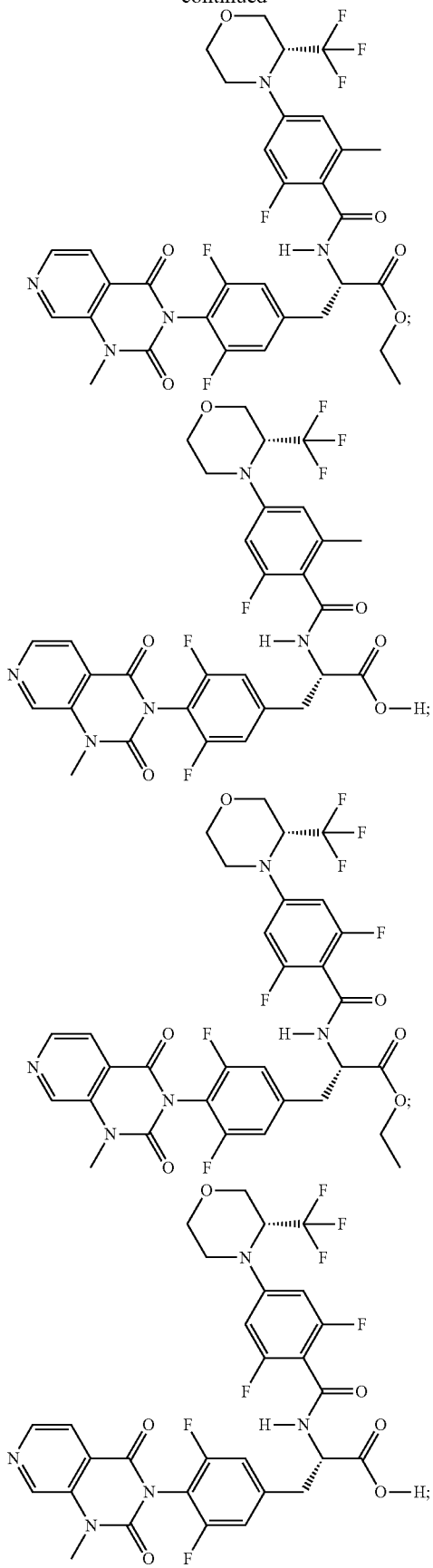

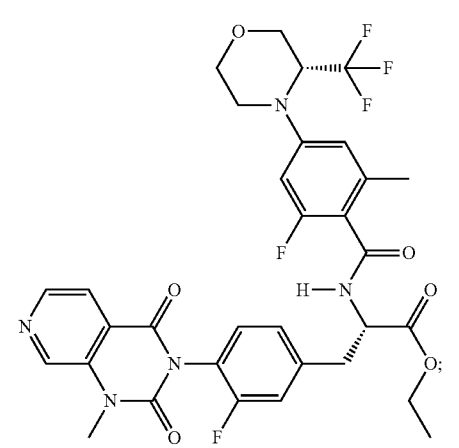
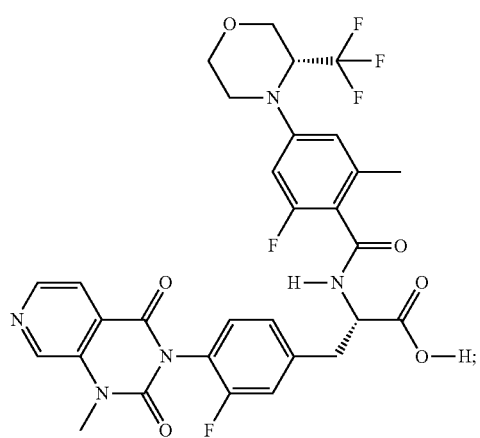
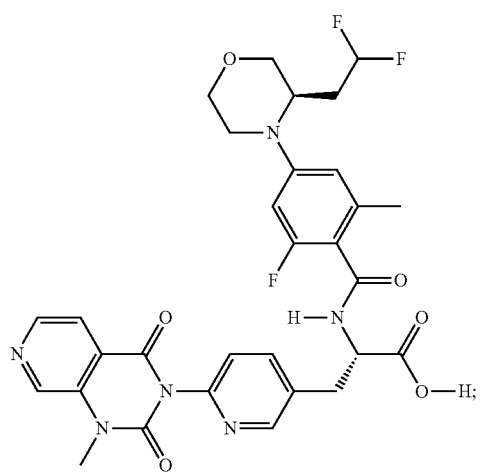
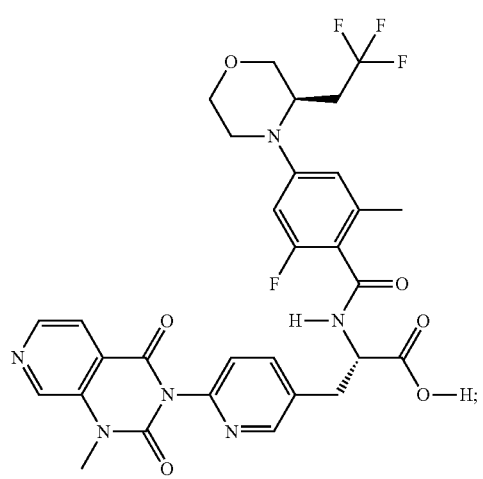
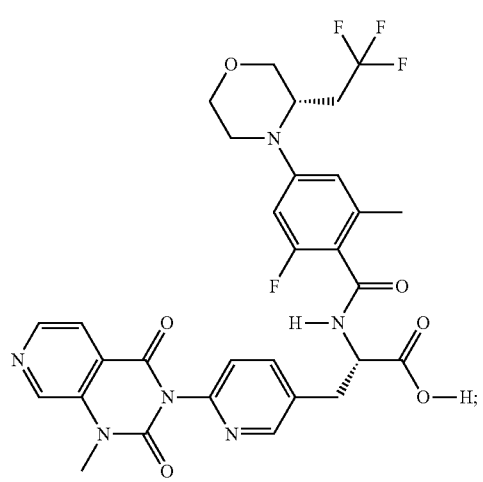
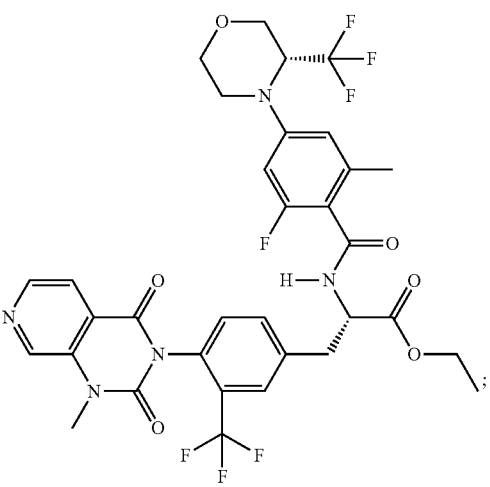

175
-continued
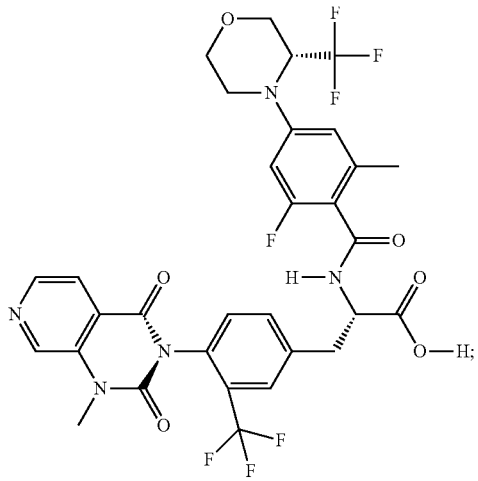
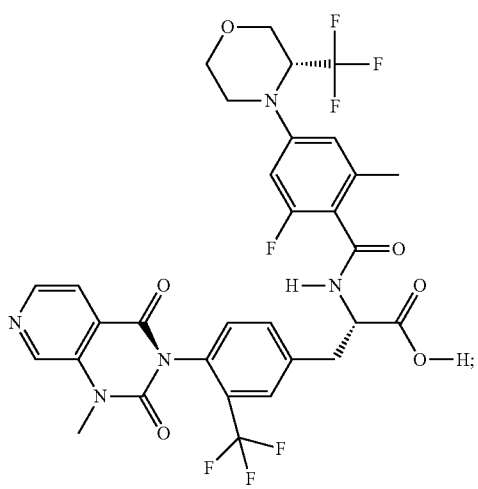
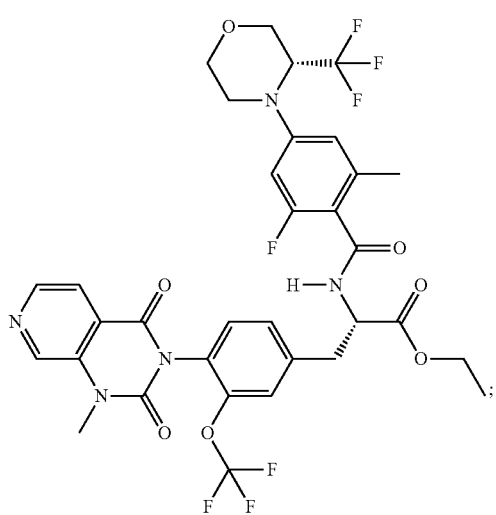
176
-continued
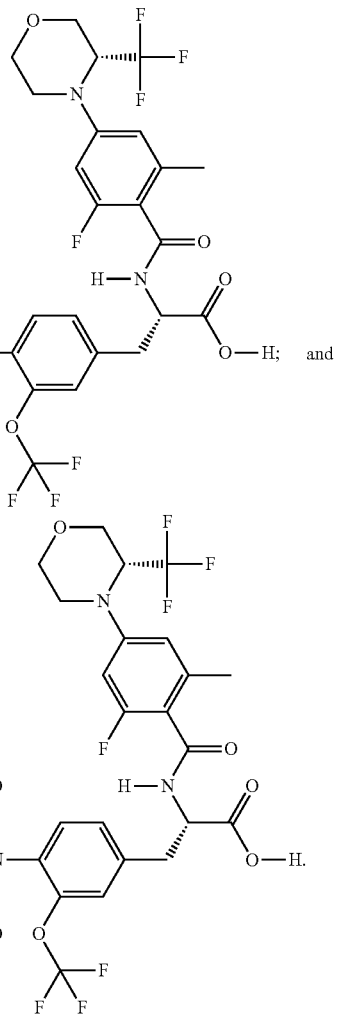
11. A compound, or a pharmaceutically acceptable salt thereof, wherein the compound is selected from the group consisting of:
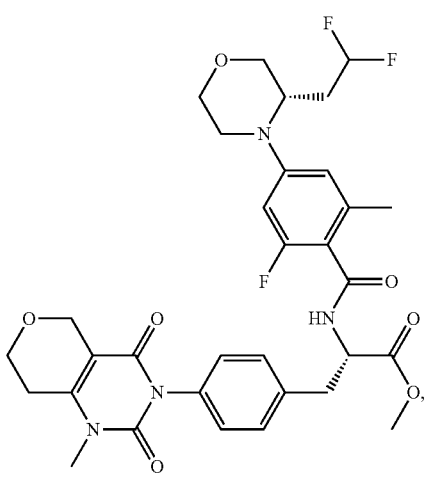

177
-continued
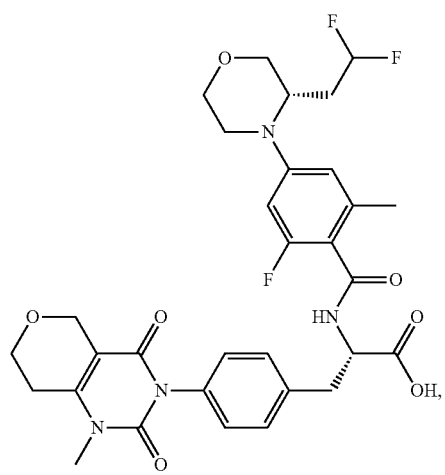
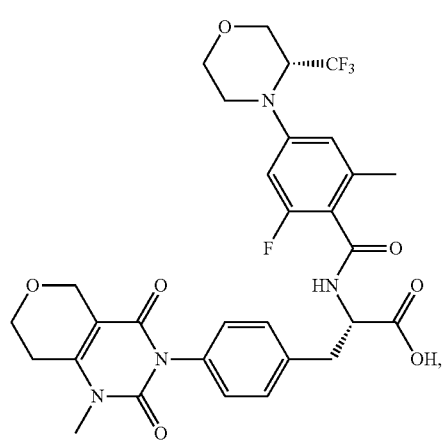
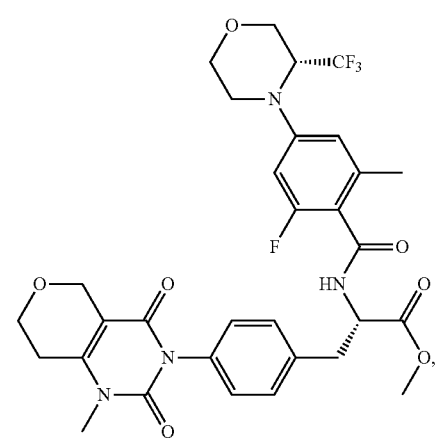
178
-continued
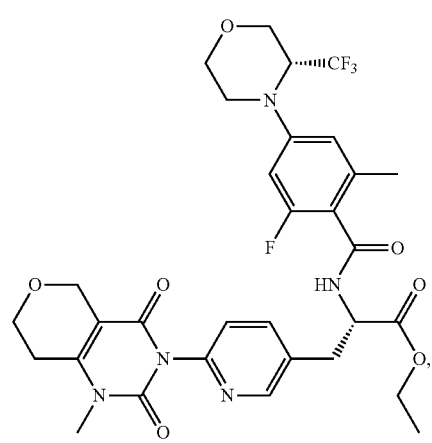
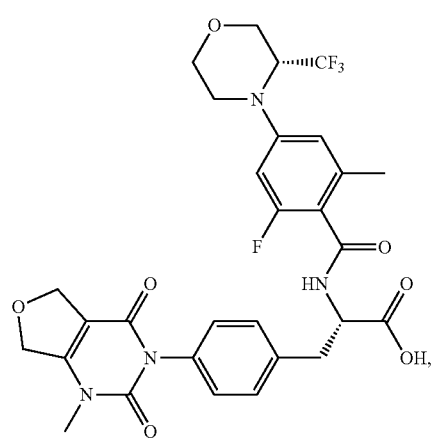
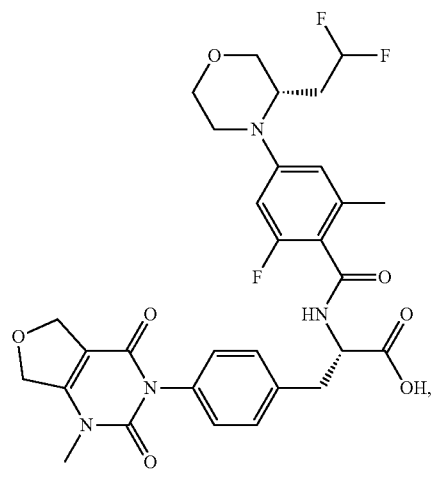

179
-continued
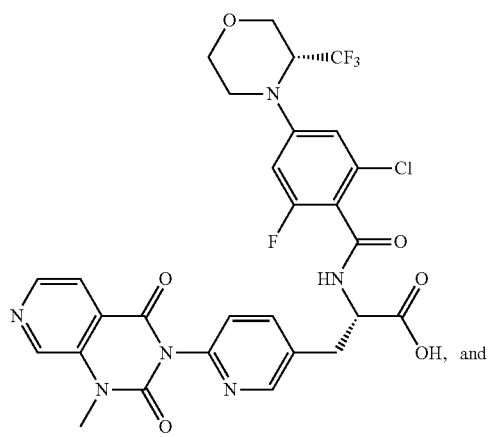
, and
180
-continued
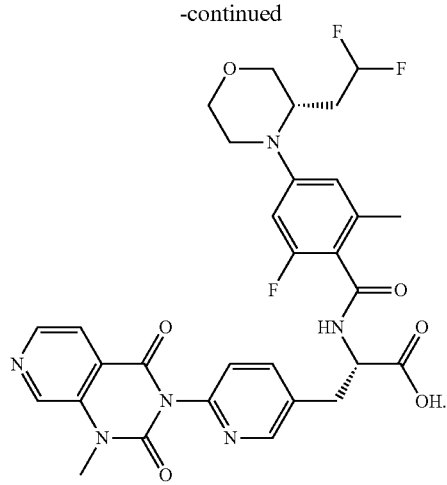
* * * * *